United States Patent
Bayever et al.

(10) Patent No.: US 11,344,552 B2
(45) Date of Patent: May 31, 2022

(54) METHODS FOR TREATING METASTATIC PANCREATIC CANCER USING COMBINATION THERAPIES COMPRISING LIPOSOMAL IRINOTECAN AND OXALIPLATIN

(71) Applicant: Ipsen Biopharm Ltd., Wrexham (GB)

(72) Inventors: Eliel Bayever, New York, NY (US); Sarah F. Blanchette, Lynnfield, MA (US); Jonathan Basil Fitzgerald, Arlington, MA (US); Daniel F. Gaddy, Cambridge, MA (US); Bart S. Hendriks, Belmont, MA (US); Ashish Kalra, Belmont, MA (US); Helen Lee, Arlington, MA (US)

(73) Assignee: Ipsen Biopharm Ltd.

( * ) Notice: Subject to any disclaimer, the term of this patent is extended or adjusted under 35 U.S.C. 154(b) by 0 days.

(21) Appl. No.: 15/809,815

(22) Filed: Nov. 10, 2017

(65) Prior Publication Data

US 2018/0078556 A1 Mar. 22, 2018

Related U.S. Application Data

(63) Continuation of application No. 15/241,106, filed on Aug. 19, 2016, now abandoned.
(Continued)

(51) Int. Cl.
*A61K 31/519* (2006.01)
*A61K 31/282* (2006.01)
(Continued)

(52) U.S. Cl.
CPC .......... *A61K 31/519* (2013.01); *A61K 9/0019* (2013.01); *A61K 9/127* (2013.01);
(Continued)

(58) Field of Classification Search
CPC .. A61K 31/519; A61K 9/1271; A61K 9/0019; A61K 31/475; A61K 31/436;
(Continued)

(56) References Cited

U.S. PATENT DOCUMENTS

| 4,604,463 A | 8/1986 | Miyasaka et al. |
| 5,013,556 A | 5/1991 | Woodle et al. |

(Continued)

FOREIGN PATENT DOCUMENTS

| CA | 2412790 A1 | 1/2002 |
| CN | 1829741 A | 9/2006 |

(Continued)

OTHER PUBLICATIONS

Conroy T Folfirinox versus gemcitabine for metastatic pancreatic cancer, nejm, 34(19), 2011, 1817.*
(Continued)

*Primary Examiner* — Gollamudi S Kishore
(74) *Attorney, Agent, or Firm* — McNeill Baur PLLC

(57) ABSTRACT

Combination therapy regimens including liposomal irinotecan, oxaliplatin and 5-fluorouracil are useful in the treatment of pancreatic cancer, including treatment of patients diagnosed with previously untreated metastatic adenocarcinoma of the pancreas. The combination therapy can include the administration of liposomal irinotecan, oxaliplatin, leucovorin and 5-fluorouracil once every two weeks.

15 Claims, 22 Drawing Sheets

Related U.S. Application Data

(60) Provisional application No. 62/343,313, filed on May 31, 2016, provisional application No. 62/323,245, filed on Apr. 15, 2016, provisional application No. 62/302,341, filed on Mar. 2, 2016, provisional application No. 62/281,473, filed on Jan. 21, 2016, provisional application No. 62/273,244, filed on Dec. 30, 2015, provisional application No. 62/216,736, filed on Sep. 10, 2015, provisional application No. 62/208,209, filed on Aug. 21, 2015.

(51) Int. Cl.
| | |
|---|---|
| *A61K 31/4745* | (2006.01) |
| *A61K 31/513* | (2006.01) |
| *A61K 9/127* | (2006.01) |
| *A61K 9/00* | (2006.01) |
| *A61K 31/475* | (2006.01) |
| *A61K 31/436* | (2006.01) |
| *A61K 47/20* | (2006.01) |

(52) U.S. Cl.
CPC .......... *A61K 9/1271* (2013.01); *A61K 31/282* (2013.01); *A61K 31/436* (2013.01); *A61K 31/475* (2013.01); *A61K 31/4745* (2013.01); *A61K 31/513* (2013.01); *A61K 47/20* (2013.01); *A61K 2300/00* (2013.01)

(58) Field of Classification Search
CPC .. A61K 47/20; A61K 31/282; A61K 31/4745; A61K 31/513; A61K 9/127; A61K 2300/00; A61P 43/00; A61P 35/04
See application file for complete search history.

(56) References Cited

U.S. PATENT DOCUMENTS

| | | |
|---|---|---|
| 5,077,056 A | 12/1991 | Bally et al. |
| 5,192,549 A | 3/1993 | Barenolz et al. |
| 5,316,771 A | 5/1994 | Barenholz et al. |
| 5,538,954 A | 7/1996 | Koch et al. |
| 5,543,152 A | 8/1996 | Webb et al. |
| 5,593,622 A | 1/1997 | Yoshioka et al. |
| 5,676,971 A | 10/1997 | Yoshioka et al. |
| 5,783,568 A | 7/1998 | Schlessinger et al. |
| 5,785,987 A | 7/1998 | Hope et al. |
| 5,846,458 A | 12/1998 | Yoshioka et al. |
| 6,110,491 A | 8/2000 | Kirpotin |
| 6,210,707 B1 | 4/2001 | Papahadjopoulos et al. |
| 6,214,388 B1 | 4/2001 | Benz et al. |
| 6,241,999 B1 | 6/2001 | Ye et al. |
| 6,355,268 B1 | 3/2002 | Slater et al. |
| 6,403,569 B1 | 6/2002 | Achterrath |
| 6,465,008 B1 | 10/2002 | Slater et al. |
| 6,511,676 B1 | 1/2003 | Boulikas |
| 6,545,010 B2 | 4/2003 | Bissery |
| 6,720,001 B2 | 4/2004 | Chen et al. |
| 6,787,132 B1 | 9/2004 | Gabizon et al. |
| 6,794,370 B2 | 9/2004 | Achterrath |
| 7,022,336 B2 | 4/2006 | Papahadjopoulos et al. |
| 7,060,828 B2 | 6/2006 | Madden et al. |
| 7,135,177 B2 | 11/2006 | Benz et al. |
| 7,219,016 B2 | 5/2007 | Rimm et al. |
| 7,244,448 B2 | 7/2007 | Madden et al. |
| 7,244,826 B1 | 7/2007 | Marks et al. |
| 7,507,407 B2 | 3/2009 | Benz et al. |
| 7,829,113 B2 | 11/2010 | Okada et al. |
| 7,842,676 B2 | 11/2010 | Janoff et al. |
| 7,846,440 B2 | 12/2010 | Schoeberl et al. |
| 7,846,473 B2 | 12/2010 | Yoshino et al. |
| 7,850,990 B2 | 12/2010 | Tardi et al. |
| 7,871,620 B2 | 1/2011 | Benz et al. |
| 7,892,554 B2 | 2/2011 | Marks et al. |
| 8,067,432 B2 | 11/2011 | Anderson et al. |
| 8,147,867 B2 | 4/2012 | Hong et al. |
| 8,329,213 B2 | 12/2012 | Hong et al. |
| 8,496,961 B2 | 7/2013 | Hong et al. |
| 8,658,203 B2 | 2/2014 | Drummond et al. |
| 8,703,181 B2 | 4/2014 | Hong et al. |
| 8,992,970 B2 | 3/2015 | Hong et al. |
| 9,339,497 B2 | 5/2016 | Bayever et al. |
| 9,364,473 B2 | 6/2016 | Bayever et al. |
| 9,452,162 B2 | 9/2016 | Bayever et al. |
| 9,492,442 B2 | 11/2016 | Bayever et al. |
| 9,511,155 B2 | 12/2016 | Drummond et al. |
| 9,616,081 B2 | 4/2017 | Okabe |
| 9,717,723 B2 | 8/2017 | Hong et al. |
| 9,717,724 B2 | 8/2017 | Bayever et al. |
| 9,724,303 B2 | 8/2017 | Hong et al. |
| 9,730,891 B2 | 8/2017 | Hong et al. |
| 9,737,528 B2 | 8/2017 | Drummond et al. |
| 9,782,349 B2 | 10/2017 | Hong et al. |
| 9,895,365 B2 | 2/2018 | Blanchette et al. |
| 10,350,201 B2 | 7/2019 | Hong et al. |
| 10,413,510 B2 | 9/2019 | Hong et al. |
| 10,456,360 B2 | 10/2019 | Drummond et al. |
| 10,478,428 B2 | 11/2019 | Blanchette et al. |
| 10,722,508 B2 | 7/2020 | Hong et al. |
| 10,980,795 B2 | 4/2021 | Bayever et al. |
| 10,993,914 B2 | 5/2021 | Drummond et al. |
| 11,052,079 B2 | 7/2021 | Hong et al. |
| 11,071,726 B2 | 7/2021 | Fitzgerald et al. |
| 2002/0035091 A1 | 3/2002 | Govindarajan et al. |
| 2002/0102298 A1 | 8/2002 | Needham |
| 2002/0146450 A1 | 10/2002 | Slater et al. |
| 2002/0192275 A1 | 12/2002 | Zalipsky et al. |
| 2003/0138481 A1 | 7/2003 | Zadi |
| 2004/0002505 A1 | 1/2004 | Ozawa et al. |
| 2004/0071768 A1 | 4/2004 | Sarris et al. |
| 2007/0110798 A1 | 5/2007 | Drummond et al. |
| 2007/0219268 A1 | 9/2007 | Hausheer |
| 2007/0265324 A1 | 11/2007 | Wernet et al. |
| 2008/0108135 A1 | 5/2008 | Marks et al. |
| 2009/0123419 A1 | 5/2009 | Sherman et al. |
| 2009/0149397 A1 | 6/2009 | Ossovskaya et al. |
| 2010/0056761 A1 | 3/2010 | Schoeberl et al. |
| 2010/0068255 A1 | 3/2010 | Benz et al. |
| 2011/0059076 A1 | 3/2011 | McDonagh et al. |
| 2011/0104256 A1 | 5/2011 | Wang et al. |
| 2011/0123523 A1 | 5/2011 | Schoeberl et al. |
| 2012/0003160 A1 | 1/2012 | Wolf et al. |
| 2012/0034295 A1 | 2/2012 | Spiegel et al. |
| 2012/0045524 A1 | 2/2012 | Wernet et al. |
| 2012/0269812 A1 | 10/2012 | Baum et al. |
| 2012/0282325 A1 | 11/2012 | Tong et al. |
| 2013/0209481 A1 | 8/2013 | Zhou et al. |
| 2013/0236459 A1 | 9/2013 | Baum et al. |
| 2013/0274281 A1 | 10/2013 | Bradley |
| 2014/0065204 A1 | 3/2014 | Hayes et al. |
| 2014/0170075 A1 | 6/2014 | Drummond et al. |
| 2015/0182460 A1 | 7/2015 | Hong et al. |
| 2015/0182521 A1 | 7/2015 | Bayever et al. |
| 2015/0328156 A1 | 11/2015 | Bayever et al. |
| 2015/0374682 A1 | 12/2015 | Bayever et al. |
| 2016/0030341 A1 | 2/2016 | Hong et al. |
| 2016/0030342 A1 | 2/2016 | Hong et al. |
| 2016/0058704 A1 | 3/2016 | Tardi et al. |
| 2016/0074382 A1 | 3/2016 | Bayever et al. |
| 2016/0206615 A1 | 7/2016 | Tangutoori et al. |
| 2016/0303264 A1 | 10/2016 | Hendricks et al. |
| 2016/0346272 A1 | 12/2016 | Bayever et al. |
| 2017/0049767 A1 | 2/2017 | Blanchette et al. |
| 2017/0049775 A1 | 2/2017 | Bayever et al. |
| 2017/0202840 A1 | 7/2017 | Bayever et al. |
| 2017/0333421 A1 | 11/2017 | Adiwijaya et al. |

FOREIGN PATENT DOCUMENTS

| | | |
|---|---|---|
| CN | 101878229 A | 11/2010 |
| CN | 1980637 B | 2/2014 |
| WO | 1997028156 A1 | 8/1997 |
| WO | 2000023052 A1 | 4/2000 |
| WO | 2003013536 A2 | 2/2003 |

(56) References Cited

FOREIGN PATENT DOCUMENTS

| WO | 2003030864 A1 | 4/2003 |
|---|---|---|
| WO | 2003101474 A1 | 12/2003 |
| WO | 2004017940 A3 | 4/2004 |
| WO | 2004093795 A3 | 11/2004 |
| WO | 2005000900 A1 | 1/2005 |
| WO | 2005107712 A1 | 11/2005 |
| WO | 2006110816 A2 | 10/2006 |
| WO | 2007076117 A2 | 7/2007 |
| WO | 2009040426 A1 | 4/2009 |
| WO | 2009126920 A3 | 3/2010 |
| WO | 2010125462 A2 | 11/2010 |
| WO | 2011066684 A1 | 6/2011 |
| WO | 2011153010 A1 | 12/2011 |
| WO | 2012012454 A1 | 1/2012 |
| WO | 2012031293 A1 | 3/2012 |
| WO | 2012078695 A2 | 6/2012 |
| WO | 2012079582 A1 | 6/2012 |
| WO | 2012146610 A1 | 11/2012 |
| WO | 2013006547 A2 | 1/2013 |
| WO | 2013138371 A1 | 9/2013 |
| WO | 2013158803 A1 | 10/2013 |
| WO | 2013188586 A1 | 12/2013 |
| WO | WO-2013-188586 * | 12/2013 |
| WO | 2014113167 A1 | 7/2014 |
| WO | 2014157444 A1 | 10/2014 |
| WO | WO-2016-094402 * | 6/2016 |
| WO | 2016168451 A1 | 10/2016 |
| WO | 2017031442 A1 | 2/2017 |
| WO | 2017031445 A1 | 2/2017 |
| WO | 2017034957 A1 | 3/2017 |
| WO | 2017066726 A1 | 4/2017 |
| WO | 2017172678 A1 | 10/2017 |
| WO | 2017199093 A1 | 11/2017 |
| WO | 2018083470 A1 | 5/2018 |

OTHER PUBLICATIONS

Fleming D, http://www.oncologynurseadvisor.com/advisor-forum/importance-of-sequence-in-chemotherapy-administration/article/378072/ 2014.*
Alcindor et al, Curr Oncol, 2011, 18(1), 18-25.*
Melis M, Can We Downstage Regionally Advanced Pancreatic Cancer to Resectable: a Phase I/II Study of Induction Oxaliplatin and 5FU Chemo-Radiation, http://meetings.ssat.com/abstracts/11ddw/P57.cgi (Year: 2011).*
Oxaliplatin label, revised Nov. 2013.
Camptosar label, revised Dec. 2014.
Chen L, et al., "Phase 1 Study of Liposome Encapsulated Irinotecan (PEP02) in Advanced Solid Tumor Patients," Poster presented at the ASCO meeting of May 30-Jun. 3, 2008, Chicago, Illinois, 9 pages.
Chibaudel B, et al., "Pepcol: A Randomized Non-Comparative Phase II Study to Evaluate the Efficacy and Safety of PEP02 (MM-398) or Irinotecan in Combination with Leucovorin and 5-Fluorouracil as Second-Line Treatment for Patients with Unresectable Metastatic Colorectal Cancer. A Gercor Study" Poster presented at ASCO 2015, 6 pages.
Clinical Trials Identifier NCT00813163: Jan. 12, 2015 update, "A Phase II Study of PEP02 as a Second Line Therapy for Patients with Metastatic Pancreatic Cancer." Retrieved from ClinicalTrials.gov archive, 3 printed pages.
Clinical Trials Identifier NCT01359007: May 23, 2011 update, "A Phase II Study Evaluating the Rate of RO Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01359007: May 28, 2015 update, "A Phase II Study Evaluating the Rate of RO Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01446458: Oct. 4, 2011 update, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.
Clinical Trials Identifier NCT01494506: Aug. 1, 2013 update, "A Randomized, Open Label Phase 3 Study of MM-398, With or Without S~Fluorouracil and Leucovorin, Versus 5 Fluorouracil and Leucovorin in Patients with Metastatic Pancreatic Cancer Who Have Failed Prior Gemcitabine-based Therapy " Retrieved from ClinicalTrials.gov archive, 3 printed pages.
Clinical Trials Identifier NCT01494506: Jun. 16, 2016 update, "A Randomized, Open Label Phase 3 Study of MM-398, With or Without 5-Fluorouracil and Leucovorin, Versus 5 Fluorouracil and Leucovorin in Patients with Metastatic Pancreatic Cancer Who Have Failed Prior Gemcitabine-based Therapy " Retrieved from ClinicalTrials.gov archive, 5 printed pages.
Clinical Trials Identifier NCT01523457: Jan. 31, 2012 update, "Phase II Study of Modified FOLFIRINOX in Advanced Pancreatic Cancer" Retrieved from ClinicalTrials.gov archive, 4 printed pages.
Clinical Trials Identifier NCT01643499: Jul. 17, 2012 update, "A Genotype-guided Dosing Study of mFOLFIRINOX in Previously Untreated Patients with Advanced Gastrointestinal Malignancies." Retrieved from ClinicalTrials.gov archive, 5 printed pages.
Clinical Trials Identifier NCT01688336: Sep. 18, 2012 update, "Phase II Single Arm Clinical Trial of FOLFIRINOX for Unresectable Locally Advanced and Borderline Resectable Pancreatic Cancer." Retrieved from ClinicalTrials.gov archive, 5 printed pages.
Clinical Trials Identifier NCT01771146: Jan. 17, 2013 update, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.
Clinical Trials Identifier NCT01926197: Aug. 19, 2013 update, "A Randomized Phase III Study Evaluating Modified FOLFIRINOX (mHHX) With or Without Stereotactic Body Radiotherapy (SBRT) in the Treatment of Locally Advanced Pancreatic Cancer." Retrieved from ClinicalTrials.gov archive, 3 printed pages.
Clinical Trials Identifier NCT01992705: Nov. 22, 2013 update, "Neoadjuvant FOLFIRINOX and Stereotactic Body Radiotherapy (SBRT) Followed by Definitive Surgery for Patients with Borderline Resectable Pancreatic Adenocarcinoma: A Single-Arm Pilot Study." Retrieved from ClinicalTrials.gov archive, 5 printed pages.
Clinical Trials Identifier NCT02028806: Jan. 6, 2014 update, "Phase II Trial to Investigate the Efficacy and Safety of mFOLFIRINOX in Patients with Metastatic Pancreatic Cancer in China." Retrieved from ClinicalTrials.gov archive, 4 printed pages.
Clinical Trials Identifier NCT02047474: Jan. 27, 2014 update, "Phase II Study of Peri-Operative Modified FOLFIRINOX in Localized Pancreatic Cancer." Retrieved from ClinicalTrials.gov archive, 5 printed pages.
Clinical Trials Identifier NCT02109341: Apr. 8, 2014 update, "Phase I/II Study to Evaluate Nab paclitaxel in Substitution of CPT11 or Oxaliplatin in FOLFIRINOX Schedule as First Line Treatment on Metastatic Pancreatic Cancer." Retrieved from ClinicalTrials.gov archive, 5 printed pages.
Clinical Trials Identifier NCT02143219: May 20, 2014 update, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma " Retrieved from ClinicalTrials.gov archive, 5 printed pages.
Clinical Trials Identifier NCT02148549: May 27, 2014 update, "The Pilot Study of Neoadjuvant Chemotherapy of FIRINOX for Patients With Borderline Resectable Pancreatic Cancer." Retrieved from ClinicalTrials.gov archive, 4 printed pages.
Clinical Trials Identifier NCT02896803: Sep. 11, 2016 update, "A Phase II Trial of Bolus Fluorouracil and Oxaliplatin (mFLOX) as First-line Regimen for Patients With Unresectable or Metastatic

(56) References Cited

OTHER PUBLICATIONS

Pancreatic Cancer Not Eligible for Infusional Fluorouracil, Irinotecan and Oxaliplatin." Retrieved from ClinicalTrials.gov archive, 4 printed pages.
Clinical Trials Identifier NCT02896907: Sep. 11, 2016 update, "A Pilot Study of Intravenous Ascorbic Acid and FOLFIRINOX in the Treatment of Advanced Pancreatic Cancer." Retrieved from ClinicalTrials.gov archive, 4 printed pages.
Dean A, et al., "A Phase 2, Open-Label Dose-Exploration Study of Liposomal Irinotecan (nal-IRI) Plus 5-Flurouracil/Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages.
Gaddy D, et al., "Preclinical Anti-tumor Activity of Nanoliposomal Irinotecan (nal-IRI, MM-398) + 5-FU + Oxaliplatin in Pancreatic Cancer" Poster presented at AACR 2016, 5 pages.
Gaddy D., "Preclinical Anti-tumor Activity of Nanoliposomal Irinotecan (Nal-IRI, MM-398) + 5-FU + Oxaliplatin in Pancreatic Cancer" Abstract presented at AACR 2016, 1 page.
Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).
Kalra A, et al. "Preclinical Activity of Nanoliposomal Irinotecan Is Governed by Tumor Deposition and Intratumor Pro-Drug Conversion," Cancer Res. Author Manuscript Published OnlineFirst Oct. 1, 2014, 31 pages.
Kalra A, et al., "Preclinical Activity of Nanoliposomal Irinolecan Is Governed by Tumor Deposition and Intratumor Drodrug Conversion," Cancer Res. 74(23)7003-13 (2014), published OnlineFirst, OF1-OF11, Oct. 1, 2014, 12 pages.
Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.
Kim J, et al., "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.
Klinz S, et al., "Identifying Differential Mechanisms of Action for MM-398/PEP02, a Novel Nanotherapeutic Encapsulation of Irinotecan." Poster presented at MCR, Nov. 12-16, 2011, 8 pages.
Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).
Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.
Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).
Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.
PCT/US2016/047727: International Preliminary Reporton Patentability dated Feb. 27, 2018, 6 pages.
PCT/US2016/047727: PCT International Search Report and Written Opinion dated Nov. 16, 2016, 8 pages.
Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.
Siegel R, et al., "Cancer Statistics, 2015," CA Cancer J Clin. 65(1):5-29 (2015).
Stein S, et al., "Final Analysis of a Phase II Study of Modified FOLFIRINOX in Locally Advanced and Metastatic Pancreatic Cancer," Br J Cancer. 114(7):737-43 (2016).
Takahara N, et al., "Uridine Disphosphate Glucuronosyl Transferase 1 Family Polypeptide A1 Gene (UGT1A1) Polymorphisms are Associated with Toxicity and Efficacy in Irinotecan Monotherapy for Refractory Pancreatic Cancer," Cancer Chemother Pharmacol. 71(1):85-92 (2013), Epub Sep. 29, 2012.
Tanaka R, et al., "Synergistic Interaction Between Oxaliplatin and SN-38 in Human Gastric Cancer Cell Lines In Vitro," Oncol Rep. 14(3):683-8 (2005).
Tsai C, et al., "Nanovector-Based Therapies in Advanced Pancreatic Cancer," J Gastroint Oncol 2(3):185-94 (2011).
Tsubamoto H, et al., "Combination Chemotherapy with Itraconazole for Treating Metastatic Pancreatic Cancer in the Second-line or Additional Setting,". Anticancer Res. 35(7):4191-6 (2015).
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul. 20, 2006.
Ulrich-Pur H, et al., "Irinotecan Plus Raltitrexed vs Raltitrexed Alone in Patients with Gemcitabine-Pretreated Advanced Pancreatic Adenocarcinoma," Br J Cancer. 88(8):1180-4 (2003).
Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
Van Cutsem E, et al., "A Phase Ib Dose-Escalation Study of Erlotinib, Capecitabine and Oxaliplatin in Metastatic Colorectal Cancer Patients," Ann Oncol. 19(2):332-9 (2008), Epub Nov. 6, 2007.
Wagener D, et al., "Phase II Trial of CPT-11 in Patients with Advanced Pancreatic Cancer: An EORTC Early Clinical Trials Group Study," Ann Oncol. 6(2):129-32 (1995).
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/50140-6736(15)00986-1, pp. 1-13 (2015).
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).
Ychou, M, et al., "An Open Phase I Study Assessing the Feasibility of the Triple Combination: Oxaliplatin Plus Irinotecan Plus Leucovorin/5-Fluorouracil Every 2 Weeks in Patients With Advanced Solid Tumors," Ann Oncol. 14(3):481-9 (2003).
Yi S, et al., "Irinotecan Monotherapy As Second-Line Treatment in Advanced Pancreatic Cancer," Cancer Chemother Pharmacol 63(6):1141-5 (2009), Epub Oct. 7, 2008.
Yoo C, et al., "A Randomised Phase II Study of Modified FOLFIRL3 vs Modified FOLFOX as Second-Line Therapy in Patients with Gemcitabine-Refractory Advanced Pancreatic Cancer," Br J Cancer. 101(10):1658-63 (2009).
Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
Alberts S., et al. "Gemcitabine and Oxaliptatin for Metastatic Pancreatic Adenocarcinoma: A North Central Cancer Treatment Group Phase II Study," Ann Oncol. 14(4):580-5 (2003).
American Chemical Society (ACS), http://www.cancer.org/cancer/pancreaticcancer/detailedguide/pancreatic-cancer-what-is-pancreatic-cancer, retrieved Dec. 1, 2016, 4 printed pages.

(56) References Cited

OTHER PUBLICATIONS

Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).
Azrak R, et al., "Therapeutic Synergy Between Irinotecan and 5-Fluorouracil against Human Tumor Xenografts," Clin Cancer Res. 10(3):1121-9 (2004).
Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.
Burris H, et al. , "Phase II Trial of Oral Rubitecan in Previously Treated Pancreatic Cancer Patients," Oncologist 10(3):183-90 (2005).
Cantore M, et al., "Combined Irinotecan and Oxaliplatin in Patients with Advanced Pre-Treated Pancreatic Cancer," Oncology 67(2):93-7 (2004).
Oereda S, et al., "XELIRI or FOLFIRI as Salvage Therapy in Advanced Pancreatic Cancer," Anticancer Res 30(11):4785-90 (2010).
Chang T, et al., "Phase I Study of Nanoliposomal Irinotecan (PEP02) in Advanced Solid Tumor Patients," Cancer Chemother Pharmacol. 75(3):579-86 (2015).
Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.
Chen L, et al., "Phase 1 Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page.
Chiesa M, et al., "A Pilot Phase II Study of Chemotherapy with Oxaliplatin, Folinic Acid, 5-Fluorouracil and Irinotecan in Metastatic Gastric Cancer," Tumori. 93(3):244-7 (2007).
Conroy T, et al., "Irinotecan Plus Oxaliplatin and Leucovorin-Modulated Fluorouracil in Advanced Pancreatic Cancer—A Groupe Tumeurs Digestives of the Fédération Nationale des Centres de Lutte Contre le Cancer Study," J Clin Oncol. 23(6):1228-36 (2005).
Delord J, et al., "Population Pharmacokinetics of Oxaliplatin," Cancer Chemother Pharmacol. 51(2):127-31 (2003), Epub Dec. 4, 2002.
Ducreax M, et al., "Randomized Phase II Study Evaluating Oxaliplatin Alone, Oxaliplatin Combined with Infusional 5-FU, and Infusional 5-FU Alone in Advanced Pancreatic Carcinoma Patients," Ann Oncol 15(3): 467-73 (2004).
Eloxatin package insert, revision Dec. 28, 2011, retrieved from https://www.accessdata.fda.gov/drugsatfda_docs/label/2011/021492s012lbl.pdf, 51 pages.
Fischel J, et al., "Ternary Combination of Irinotecan, Fluorouracil-Folinic Acid and Oxaliplatin: Results on Human Colon Cancer Cell Lines," Br J Cancer. 84(4):579-85 (2001).
Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010).
Globocan Cancer Facts Sheets: All Cancers 2012. Available from: http://globocan.iarc.fr/old/FactSheets/cancers/all-new.asp, accessed on Oct. 3, 2016, 9 printed pages.
Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).
Grant S, et al., "Dose-Ranging Evaluation of the Substituted Benzamide Dazopride When Used as an Antiemetic in Patients Receiving Anticancer Chemotherapy," Cancer Chemother Pharmacol 31(6):442-44 (1993).
Guichard S, et al., "Combination of Oxaliplatin and Irinotecan on Human Colon Cancer Cell Lines: Activity In Vitro and In Vivo," Anticancer Drugs. 12(9):741-51 (2001).

Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).
Hoskins J, et al., "UGT1A1*28 Genotype and Irinotecan-Induced Neutropenia: Dose Matters," J Natl Cancer Inst. 99(17):1290-95 (2007).
Jacobs A, et al., "A Randomized Phase III Study of Rubitecan (ORA) vs. Best Choice (BC) in 409 Patients with Reflactory Pancreatic Cancer Report from a North-American Multi-Center Study," J Clin Oncol., 2004 ASCO Annual Meeting Proceedings 22(14S):4013 (2004).
Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).
Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).
Lee M, et al., "5-Fluorouracil/Leucovorin Combined wtih Irinotecan and Oxaliplatin (FOLFIRINOX) as Second-Line Chemotherapy in Patients with Advanced Pancreatic Cancer Who Have Progressed on Gemcitabine-Based Therapy," Chemotherapy. 59(4):273-9 (2013).
Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer. 93(2):190-4 (2005).
Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23(15):3509-16 (2005).
Mahaseth H, et al., "Modified FOLFIRINOX Regimen With Improved Safety and Maintained Efficacy in Pancreatic Adenocarcinoma," Pancreas 42(8):1311-5 (2013).
Mans D, et al., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).
Mullany S, et al., "Effect of Adding the Topoisomerase I Poison 7-ethyl-10-hydroxy-camptothecin (SN-38) to 5-Fluorouracil and Folinic Acid in HCT-8 Cells: Elevated dTTP Pools and Enhanced Cytotoxicity," Cancer Chemother Pharmacol. 42(5):391-9 (1998).
Münstedt K, et al., "Role of Dexamethasone Dosage in Combination with 5-HT3 Antagonists for Prophylaxis of Acute Chemotherapy-Induced Nausea and Vomiting," Br J Cancer. 79(3-4):637-9 (1999).
Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).
Oettle H, et al., "Second-Line Oxaliplatin, Folinic Acid, and Fluorouracil Versus Folinic Acid and Fluorouracil Alone for Gemcitabine-Refractory Pancreatic Cancer: Outcomes From the CONKO-003 Trial," J Clin Oncol. 32(23):2423-9 (2014).
Oh S, et al., "Pilot Study of Irinotecan/Oxaliplatin (IROX) Combination Chemotherapy for Patients with Gemcitabine- and 5-Fluorouracil-Refractory Pancreatic Cancer," Invest New Drugs. 28(3):343-9 (2010), Epub May 15, 2009.
Ohkawa S, et al., "Randomised Phase II Trial of S-1 Plus Oxaliplatin vs S-1 in Patients with Gemcitabine-Refractory Pancreatic Cancer," Br J Cancer 112(9):1428-34 (2015).
Okusaka T, et al., "Phase II Study of FOLFIRINOX for Chemotherapy-Naïve Japanese Patients with Metastatic Pancreatic Cancer," Cancer Sci. 105(10):1321-6 (2014).
Onivyde [MM-398] package insert, revision Oct. 22, 2015, retrieved from http://www.accessdata.fda.gov/drugsatfda_docs/label/2015Z207793lbl.pdf, 18 pages.
Pavillard V, et al., "Combination of Irinotecan (CPT11) and 5-Fluorouracil with an Analysis of Cellular Determinants of Drug Activity," Biochem Pharmacol. 56(10):1315-22 (1998).
Peddi P, et al., "Multi-Institutional Experience with FOLFIRINOX in Pancreatic Adenocarcinoma," Journal of the Pancreas (JOP). 13(5):497-501 (2012), online access, 11 printed pages.
Pelzer U, et al., "A Randomized Trial in Patients With Gemcitabine Refractory Pancreatic Cancer. Final Results of the CONKO 003

(56) References Cited

OTHER PUBLICATIONS

Study," J Clin Oncol 2008 ASCO Annual Meeting Proceedings 26(15S):4508 (2008), 2 printed pages.
Pelzer U, et al., "Second-Line Therapy in Refractory Pancreatic Cancer. Results of a Phase II Study," Onkologie. 32(3):99-102 (2009).
Petrioli R, et al., "Gemcitabine, Oxaliplatin, and Capecitabine (GEMOXEL) Compared with Gemcitabine Alone in Metastatic Pancreatic Cancer: A Randomized Phase II Study," Cancer Chemother Pharmacol. 75(4):683-90 (2015).
Qin B, et al., "In-vitro Schedule-Dependent Interaction Between Oxaliplatin and 5-Fluorouracil in Human Gastric Cancer Cell Lines," Anti-Cancer Drugs. 17(4):445-53 (2006).
Rahib L, et al., "Projecting Cancer Incidence and Deaths to 2030: The Unexpected Burden of Thyroid, Liver, and Pancreas Cancers in the United States," Cancer Res 74(11):2913-21 (2014).
Reni M, et al., "Salvage Chemotherapy with Mitomycin, Docetaxel, and Irinotecan (MDI Regimen) in Metastatic Pancreatic Adenocarcinoma: A Phase I and II Trial," Cancer Invest. 22(5):688-96 (2004).
Rombouts S, et al., "FOLFIRINOX in Locally Advanced and Metastatic Pancreatic Cancer: A Single Centre Cohort Study," J Cancer. 7(13):1861-6 (2016).
U.S. Appl. No. 11/121,294: Aug. 17, 2009 Nonfinal Office Action, 33 pages.
U.S. Appl. No. 11/121,294: Mar. 12, 2010 Final Office Action, 15 pages.
U.S. Appl. No. 11/121,294: May 19, 2010 Advisory Action, 3 pages.
U.S. Appl. No. 11/121,294: Aug. 24, 2010 Nonfinal Office Action, 14 pages.
U.S. Appl. No. 11/121,294: Dec. 6, 2010 Final Office Action, 17 pages.
U.S. Appl. No. 11/121,294: Apr. 13, 2011 Nonfinal Office Action, 10 pages.
U.S. Appl. No. 11/121,294: Jul. 12, 2011 Examiner Interview Summary, 3 pages.
U.S. Appl. No. 11/121,294: Nov. 23, 2011 Final Office Action, 20 pages.
U.S. Appl. No. 11/601,451: Jan. 11, 2010 Nonfinal Office Action, 14 pages.
U.S. Appl. No. 11/601,451: Aug. 27, 2010 Final Office Action, 17 pages.
U.S. Appl. No. 11/601,451: Jul. 12, 2011 Examiner Interview Summary, 4 pages.
U.S. Appl. No. 13/416,204: May 8, 2012 Pre-Interview Communication, 4 pages.
U.S. Appl. No. 13/416,204: Jun. 29, 2012 Interview Summary and First Action Interview Office Action, 6 pages.
U.S. Appl. No. 13/654,373: Aug. 12, 2013 Nonfinal Office Action and Interview Summary, 10 pages.
U.S. Appl. No. 14/151,632: Apr. 18, 2016 Nonfinal Office Action, 9 pages.
U.S. Appl. No. 14/175,365: Jun. 26, 2014 Nonfinal Office Action, 20 pages.
U.S. Appl. No. 14/406,776: Feb. 26, 2016 Nonfinal Office Action, 9 pages.
U.S. Appl. No. 14/406,776: Apr. 25, 2016 Response to Non-final Office Action dated Feb. 26, 2016, 71 pages.
U.S. Appl. No. 14/632,422: Jan. 10, 2017 Nonfinal Office Action, 18 pages.
U.S. Appl. No. 14/812,950: Oct. 2, 2015 Pre-Interview Communication, 3 pages.
U.S. Appl. No. 14/812,950: Oct. 22, 2015 Preliminary amendment in response to Pre-Interview Communication dated Oct. 2, 2015, 7 pages.
U.S. Appl. No. 14/844,500: Dec. 16, 2015 Nonfinal Office Action, 25 pages.
U.S. Appl. No. 14/844,500: Feb. 25, 2016 Response to Non-final Office Action dated Dec. 16, 2015, 15 pages.
U.S. Appl. No. 14/851,111: Feb. 25, 2016 Nonfinal Office Action, 13 pages.
U.S. Appl. No. 14/851,111: May 12, 2016 Response to Non-final Office Action dated Feb. 25, 2016, 71 pages.
U.S. Appl. No. 14/879,302: Aug. 15, 2016 Nonfinal Office Action, 30 pages.
U.S. Appl. No. 14/879,302: Dec. 15, 2016 Nonfinal Office Action, 14 pages.
U.S. Appl. No. 14/879,358: Dec. 28, 2015 Nonfinal Office Action, 20 pages.
U.S. Appl. No. 14/879,358: Jul. 12, 2016 Nonfinal Office Action, 14 pages.
U.S. Appl. No. 14/964,239: Nov. 4, 2016 Nonfinal Office Action, 21 pages.
U.S. Appl. No. 14/964,239: Apr. 26, 2017 Examiner Interview Summary, 2 pages.
U.S. Appl. No. 14/964,239: Jun. 21, 2017 Nonfinal Office Action, 16 pages.
U.S. Appl. No. 14/964,239: Dec. 11, 2017 Nonfinal Office Action, 15 pages.
U.S. Appl. No. 14/964,571: Feb. 13, 2017 Nonfinal Office Action, 8 pages.
U.S. Appl. No. 14/964,571: Nov. 1, 2017 Final Office Action, 14 pages.
U.S. Appl. No. 14/964,571: Sep. 25, 2018 Nonfinal Office Action, 12 pages.
U.S. Appl. No. 14/965,140: Mar. 10, 2016 Nonfinal Office Action, 24 pages.
U.S. Appl. No. 14/965,140: Jul. 13, 2016 Interview Summary and Nonfinal Office Action, 14 pages.
U.S. Appl. No. 14/965,140: Dec. 19, 2016 Nonfinal Office Action, 9 pages.
U.S. Appl. No. 14/966,458: Dec. 6, 2016 Nonfinal Office Action, 34 pages.
U.S. Appl. No. 14/966,458: Apr. 27, 2017 Examiner Interview Summary, 2 pages.
U.S. Appl. No. 14/979,666: Dec. 9, 2016 Nonfinal Office Action, 20 pages.
U.S. Appl. No. 15/059,640: Dec. 2, 2016 Nonfinal Office Action, 9 pages.
U.S. Appl. No. 15/227,561: Jul. 14, 2017 Nonfinal Office Action, 25 pages.
U.S. Appl. No. 15/227,561: Apr. 26, 2018 Nonfinal Office Action, 13 pages.
U.S. Appl. No. 15/227,561: Dec. 10, 2018 Final Office Action, 18 pages.
U.S. Appl. No. 15/227,631: Jul. 17, 2017 Nonfinal Office Action, 24 pages.
U.S. Appl. No. 15/227,631: Apr. 10, 2018 Nonfinal Office Action, 13 pages.
U.S. Appl. No. 15/227,631: Aug. 31, 2018 Nonfinal Office Action, 15 pages.
U.S. Appl. No. 15/227,631: Dec. 19, 2018 Final Office Action, 15 pages.
U.S. Appl. No. 15/241,106: Oct. 28, 2016 Pre-Interview Communication, 4 pages.
U.S. Appl. No. 15/241,106: Dec. 29, 2016 Nonfinal Office Action, 15 pages.
U.S. Appl. No. 15/241,106: Jul. 10, 2017 Final Office Action, 16 pages.
U.S. Appl. No. 15/241,128: Nov. 25, 2016 Nonfinal Office Action, 6 pages.
U.S. Appl. No. 15/296,536: Mar. 8, 2017 Nonfinal Office Action, 6 pages.
U.S. Appl. No. 15/331,393: Jan. 19, 2017 Pre-Interview Communication, 4 pages.
U.S. Appl. No. 15/331,393: Mar. 20, 2017 Examiner's Interview Summary and First Action Interview Office Action Summary, 5 pages.
U.S. Appl. No. 15/331,648: Jan. 19, 2017 Pre-Interview Communication, 4 pages.
U.S. Appl. No. 15/331,648: Mar. 17, 2017 Examiner's Interview Summary, 3 pages.

(56) References Cited

OTHER PUBLICATIONS

U.S. Appl. No. 15/337,274: Mar. 24, 2017 Nonfinal Office Action, 10 pages.
U.S. Appl. No. 15/341,377: Jan. 30, 2017 Nonfinal Office Action, 12 pages.
U.S. Appl. No. 15/341,377: Apr. 18, 2017 Final Office Action, 13 pages.
U.S. Appl. No. 15/341,619: Apr. 3, 2017 Pre-Interview Communication, 3 pages.
U.S. Appl. No. 15/363,761: Jan. 18, 2017 Nonfinal Office Action, 15 pages.
U.S. Appl. No. 15/363,761: Aug. 1, 2017 Final Office Action, 18 pages.
U.S. Appl. No. 15/363,761: Dec. 14, 2017 Examiner Interview Summary, 3 pages.
U.S. Appl. No. 15/363,923: Feb. 1, 2017 Nonfinal Office Action, 24 pages.
U.S. Appl. No. 15/363,923: Sep. 13, 2017 Final Office Action, 29 pages.
U.S. Appl. No. 15/363,978: Feb. 7, 2017 Nonfinal Office Action, 16 pages.
U.S. Appl. No. 15/363,978: Aug. 21, 2017 Final Office Action, 19 pages.
U.S. Appl. No. 15/363,978: Dec. 14, 2017 Examiner Interview Summary, 3 pages.
U.S. Appl. No. 15/364,021: Mar. 9, 2017 Nonfinal Office Action, 18 pages.
U.S. Appl. No. 15/364,021: Oct. 4, 2017 Final Office Action, 20 pages.
U.S. Appl. No. 15/375,039: Feb. 16, 2018 Nonfinal Office Action, 11 pages.
U.S. Appl. No. 15/403,441: Dec. 21, 2017 Nonfinal Office Action, 9 pages.
U.S. Appl. No. 15/645,645: Dec. 1, 2017 Nonfinal Office Action, 16 pages.
U.S. Appl. No. 15/652,513: Dec. 20, 2017 Nonfinal Office Action, 13 pages.
U.S. Appl. No. 15/661,868: Dec. 1, 2017 Nonfinal Office Action, 15 pages.
U.S. Appl. No. 15/664,930: Dec. 20, 2017 Nonfinal Office Action, 7 pages.
U.S. Appl. No. 15/664,976: Sep. 11, 2018 Nonfinal Office Action, 23 pages.
U.S. Appl. No. 15/809,815: Mar. 6, 2018 Nonfinal Office Action, 12 pages.
U.S. Appl. No. 15/809,815: Sep. 11, 2018 Final Office Action, 14 pages.
U.S. Appl. No. 15/852,551: Jan. 11, 2019 Nonfinal Office Action, 5 pages.
U.S. Appl. No. 15/967,638: Jan. 14, 2019 Nonfinal Office Action, 14 pages.
Extra J, et al., "Phase 1 Study of Oxaliplatin in Patients with Advanced Cancer," Cancer Chemother Pharmacol. 25(4):299-303 (1990).
Mathé G, et al., "A Phase I Trial of Trans-1-diamino-cyclohexane Oxalate-platinum (I-OHP)," Biomed Pharmacother, 40:372-6 (1986).
U.S. Appl. No. 11/121,294, filed May 2, 2005, U.S. Pat. No. 8,147,867, Issued.
U.S. Appl. No. 11/601,451, filed Nov. 17, 2006, U.S. Pat. No. 8,658,203, Issued.
U.S. Appl. No. 13/416,204, filed Mar. 9, 2012, U.S. Pat. No. 8,329,213, Issued.
U.S. Appl. No. 13/654,373, filed Oct. 17, 2012, U.S. Pat. No. 8,703,181, Issued.
U.S. Appl. No. 14/151,632, filed Jan. 9, 2014, Abandoned.
U.S. Appl. No. 14/175,365, filed Feb. 7, 2014, U.S. Pat. No. 8,992,970, Issued.
U.S. Appl. No. 14/632,422, filed Feb. 26, 2015, U.S. Pat. No. 9,717,723, Issued.
U.S. Appl. No. 14/879,302, filed Oct. 9, 2015, U.S. Pat. No. 9,730,891, Issued.
U.S. Appl. No. 14/879,358, filed Oct. 9, 2015, Abandoned.
U.S. Appl. No. 14/964,239, filed Dec. 9, 2015, Abandoned.
U.S. Appl. No. 14/695,140, filed Dec. 10, 2015, U.S. Pat. No. 9,724,303, Issued.
U.S. Appl. No. 14/966,458, filed Dec. 11, 2015, U.S. Pat. No. 9,782,349, Issued.
U.S. Appl. No. 14/979,666, filed Dec. 28, 2015, Abandoned.
U.S. Appl. No. 15/227,561, filed Aug. 3, 2016, Published.
U.S. Appl. No. 15/227,631, filed Aug. 3, 2016, Published.
U.S. Appl. No. 15/213,127, filed Jul. 18, 2016, Abandoned.
U.S. Appl. No. 15/296,536, filed Oct. 18, 2016, U.S. Pat. No. 9,737,528, Issued.
U.S. Appl. No. 15/363,761, filed Nov. 29, 2016, Published.
U.S. Appl. No. 15/363,923, filed Nov. 29, 2016, Abandoned.
U.S. Appl. No. 15/363,978, filed Nov. 29, 2016, Published.
U.S. Appl. No. 15/364,021, filed Nov. 29, 2016, Abandoned.
U.S. Appl. No. 15/664,976, filed Jul. 31, 2017, Published.
U.S. Appl. No. 15/896,389, filed Feb. 14, 2018, Published.
U.S. Appl. No. 15/896,436, filed Feb. 14, 2018, Published.
U.S. Appl. No. 14/406,776, filed Dec. 10, 2014, U.S. Pat. No. 9,452,162, Issued.
U.S. Appl. No. 14/812,950, filed Jul. 29, 2015, U.S. Pat. No. 9,339,497, Issued.
U.S. Appl. No. 14/844,500, filed Sep. 3, 2015, U.S. Pat. No. 9,364,473, Issued.
U.S. Appl. No. 14/851,111, filed Sep. 11, 2015, U.S. Pat. No. 9,492,442, Issued.
U.S. Appl. No. 15/059,640, filed Mar. 3, 2016, Abandoned.
U.S. Appl. No. 15/241,128, filed Aug. 19, 2016, U.S. Pat. No. 9,717,724, Issued.
U.S. Appl. No. 15/341,377, filed Nov. 2, 2016, Abandoned.
U.S. Appl. No. 15/341,619, filed Nov. 2, 2016, Abandoned.
U.S. Appl. No. 15/652,513, filed Jul. 18, 2017, Abandoned.
U.S. Appl. No. 15/664,930, filed Jul. 31, 2017, Abandoned.
U.S. Appl. No. 16/012,351, filed Jun. 19, 2018, Pending.
U.S. Appl. No. 16/012,372, filed Jun. 19, 2018, Pending.
U.S. Appl. No. 14/964,571, filed Dec. 9, 2015, Published.
U.S. Appl. No. 15/375,039, filed Dec. 9, 2016, Abandoned.
U.S. Appl. No. 15/928,649, filed Mar. 22, 2018, Abandoned.
U.S. Appl. No. 16/036,885, filed Jul. 16, 2018, Pending.
U.S. Appl. No. 15/337,274, filed Oct. 28, 2016, U.S. Pat. No. 9,895,365, Issued.
U.S. Appl. No. 15/852,551, filed Dec. 22, 2017, Published.
U.S. Appl. No. 15/241,106, filed Aug. 19, 2016, Abandoned.
U.S. Appl. No. 15/809,815, filed Nov. 10, 2017, Published.
U.S. Appl. No. 15/403,441, filed Jan. 11, 2017, Abandoned.
U.S. Appl. No. 15/331,648, filed Oct. 21, 2016, Abandoned.
U.S. Appl. No. 15/331,393, filed Oct. 21, 2016, Abandoned.
U.S. Appl. No. 15/331,318, filed Oct. 21, 2016, Abandoned.
U.S. Appl. No. 15/645,645, filed Jul. 10, 2017, Abandoned.
U.S. Appl. No. 15/655,592, filed Jul. 20, 2017, Abandoned.
U.S. Appl. No. 15/661,868, filed Jul. 27, 2017, Abandoned.
U.S. Appl. No. 15/908,443, filed Feb. 28, 2018, Abandoned.
U.S. Appl. No. 15/768,352, filed Apr. 13, 2018, Pending.
U.S. Appl. No. 15/967,633, filed May 1, 2018, Abandoned.
U.S. Appl. No. 15/967,638, filed May 1, 2018, Pending.
U.S. Appl. No. May 18, 2017, Abandoned.
U.S. Appl. No. 15/948,571, filed Apr. 9, 2018, Abandoned.
Abraxane package insert, revision Dec. 23, 2011, retrieved from https://www.accessdata.fda.gov/drugsatfda_docs/label/2011/021660s025s026s029lbl.pdf, 13 pages.
Abraxane package insert, revision Jul. 21, 2015, retrieved from https://www.accessdata.fda.gov/drugsatfda_docs/label/2015/021660s041lbl.pdf, 24 pages.
Ahmad I, et al., "Antibody-Targeted Delivery of Doxorubicin Entrapped in Sterically Stabilized Liposomes Can Eradicate Lung Cancer in Mice," Cancer Res. 53(7):1484-8 (1993).
American Chemical Society (ACS), http://www.cancer.org/cancer/pancreaticcancer/detailedguide/pancreatic-cancer-what-is-pancreatic-cancer, retrieved Dec. 10, 2017, 7 printed pages.

(56) References Cited

OTHER PUBLICATIONS

Author Unknown, "From Antinutrient to Phytonutrient: Phytic Acid Gains Respect." HighBeam Research, Environmental Nutrition, Apr. 1, 2004, 2 printed pages. URL: http://www.highbeam.com/doc/1G1-116341390.html/print (accessed Nov. 4, 2011).
Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).
Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011).
Camptosar package insert, revised May 16, 2002, 37 pages.
Camptosar package insert, revision May 14, 2010, retrieved from https://www.accessdata.fda.gov/drugsatfda_docs/label/2010/020571s031s032s033s036s037lbl.pdf, 37 pages.
CAS Registry Record for 23214-92-8 (doxorubicin), entered STN Nov. 16, 1984, 2 pages.
CAS Registry Record for 97682-44-5 (irinotecan), entered STN Aug. 18, 1985, 1 page.
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster presented at the Gastrointestinal Cancers Symposium of the ASCO meeting of Jan. 21-23, 2016, San Francisco, California, 16 pages.
Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy " Poster presented at the ASCO meeting of May 29-Jun. 2, 2015, Chicago, Illinois, 7 pages.
Chou T, et al., "Effect of Composition on the Stability of Liposomal Irinotecan Prepared by a pH Gradient Method," J Biosci Bioeng. 95(4):405-8 (2003).
Chuang V and M. Suno, "Levoleucovorin as Replacement for Leucovorin in Cancer Treatment," Ann Pharmacother. 46(10):1349-57 (2012).
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Mar. 1, 2012 update, "A Phase II Study of PEP02 as a Second Line Therapy for Patients With Metastatic Pancreatic Cancer " Retrieved from ClinicalTrials.gov archive, 3 printed pages.
Clinical Trials Identifier NCT00813163: Apr. 6, 2017 update, first posted Dec. 22, 2008, "A Phase II Study of PEP02 as a Second Line Therapy for Patients With Metastatic Pancreatic Cancer." Retrieved from ClinicalTrials.gov archive, 6 printed pages.
Clinical Trials Identifier NCT00940758: Jul. 16, 2009 update, "Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Feb. 3, 2010 update, "Phase I and Pharmacokinetic Study of Biweekly PEP02 Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Mar. 1, 2012 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01375816: Jun. 16, 2011 update, "A Randomized Phase II Study of PEP02 or Irinotecan in Combination With Leucovorin and 5-Flourouracil in Second Line Therapy of Metastatic Colorectal Cancer." Retrieved Tom ClinicalTrials.gov archive, 5 printed pages.
Clinical Trials Identifier NCT01375816: Jun. 4, 2015 update, first posted Jun. 17, 2011, "A Randomized Phase II Study of PEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT01494506: Dec. 16, 2011 update, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages.
Clinical Trials Identifier NCT01494506: Aug. 9, 2012 update, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy " Retrieved from ClinicalTrials.gov archive, 3 printed pages.
Clinical Trials Identifier NCT02884128: Aug. 25, 2016 update, "A Study of PEP02 in Combination With 5-fluorouracil (5-FU) and Leucovorin (LV) in Advanced Solid Tumors." Retrieved from ClinicalTrials.gov archive, 3 printed pages.
Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.
Dawidczyk C, et al., "State-of-the-art in Design Rules for Drug Delivery Platforms: Lessons Learned from FDA-Approved Nanomedicines," J Control Release. 187:133-44 (2014).
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster handout at the Gastrointestinal Cancers Symposium ASCO 2016, 2 pages.
Douillard J, et al.,"Irinotecan Combined with Fluorouracil Compared with Fluorouracil Alone as First-line Treatment tor Metastatic Colorectal Cancer: A Multicentre Randomised Trial," Lancet. 355(9209):1041-7 (2000).
Doxil package insert, revision Apr. 16, 2015, retrieved from https://www.accessdata.fda.gov/drugsatfda_docs/label/2015/050718s048lbl.pdf, 28 pages.
Doxil package insert, revision Aug. 30, 2013, retrieved from https://www.accessdata.fda.gov/drugsatfda_docs/label/2013/050718s045lbl.pdf, 35 pages.
Doxil package insert, revision Jun. 10, 2008, retrieved from https://www.accessdata.fda.gov/drugsatfda_docs/label/2008/050718s033lbl.pdf, 34 pages.
Drummond D, et al., "Development of a Highly Active Nanoliposomal Irinotecan Using a Novel Intraliposomal Stabilization Strategy," Cancer Res. 66(6):3271-77 (2006).
Drummond D, et al., "Optimizing Liposomes for Delivery of Chemotherapeutic Agents to Solid Tumors," Pharmacol Rev. 51(4):691-743 (1999).
Eisenhauer E, et al., "New Response Evaluation Criteria in Solid Tumours: Revised RECIST Guideline (version 1.1)," Eur J Cancer. 45(2):228-47 (2009).
EP2861210: Communication of Notices of Opposition (R. 79(1) EPC), dated Feb. 16, 2018, 1 page.
EP2861210: Notice of Opposition dated Feb. 5, 2018, 6 pages.
EP2861210: Opposition dated Feb. 5, 2018, Annex to Notice of Opposition, Facts and Arguments, 8 pages.
EP2861210: Opposition dated Feb. 5, 2018, D1 (Fusilev package insert, 2008, 7 pages).
EP2861210: Opposition dated Feb. 5, 2018, D2 (Gebbia V, et al., "Irinotecan Plus Bolus/Infusional 5-Fluorouracil and Leucovorin in Patients With Pretreated Advanced Pancreatic Carcinoma: A Mul-

(56) References Cited

OTHER PUBLICATIONS ticenter Experience of the Gruppo Oncologico Italia Meridionale," Am J Clin Oncol. 33(5):461-64 (2010)).
EP2861210: Opposition dated Feb. 5, 2018, D3 (Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012)).
EP2861210: Opposition dated Feb. 5, 2018, D4 (Neuzillet C, et al., "FOLFIRI Regimen in Metastatic Pancreatic Adenocarcinoma Resistant to Gemcitabine and Platinum-Salts," World J Gastroenterol 18(33):4533-41 (2012)).
EP2861210: Opposition dated Feb. 5, 2018, D5 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP2861210: Opposition dated Feb. 5, 2018, D6 (Taïeb J., "FOLFIRI. 3, A New Regimen Combining 5-Fluorouracil, Folinic Acid and Irinotecan, For Advanced Pancreatic Cancer: Results of an Association des Gastro-Enterologues Oncologues (Gastroenterologist Oncologist Association) Multicenter Phase II Study," Ann Oncol 18(3)498-503 (2007), epub Dec. 8, 2006).
EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).
EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5):699-705 (2012)).
EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).
EP2861210: Opposition filed Feb. 5, 2018, D10 (Camptosar package insert, 2012, 39 pages).
Adiwijaya B, et al., "Population Pharmacokinetics of Liposomal Irinotecan in Patients With Cancer," Clin Pharmacol Ther. 102(6):997-1005 (2017).
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster handout at the Gastrointestinal Cancers Symposium of the ASCO meeting of Jan. 21-23, 2016, San Francisco, California, 2 pages.
Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).
Waterhouse D, et al., "Lipid-Based Nanoformulation of Irinotecan: Dual Mechanism of Action Allows for Combination Chemo/ Angiogenic Therapy," Nanomedicine 6(9):1645-54 (2011).
Wilson W, et al., "Targeting Hypoxia in Cancer Therapy," Nat Rev Cancer. 11(6):393-410 (2011).
Yeh B, et al., "Structural Basis for Activation of Fibroblast Growth Factor Signaling by Sucrose Octasulfate," Mol Cell Biol. 22(20):7184-92 (2002).
Amodeo S, et al., "Can we downstage locally advanced pancreatic cancer to resectable? A phase I/II study of induction oxaliplatin and 5-FU chemoradiation," J Gastrointest Oncol. 9(5):922-35 (2018).
Clinical Trials Identifier NCT02551991: Sep. 30, 2019 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Retrieved from ClinicalTrials.gov archive, 5 printed pages.

Maxwell F, et al., "CA 19-9 levels in patients with metastatic pancreatic adenocarcinoma receiving first-line therapy with liposomal irinotecan plus 5-fluorouracil/leucovorin and oxaliplatin (NAPOX)," Poster presented at the American Association for Cancer Research (AACR) Special Conference on Pancreatic Cancer: Advances in Science and Clinical Care, Sep. 6-9, 2019, Boston, MA, 7 pages.
Wainberg Z, et al., "A phase 1/2, open-label, dose-expansion study of liposomal irinotecan (nal-IRI) plus 5-fluorouracil/leucovorin (5-FU/LV) and oxaliplatin (OX) in patients with previously untreated metastatic pancreatic cancer (mPAC)" Presentation presented at the ESMO 21st World Congress on Gastrointestinal Cancer, Barcelona, Spain, Jul. 3-6, 2019, 13 pages.
Wainberg Z, et al., Abstract SO-005: "A Phase 1/2, Open-Label, Dose-Expansion Study of Liposomal Irinotecan (Nal-IRI) Plus 5-Fluorouracil/Leucovorin (5-FU/LV) and Oxaliplatin (OX) in Patients with Previously Untreated Metastatic Pancreatic Cancer," Ann Oncol. 30(Suppl 4): doi:10.1093/annonc/mdz157 | iv123 (Jul. 2019), 1 page.
FP2861210: Opposition filed Feb. 5, 2018, D11 (Hoskins J, et al., "UGT1 A1*28 Genotype and Irinotecan-Induced Neutropenia: Dose Matters," J Natl Cancer Inst. 99(17):1290-95 (2007)).
EP2861210: Opposition dated Feb. 5, 2018, D12 (Tsai C, et al., "Nanovector-Based Therapies in Advanced Pancreatic Cancer," J Gastroint Oncol 2(3):185-94 (2011)).
EP2861210: Opposition dated Feb. 5, 2018, D13 (Ko A, et al., "A Multinational Phase II Study of Liposome Irinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).
EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus 5 Fluorouracil and Leucovorin in Patients With Metastatic Pancreatic Cancer Who Have Failed Prior Gemcitabine-based Therapy," Retrieved from ClinicalTrials.gov archive, 1 printed page).
EP2861210: Response to EP Opposition Proceedings filed Aug. 24, 2018, 22 pages.
EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).
EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://ww.fda. gov/NewsEvents/Newsroom/PressAnnouncements/ucm468654. htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/50140-6736(15)00986-1, pp. 1-13 (2015)).
EP2861210: Response to EP Opposition Proceedings filed Aug. 24, 2018, D20 (MHRA Public Assessment Report tor 5-Fluorouracil, 2006, 60 pages).
EP2861210: Summons to attend oral proceedings including preliminary opinion of the Opposition Division dated Jan. 30, 2019, 12 pages.
EP2861210: Opponent submission in opposition proceedings made following summons to attend oral proceedings, dated May 10, 2019, 20 pages.
EP2861210: Opponent submission in opposition proceedings made following summons to attend oral proceedings, dated May 10, 2019, D1b (Leucovorin calcium injection product label, Nov. 2011, 2 pages).

(56) References Cited

OTHER PUBLICATIONS

EP2861210: Opponent submission in opposition proceedings made following summons to attend oral proceedings, dated May 10, 2019, D22 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15 suppl) (May 20 Suppl):e13024 (2010), 1 page).
EP2861210: Proprietor's Auxiliary Requests in Opposition Proceedings filed Jun. 28, 2019, including cover letter and clean and marked-up AR1, AR2, and AR3, 12 pages.
EP2861210: Minutes of the oral proceedings before the Opposition Division, dated Aug. 28, 2019, 9 pages.
EP2861210: Opposition Division's decision to revoke patent, dated Aug. 28, 2019, 27 pages.
FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages.
Fuchs C, et al., "Phase III Comparison of Two Irinotecan Dosing Regimens in Second-Line Therapy of Metastatic Colorectal Cancer," J Clin Oncol. 21(5):807-14 (2003).
Gemzar package insert, revision Feb. 4, 2011, retrieved from https://www.accessdata.fda.gov/drugsatfda_docs/label/2011/020509s069lbl.pdf, 21 pages.
Gemzar package insert, revision May 8, 2014, retrieved from https://www.accessdata.fda.gov/drugsatfda_docs/label/2014/020509s077lbl.pdf, 18 pages.
Hong K, et al., "Anti-HER2 Immunoliposomes for Targeted Drug Delivery," Ann N Y Acad Sci. 886:293-6 (1999).
Kambe M, et al., "Phase 1 Study of Irinotecan by 24-h Intravenous Infusion in Combination with 5-Fluorouracil in Metastatic Colorectal Cancer," Int J Clin Oncol. 17(2):150-4 (2012).
Katsu T, et al., "Ion-Selective Electrode for Transmembrane pH Difference Measurements," Anal. Chem. 73(8):1849-54 (2001).
Ko A, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.
Ko A, et al., "A Multinational Phase II Study of PEP02 (MM-398), Liposome Irinotecan, for Patients with Gemcitabine-refractory Metastatic Pancreatic Cancer." Poster presented at the American Society of Clinical Oncology meeting, Jun. 3-Jun. 7, 2011, Chicago, Illinois, 9 pages.
Köhne C, et al., "Randomized Phase III Study of High-Dose Fluorouracil Given As a Weekly 24-Hour Infusion With or Without Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).
Lee C, et al., "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).
Maddison J, et al., "Sucralfate," In Small Animal Clinical Pharmacology at p. 474, published by W. B. Saunders (2002).
Makrilia N, et al., "Treatment for Refractory Pancreatic Cancer. Highlights from the '2011 ASCO Gastrointestinal Cancers Symposium' San Francisco, CA, USA, Jan. 20-22, 2011," J Pancreas 12(2):110-3 (2011).
Merrimack Pharmaceuticals, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releases/news-release-details/merrimack-announces-inclusion-onivyder-irinotecan-liposome, 2 printed pages.
Minami H, et al., "Irinotecan Pharmacokinetics/Pharmacodynamics and UGT1A Genetic Polymorphisms in Japanese Roles of UGT1 A1*6 and *28," Pharmacogenet Genomics. 17(7):497-504 (2007).
Morgan R, et al., "Human Cell Line (COLO 357) of Metastatic Pancreatic Adenocarcinoma," Int J Cancer 25(5):591-8 (1980).

National Comprehensive Cancer Network Clinical Practice Guidelines In Oncology (NCCN Guidelines). "Pancreatic Adenocarcinoma." Version I.2016. Mar. 22, 2016 (PANC-9), 133 pages.
Nentwich, F., "Doxorubicin Hydrochloride," In Intravenous Therapy: A Comprehensive Application of Intravenous Therapy and Medication Administralion at p. 310 Published by Jones & Bartlett Learning, 1990.
Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective Series of 70 Patients." J Clin Oncol. 29: 2011 (Suppl 4; Abstract 272). 2011 Gastrointestinal Cancers Symposium (2011), 2 printed pages.
NIH National Cancer Institute, "FDA Approves Irinotecan Liposome to Treat Pancreatic Cancer," Nov. 24, 2015 by NCI Staff, 2 printed pages.
O'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).
Palomaki G, et al., "Can UGT1A1 Genotyping Reduce Morbidity and Mortality in Patients with Metastatic Colorectal Cancer Treated with Irinotecan? An Evidence-Based Review," Genet Med. 11(1):21-34 (2009).
PCT/US2013/045495: International Preliminary Reporton Patentability dated Dec. 16, 2014, 8 pages.
PCT/US2013/045495: International Search Report and Written Opinion dated Aug. 22, 2013, 11 pages.
Pliarchopoulou K, et al., "Pancreatic Cancer: Current and Future Treatment Strategies," Cancer Treat Rev. 35(5):431-6 (2009).
Rahma O, et al., "Second-Line Treatment in Advanced Pancreatic Cancer: A Comprehensive Analysis of Published Clinical Trials," Ann Oncol 24(8):1972-9 (2013), epub doi:10.1093/annonc/mdt166, May 12, 2013, pp. 1-8.
Rivory L, et al., "Pharmacokinetic Interrelationships of Irinotecan (CPT-11) and Its Three Major Plasma Metabolites in Patients Enrolled in Phase I/II Trials," Clin Cancer Res 3(8):1261-6 (1997).
Rothenberg M, et al., "Phase I and Pharmacokinetic Trial of Weekly CPT-11," J Clin Oncol. 11(11):2194-204 (1993).
Sadzuka Y, et al. "Effect of Liposomalization on the Antitumor Activity, Side-Effects and Tissue Distribution of CPT-11," Cancer Lett. 127(1-2): 99-106 (1998).
Saltz L, et al., "Irinotecan Plus Fluorouracil and Leucovorin for Metastatic Colorectal Cancer. Irinotecan Study Group," N Engl J Med. 343(13):905-14 (2000).
Shimada S, et al., "Irinotecan Plus Low-Dose Cisplatin for α-Fetoprotein-Producing Gastric Carcinoma with Multiple Liver Metastases: Report of Two Cases," Surg Today. 32(12):1075-80 (2002).
Slatter J, et al., "Pharmacokinetics, Metabolism, and Excretion of Irinotecan (CPT-11) Following I.V. Infusion of [14C]CPT-11 in Cancer Patients," Drug Metab Dispos. 28(4):423-33 (2000).
Taïeb J., "FOLFIRI.3, A New Regimen Combining 5-Fluorouracil, Folinic Acid and Irinotecan, For Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006.
PCT/US2013/046914: International Preliminary Reporton Patentability dated Dec. 23, 2014, 7 pages.
PCT/US2013/046914: PCT International Search Report dated Sep. 2, 2013, 3 pages.
PCT/US2013/075513: PCT International Preliminary Report on Patentability dated Jun. 16, 2015, 7 pages.
PCT/US2013/075513: PCT International Search Report dated Jun. 6, 2014, 2 pages.
PCT/US2014/062007: PCT International Preliminary Report on Patentability dated Apr. 26, 2016, 10 pages.
PCT/US2014/062007: PCT International Search Report dated Jan. 9, 2015, 3 pages.
PCT/US2015/064491: PCT International Preliminary Report on Patentability dated Jun. 13, 2017, 7 pages.
PCT/US2015/064491: PCT International Search Report dated Feb. 19, 2016, 4 pages.

(56) References Cited

OTHER PUBLICATIONS

PCT/US2016/047814: International Search Report dated Nov. 17, 2016, 3 pages.
PCT/US2016/047814: PCT International Preliminary Report on Patentability dated Feb. 20, 2018, 6 pages.
PCT/US2016/047827: International Search Report dated Nov. 17, 2016, 3 pages.
PCT/US2016/047827: PCT International Preliminary Report on Patentability dated Feb. 20, 2018, 6 pages.
Pfizer Background Document on the UGT1A1 Polymorphisms and Irinotecan Toxicity: ACPS Nov. 3, 2004 Advisory Committee Meeting, 19 pages.
Ramanathan R, et al., "Correlation between Ferumoxytol Uptake in Tumor Lesions by MRI and Response to Nanoliposomal Irinotecan in Patients with Advanced Solid Tumors: A Pilot Study," Clin Cancer Res. 23(14):3638-48 (2017).
Ramanathan R, et al., "Lesion Characterization with Ferumoxytol MRI in Patients with Advanced Solid Tumors and Correlation with Treatment Response to MM-398, Nanoliposomal Irinotecan (nal-IRI)." Poster presented at EORTC-NCI-AACR International Conference on Molecular Targets and Cancer Therapeutics on Nov. 20, 2014, 7 pages.
Ramanathan R, et al., "Lesion Characterization with Ferumoxytol MRI in Patients with Advanced Solid Tumors and Correlation with Treatment Response to MM-398, Nanoliposomal Irinotecan (nal-IRI)," Abstract No. 261. Eur. J. Cancer, 50:87 (2014).
Ramanathan R, et al., "Pilot Study in Patients with Advanced Solid Tumors to Evaluate Feasibility of Ferumoxytol (FMX) As a Tumor Imaging Agent Prior to MM-398, a Nanoliposomal Irinotecan (nal-IRI)." Poster presented at AACR Annual Meeting 2014, San Diego, CA, 9 pages.
Sachdev J, et al., "A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398)." Poster presented at 38th Annual San Antonio Breast Cancer Symposium on Dec. 8, 2015, 10 pages.
Sachdev J, et al., "Characterization of Metastatic Breast Cancer Lesions with Ferumoxytol MRI and Clinical Response to MM-398, Nanoliposomal Irinotecan (nal-IRI), in 3 Subjects." Poster presented at San Antonio Breast Cancer Symposium 2014, 8 pages.
Sachdev J, et al., "Characterization of Metastatic Breast Cancer Lesions with Ferumoxytol MRI and Treatment Response to MM-398, Nanoliposomal Irinotecan (nal-IRI)," Cancer Res.75(9 Suppl): Abstract P5-01-06 (2015), 3 printed pages.
Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).
Saito R, et al., "Gadolinium-loaded Liposomes Allow for Real-Time Magnetic Resonance Imaging of Convection-Enhanced Delivery in the Primate Brain," Exp Neurol. 196(2):381-9 (2005).
Saito R, et al., "Tissue Affinity of the Infusate Affects the Distribution Volume During Convection-Enhanced Delivery Into Rodent Brains: Implications for Local Drug Delivery," J Neurosci Methods. 154(1-2):225-32 (2006).
Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014).
Tardi P, et al., "Drug Ratio-Dependent Antitumor Activity of Irinotecan and Cisplatin Combinations In Vitro and In Vivo," Mol Cancer Ther. 8(8):2266-75 (2009).
Tentori L, et al., "Influence of MLH1 on Colon Cancer Sensitivity to Poly(ADP-ribose) Polymerase Inhibitor Combined with Irinotecan," Int J Oncol. 43(1):210-8 (2013).
U.S. Appl. No. 14/964,571: Jun. 12, 2019 Final Office Action, 15 pages.
U.S. Appl. No. 15/664,976: May 21, 2019 Nonfinal Office Action, 11 pages.
U.S. Appl. No. 15/768,352: Feb. 14, 2019 Non-Final Office Action, 15 pages.
U.S. Appl. No. 15/768,352: Jun. 3, 2019 Examiner Interview Summary, 5 pages.
U.S. Appl. No. 15/768,352: Jun. 12, 2019 Notice of Allowance including Examiner's Reasons for Allowance and Examiner Interview Summary, 21 pages.
U.S. Appl. No. 15/768,352: Jul. 12, 2019 Examiner Interview Summary, 4 pages.
U.S. Appl. No. 15/768,352: Aug. 28, 2019 Notice of Allowance including Examiner's Reasons for Allowance and Examiner Interview Summary, 16 pages.
U.S. Appl. No. 15/809,815: Jul. 8, 2019 Non-Final Office Action, 13 pages.
U.S. Appl. No. 15/896,389: Jul. 18, 2019 Nonfinal Office Action, 24 pages.
U.S. Appl. No. 15/896,436: Jul. 5, 2019 Nonfinal Office Action, 18 pages.
U.S. Appl. No. 16/012,351: Mar. 8, 2019 Non-Final Office Action, 13 pages.
U.S. Appl. No. 16/012,372: Mar. 8, 2019 Non-Final Office Action, 8 pages.
U.S. Appl. No. 16/036,885: Sep. 3, 2019 Non-Final Office Action, 15 pages.
Ventura M, et al., "Imaging-Based Assessment of the Treatment Efficacy of Nanoliposomal Irinotecan (nal-IRI) in a Triple Negative Breast Cancer Model of Spontaneous Metastasis." Poster presented at Annual World Molecular Imaging Congress, Sep. 7-10, 2016, 8 pages.
Von Pawel J, et al., "Randomized Phase III Trial of Amrubicin Versus Topotecan as Second-Line Treatment for Patients with Small-Cell Lung Cancer," J Clin Oncol. 32(35):4012-9 and appendix (1 page) (2014).
Von Pawel J, et al., "Topotecan Versus Cyclophosphamide, Doxorubicin, and Vincristine for the Treatment of Recurrent Small-Cell Lung Cancer," J Clin Oncol 17(2):658-67 (1999).
Wählby C, et al., "Sequential Immunofluorescence Staining and Image Analysis for Detection of Large Numbers of Antigens in Individual Cell Nuclei," Cytometry. 47(1):32-41 (2002).
Zander S, et al., "EZN-2208 (PEG-SN38) Overcomes ABCG2-Mediated Topotecan Resistance in BRCA1-Deficient Mouse Mammary Tumors," PLoS One. 7(9):345248 (2012), pp. 1-9.
Zhang Y, et al., "Poly(ADP-ribose) Polymerase and XPF-ERCC1 Participate in Distinct Pathways for the Repair of Topoisomerase I-Induced DNA Damage in Mammalian Cells," Nucleic Acids Res 39(9):3607-20 (2011).
Zhao M, et al., "Clinical Observation of Irinotecan or Topotecan as Second-Line Chemotherapy on Treating 43 Patients with Small-Cell Lung Cancer," Chin Oncol. 21(2):156-8 (2011), text in Chinese with Tables 1-3 and Figure 1 in English.
Zheng J, et al., "[18F]FAZA-PET Detection of Hypoxia Changes following Anti-cancer Therapy." Poster presented at Annual World Molecular Imaging Congress, Sep. 18-21, 2013, 7 pages.
Zheng J, et al., "Longitudinal Tumor Hypoxia Imaging with [18F[FAZA-PET Provides Early Prediction of Nanoliposomal Irinotecan (nal-IRI) Treatment Activity," EJNMMI Res 5(1):57, 10 pages (2015).
Znojek P, et al., "Preferential Potentiation of Topoisomerase I Poison Cytotoxicity by PARP Inhibition in S Phase," Br J Cancer. 111(7):1319-26 (2014).
Kalra A, et al., "Preclinical Activity of Nanoliposomal Irinotecan Is Governed by Tumor Deposition and Intratumor Prodrug Conversion," Cancer Res. 74(23):7003-13 (2014).
Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.
Kalra A., "Magnetic Resonance Imaging (MRI) to Predict Tumor Drug Delivery and Response to Nanoliposomal Therapy." Presentation presented at Tumor Models Boston 2014, 32 pages.
Kang M, et al., "Activity of MM-398, Nanoliposomal Irinotecan (nal-IRI), in Ewing's Family Tumor Xenografts Is Associated with

(56) References Cited

OTHER PUBLICATIONS

High Exposure of Tumor to Drug and High SLFN11 Expression," Clin Cancer Res. 21(5):1139-50 (2015).

Kim J, et al., "Systems Pharmacology Based Biomarker Potentially Predicts Clinical Anti-Cancer Activity of MM-398, Nanoliposomal Irinotecan, nal-IRI." Poster presented at American Conference on Pharmacometrics, Oct. 12-15 2014, 10 pages.

Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).

Klinz S, et al., "Identifying Differential Mechanisms of Action for MM-398/PEP02, a Novel Nanotherapeutic Encapsulation of Irinotecan," Mol Cancer Ther. 10(11 Suppl):Abstract C207. Molecular Targets and Therapeutics Meeting (2011), 2 printed pages.

Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACR Pancreatic meeting Orlando, FL, May 12-15, 2016, 10 pages.

Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenografl Model." Poster presented at AACR-NCI-EORTC International Conference on Molecular Targets and Cancer Therapeutics on Oct. 19, 2013, 7 pages.

Klinz S, et al.,"MM-302 a HER2-targeted Liposomal Doxorubicin, Shows Binding/Uptake and Efficacy in HER2 2+ Cells and Xenograft Models," Cancer Res 71 Abstract 3637 (2011), 1 printed page.

Korn R, "Advanced Imaging with Ferumoxytol MRI to Predict Drug Delivery." Presentation presented at Pancreatic Cancer 2014, Feb. 22, 2014, 23 pages.

Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting on Apr. 16-20, 2016, 5 pages.

Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).

Kummar S, et al. "Phase I Study of PARP Inhibitor ABT-888 in Combination with Topotecan in Adults with Refractory Solid Tumors and Lymphomas," Cancer Res. 71(17):5626-34 (2011), Epub Jul. 27, 2011.

Landry R, et al., "Pharmacokinetic Study of Ferumoxytol: A New Iron Repalcement Therapy in Normal Subjects and Hemodialysis Patients," Am J Nephrol. 25(4):400-10 (2005).

Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast Cancer Symposium, Dec. 4-8, 2012, 2 printed pages.

Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.

Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.

Leonard S, et al., "Extended Topoisomerase 1 Inhibition Through Liposomal Irinotecan Results in Improved Efficacy over Topotecan and Irinotecan in Models of Small-Cell Lung Cancer," Anti-Cancer Drugs. 28(10):1086-96 (2017).

Leonard S, et al., "Irinotecan Liposome Injection has Greater Anti-Tumor Activity than Topotecan and Irinotecan in Mouse Models of Small Cell Lung Cancer," Poster presented at AACR 110th Annual World Congress 2017, Washington, DC, Apr. 1-5, 2017, 6 pages.

Leonard S, et al., "Preclinical Support for Evaluation of Irinotecan Liposome Injection (nal-IRI, MM-398) in Small Cell Lung Cancer," Abstracts from the IASLC 17th World Conference on Lung Cancer held Dec. 4-7, 2016, J Thoracic Oncology. 12(1)(Suppl):S699 (2016), 1 page.

Leonard S, et al., "Preclinical Support for Evaluation of Irinotecan Liposome Injection (nal-IRI, MM-398) in Small Cell Lung Cancer," Poster presented at 17th World Conference on Lung Cancer, Vienna, Austria, Dec. 4-7, 2016, 5 pages.

Lo Russo P, et al., "Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors," Clin Cancer Res. 22(13):3227-37 (2016), Epub Feb. 3, 2016.

Lo Russo P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Supplement ASCO Meeting Library, Jun. 5, 2011, 1 page.

Lo Russo P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages.

Lynparza™ (olaparib) capsules package insert, ©AstraZeneca. 2014, Revised: Dec. 2014, 6 pages.

Mamot C, et al., "Epidermal Growth Factor Receptor-Targeted Immunoliposomes Significantly Enhance the Efficacy of Multiple Anticancer Drugs In Vivo," Cancer Res. 65(24):11631-8 (2005).

Mamot C, et al., "Extensive Distribution of Liposomes in Rodent Brains and Brain Tumors Following Convection-Enhanced Delivery," J Neurooncol 68(1):1-9 (2004).

Masuda N, et al., "CPT-11: A New Derivative of Camptothecin for the Treatment of Refractory or Relapsed Small-Cell Lung Cancer," J Clin Oncol. 10(8):1225-9 (1992).

Merrimack Pharmaceuticals, "Merrimack Pharmaceuticals Initiates Cross-Tumor Study to Investigate Potential Predictive Response Markers for a Developmental Nanotherapeutic Chemotherapy," Dec. 19, 2012. Retrieved from http://investors.merrimack.com/news-releases/news-release-details/merrimack-pharmaceuticals-initiates-cross-tumor-study, 2 printed pages.

Messerer C, et al., "Liposomal Irinotecan: Formulation Development and Therapeutic Assessment in Murine Xenograft Models of Colorectal Cancer," Clin Cancer Res. 10(19):6638-49 (2004).

Miles D, et al., "Combination Versus Sequential Single-Agent Therapy in Metastatic Breast Cancer," Oncologist. 7(suppl 6):13-19 (2002).

Miller M, et al. "Predicting Therapeutic Nanomedicine Efficacy Using a Companion Magnetic Resonance Imaging Manoparticule," Sci Transl Med. 7:314ra183 (2015), pp. 1-12, Editor's Summary (1 page), and Supplementary Materials (24 pages).

Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).

Mohammad A, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.

Mukhtar R, et al., "Elevated PCNA+ Tumor-Associated Macrophages in Breast Cancer are Associated with Early Recurrence and Non-Caucasian Ethnicity," Breast Cancer Res Treat. 130(2):635-44 (2011).

Murai J, et al., "Identification of Novel PARP Inhibitors Using a Cell-Based TDP1 Inhibitory Assay in a Quantitative High-Throughput Screening Platform," Author manuscript; Published in final edited form as: DNA Repair (Arnst). 21:177-82 (2014), 13 pages.

(56) References Cited

OTHER PUBLICATIONS

Murai J, et al., "Rationale for Poly(ADP-ribose) Ploymerase (PARP) Inhibitors in Combination Therapy with Campothecins or Temozolomide Based on PARP Trapping versus Catalytic Inhibition," J Pharmacol Exp Ther. 349(3):408-16 (2014).
Noble C, et al., "Novel Nanoliposomal CPT-11 Infused by Convection-Enhanced Delivery in Intracranial Tumors Pharmacology and Efficacy," Cancer Res. 66(5):2801-6 (2006).
Noble C, et al., "Pharmacokinetics, Tumor Accumulation and Antitumor Activity of Nanoliposomal Irinotecan Following Systemic Treatment of Intracranial Tumors," Nanomedicine. 9(14):2099-108 (2014).
O'Brien M, et al., "Phase III Trial Comparing Supportive Care Alone With Supportive Care With Oral Topotecan in Patients With Relapsed Small-Cell Lung Cancer," J Clin Oncol. 24(34):5441-7 (2006).
Owonikoko T, et al., "A Systematic Analysis of Efficacy of Second-Line Chemotherapy in Sensitive and Refractory Small-Cell Lung Cancer," J Thorac Oncol. 7(5):866-72 (2012).
Pallis A, et al., "A Multicenter Randomized Phase II Study of the Irinotecan/Gemcitabine Doublet Versus Irinotecan Monotherapy in Previously Treated Patients with Extensive Stage Small-Cell Lung Cancer," Lung Cancer. 65(2):187-91 (2009), Epub Dec. 18, 2008.
Park J, et al., "Anti-HER2 Immunoliposomes: Enhanced Efficacy Attributable to Targeted Delivery," Clin Cancer Res. 8(4):1172-81 (2002).
Patton W, "Detection Technologies in Proteome Analysis," J Chromatogr B. 771(1-2):3-31 (2002).
Paz-Ares L, et al., "Liposomal Irinotecan vs Topotecan in Patients with Small Cell Lung Cancer Who Have Progressed On/After Platinum-Based Therapy." Poster presented Sep. 23-26, 2018 at 19th World Conference on Lung Cancer meeting, 9 pages.
Paz-Ares L, et al., "RESILIENT: Study of Irinotecan Liposome Injection (nal-IRI) in Patients with Small Cell Lung Cancer—Preliminary Findings from Part 1 Dose-Defining Phase," Poster presented at ASCO in Chicago, IL May 31-Jun. 4, 2019, 6 pages.
Paz-Ares L, et al., "RESILIENT: Study of Irinotecan Liposome Injection (nal-IRI) in Patients with Small Cell Lung Cancer—Preliminary Findings from Part 1 Dose-Defining Phase," Abstract No. 8562, J Clin Oncol. 37(15)(Suppl):8562 (2019).
PCT/IB2017/000681: PCT International Preliminary Report on Patentability dated Nov. 20, 2018, 6 pages.
PCT/IB2017/000681: PCT International Search Report and Written Opinion dated Aug. 25, 2017, 8 pages.
Alagoz M, et al., "DNA Repair and Resistance to Topoisomerase I Inhibitors: Mechanisms, Biomarkers and Therapeutic Targets," Curr Med Chem. 19(23):3874-85 (2012).
Alfert M, et al., "A Selective Staining Method for the Basic Proteins of Cell Nuclei," Proc Natl Acad Sci USA. 39(10):991-9 (1953).
Ardizzoni A, et al., "Topotecan, A New Active Drug in the Second-Line Treatment of Small-Cell Lung Cancer: A Phase II Study in Patients with Refractory and Sensitive Disease," J Clin Oncol. 15(5):2090-6 (1997).
Butt R, et al., "Postfractionation for Enhanced Proteomic Analyses: Routine Electrophoretic Methods Increase the Resolution of Standard 2D-PAGE," J Proteome Res. 4(3):982-91 (2005).
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Cancer Res.74(19 Suppl): Abstract 4626 (2014), 2 printed pages.
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Poster presented at AACR Annual Meeting Apr. 5-9, 2014, 6 pages.
Chan D, et al., "PEP02 (Liposome Irinotecan) Effectively Inhibits Human Lung Squamous Cell Carcinoma and Small Cell Lung Cancers in Subcutaneous and Orthotopic Xenograft Tumor Models," J Thoracic Oncology. 6(6)(Suppl 2): S420-1 (2011).
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at the 14th World Conference on Lung Cancer, 2011, 11 pages.
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at Santa Monica Lung Cancer Meeting, 2012, 9 pages.
Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.
Clarke J, et al., "A Phase 1 Trial of Intravenous Liposomal Irinotecan in Patients with Recurrent High-Grade Glioma," Cancer Chemother Pharmacol. 79(3):603-10 (2017).
Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.
Clinical Trials Identifier NCT00311610: Jun. 29, 2016 update, first posted Apr. 6, 2006, "Phase II Trial of LE SN38 in Patients with Metastatic Colorectal Cancer After Progression on Oxaliplatin." Retrieved from ClinicalTrials.gov archive, 3 printed pages.
Clinical Trials Identifier NCT00364143: Jan. 26, 2012 update, first posted Aug. 15, 2006, "A Phase I Study of IHL-305 Irinotecan Liposome Injection) in Patients With Advanced Solid Tumors." Retrieved from ClinicalTrials.gov archive, 6 printed pages.
Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.
Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: May 6, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.
Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment" Retrieved from ClinicalTrials.gov archive, 4 printed pages.
Clinical Trials Identifier NCT01770353: Jun. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment" Retrieved from ClinicalTrials.gov archive, 4 printed pages.
Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Reflactory Pediatric Solid Tumors." Retrieved from ClinicalTrials.gov archive, 6 printed pages.
Clinical Trials Identifier NCT02022644: May 8, 2017 update, first posted Dec. 30, 2013, "A Phase I Study of Convection-Enhanced Delivery of Liposomal-Irinotecan Using Real-Time Imaging With

(56) References Cited

OTHER PUBLICATIONS

Gadolinium in Patients With Recurrent High Grade Glioma." Retrieved from ClinicalTrials.gov archive, 9 printed pages.
Clinical Trials Identifier NCT02631733: Dec. 15, 2015 update, "A Phase I Study of a Combination of MM-398 and Veliparib in Solid Tumors" Retrieved from ClinicalTrials.gov archive, 6 printed pages.
Clinical Trials Identifier NCT02631733: Feb. 16, 2016 update, "A Phase I Study of a Combination of MM-398 and Veliparib in Solid Tumors" Retrieved from ClinicalTrials.gov archive, 6 printed pages.
Clinical Trials Identifier NCT02631733: Jun. 20, 2016 update, "A Phase I Study of a Combination of MM-398 and Veliparib in Solid Tumors" Retrieved from ClinicalTrials.gov archive, 6 printed pages.
Clinical Trials Identifier NCT02631733: Jun. 21, 2016 update, "A Phase I Study of a Combination of MM-398 and Veliparib in Stolid Tumors." Retrieved from ClinicalTrials.gov archive, 6 printed pages.
Clinical Trials Identifier NCT02631733: Jul. 6, 2016 update, "A Phase I Study of a Combination of MM-398 and Veliparib in Solid Tumors" Retrieved from ClinicalTrials.gov archive, 6 printed pages.
Clinical Trials Identifier NCT02631733: Jul. 11, 2016 update, "A Phase I Study of a Combination of MM-398 and Veliparib in Solid Tumors" Retrieved from ClinicalTrials.gov archive, 6 printed pages.
Clinical Trials Identifier NCT02631733: Jul. 19, 2016 update, "A Phase I Study of a Combination of MM-398 and Veliparib in Solid Tumors" Retrieved from ClinicalTrials.gov archive, 6 printed pages.
Clinical Trials Identifier NCT02631733: Aug. 7, 2016 update, "A Phase I Study of a Combination of MM-398 and Veliparib in Solid Tumors" Retrieved from ClinicalTrials.gov archive, 6 printed pages.
Clinical Trials Identifier NCT02631733: Sep. 21, 2016 update, "A Phase I Study of a Combination of MM-398 and Veliparib in Solid Tumors" Retrieved from ClinicalTrials.gov archive, 6 printed pages.
Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.
Clinical Trials Identifier NCT03088813: Sep. 30, 2019 update, first posted Mar. 23, 2017, "Study of Irinotecan Liposome Injection (Onivyde®) in Patients With Small Cell Lung Cancer." Retrieved from ClinicalTrials.gov archive, 8 printed pages.
Davidson D, et al., "The PARP Inhibitor ABT-888 Synergizes Irinotecan Treatment of Colon Cancer Cell Lines," Invest New Drugs. 31(2);461-8 (2013) DOI: 10.1007/S10637-012-9886-7; Epub Oct. 9, 2012, 8 pages.
Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).
Dickinson P, et al., "Canine Spontaneous Glioma: A Translational Model System for Convection-Enhanced Delivery," Neuro Oncol. 12(9):928-40; Epub 10:1093/neuonc/noq046, 1-13 (2010).
Dósa E, et al., "Magnetic Resonance Imaging of Intracranial Tumors: Intra-Patient Comparison of Gadoteridol and Ferumoxytol," Neuro Oncol. 13(2):251-60 (2011) doi: 10.1093/neuonc/noq172. Epub 2010.
Eckardt J, et al., "Phase III Study of Oral Compared With Intravenous Topotecan As Second-Line Therapy in Small-Cell Lung Cancer," J Clin Oncol. 25(15):2086-92 (2007).
Fitzgerald J, et al., "Systems Pharmacology Identification of Tumour Nanoparticle Permeability as Predictor of Clinical Anti-Cancer Activity of MM-398, Nanoliposomal Irinotecan, nal-IRL" Poster presented at 15th International Conference on Systems Biology. Sep. 14-18, 2014, 10 pages.
Gahramanov S, et al., "Pseudoprogression of Glioblastoma After Chemo- and Radiation Therapy: Diagnosis by Using Dynamic Susceptibility-Weighted Contrast-Enhanced Perfusion MR Imaging with Ferumoxytol versus Gadoteridol and Correlation with Survival," Radiology 266(3):842-52 (2013). doi: 10.1148/radiol. 12111472 Epub Nov. 30, 2012.
Genther Williams S, et al., "Treatment with the PARP Inhibitor, Niraparib, Sensitizes Colorectal Cancer Cell Lines to Irinotecan Regardless of MSI/MSS Status," Cancer Cell Int. 15(1):14, doi: 10.1186/s12935-015-0162-8 (2015), pp. 1-11.

Gilbert D, et al., "Topoisomerase I Inhibition In Colorectal Cancer: Biomarkers and Therapeutic Targets," Br J Cancer. 106(1):18-24 (2012), doi: 10.1038/bjc.2011.498, Epub Nov. 22, 2011.
Hanna N, et al., "Randomized Phase III Trial Comparing Irinotecan/Cisplatin with Etoposide/Cisplatin in Patients with Previously Untreated Extensive-Stage Disease Small-Cell Lung Cancer," J Clin Oncol. 24(13):2038-43 (2006).
Hare J, et al., "Treatment of Colorectal Cancer Using a Combination of Liposomal Irinotecan (Irinophore C(TM)) and 5-Fluorouracil," PLoS One. 8(4):e62349, doi: 10.1371/journal.pone.0062359, 12 pages (2013).
Hayashi H, et al., "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.
Hayes M, et al., "Assembly of Nucleic Acid-Lipid Nanoparticles from Aqueous-Organic Monophases," Biochim Biophys Acta. 1758(4):429-42 (2006).
Huber R, et al., "Efficacy of a Toxicity-Adjusted Topotecan Therapy in Recurrent Small Cell Lung Cancer," Eur Respir J. 27(6):1183-9 (2006).
Hycamtin (topotecan hydrochloride) for injection package insert, revision Feb. 28, 2014, retrieved from https://www.accessdata.fda.gov/drugsatfda_docs/label/2014/020671s020lbl.pdf, 23 pages.
Hycamtin (topotecan) for injection package insert, revision Jun. 2, 2015, retrieved from https://www.accessdata.fda.gov/drugsatfda_docs/label/2015/020671s021lbl.pdf, 21 pages.
Stathopoulos G and Boulikas T, "Lipoplatin Formulation Review Article," J Drug Deliv. 2012:581363, Article ID 581363, doi:10.1155/2012/581363, Epub 2011, 10 pages.
Stathopoulos G, et al., "Liposomal Oxaliplatin in the Treatment of Advanced Cancer: A Phase I Study," Anticancer Res 26(2B):1489-93 (2006).
Stylianopoulos T and Jain R, "Combining Two Strategies to Improve Perfusion and Drug Delivery in Solid Tumors," Proc Natl Acad Sci USA. 110(46):18632-7 (2013).
Takano S, et al., "Metronomic Treatment of Malignant Glioma Xenografts with Irinotecan (CPT-11) Inhibits Angiogenesis and Tumor Growth," J Neurooncol. 99(2):177-85 (2010).
Tardi P, et al., "Liposomal Encapsulation of Topotecan Enhances Anticancer Efficacy in Murine and Human Xenograft Models," Cancer Res. 60(13):3389-93 (2000).
Tardi P, et al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006.
Toutain P and Bousquet-Melou A, "Plasma terminal half-life," J Vet Pharmacol Ther. 27(6):427-39 (2004).
U.S. Appl. No. 15/664,976: Nov. 4, 2019 Nonfinal Office Action, 9 pages.
U.S. Appl. No. 15/664,976: May 18, 2020 Final Office Action, 11 pages.
U.S. Appl. No. 15/664,976: Oct. 13, 2020 Notice of Allowance including Examiner's Reasons for Allowance, 13 pages.
U.S. Appl. No. 15/809,815: Feb. 27, 2020 Final Office Action, 16 pages.
U.S. Appl. No. 15/896,389: Jan. 31, 2020 Final Office Action, 28 pages.
U.S. Appl. No. 15/896,389: Mar. 26, 2020 Examiner Interview Summary and Applicant slides, 22 pages.
U.S. Appl. No. 15/896,389: Apr. 9, 2020 Advisory Action, 3 pages.
U.S. Appl. No. 15/896,389: Jun. 5, 2020 Notice of Allowance including Examiner's Reasons for Allowance and Examiner Interview Summary, 13 pages.
U.S. Appl. No. 16/012,351: Jan. 7, 2020 Final Office Action, 9 pages.
U.S. Appl. No. 16/012,372: Jan. 7, 2020 Final Office Action, 9 pages.
U.S. Appl. No. 16/012,372: Jul. 27, 2020 Non-Final Office Action, 8 pages.
U.S. Appl. No. 16/302,050: Jan. 17, 2020 Non-Final Office Action, 17 pages.

(56) References Cited

OTHER PUBLICATIONS

U.S. Appl. No. 16/510,394: Mar. 6, 2020 Non-Final Office Action, 15 pages.
U.S. Appl. No. 16/567,902: Apr. 27, 2020 Non-Final Office Action, 20 pages.
U.S. Appl. No. 16/567,902: Aug. 10, 2020 Final Office Action, 21 pages.
U.S. Appl. No. 16/586,609: Oct. 5, 2020 Non-Final Office Action, 5 pages.
Vaage J, et al., "Therapy of a Xenografted Human Colonic Carcinoma Using Cisplatin or Doxorubicin Encapsulated in Long Circulating Pegylated Stealth Liposomes," Int J Cancer. 80(1):134-7 (1999).
Veal G, et al., "A Phase I Study in Paediatric Patients to Evaluate the Safety and Pharmacokinetics of SPI-77, A Liposome Encapsulated Formulation of Cisplatin," Br J Cancer. 84(8):1029-35 (2001).
Venook A, "Critical Evaluation of Current Treatments in Metastatic Colorectal Cancer," Oncologist. 10(4):250-61 (2005).
Ventura M, et al., "Ferumoxytol as an MR Imaging Surrogate Marker of Liposomal Drug Deposition and Longitudinal Efficacy in a Preclinical Model of Breast Cancer." Poster presented at World Molecular Imaging Congress, Sep. 13-16, 2017, Philadelphia, Pennsylvania, 6 pages.
Villalona-Calero M, et. al., "Phase I Study of Low-Dose Suramin as a Chemosensitizer in Patients With Advanced Non-Small Cell Lung Cancer," Clin Cancer Res. 9(9):3303-11 (2003).
Walker S, et al., "Simulation of Y-Site Compatibility of Irinotecan and Leucovorin at Room Temperature in 5% Dextrose in Water in 3 Different Containers," Can J Hosp Pharm. 58(4):212-22 (2005).
Wang W, et. al., "Weekly 24-Hour Infusion of High-dose 5-Fluorouracil and Leucovorin in Patients with Advanced Colorectal Cancer: Taiwan Experience," Jpn J Clin Oncol. 28(1):16-19 (1998).
Wei H, et al., "Active Loading Liposomal Irinotecan Hydrochloride: Preparation, In Vitro and In Vivo Evaluation," Asian J Pharm Sci. 8(5):303-11 (2013).
Weng K, et al., "Convection-Enhanced Delivery of Targeted Quantum Dot-lmmunoliposome Hybrid Nanoparticles to Intracranial Brain Tumor Models," Nanomedicine (Lond). 8(12):1913-25. 2013.
Weng K, et al., "Targeted Tumor Cell Internalization and Imaging of Multifunctional Quantum Dot-Conjugated Immunoliposomes in Vitro and in Vivo," Nano Lett. 8(9):2851-7 (2008).
Willett C, et al., "Direct Evidence That the VEGF-Specific Antibody Bevacizumab Has Antivascular Effects in Human Rectal Cancer," Nat Med 10(2):145-7 (2004), author manuscript version, 7 pages.
Wulaningsih W, et al., "Irinotecan Chemotherapy Combined With Fluoropyrimidines Versus Irinotecan Alone for Overall Survival and Progression-Free Survival in Patients With Advanced and/or Metastatic Colorectal Cancer," Cochrane Database Syst Rev. 2:CD008593 doi: 10.1002/14651858.CD008593.pub3. (2016), 36 pages.
Xeloda (capecitabine) package insert, Roche, revised Nov. 2000, 19 pages.
Yamashita Y, et al., "Convection-Enhanced Delivery of a Topoisomerase I Inhibitor (Nanoliposomal Topotecan) and a Topoisomerase II Inhibitor (Pegylated Liposomal Doxorubicin) in Intracranial Brain Tumor Xenografts," Neuro Oncol. 9(1):20-8 (2007). Epub 2006.
Yamashita Y, et al., "Convection-Enhanced Delivery of Liposomal Doxorubicin in Intracranial Brain Tumor Xenografts," Targ Oncol. 1:79-85 (2006).
Yang W, et al. "Development of a Method to Quantify Total and Free Irinotecan and 7-ethyl-10-hydroxycamptothecin (SN-38) for Pharmacokinetic and Bio-Distribution Studies After Administration of Irinotecan Liposomal Formulation," Asian J Pharm Sci. 14(6):687-97 (2019). Epub 2018.
Yang W, et al., "The Influence of Trapping Agents on the Antitumor Efficacy of Irinotecan Liposomes: Head-to-Head Comparison of Ammonium Sulfate, Sulfobutylether-β-Cyclodextrin and Sucrose Octasulfate," Biomater Sci., 7(1):419-28 (2019).
Yang, et al., "Oxaliplatin Long-Circulating Liposomes Improved Therapeutic Index of Colorectal Carcinoma," BMC Biotechnology. 11:21 doi: 10 1186/1472-6750-11-21 (2011), 8 pages.

Yoo C, et al., "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial." Poster presented at the European Society for Medical Oncology (ESMO) 2019 Congress, Barcelona, Spain, Sep. 27-Oct. 1, 2019, 6 pages.
Yoo C, et al., Abstract 829TiP. "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial," Ann Oncol. 30(Supp_5):v318 /doi.org/10.1093/annonc/mdz247.155 (2019).
Younis I, et al., "Enterohepatic Recirculation Model of Irinotecan (CPT-11) and Metabolite Pharmacokinetics in Patients With Glioma," Cancer Chemother Pharmacol 63(3):517-24 (2009), author manuscript version, 16 pages.
Zamboni W, et al., "Phase 1 and Pharmacokinetic Study of Pegylated Liposomal CKD-602 in Patients with Advanced Malignancies," Clin Cancer Res. 15(4):1466-72 (2009) and correction found at Clin Cancer Res. 15(8):2949-50 (2009).
Zhang K, et al., "Comprehensive Optimization of a Single-Chain Variable Domain Antibody Fragment as a Targeting Ligand for a Cytotoxic Nanoparticle," MAbs. 7(1):42-52 (2015).
Zhang L, et al., PEG-Coated Irinitecan Cationic Liposomes Improve the Therapeutic Efficacy of Breast Cancer in Animals, Eur Rev Med Pharmacol Sci. 17(24):3347-61 (2013).
Zhou X, et al., "Clinical Analysis of Bevacizumab Plus FOLFIRI Regimen as Front-Line Therapy for Chinese Patients with Advanced Colorectal Cancer," J Cancer Ther. 2(4):470-4 (2011).
Rocha Lima C, et al., "Irinotecan Plus Gemcitabine Results in No Survival Advantage Compared With Gemcitabine Monotherapy in Patients With Locally Advanced or Metastatic Pancreatic Cancer Despite Increased Tumor Response Rate," J Clin Oncol. 22(18):3776-83 (2004).
Sancho A, et al., Abstract 15625. "Oxaliplatin and Capecitabine After Gemcitabine Failure in Patients With Advanced Pancreatic, Biliary, and Gallbladder Adenocarcinoma (APBC)," J Clin Oncol. 26(15_suppl):15625 (2008), 5 printed pages.
Shi S, et al., "Combinational Therapy: New Hope for Pancreatic Cancer?" Cancer Lett. 317(2):127-35 (2012). Epub 2011.
Siveke J, et al., "Subgroup Analysis by Measurable Metastatic Lesion (ML) Number and Selected Lesion Locations (LL) at Baseline (BL) in NAPOLI-1: A Phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.
Siveke J, et al., Abstract 460. "Subgroup Analysis by Measurable Metastatic Lesion (ML) Number and Selected Lesion Locations (LL) at Baseline (BL) in NAPOLI-1: A Phase III Study of Liposomal Irinotecan (nal-IRI) ±5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):460 DOI: 10.1200/JCO.2018.36.4_suppl.460 (2018), 2 printed pages.
Siveke J, et al., Abstract ID0596. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," Oncol Res Treat. 39(Suppl 1):170 (2016).
Siveke J, et al., Abstract P863. "Effects of Nanoliposomal Irinotecan (nal-IRI;MM-398) ± 5-Fluorouracil und Leucavorin (5-FU/LV) on Quality of Life (QoL) in NAPOLI-1: A Phase 3 Study in Patients (pts) With Metastatic Pancreatic Adenocarcinoma (mPAC) Previously Treated With Gemcitabine-Based Therapy," Oncol Res Threat. 39 (Suppl 3):259 (2016).
Soares H, et al., "A Phase II Study of Capecitabine Plus Docetaxel in Gemcitabine-Pretreated Metastatic Pancreatic Cancer Patients: CapTere," Cancer Chemother Pharmacol. 73(4):839-45 (2014).

(56) References Cited

OTHER PUBLICATIONS

Sohal D et. al., "Metastatic Pancreatic Cancer: ASCO Clinical Practice Guideline Update," J Clin Oncol. 36(24):2545-2556 and appendix (2018).
Sohal D, et. al., "Metastatic Pancreatic Cancer: American Society of Clinical Oncology Clinical Practice Guideline," J Clin Oncol 34(23):2784-96 and Appendix (2016).
Sohal D, et al., "Reply to A. Wang-Gillam et al.," J Clin Oncol. 35(6):690-1 (2017). Epub 2016.
Son J, et al., "Glutamine Supports Pancreatic Cancer Growth Through a Kras-Regulated Metabolic Pathway," Nature. 496(7443):101-5 (2013), author manuscript version, 16 pages.
Sousa C and Kimmelman A, "The Complex Landscape of Pancreatic Cancer Metabolism," Carcinogenesis. 35(7):1441-50 (2014).
Starling N, et. al., "A Dose Escalation Study of Gemcitabine Plus Oxaliplatin in Combination With Imatinib for Gemcitabine-Refractory Advanced Pancreatic Adenocarcinoma," Ann Oncol. 23(4):942-7 (2012). Epub 2011.
Stathis A and Moore M, "Advanced Pancreatic Carcinoma: Current Treatment and Future Challenges," Nat Rev Clin Oncol. 7(3):163-72 (2010).
Stathopoulos G, et. al., "A Multicenter Phase III Trial Comparing Irinotecan-Gemcitabine (IG) With Gemcitabine (G) Monotherapy as First-Line Treatment in Patients With Locally Advanced or Metastatic Pancreatic Cancer," Br J Cancer. 95(5):587-92 (2006).
Stathopoulos G, et al., "Lipsomal Cisplatin Combined With Gemcitabine in Pretreated Advanced Pancreatic Cancer Patients: A phase I-II Study," Oncol Rep. 15(5):1201-4 (2006).
Takada T et. al., "Comparison of 5-Fluorouracil, Doxorubicin and Mitomycin C with 5-Fluorouracil Alone in the Treatment of Pancreatic-Biliary Carcinomas," Oncology. 51(5):396-400 (1994).
Takahara N, et. al., "A Retrospective Study of S-1 and Oxaliplatin Combination Chemotherapy in Patients With Refractory Pancreatic Cancer," Cancer Chemother Pharmacol. 72(5):985-90 (2013).
Tempero M, et al., "NCCN Clinical Practice Guidelines in Oncology: Pancreatic Adenocarcinoma," Version 1.2012. National Comprehensive Cancer Network, Inc. (2011), 79 pages.
Tempero M, et al., "NCCN Clinical Practice Guidelines in Oncology: Pancreatic Adenocarcinoma," Version 2.2012. National Comprehensive Cancer Network, Inc. (2011), 94 pages.
Tempero M, et al., "NCCN Clinical Practice Guidelines in Oncology: Pancreatic Adenocarcinoma," Version 2.2014. National Comprehensive Cancer Network, Inc. (2014), 122 pages.
Tempero M, et. al., "Pancreatic Adenocarcinoma: Clinical Practice Guidelines in Oncology," J Natl Compr Canc Netw. 8(9):972-1017 (2010).
Thota R, et. al., "Treatment of Metastatic Pancreatic Adenocarcinoma: A Review," Oncology. 28(1):70-4 (2014). Available at cancernetwork. com/view/treatment-metastatic-pancreatic-adenocarcinoma-review, 6 printed pages.
Todaka A, et. al., "S-1 Monotherapy as Second-line Treatment for Advanced Pancreatic Cancer after Gemcitabine Failure," Jpn J Clin Oncol. 40(6):567-72 (2010).
Togawa A, et. al., "Treatment With an Oral Fluoropyrimidine, S-1, Plus Cisplatin in Patients Who Failed Postoperative Gemcitabine Treatment for Pancreatic Cancer: A Pilot Study," Int J Clin Oncol. 12(4):268-73 (2007).
Tomicki S, et al., "Utilization of Hospital Inpatient Services Among Patients With Metastatic Pancreatic Cancer With Commercial and Medicare Insurance Treated With FDA-Approved/NCCN Category 1 Regimens." Poster presented at the Academy of Managed Care Pharmacy, Nexus (AMCP, Nexus): virtual meeting, week of Oct. 19, 2020, 6 pages.
Tsavaris N, et. al., "Second-Line Treatment With Oxaliplatin, Leucovorin and 5-Fluorouracil in Gemcitabine-Pretreated Advanced Pancreatic Cancer: A Phase II Study," Invest New Drugs. 23(4):369-75 (2005).
Van Cutsem E et. al., "Phase III Trial of Bevacizumab in Combination With Gemcitabine and Erlotinib in Patients With Metastatic Pancreatic Cancer," J Clin Oncol. 27(13):2231-7 (2009).

Van Rijswijk R, et. al., "Weekly High-Dose 5-Fluorouracil and Folinic Acid in Metastatic Pancreatic Carcinoma: A Phase II Study of the EORTC GastroIntestinal Tract Cancer Cooperative Group," Eur J Cancer. 40(14):2077-81 (2004).
Ventura M, et al., "Efficacy of nal-IRI and Hypoxia Modulation in Orthotopic Patient-Derived Pancreatic Tumor Models of High (OCIP51) and Low (OCIP19) Hypoxia," Presentation presented at the World Molecular Imaging Congress 2017, Philadelphia, Pennsylvania, Sep. 13-16, 2017, 15 pages.
Ventura M, et al., Abstract. "Efficacy of nal-IRI and Hypoxia Modulation in Orthotopic Patient-Derived Pancreatic Tumor Models of High (OCIP51) and Low (OCIP19) Hypoxia," The World Molecular Imaging Congress 2017, Philadelphia, Pennsylvania, Sep. 13-16, 2017, 1 page.
Vickers M, et al., "Comorbidity, Age and Overall Survival in Patients With Advanced Pancreatic Cancer—Results from NCIC CTG PA.3: A Phase III Trial of Gemcitabine Plus Erlotinib or Placebo," Eur J Cancer. 48(10):1434-42 (2012). Epub 2011.
Von Hoff D, et al., "Gemcitabine Plus nab-Paclitaxel Is an Active Regimen in Patients With Advanced Pancreatic Cancer: A PhaseI/II Trial," J Clin Oncol. 29(34):4548-54 (2011).
Von Hoff D, et al., "Increased Survival in Pancreatic Cancer with nab-Paclitaxel plus Gemcitabine," N Engl J Med. 369(18):1691-703 (2013).
Wainberg Z, et al., "First-line liposomal irinotecan + 5-fluorouracil/ leucovorin + oxaliplatin in patients with pancreatic ductal adenocarcinoma: long-term follow-up results from a phase 1/2 study." Presentation presented at the ESMO World Congress on Gastrointestinal Cancer, Jul. 1-4, 2020, 13 pages.
Wainberg Z, et al., "First-Line Liposomal Irinotecan + 5-Fluorouracil/ Leucovorin + Oxaliplatin in Patients With Pancreatic Ductal Adenocarcinoma: Long-Term Follow-Up Results From a Phase 1/2 Study." Poster presented at the European Society for Medical Oncology (ESMO) World Congress on Gastrointestinal Cancer, virtual format, Jul. 1-4, 2020, 7 pages.
Wainberg Z, et al., "NAPOLI-3: An Open-Label, Randomized, Phase 3 Study of First-Line Liposomal Irinotecan + 5 Fluorouracil/ Leucovorin + Oxaliplatin Versus Nab-Paclitaxel + Gemcitabine in Patients With Metastatic Pancreatic Ductal Adenocarcinoma." Poster presented at the American Society of Clinical Oncology (ASCO) Annual Conference, virtual format, May 29-Jun. 2, 2020, 6 pages.
Wainberg Z, et al., Abstract LBA-1. "First-line liposomal irinotecan + 5 fluorouracil/leucovorin + oxaliplatin in patients with pancreatic ductal adenocarcinoma: Long-term follow-up results from a phase 1/2 study," Ann Oncol. 31(Suppl 3): S241 doi.org/10.1016/j.annonc. 2020.04.076 (2020).
Wainberg Z, et al., Abstract TPS4661. "NAPOLI-3: An Open-Label, Randomized, Phase III Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma," J Clin Oncol. 38(15 Suppl):TPS4461 DOI: 10.1200/ JCO.2020.38.15_suppl.TPS4661 (2020), 2 printed pages.
Walker E and Ko A, "Beyond First-Line Chemotherapy for Advanced Pancreatic Cancer: An Expanding Array of Therapeutic Options?" World J Gastroenterol. 20(9):2224-36 (2014).
Wang-Gillam A, et al., "Characteristics of Long-Term Survivors in a Randomized Phase 3 Trial (NAPOLI-1) of Patients With Metastatic Pancreatic Ductal Adenocarcinoma (mDPAC) Treated With Liposomal Irinotecan (nal-IRI MM-398) + 5-FU/LV." Poster presented at the American Society of Clinical Oncology Gastrointestinal Cancers Symposium (ASCO GI), San Francisco, CA, Jan. 19-21, 2017, 9 pages.
Wang-Gillam A, et al., "Dose Modifications of Liposomal Irinotecan (nal-IRI) + 5-Fluorouracil/Leucovorin (5-FU/LV) n NAPOLI-1: Impact on Efficacy." Poster presented at the American Society of Clinical Oncology Gastrointestinal Cancers Symposium (ASCO GI), San Francisco, CA, Jan. 18-20, 2018, 8 pages.
Wang-Gillam A, et al., "Nomogram for Predicting Overall Survival in Patients Treated With Liposomal Irinotecan (nal-IRI) ± 5-Fluorouracil/ Leucovorin (5-FU/LV) in Metastatic Pancreatic Ductal Adenocarcinoma (mPDAC) Previously Treated With Gemcitabine-Based Therapy in NAPOLI-1." Poster presented at the American Society of Clinical

(56) References Cited

OTHER PUBLICATIONS

Oncology Gastrointestinal Cancers Symposium (ASCO GI), San Francisco, CA, Jan. 18-20, 2018, 9 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Treated With Gemcitabine-Based Therapy." Poster presented at the American Society of Clinical Oncology Gastrointestinal Cancers Symposium (ASCO GI), San Francisco, CA, Jan. 21-23, 2016, 11 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin, vs 5-Fluorouracil and Leucovorin in Metastatic Pancreatic Ductal Adenocarcinoma Previously Treated With Gemcitabine." Poster presented at the American Society of Clinical Oncology (ASCO) Annual Meeting, Chicago, Illinois, Jun. 3-7, 2016, 8 pages.
Wang-Gillam A, et al., Abstract 293. "Characteristics of Long-Term Survivors in a Randomized Phase III Trial (NAPOLI-1) of Patients With Metastatic Pancreatic Ductal Adenocarcinoma (mPDAC) Treated With Liposomal Irinotecan (nal-IRI; MM-398) + 5-FU/LV," J Clin Oncol. 35(4_Suppl):293 DOI: 10.1200/JCO.2017.35.4_suppl.293 (2017), 2 printed pages.
Wang-Gillam A, et al., Abstract 388. "Dose Modifications of Liposomal Irinotecan (nal-IRI) + 5-Fluorouracil/Leucovorin (5-FU/LV) in NAPOLI-1: Impacton Efficacy," J Clin Oncol. 36(4_Suppl):388 DOI: 10.1200/JCO.2018.36.4_suppl.388 (2018), 2 printed pages.
Wang-Gillam A, et al., Abstract 4126. "Updated Overall Survival (OS) Analysis of NAPOLI-1: Phase 3 Study of Nanoliposomal Irinotecan (nal-IRI, MM-398), With or Without 5-Fluorouracil and Leucovorin (5-FU/LV), vs 5-FU/LV in Metastatic Pancreatic Cancer (mPAC) Previously Treated With Gemcitabine (Gem)-Based Therapy," J Clin Oncol. 34(15_Suppl):4126 DOI: 10.1200/JCO.2016.34.15_suppl.4126 (2016), 5 printed pages.
Wang-Gillam A, et al., Abstract 417. "Updated Overall Survival Analysis of NAPOLI-1: Phase III Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Rreated With Gemcitabine-Based Therapy," J Clin Oncol. 34(4_Suppl):417 DOI: 10.1200/jco.2016.34.4_suppl.417 (2016), 2 printed pages.
Macarulla Mercadé T, et al., Abstract 379. "Subgroup Analysis by Baseline Pain Intensity (BPI) and Analgesic Use (BAU) in NAPOLI-1: A phase III Study of Liposomal Irinotecan (nal IRI)±5-Fluorouracil/ Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):379 DOI: 10.1200/JCO.2018.36.4_suppl.379 (2018), 4 printed pages.
Macarulla Mercadé T, et al., Abstract 410. "Subgroup Analysis by Baseline (BL) Weight-Associated Parameters: A phase III Study of Liposomal Irinotecan (nal-IRI)±5-Fluorouracil/Leucovorin (5-FU/LV) in Patients (pts) With Metastatic Pancreatic Ductal Adenocarcinoma (mPDAC) Previously Treated With Gemcitabine-Based (Gem) Therapy," J Clin Oncol. 36(4_Suppl):410 DOI: 10.1200/JCO.2018.36.4_suppl.410 (2018), 6 printed pages.
Macarulla Mercadé T, et al., Abstract 733P. "NAPOLI-1 Phase III Trial Outcomes by Prior Surgery, and Disease Stage, in Patients With Metastatic Pancreatic Ductal Adenocarcinoma (mPDAC)," Ann Oncol. 29(Supp_8)viii249-viii250 doi:10.1093/annonc/mdy282 (2018).
Macarulla Mercadé T, et al., Abstract O-004. "Selected Subgroup Analyses of Liposomal Irinotecan (nal-IRI) in Patients With Metastatic Pancreatic Ductal Adenocarcinoma (mPDAC) in the Global NAPOLI-1 Phase III Trial," Ann Oncol. 29(Suppl_5)v101 doi:10.1093/annonc/mdy149(2018).
Macarulla Mercadé T, et al., Abstract P-150. "Prognostic Effect of Primary Tumour Location in the NAPOLI-1 Phase 3 Study in Metastatic Pancreatic Ductal Adenocarcinoma (mPDAC)," Ann Oncol. 29(Suppl_5)v41-v42 doi:10.1093/annonc/mdy151 (2018).
Macarulla Mercadé T, et al., Abstract P-152. "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy," Ann Oncol. 29(Suppl_5):v42 doi:10.1093/annonc/mdy151 (2018).
Macarulla T, et al., "Integrated Population Pharmacokinetic Modelling of Liposomal Irinotecan in Patients With Various Tumour Types, Including Untreated Metastatic Pancreatic Cancer (mPC)." Poster presented at the European Society for Medical Oncology (ESMO) Congress 2019, Barcelona, Spain, Sep. 27-Oct. 1, 2019, 6 pages.
Macarulla T, et al., "Subgroup Analysis by Prior Lines of Metastatic Therapy in NAPOLI-1, A Global, Randomized Phase 3 Study of Liposomal Irinotecan ± 5-Fluorouracil and Leucovorin, vs. 5-Fluorouracil and Leucovorin in Patients With Metastatic Pancreatic Ductal Adenocarcinoma Who Have Progressed Following Gemcitabine-Based Therapy." Poster presented at the American Society of Clinical Oncology (ASCO) Annual Conference, Chicago, IL, Jun. 2-6, 2017, 7 pages.
Macarulla T, et al., Abstract 4127. "Subgroup Analysis by Prior Lines ot Metastatic Therapy (mtx) in NAPOLI-1: A Global, Randomized Phase 3 Study of Liposomal Irinotecan (nal-IRI) ± 5-Fluorouracil and Leucovorin (5-FU/LV), vs. 5-FU/LV in Patients (pts) With Metastatic Pancreatic Ductal Adenocarcinoma (mPDAC) Who Have Progressed Following Gemcitabine-Based Therapy," J Clin Oncol. 35(15_Suppl):4127 DOI: 10.1200/JCO.2017.35.15_suppl.4127 (2017), 2 printed pages.
Macarulla T, et al., Abstract 691P. "Integrated Population Pharmacokinetic Modelling of Liposomal Irinotecan in Patients With Various Tumour Types, Including Untreated Metastatic Pancreatic Cancer (mPC)," Ann Oncol. 30(Suppl_5):v263 doi:10.1093/annonc/mdz247 (2019).
Markham C, et al., "A Phase II Irinotecan-Cisplatin Combination in Advanced Pancreatic Cancer," Br J Cancer. 89(10):1860-4 (2003).
Matrisian , et. al., "The Past, Present, and Future of Pancreatic Cancer Clinical Trials," American Society of Clinical Oncology Educational Book. 35:e205-15 (2016).
Melisi D, et al., Abstract B04. "Effects of Nanoliposomal Irinotecan (nal-IRI; MM-398) ± 5-Fluorouracil and Leucavorin 5-FU/LV) on Quality of Life (QoL) in Patients (pts) With Metastatic Pancreatic Adenocarcinoma (mPAC) Previously Treated With Gemcitabine-Based Therapy: Results From the Phase 3 NAPOLI-1 Study," Ann Oncol. 27(Supp_4):iv18 doi:10.1093/annonc/mdw333.4 (2016).
Moore M, et. al., "Erlotinib Plus Gemcitabine Compared With Gemcitabine Alone in Patients With Advanced Pancreatic Cancer: A Phase III Trial of the National Cancer Institute of Canada Clinical Trials Group," J Clin Oncol. 25(15):1960-6 (2007).
Muldoon L, et al., "Comparing Service Utilization and Costs for Medicare FFS Patients With Metastatic Pancreatic Cancer by Chemotherapy Regimen and Line of Therapy." Poster presented at the International Society for Pharmacoeconomics and Outcomes Research (ISPOR) Annual Meeting, New Orleans, LA, May 18-22, 2019, 6 pages.
Muldoon L, et al., Abstract e18357. "Treatment Patterns, Survival Rate, and Parts A and B Costs by Line of Therapy for FDA-Approved/NCCNCategory 1 Treatments for Patients With Metastatic Pancreatic Cancer," J Clin Oncol. 37(15_Suppl):e18357 DOI: 10.1200/JCO.2019.37.15_suppl.e18357 (2019), 2 printed pages.
Muldoon L, et al., Abstract PCN302. "Comparing Service Utilization and Costs for Medicare FFS Patients With Metastatic Pancreatic Cancer by Chemotherapy Regimen and Line of Therapy," Value in Health. 22(Suppl 2):S113-S114 (2019).
Nakai Y, et. al., "Inhibition of Renin-Angiotensin System Affects Prognosis of Advanced Pancreatic Cancer Receiving Gemcitabine," Br J Cancer. 103(11):1644-8 (2010).
Neesse A, et al., "Stromal Biology and Therapy in Pancreatic Cancer," Gut. 60(6):861-8 (2011). Epub 2010.
Nelson R, "Lipsomal Irinotecan Boosts Survival in Pancreatic Cancer," Medscape, available at medscape.com/viewarticle/838501, 2015, 2 printed pages.

(56) References Cited

OTHER PUBLICATIONS

Nieto J, et. al., "Metastatic Pancreatic Cancer 2008: Is the Glass Less Empty?," Oncologist. 13(5):562-76 (2008) and erratum found at Oncologist 13(6):738 (2008).
Novarino A, et. al., "Oxaliplatin, 5-Fluorouracil, and Leucovorin as Second-Line Treatment for Advanced Pancreatic Cancer," Am J Clin Oncol. 32(1):44-8 (2009).
Oberstein P and Olive K, "Pancreatic Cancer: Why Is It So Hard to Treat?" Ther Adv Gastroenterol. 6(4):321-37 (2013).
Oettle H and Lehmann T, "Gemcitabine-Resistant Pancreatic Cancer: A Second-Line Option," Lancet. 387(10018):507-8 (2016). Epub 2015.
Olszewski A, et. al., "Phase I Study of Oxaliplatin in Combination with Gemcitabine, Irinotecan, and 5-Fluorouracil/Leucovorin(G-FLIE) in Patients with Metastatic Solid Tumors Including Adenocarcinoma of the Pancreas," J Gastrointest Cancer. 44(2):182-9 (2013).
O'Reilly E, et al., "Impact of Prior Irinotecan Exposure on Outcomes of Metastatic Pancreatic Cancer Patients." Poster presented at the American Society of Clinical Oncology Gastrointestinal Cancers Symposium (ASCO GI), San Francisco, CA, Jan. 23-25, 2020, 6 pages.
O'Reilly E, et al., "Real-World Patterns of Care Among Patients With Metastatic Pancreatic Cancer." Poster presented at the American Society of Clinical Oncology Gastrointestinal Cancers Symposium (ASCO GI), San Francisco, CA, Jan. 23-25, 2020, 6 pages.
O'Reilly E, et al., Abstract 666. "Real-World Patterns of Care Among Patients With Metastatic Pancreatic Cancer (mPC)," J Clin Oncol. 38(4_Suppl):666 DOI: 10.1200/JCO.2020.38.4_suppl.666 (2020), 2 printed pages.
O'Reilly E, et al., Abstract 667. "Impact of Prior Irinotecan Exposure on Outcomes of Metastatic Pancreatic Cancer (mPC) Patients," J Clin Oncol. 38(4_Suppl):667 DOI: 10.1200/JCO.2020.38.4_suppl. 667 (2020), 2 printed pages.
O'Reilly E, et. al., "A Cancer and Leukemia Group B Phase II Study of Sunitinib Malate in Patients with Previously Treated Metastatic Pancreatic Adenocarcinoma (CALGB 80603)," Oncologist. 15(12):1310-9 (2010).
Pan-Canadian Oncology Drug Review (pCODR) Expert Review Committee (pERC) Final Recommendation for Irinotecan Liposome (Onivyde) for Metastatic Pancreatic Cancer, pERC Meeting: Oct. 19, 2017, pERC Reconsideration Meeting: Dec. 17, 2017, pp. 1-14.
Papadatos-Pastos D, et.al., "FOLFIRINOX—A New Paradigm in the Treatment of Pancreatic Cancer," Expert Rev Anticancer Ther. 14(10):1115-25 (2014).
Parekh H, et al., "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study)." Poster presented at the American Society of Clinical Oncology Gastrointestinal Cancers Symposium (ASCO GI), San Francisco, CA, Jan. 23-25, 2020, 3 pages.
Parekh H, et al., Abstract TPS790. "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study) (NCT03483038)," J Clin Oncol. 38(4_Suppl):TPS790 (2020), 2 printed pages.
Park J, English abstract and Table 1 and Figure 1 of "Second Line Chemotherapy for Pancreatic Cancer," Korean J Gastroenterol. 57(4):207-12 (2011).
Pellino A, et al., "Observational Retrospective Evaluation of Treatment With Liposomal Irinotecan Plus Fluorouracil/Leucovorin for Metastatic Pancreatic Cancer Patients: An Italian Large Real-World Analysis." Poster presented at the American Society of Clinical Oncology Gastrointestinal Cancers Symposium (ASCO GI), San Francisco, CA, Jan. 23-25, 2020, 5 pages.
Pellino A, et al., Abstract 660. "Observational Retrospective Evaluation of Treatment With Liposomal Irinotecan Plus Fluorouracil/Leucovorin for Metastatic Pancreatic Cancer Patients: An Italian Large Real-World Analysis," J Clin Oncol. 38(4_Suppl):660 DOI: 10.1200/JCO.2020.38.4_suppl.660 (2020), 2 printed pages.
Pelzer U, et al., "A Randomized Trial in Patients With Gemcitabine Refractory Pancreatic Cancer. Final Results of the CONKO-003 Study." Presentation presented at the American Society of Clinical Oncology (ASCO) Annual Meeting, Chicago, Illinois, May 30-Jun. 3, 2008, 18 pages.
Pelzer U, et al., "Best Supportive Care (BSC) Versus Oxaliplatin, Folinic Acid and 5-Fluorouracil (OFF) Plus BSC in Patients for Second-Line Advanced Pancreatic Cancer: A Phase III-Study from the German CONKO-Study Group," Eur J Cancer. 47(11):1676-81 (2011).
Pelzer U, et al., Abstract P865. "Quality-Adjusted Time Without Symptoms or Toxicity (Q-TWiST) of Nanoliposomal Irinotecan (nal-IRI;MM-398) Plus 5-Fluorouracil and Leucovorin (5-FU/LV) vs 5-FU/LV alone in patients (pts) With Metastatic Pancreatic Adenocarcinoma (mPAC) Previously Treated With Gemcitabine-Based Therapy," Oncol Res Treat. 39(Suppl 3):260 (2016).
Petrelli F, et al., "What Else in Gemcitabine-Pretreated Advanced Pancreatic Cancer? An Update of Second Line Therapies," Rev Recent Clin Trials. 5(1):43-56 (2010).
Philip P, et al., "Consensus Report of the National Cancer Institute Clinical Trials Planning Meeting on Pancreas Cancer Treatment," J Clin Oncol. 27(33):5660-9 (2009).
Picozzi V, et al., "An Assessment of the Total Cost of Pancreatic Cancer Using Real-World Evidence." Poster presented at the American Society of Clinical Oncology Gastrointestinal Cancers Symposium (ASCO GI), San Francisco, CA, Jan. 23-25, 2020, 6 pages.
Picozzi V, et al., Abstract 773. "An Assessment of the Total Cost of Pancreatic Cancer Using Real-World Evidence," J Clin Oncol 38(4_Suppl):773 DOI: 10.1200/JCO.2020 38.4_suppl.773 (2020), 2 printed pages.
Pino M, et. al., "Capecitabine and Celecoxib as Second-Line Treatment of Advanced Pancreatic and Biliary Tract Cancers," Oncology. 76(4):254-61 (2009).
Poplin E, et. al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009).
Rahib L, et. al., "Evaluation of Pancreatic Cancer Clinical Trials and Benchmarks for Clinically Meaningful Future Trials: A Systematic Review," JAMA Oncol. 2(9):1209-16 (2016).
Ramnani K, et al., Abstract CT13. "Impact of Treatment Sequence on Overall Survival in Metastatic Pancreatic Cancer Patients Treated with Liposomal Irinotecan in the Real-World Setting," Hematology Oncology Pharmacy Association (HOPA) Annual Conference, Mar. 11-14, 2020, available at eventscribe.com/2020/posters/HOPAahead/SplitViewer.asp?PID=Njg0NzMyODlyNzY, (2020), 2 pages.
Reni M, et. al., "Raltitrexed-Eloxatin Salvage Chemotherapy in Gemcitabine-Resistant Metastatic Pancreatic Cancer," Br J Cancer. 94(6):785-91 (2006).
Renouf D, et al., "A Phase II Study of Erlotinib in Gemcitabine Refractory Advanced Pancreatic Cancer," Eur J Cancer. 50(11):1909-15 (2014).
Bouché O, et al. "Randomized Multicenter Phase II Trial of a Biweekly Regimen of Fluorouracil and Leucovorin (LV5FU2), LV5FU2 Plus Cisplatin, or LV5FU2 Plus Irinotecan in Patients With Previously Untreated Metastatic Gastric Cancer: A Fédération Francophone De Cancérologie Digestive Group Study—FFCD 9803," J Clin Oncol. 22(21):4319-28 (2004).
Chiang, N.-J, et al., "Development of Nanoliposomal Irinotecan (nal-IRI, MM-398, PEP02) in the Management of Metastatic Pancreatic Cancer," Expert Opin Pharmacother. 17(10):1413-20 (2016).
EP3337478: EPO Notice of Sandoz AG Opposition dated May 6, 2021, 5 pages.
EP3337478: Sandoz AG Opposition dated May 6, 2021, 22 pages.
EP3337478: Sandoz AG Opposition dated May 6, 2021, D1 (History of Changes for Study NCT02551991, retrieved from ClinicalTrials. gov archive on May 3, 2021, 4 pages).
EP3337478: Sandoz AG Opposition dated May 6, 2021, D2 (Abstract 0-0003. Von Hoff D, et al., "NAPOL11 Randomized Phase 3 Study of MM-398 (nal-IRI), With or Without 5-Fluorouracil and Leucovorin,

(56) References Cited

OTHER PUBLICATIONS

Versus 5-Fluorouracil and Leucovorin, in Metastatic Pancreatic Cancer Progressed on or Following Gemcitabine-Based Therapy." Ann Oncol. 25(Suppl 2):ii105 (2014)).
EP3337478: Sandoz AG Opposition dated May 6, 2021, D3 (Marsh R, et al., "Pancreatic Cancer and FOLFIRINOX: A New Era and New Questions," Cancer Med. 4(6):853-63 (2015)).
EP3337478: Sandoz AG Opposition dated May 6, 2021, D4 (Onivyde [MM-398] package insert, revision Oct. 22, 2015, 18 pages).
EP3337478: Sandoz AG Opposition dated May 6, 2021, D5 (Carnevale J and Ko A, "MM-398 (Nanoliposomal Irinotecan): Emergence of a Novel Therapy for the Treatment of Advanced Pancreatic Cancer," Future Oncol. 12(4):453-64 (2016). Epub 2015).
EP3337478: Sandoz AG Opposition dated May 6, 2021, D6 (Dean A, et al., Abstract TPS482. "A Randomized, Open-Label Phase II Study of Nanoliposomal Irinotecan (nal-IRI)-Containing Regimens Versus nab-Paclitaxel Plus Gemcitabine in Patients With Previously Untreated Metastatic Pancreatic Adenocarcinoma (mPAC)," J Clin Oncol. 34(4_Suppl):tps482 (2016), DOI: 10.1200/jco.2016.34.4_suppl.tps482, 5 printed pages).
EP3337478: Sandoz AG Opposition dated May 6, 2021, D7 (Zhang H, "Onivyde for the Therapy of Multiple Solid Tumors," Onco Targets Ther. 9:3001-3007 (2016)).
EP3337478: Sandoz AG Opposition dated May 6, 2021, D8 (Gaddy D, et al., "Abstract 4830: Preclinical Anti-tumor Activity of Nanoliposomal Irinotecan (Nal-IRI, MM-398) + 5-FU + Oxaliplatin in Pancreatic Cancer." In: Proceedings of the 107th Annual Meeting of the American Association for Cancer Research; Apr. 16-20, 2016; New Orleans, LA. Cancer Res. 76(14 Suppl):Abstract nr 4830 (2016), 4 printed pages).
EP3337478: Sandoz AG Opposition dated May 6, 2021, D9 (Priyambada P, et al., "Nanotechnology-Based Dombinational Drug Delivery: An Emerging Approach for Cancer Therapy," Drug Discov Today. 17(17-18):1044-52 (2012)).
EP3337478: EPO Notice of Generics [UK] Limited Opposition dated May 12, 2021, 5 pages.
EP3337478: Generics [UK] Limited Opposition dated May 12, 2021, 9 pages.
EP3337478: Generics [UK] Limited Opposition dated May 12, 2021, D10 (Conroy T, et al., "FOLFIRINOX versus Gemcitabine for Metastatic Pancreatic Cancer," N Engl J Med. 364(19):1817-25 (2011)).
EP3337478: Generics [UK] Limited Opposition dated May 12, 2021, D11 (Gourgou-Bourgade S, et al., "Impact of FOLFIRINOX Compared With Gemcitabine on Quality of Life With Metastatic Pancreatic Cancer: Results From the PRODIGE 4/ACCORD 11 Randomized Trial," J Clin Oncol. 31(1):23-9 (2013). Epub 2012.).
EP3337478: Generics [UK] Limited Opposition dated May 12, 2021, D12 (Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013)).
EP3337478: Generics [UK] Limited Opposition dated May 12, 2021, D13 (Hann B, et al., Abstract 5648. "Lipidic Nanoparticle CPT-11 in a Bioluminescent Orthotopic Pancreas Cancer Model," Cancer Res. 67(9 Suppl):5648 (2007), 4 printed pages).
EP3337478: Generics [UK] Limited Opposition dated May 12, 2021, D14 (Chang T, et al., "Phase I Study of Nanoliposomal Irinotecan (PEP02) in Advanced Solid Tumor Patients," Cancer Chemother Pharmacol. 75(3):579-86 (2015).
EP3337478: Generics [UK] Limited Opposition dated May 12, 2021, D15 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 4 printed pages).
EP3337478: Generics [UK] Limited Opposition dated May 12, 2021, D16 (Pubmed abstract retrieved on May 6, 2021 for Mahaseth H, et al., "Modified FOLFIRINOX Regimen With Improved Safety and Maintained Efficacy in Pancreatic Adenocarcinoma," Pancreas. 42(8):1311-5 (2013), 2 printed pages).
EP3337478: Generics [UK] Limited Opposition dated May 12, 2021, D17 (Drummond D, et al., "Development of a Highly Active Nanoliposomal Irinotecan Using a Novel Intraliposomal Stabilization Strategy," Cancer Res. 66(6):3271-77 (2006)).
Koizumi W, at aL, "Phase I/II Study of Bi-weekly Irinotecan plus Cisplatin in the Treatment of Advanced Gastric Cancer," Anticancer Res. 25(2B):1257-62 (2005).
Lorusso P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Journal of Clinical Oncology 29.15_suppl: Abstract 3000 (2011), 3 printed pages.
Morise M, et al., "Low-dose Irinotecan as a Second-line Chemotherapy for Recurrent Small Cell Lung Cancer," Jpn J Clin Oncol. 44(9):846-51 (2014).
Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021).
Colucci G, et. al., "Randomized Phase III Trial of Gemcitabine Plus Cisplatin Compared With Single-Agent Gemcitabine as First-Line Treatment of Patients With Advanced Pancreatic Cancer: The GIP-1 Study," J Clin Oncol. 28(10):1645-51 (2010).
Conroy T et al., Abstract 4010. "Randomized Phase III Trial Comparing FOLFIRINOX (F: 5FU/Leucovorin [LV], Irinotecan [I}, and Oxaliplatin [0]) Versus Gemcitibine (G) as First-Line Treatment for Metastatic Pancreatic Adenocarcinoma (MPA): Preplanned Interim Analysis Results of the PRODIGE 4/ACCORD 11 Trial" J Clin Oncol. 28(15_Suppl):4010 (2010), 3 printed pages.
Custodio A, et. al., "Second-Line Therapy for Advanced Pancreatic Cancer: A Review of the Literature and Future Directions," Cancer Treat Rev. 35(8):676-84 (2009).
De Jong F, et al., "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma Previously Treated With Gemcitabine," Poster presented at the Australian Gastro-Intestinal Trials Group, 18th Annual Scientific Meeting, Melbourne, Australia, Sep. 14-16, 2016, 10 pages.
De Jong F, et al., Abstract. "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma (mPDAC) Previously Treated With Gemcitabine," Australian Gastro-Intestinal Trials Group, 18th Annual Scientific Meeting, Melbourne, Australia, Sep. 14-16, 2016, 2 pages.
Dean A, et al., "First-Line (1L) Liposomal Irinotecan + 5-Fluorouracil/ Leucovorin (5-FU/LV) + Oxaliplatin (OX) in Patients With Locally Advanced or Metastatic Pancreatic Ductal Adenocarcinoma: Exploratory Subgroup Analyses of Survival by Changes in CA 19-9 Levels." Poster presented at the European Society for Medical Oncology (ESMO) Virtual Congress 2020, Sep. 19-21, 2020, 7 pages.
Dean A, et al., "First-Line Liposomal Irinotecan + 5-Fluorouracil/ Leucovorin + Oxaliplatin in Patients With Pancreatic Ductal Adenocarcinoma: Results From a Phase 1/2 Study." Presentation presented at the Clinical Oncology Society of Australia (COSA): Virtual meeting, Nov. 11-13, 2020, 10 pages.
Dean A, et al., "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Poster presented at the 18th European Society of Medical Oncology World Congress on Gastrointestinal Cancer; Barcelona, Spain; Jun. 29-Jul. 2, 2016, 14 pages.
Dean A, et al., "NAPOLI-3: An Open-Label, Randomized, Phase III Study of First-Line Liposomal Irinotecan + 5-Fluorouracil/ Leucovorin + Oxaliplatin Versus nab-Paclitaxel + Gemcitabine in Patients With Metastatic Pancreatic Ductal Adenocarcinoma." Pre-

(56) References Cited

OTHER PUBLICATIONS sentation presented at the Clinical Oncology Society of Australia (COSA): Virtual meeting, Nov. 11-13, 2020, 10 pages.
Dean A, et al., Abstract 1529P. "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma (mPDAC) Exploratory Subgroup Analyses of Survival by Changes in CA 19-9 Levels," Ann Oncol. 31(Suppl_4):S881-S897 10.1016/annonc/annonc285 (2020), 3 printed pages.
Dean A, et al., Abstract 222. "First-Line Liposomal Irinotecan + 5-Fluorouracil/Leucovorin + Oxaliplatin in Patients With Pancreatic Ductal Adenocarcinoma: Results From a Phase 1/2 Study," Asia-Pac J Clin Oncol. 16(Suppl. 8):118-119 (2020).
Dean A, et al., Abstract 407. "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma," Asia-Pac J Clin Oncol. 16(Suppl. 8):202-3 (2020).
Dean A, et al., Abstract 4111. "A Phase 1/2, Open-Label Dose-Escalation Study of Liposomal Irinotecan (nal-IRI) Plus 5-Fluorouracil/Leucovorin (5-FU/LV) and Oxaliplatin (OX) in Patients with Previously Untreated Metastatic Pancreatic Cancer (mPAC)," J Clin Oncol. 36(15_Suppl):4111 10.1200/JCO.2018.36.15_suppl.4111 (2018), 1 page.
Dean A, et al., Abstract P-287. "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Annals of Oncology. 27(Suppl 2):ii1-i85 (2016), 1 page.
Dean A, et al., Abstract. "Expanded Analyses of NAPOLI-1: Phase 3 Study of MM-398 (nal-IRI), With or Without 5-Fluorouracil and Leucovorin (5-FU/LV), Versus 5-FU/LV, in Metastatic Pancreatic Cancer (mPAC) Previously Treated With Gemcitabine-Based Therapy," 18th Annual Scientific Meeting of the Australasian Gastro-Intestinal Trials Group (AGITG), Melbourne, Australia, Sep. 14-16, 2016, 2 pages.
Dean A, et al., Abstract. "Liposomal Irinotecan (nal-IRI, MM-398)-Containing Regimens Versus nab-Paclitaxel Plus Gemcitabine as First-Line Therapy in Patients With Metastatic Pancreatic Adenocarcinoma (mPAC): A Randomized, Open-Label Phase 2 Study," 18th Annual Scientific Meeting of the Australasian Gastro-Intestinal Trials Group (AGITG), Melbourne, Australia, Sep. 14-16, 2016, 2 pages.
Dieguez G, et al., "Real-World Rates of Hematologic Laboratory Abnormalities and Associated Cost Among Metastatic Pancreatic Cancer Therapeutic Regimens," Poster presented at the American Society of Clinical Oncology Gastrointestinal Cancers Symposium (ASCO GI), San Francisco, CA, Jan. 23-25, 2020, 6 pages.
Dieguez G, et al., Abstract 670. "Real-World Rates of Hematology Lab Abnormalities and Associated Cost Among Metastatic Pancreatic Cancer (mPC) Therapeutic Regimens," J Clin Oncol. 38(4_Suppl):670 DOI: 10.1200/JCO.2020.38.4_suppl.670 (2020), 2 printed pages.
Doris J, et al., Abstract CT12. "The Cost of Adverse Events for FDA-Approved/NCCN Category 1 Treatments for Medicare Fee-For-Service (FFS) Patients With Metastatic Pancreatic Cancer: Focus on Liposomal Irinotecan-Based Regimens," Hematology Oncology Pharmacy Association (HOPA) Annual Conference, Mar. 11-14, 2020, available at eventscribe.com/2020/posters/HOPAahead/SplitViewer.asp?PID=NjgONzA2NjU1NjE, (2020), 2 pages.
Figer A, et. al., "A Comparison of Two Dose Regimens in Pancreatic Cancer," J Chemother. 12(5):442-5 (2000).
Gaddy D, et al., "A Systematic Literature Review to Identify and Compare Clinical Trials Evaluating Novel Therapeutic Agents in Post-Gemcitabine Advanced Pancreatic Cancer Patients." Poster presented at the International Society for Pharmacoeconomics and Outcomes Research (ISPOR) 18th Annual European Congress, Milan, Italy, Nov. 7-11, 2015, 6 pages.
Gaddy D, et al., "Preclinical Anti-tumor Activity of Nanoliposomal Irinotecan (Nal-IRI, MM-398) Supports Utilization as a Foundation of Front-Line Pancreatic Cancer Regimens." Poster presented at the American Society of Clinical Oneology Gastrointestinal Cancers Symposium (ASCO GI), San Francisco, CA, Jan. 19-21, 2017, 5 pages.
Gaddy D, et al., Abstract 336. "Preclinical Antitumor Activity of Nanoliposomal Irinotecan (Nal-IRI, MM-398) and Utilization as a Foundation of Front-Line Pancreatic Cancer Regimens," J Clin Oncol. 35(4_Suppl):336 DOI: 10.1200/JCO.2017.35.4_suppl.336 (2017), 2 printed pages.
Gaddy D, et al., Abstract PCN29. "A Systematic Literature Review to Identify and Compare Clinical Trials Evaluating Hovel Therapeutic Agents in Post-Gemcitabine Advanced Pancreatic Cancer," Value in Health. 18(7):A434 (2015).
Gebbia V, et al., "Second-Line Chemotherapy in Advanced Pancreatic Carcinoma: A Multicenter Survey of the Gruppo Oncologico Italia Meridionale on the Activity and Safety of the FOLFOX4 Regimen in Clinical Practice," Ann Oncol. 18(Suppl 6):vi124-7 (2007).
Gill S, et al., "PANCREOX: A Randomized Phase III Study of Fluorouracil/Leucovorin With or Without Oxaliplatin for Second-Line Advanced Pancreatic Cancer in Patients Who Have Received Gemcitabine-Based Chemotherapy," J Clin Oncol. 34(32):3914-20 and Appendix (2016).
Glassman D, et al., "Nanoliposomal Irinotecan With Flurouracil for the Treatment of Advanced Pancreatic Cancer." Poster presented at the American Society of Clinical Oncology Gastrointestinal Cancers Symposium (ASCO GI), San Francisco, CA, Jan. 18-20, 2018, 7 pages.
Glassman D, et al., Abstract 471. "Nano-Liposomal Irinotecan and 5-FU/LV (N+F) for the Treatment of Advanced DDAC: Memorial Sloan Kettering (MSK) Single Cancer Center Evaluation," J Clin Oncol. 36(4 Suppl):471 DOI: 10.1200/JCO.2018.36.4_suppl.471 (2018), 2 printed pages.
Gounaris I, et. al., "Options for the Treatment of Gemcitabine-Resistant Advanced Pancreatic Cancer," JOP. J Pancreas (Online) 11(2):113-23 (2010).
Gourzoulidis G, et al., "The Cost-Effectiveness of Nanoliposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece." Poster presented at the Virtual International Society for Pharmacoeconomics and Outcomes Research (ISPOR) European Congress, Milan, Italy, Nov. 16-19, 2020, 9 pages.
Gourzoulidis G, et al., Abstract PCN57. "The Cost-Effectiveness of Nanoliposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece," Virtual International Society for Pharmacoeconomics and Outcomes Research (ISPOR) European Congress, Milan, Italy, Nov. 16-19, 2020, available at ispor.org/heor-resources/presentations-database/presentation/euro2020-3282/105175, 2 printed pages.
Haller D, "Chemotherapy for Advanced Pancreatic Cancer," Int J Radiat Oncol Biol Phys. 56(4 Suppl):16-23 (2003).
Hann B, et al., Abstract 5648. "Lipidic Nanoparticle CPT-11 in a Bioluminescent Orthotopic Pancreas Cancer Model," Cancer Res. 67(9 Suppl):5648 (2007), 4 printed pages.
Heinemann V, et. al., "Randomized Phase III Trial of Gemcitabine Plus Cisplatin Compared With Gemcitabine Alone in Advanced Pancreatic Cancer," J Clin Oncol. 24(24):3946-52 (2006).
Herrera-Restrepo O, et al., "Budget Impact in the USA of Liposomal Irinotecan as a Post-Gemcitabine Treatment Option for Patients With Metastatic Pancreatic Adenocarcinoma (mPC)." Poster presented at the International Society for Pharmacoeconomics and Outcomes Research (ISPOR) Annual Meeting, New Orleans, LA, May 18-22, 2019, 12 pages.
Herrera-Restrepo O, et al., Abstract PCN80. "Budget Impact in the USA of Liposomal Irinotecan as a Post-Gemcitabine Treatment Option for Patients With Metastatic Pancreatic Adenocarcinoma (mPC)," Value in Health. 22(Suppl 2):S70 (2019).
Hidalgo M, "Pancreatic Cancer," N Engl J Med. 362(17):1605-17 (2010).

(56) References Cited

OTHER PUBLICATIONS

Hirsch J, et al., "Comparing Total Cost of Care For Medicare Fee-For-Service Patients With Pancreatic Cancer, By Chemotherapy Regimen." Poster presented at the American Society of Clinical Oncology Gastrointestinal Cancers Symposium (ASCO GI), San Francisco, CA, Jan. 23-25, 2020, 5 pages.

Hirsch J, et al., "Comparing Total Costs of Care for Medicare Fee-For-Service (FFS) Patients With Metastatic Pancreatic Cancer by Chemotherapy Regimen," Poster presented at the Academy of Managed Care Pharmacy, Nexus (AMCP, Nexus): virtual meeting, week of Oct. 19, 2020, 8 pages.

Hirsch J, et al., "The Cost of Adverse Events for FDA-Approved/NCCN Category 1 Treatments for Medicare Fee-For-Service (FFS) Patients With Metastatic Pancreatic Cancer." Poster presented at the Hematology Oncology Pharmacy Association (HOPA) Annual Conference, Tampa, FL, Mar. 11-14, 2020, 6 pages.

Hirsch J, et al., "The Cost of Adverse Events for FDA-Approved/NCCN Category 1 Treatments for Medicare Fee-For-Service Patients With Metastatic Pancreatic Cancer." Poster presented at the American Society of Health-System Pharmacists (ASHP) Midyear 2019 Clinical Meeting and Exhibition, Las Vegas, NV, Dec. 8-12, 2019, 6 pages.

Hirsch J, et al., Abstract 4-138. "The Cost of Adverse Events for FDA-Approved/NCCN Category 1 Treatments for Medicare Fee-For-Service Patients With Metastatic Pancreatic Cancer," American Society of Health-System Pharmacists (ASHP) Midyear Clinical Meeting Professional Poster Abstracts, (2019), 2 pages.

Hirsch J, et al., Abstract 721. "Comparing Total Cost of Care For Medicare FFS Patients With Pancreatic Cancer By Chemotherapy Regimen," J Clin Oncol. 38(4_Suppl):721 DOI: 10.1200/JCO.2020.38.4_suppl.721 (2020), 4 printed pages.

Hirsch J, et al., Abstract e19394. "Comparing Total Cost of Care for Medicare FFS Patients With Pancreatic Cancer by Chemotherapy Regimen," J Clin Oncol. 38(15_Suppl):e19394 DOI: 10.1200/JCO.2020.38.15_suppl.e19394 (2020), 2 printed pages.

Hsueh C-T, et al., "Nanovectors for Anti-Cancer Drug Delivery in the Treatment of Advanced Pancreatic Adenocarcinoma," World J Gastroenterol. 22(31):7080-90 (2016).

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 9 pages.

Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated With Gemcitabine," Presentation presented at the European Society for Medical Oncology (ESMO) World Congress on Gastrointestinal Cancer, Barcelona, Spain, Jun. 29-Jul. 2, 2016, 13 pages.

Hubner R, et al., "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone." Poster presented at the European Society for Medical Oncology (ESMO) Annual Congress, Madrid, Spain, Sep. 8-12, 2017, 5 pages.

Hubner R, et al., "Time Course of Selected Treatment-Emergent Adverse Events in NAPOLI-1: A Phase 3 Study of Liposomal Irinotecan (nal-IRI; MM-398) ± 5-Fluorouracil and Leucovorin (5-FU/LV) vs 5-FU/LV in Metastatic Pancreatic Cancer Previously Treated With Gemcitabine-Based Therapy." Poster presented at the European Society for Medical Oneology (ESMO) Annual Congress, Copenhagen, Denmark, Oct. 7-11, 2016, 8 pages.

Hubner R, et al., Abstract 242P. "Effects of nal-IRI (MM-398) ± 5-Fluorouracil on Quality of Life (QoL) of Patients With Metastatic Pancreatic Ductal Adenocarcinoma (mPDAC) Previously Treated With Gemcitabine Based Therapy Results From NAPOLI-1," Ann Oncol. 27(Supp_9):ix76 doi:10.1093/annonc/mdw582 (2016).

Hubner R, et al., Abstract 3832. "Time Course of Selected Treatment Emergent Adverse Events (TEAES) in NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.

Hubner R, et al., Abstract 741P. "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone," Ann Oncol. 28(Suppl_5):253 doi:10.1093/annonc/mdx369 (2017).

Hubner R, et al., Abstract O-004. "Effects of nal-IRI (MM-398) ± 5-fluorouracil on Quality of Life (QoL) in NAPOLI-1 X Phase 3 Study in Patients with Metastatic Pancreatic Ductal Adenocarcinoma (mPDAC) Previously Treated with Gemcitabine." Annals of Oncology. 27(Suppl 2):ii118-ii128 (2016), 1 page.

Hubner R, et al., Abstract. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," 2015 National Cancer Research Institute (NCRI) Cancer Conference, Nov. 1-4, 2015, 2 printed pages.

Hwang J, et al., Abstract 4618. "A Randomized Phase II Study of FOLFOX or FOLFIRI.3 as Second-Line Therapy in Patients With Advanced Pancreatic Cancer Previously Treated With Gemcitabine-Based Chemotherapy," J Clin Oncol. 27(15_Suppl):4618 (2009), 2 printed pages.

Hwang J, et. al., "Improving the Toxicity of Irinotecan/5-FU/Leucovorin: A 21-Day Schedule," Oncology. 17(9):37-43 (2003). Available at cancernetwork.com/view/improving-toxicity-irinotecan5-fu-leucovorin-21-day-schedule, 13 printed sages.

Ignatius R, et al., "Presentation of Proteins Encapsulated in Sterically Stabilized Liposomes by Dendritic Cells Initiates CD8+ T-cell Responses in Vivo," Blood. 96(10):3505-13 (2000).

Ilson D, "Nanolipoosomal Irinotecan Effective for Pancreatic Cancer," NEJM journal Watch, available at jwatch.org/na39795/2015/12/08/nanoliposomal-irinotecan-effective-pancreatic-cancer, (2015), 7 printed pages.

Ioka T, et al., "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)." Poster presented at the European Society for Medical Oncology (ESMO) Asia 2019 Congress, Singapore, Nov. 22-24, 2019, 9 pages.

Ioka T, et al., Abstract 132P. "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)," Ann Oncol. 30(Suppl_9):ix47-ix48 doi:10.1093/annonc/mdz422 (2019).

Ioka T, et al., Abstract 274TiP. "A Randomized Phase 2 Study of Nanoliposomal Irinotecan (nal-IRI, BAX2398)-Containing Regimen in Japanese Patients With Metastatic Pancreatic Adenocarcinoma (mPAC)," Ann Oncol. 27(Supp_9):ix84-ix85 doi:10.1093/annonc/mdw582 (2016).

Jameson G, et al., "Adverse Events in Patients with Metastatic Pancreatic Cancer Receiving Liposomal Irinotecan Understanding the Occurrence and How Management Affects Patient Outcomes." Poster presented at the Oncology Nursing Society (ONS) Annual Conference, Washington, DC, May 17-20, 2018, 7 pages.

Jameson G, et al., Abstract 1. "Adverse Events in Patients with Metastatic Pancreatic Cancer Receiving Liposomal Irinotecan: Understanding the Occurrence and How Management Affects Patient Outcomes," Oncology Nursing Society (ONS) 43rd Annual Congress, available at ons.confex.com/ons/2018/meetingapp.cgi/Paper/2970, (2018), 2 pages.

Kang S and Saif M, "Optimal Second Line Treatment Options for Gemcitabine Refractory Advanced Pancreatic Cancer Patients. Can We Establish Standard of Care with Available Data?," JOP. J Pancreas (Online) 9(2):83-90 (2008).

(56) References Cited

OTHER PUBLICATIONS

Katopodis O, et al., "Second-Line Chemotherapy With Capecitabine (Xeloda) and Docetaxel (Taxotere) in Previously Treated, Unresectable Adenocarcinoma of Pancreas: The Final Results of a Phase II Trial," Cancer Chemother Pharmacol. 67(2):361-8 (2011). Epub 2010.

Kim G, et al., "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens." Poster presented at the European Society for Medical Oncology (ESMO) Virtual Congress 2020, Sep. 19-21, 2020, 6 pages.

Kim G, et al., "Impact of Treatment Sequence on Overall Survival in Metastatic Pancreatic Cancer Patients Treated with Liposomal Irinotecan in the Real-World Setting." Poster presented at the Hematology Oncology Pharmacy Association (HOPA) Annual Conference, Tampa, FL, Mar. 11-14, 2020, 7 pages.

Kim G, et al., Abstract 1564P. "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens," Ann Oncol. 31(Suppl_4):S881-S897 10.1016/annonc/annonc285 (2020), 2 printed pages.

Kim G, et al., Abstract e16740. "Real-World Use of Liposomal Irinotecan-Based Regimens Among Patients (pts) With Metastatic Pancreatic Adenocarcinoma (mPDAC) in the United States (U.S.)," J Clin Oncol. 38(15 Suppl):e16740 DOI: 10.1200/JCO.2020.38.15_suppl.e16740 (2020), 2 printed pages.

Kim H, et. al., "Phase II Study of Palliative S-1 in Combination With Cisplatin as Second-Line Chemotherapy for Gemcitabine-Refractory Pancreatic Cancer Patients," Oncol Lett. 3(6):1314-8 (2012).

Kim Y, et. al., "Phase II Study of 5-Fluorouracil and Paclitaxel in Patients With Gemcitabine-Refractory Pancreatic Cancer," Cancer Chemother Pharmacol. 63(3):529-33 (2009). Epub 2008.

Kindler H, et. al., "Arsenic Trioxide in Patients With Adenocarcinoma of the Pancreas Refractory to Gemcitabine: A Phase II Trial of the University of Chicago Phase II Consortium," Am J Clin Oncol. 31(6):553-6 (2008).

Kindler H, et. al., "Gemcitabine Plus Bevacizumab Compared With Gemcitabine Plus Placebo in Patients With Advanced Pancreatic Cancer: Phase III Trial of the Cancer and Leukemia Group B (CALGB 80303)," J Clin Oncol. 28(22):3617-22 (2010).

Kipps E, et. al., "Liposomal Irinotecan in Gemcitabine-Refractory Metastatic Pancreatic Cancer: Efficacy, Safety and Place in Therapy," Ther Adv Med Oncol. 9(3):159-70 (2017).

Klapdor R and Fenner C, "Irinotecan(Campto R): Efficacy as Third/Forth Line Therapy in Advanced Pancreatic Cancer," Anticancer Res. 20(6D): 5209-12 (2000).

Klapdor R, et. al., "Reflections on Treatment Strategies for Palliative Chemotherapy of Pancreatic Cancer," Anticancer Res. 27(4A): 1789-94 (2007).

Klinz S, et al., Abstract e16205. "DNA Damage With Liposomal Irinotecan (nal-IRI) in Pancreatic Cancer Xenografts Multimodal Analysis of Deposition Characteristics," J Clin Oncol. 36(15_Suppl):e16205 DOI: 10.1200/JCO.2018.36.15_suppl.e16205 (2018), 2 printed pages.

Ko A, "Nanomedicine Developments in the Treatment of Metastatic Pancreatic Cancer: Focus on Nanoliposomal Irinotecan," Int J Nanomedicine. 11:1225-35 (2016).

Ko A, et. al., "A Phase II Study of Bevacizumab Plus Erlotinib for Gemcitabine-Refractory Metastatic Pancreatic Cancer," Cancer Chemother Pharmacol. 66(6):1051-7 (2010).

Koeller J, et al., Abstract e16751. "Trends in Real-World Clinical Outcomes Among Patients (pts) With Metastatic Pancreatic Adenocarcinoma (mPDAC) Treated With Liposomal Irinotecan Based Regimens in the United States (US)," J Clin Oncol. 38(15_Suppl):e16751 DOI: 10.1200/JCO.2020.38.15_suppl.e16751 (2020), 2 printed pages.

Kulke M, et. al., "Capecitabine Plus Erlotinib in Gemcitabine-Refractory Advanced Pancreatic Cancer," J Clin Oncol. 25(30):4787-92 (2007).

Kulke M, et. al., "Randomized Phase II Study of Gemcitabine Administered at a Fixed Dose Rate or in Combination With Cisplatin, Docetaxel, or Irinotecan in Patients With Metastatic Pancreatic Cancer: CALGB 89904," J Clin Oncol. 27(33):5506-12 (2009).

Lakatos G, et al., "Prognostic Value of Baseline Biliary Stents on Outcomes in Patients With Metastatic Pancreatic Ductal Adenocarcinoma (mPDAC) in the NAPOLI-1 Trial." Poster presented at the European Society for Medical Oncology 20th World Congress on Gastrointestinal Cancer, Barcelona, Spain, Jun. 20-23, 2018, 10 pages.

Lakatos G, et al., Abstract P-151. "Prognostic Value of Baseline Biliary Stents on Outcomes in Patients With Metastatic Pancreatic Ductal Adenocarcinoma (mPDAC) in the NAPOLI-1 Trial," Ann Oncol. 29(Suppl_5):v42 doi:10.1093/annonc/mdy151 (2018).

Latimer H, et al., Abstract C5. "Utilization of Hospital Inpatient Services Among Patients With Metastatic Pancreatic Cancer With Commercial and Medicare Insurance Treated With FDA-Approved/NCCN Category 1 Regimens," J Manag Care Spec Pharm. 26(10-a):S20 (2020).

Le A, et. al., "Conceptual Framework for Cutting the Pancreatic Cancer Fuel Supply," Clin Cancer Res. 18(16):4285-90 (2012).

Lee K, et al., Abstract P-153. "Decreased Appetite (DA) at Baseline Impacts Prognosis in the NAPOLI-1 Phase 3 Study in Metastatic Pancreatic Ductal Adenocarcinoma (mPDAC)," Ann Oncol. 29(Suppl_5):v42-v43 doi: 10.1093/annonc/mdy151 (2018).

Lee K-H, et al., "Decreased Appetite (DA) at Baseline Impacts Prognosis in the NAPOLI-1 Phase 3 Study in Metastatic Pancreatic Ductal Adenocarcinoma (mPDAC)." Poster presented at the European Society for Medical Oncology 20th World Congress on Gastrointestinal Cancer, Barcelona, Spain, Jun. 20-23, 2018, 9 pages.

Leonard S, et al., "Deposition Characteristics and Resulting DNA Damage Patterns of Liposomal Irinotecan (nal-IRI) in Pancreatic Cancer Xenografts." Poster presented at the American Society of Clinical Oncology Gastrointestinal Cancers Symposium (ASCO GI), San Francisco, CA, Jan. 18-20, 2018, 9 pages.

Leonard S, et al., Abstract 335. "Deposition Characteristics and Resulting DNA Damage Patterns of Liposomal Irinotecan (nal-IRI) in Pancreatic Cancer Xenografts," J Clin Oncol. 36(4_Suppl):335 DOI: 10.1200/JCO.2018.36.4_suppl.335 (2018), 2 printed pages.

Li J and Saif M, "Any Progress in the Management of Advanced Pancreatic Cancer? Highlights from the 45th ASCO Annual Meeting." JOP. J Pancreas (Online) 10(4):361-5 (2009).

Li J, et. al., "Any Second-Line Therapy for Advanced Pancreatic Cancer? Highlights from the 2010 ASCO Gastrointestinal Cancers Symposium " JOP. J Pancreas (Online). 11(2):151-3 (2010).

Löhr J, et. al., "Cationic Liposomal Paclitaxel Plus Gemcitabine or Gemcitabine Alone in Patients With Advanced-Pancreatic Cancer: A Randomized Controlled Phase II Trial," Ann Oncology. 23(5):1214-22 (2012). Epub 2011.

Ma W, et al., Abstract 2365. "Nanoliposomal Irinotecan (MM-398, nal-IRI) Population Pharmacokinetics (PK) and its Association With Efficacy and Safety in Patients With Solid Tumors Based on the Phase 3 Study NAPOLI-1 and Five Phase 1 and 2 Studies," Eur J Cancer. 51(3):S458 10.1016/S0959-8049(16)31281-3 (2015).

Macarulla Mercadé T, et al., "NAPOLI-1 Phase 3 Trial Outcomes by Prior Surgery, and Disease Stage, in Patients With Metastatic Pancreatic Ductal Adenocarcinoma (mPDAC)." Poster presented at the European Society for Medical Oncology Annual Congress, Munich, Germany, Oct. 19-23, 2018, 7 pages.

Macarulla Mercadé T, et al., "Prognostic Effect of Primary Tumour Location in the NAPOLI-1 Phase 3 Study in Metastatic Pancreatic Ductal Adenocarcinoma (mPDAC)." Poster presented at the European Society for Medical Oncology 19th World Congress on Gastrointestinal Cancer, Barcelona, Spain, Jun. 20-23, 2018, 10 pages.

Macarulla Mercadé T, et al., "Selected Subgroup Analyses of Liposomal Irinotecan in Patients With Metastatic Pancreatic Ductal Adenocarcinoma in the Global NAPOLI-1 Phase III Trial." Presentation presented at the European Society for Medical Oncology

(56) References Cited

OTHER PUBLICATIONS (ESMO) 20th World Congress on Gastrointestinal Cancer, Barcelona, Spain, Jun. 20-23, 2018, 16 pages.
Macarulla Mercade T, et al., "Subgroup Analysis by Baseline Pain Intensity (BPI) and Baseline Analgesic Use (BAU) in NAPOLI-1, A phase 3 Study of Liposomal Irinotecan (nal IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.
Macarulla Mercadé T, et al., "Subgroup Analysis by Baseline Weight-Associated Parameters: A phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 7 pages.
Macarulla Mercadé T, et al., "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy." Poster presented at the European Society for Medical Oncology 20th World Congress on Gastrointestinal Cancer, Barcelona, Spain, Jun. 20-23, 2018, 10 pages.
Abra R, et. al., "The Next Generation of Liposome Delivery Systems: Recent Experience With Tumor-Targeted, Sterically-Stabilized Immunoliposomes and Active-Loading Gradients," J Liposome Res. 12(1-2):1-3 (2002).
Alese O, et al., "A Phase I/II Study of Trifluridine/Tipiracil (TAS-102) in Combination With Nanoliposomal Irinotecan (NAL-IRI) in Advanced GI Cancers." Poster presented at Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 1-5, 2018, 1 page.
Alese O, et al., Abstract TPS4155. "A Phase I/II Study of Trifluridine/Tipiracil (TAS-102) in Combination With Nanoliposomal Irinotecan (NAL-IRI) in Advanced GI Cancers," J Clin Oncol. 36(15 Suppl):TPS4155 DOI: 10.1200/JCO.2018.36.15_suppl.TPS4155 (2018), 5 printed pages.
Allegrini G, et. al., "A Pharmacokinetic and Pharmacodynamic Study on Metronomic Irinotecan in Metastatic Colorectal Cancer Patients," Br J Cancer. 98(8):1312-19 (2008).
Alves Da Silva A, et. al., "Standardization of the Infusion Sequence of Antineoplastic Drugs Used in the Treatment of Breast and Colorectal Cancers," Einstein (São Paulo). 16(2):eRW4074 doi: 10.1590/S1679-45082018RW4074 (2018), 9 pages.
Anders C, et al., "Phase 1 Expansion Study of Irinotecan Liposome Injection (nal-IRI) in Patients with Metastatic Breast Cancer (mBC): Findings from the Cohort with Active Brain Metastasis (BM)." Presentation presented at the Society for Neuro-Oncology Inaugural Conference on Brain Metasteses, Aug. 16-17, 2019, New York, NY, 11 pages.
Anders C, et al., Abstract e12003. "Pharmacokinetic (PK) Characterization of Irinotecan Liposome Injection in Patients (pts) With Metastatic Breast Cancer (mBC)," J Clin Oncol. 37(15_Suppl):e12003 DOI: 10.1200/JCO.2019.37.15_suppl.e12003 (2019), 2 printed pages.
Anders C, et al., Abstract TRLS-06. "Phase 1 Expansion Study of Irinotecan Liposome Injection (nal-IRI) in Patients with Metastatic Breast Cancer (mBC): Findings from the Cohort with Active Brain Metastasis (BM)," Neuro-Oncology Advances. 1(Suppl 1):i9 doi. org/10.1093/noajnl/vdz014.039 (2019).
Andre T, et. al., "Phase III Study Comparing a Semimonthly With a Monthly Regimen of Fluorouracil and Leucovorin As Adjuvant Treatment for Stage II and III Colon Cancer Patients: Final Results of GERCOR C96.1," Clin Oncol. 25(24):3732-8 (2007).

Aranda E, et. al., "Randomized Study of Weekly Irinotecan Plus High-Dose 5-Fluorouracil (FUIRI) Versus Biweekly Irinotecan Plus 5-Fluorouracil/Leucovorin (FOLFIRI) As First-Line Chemotherapy for Patients With Metastatic Colorectal Cancer: A Spanish Cooperative Group for the Treatmentof Digestive Tumors Study," Ann Oncol. 20(2):251-7 (2009).
Awasthi N, et al., "Antitumor Efficacy of a Liposomal Formulation of Irinotecan in Preclinical Gastric Cancer Models Augmenting Its Response by Antiangiogenic Agents." Poster presented at the Annual Meeting of the American Association for Cancer Research 2020, Philadelphia, PA, Apr. 27-28, 2020 and Jun. 22-24, 2020, 6 pages.
Awasthi N, et al., Abstract 553. "Antitumor Efficacy of a Liposomal Formulation of Irinotecan in Preclinical Gastric Cancer Models: Augmenting Its Response by Antiangiogenic Agents," In Proceedings of the Annual Meeting of the American Association for Cancer Research 2020; Apr. 27-28, 2020 and Jun. 22-24, 2020. Cancer Res. 2020;80(16 Suppl):Abstract nr 553, DOI: 10.1158/1538-7445. AM2020-553, 2 printed pages.
Barenholz Y, "Development of Liposomal Drugs And Nano-Drugs: From Academic Research Via Incubators and Startups to FDA and EMA Approved Products. Part I: Science and Technology," Presentation presented at Barcelona NanoMed, Mar. 4-5, 2014, 89 pages.
Barenholz Y, "Doxil@—The First FDA-Approved Nano-Drug: Lessons Learned," J Control Release. 160(2):117-34 (2012).
Barone C, et. al., "Schedule-Dependent Activity of 5-Fluorouracil and Irinotecan Combination in the Treatment of Human Colorectal Cancer: In Vitro Evidence and a Phase I Dose-Escalating Clinical Trial," Br J Cancer. 96(1):21-8 (2007). Epub 2006.
Basu S, et. al., "Development and Validation of an UPLC-MS/MS Method for the Quantification of Irinotecan, SN 38 and SN-38 Glucuronide in Plasma, Urine, Feces, Liver and Kidney: Application to a Pharmacokinetic Study of Irinotecan in Rats," J Chromatogr B Analyt Technol Biomed Life Sci. 1015-1016: 34-41 (2016).
Batist G, et al., "Safety Pharmacokinetics, and Efficacy of CPX-1 Liposome Injection in Patients with Advanced Solid Tumors," Clin Cancer Res. 15(2):692-700 (2009).
Batist G, et al., Abstract 2014. "Phase 1 Study of CPX-1, A Fixed Ratio Formulation of Irinotecan (IRI) and Floxuridine (FLOX), in Patients With Advanced Solid Tumors," J Clin Oncol. 24(18_suppl):2014 (2006), 2 printed pages.
Batist G, et al., Abstract 2549. "Ratiometric Dosing of Irinotecan (IRI) and Floxuridine (FLOX) in a Phase I Trial: A Mew Approach for Enhancing the Activity of Combination Chemotherapy," J Clin Oncol. 25(18_suppl):2549 (2007), 5 printed pages.
Bendell J, et al., "Treatment Patterns and Clinical Outcomes in Patients With Metastatic Colorectal Cancer Initially Treated with FOLFOX-Bevacizumab or FOLFIRI-Bevacizumab: Results From ARIES, a Bevacizumab Observational Cohort Study," Oncologist. 17(12):1486-95 (2012).
Bernards N, et al., "Liposomal Irinotecan Achieves Significant Survival and Tumor Burden Control in a Triple Megative Breast Cancer Model of Spontaneous Metastasis," Mol Pharm. 15(9):4132-8 (2018).
Bernards N, et al., "Liposomal Irinotecan Injection (nal-IRI) Achieves Significant Survival and Tumor Burden Control in a Triple Negative Breast Cancer Model of Spontaneous Metastasis," Poster presented at the World Molecular Imaging Congress Sep. 13-16, 2017, Philadelphia, Pennsylvania, 5 pages.
Boman N, et al., "Optimization of the Retention Properties of Vincristine in Liposomal Systems," Biochim Biophys Acta. 1152(2):253-58 (1993).
Borner M, et. al., "A Randomized Phase II Trial of Capecitabine and Two Different Schedules of Irinotecan in First-Line Treatment of Metastatic Colorectal Cancer: Efficacy, Quality-of-Life and Toxicity," Ann Oncol. 16(2): 282-8 (2005).
Boulikas T, "Clinical Overview on Lipoplatin: A Successful Liposomal Formulation of Cisplatin," Expert Opin Investig Drugs. 18(8):1197-218 (2009), author manuscript version, 22 pages.
Bozzuto G and Molinari A, "Liposomes as Nanomedical Devices," Int J Nanomedicine. 10:975-99 (2015).
Bulbake U, et al., "Liposomal Formulations in Clinical Use: An Updated Review," Pharmaceutics. 9(2):12 doi: 10.3390/pharmaceutics9020012 (2017), 33 pages.

(56) References Cited

OTHER PUBLICATIONS

Butowski N, et al., "A Phase I Study of CED of Nanoliposomal-Irinotecan Using Real-Time Imaging With Gadolinium in Patients With Recurrent High Grade Glioma." Poster presented at the American Society of Clinical Oncology (ASCO) Annual Conference, Chicago, IL, May 29-Jun. 2, 2015, 4 pages.

Butowski N, et al., Abstract TPS2081. "A Phase I Study of Convection-Enhanced Delivery of Nanoliposomal Irinotecan Using Real-Time Imaging in Patients With Recurrent High Grade Glioma," J Clin Oncol. 33(15 Suppl):2081 DOI: 10.1200/jco.2015.33.15_suppl. tps2081 (2015), 2 printed pages.

Caelyx (doxorubicin), MedBroadcast, accessed Jan. 26, 2021 from medbroadcast.com/drug/getdrug/caelyx, 11 printed pages.

Cao S, et. al., "Synergistic Antitumor Activity of Capecitabine in Combination with Irinotecan," Clin Colorectal Cancer. 4(5):336-43 (2005).

Cao Y, et al., "A Gold Nanoparticle Bouquet Held on Plasma Membrane: An Ultrasensitive Dark-Field Imaging Approach for Cancer Cell Analysis," Nanotheranostics. 4(4):201-209 (2020).

Carter K, et. al., "Sphingomyelin Liposomes Containing Porphyrin-Phospholipid for Irinotecan Chemophototherapy," Theranostics. 6(13):2329-36 (2016).

Dassileth P, et al., "Antiemetic Efficacy of Dexamethasone Therapy in Patients Receiving Cancer Chemotherapy," Arch Intern Med. 143(7):1347-9 (1983).

Chabot G, "Clinical Pharmacokinetics of Irinotecan," Clin. Pharmacokinet. 33(4):245-59 (1997).

Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 3-7, 2016, 7 pages.

Chan E, et al., Abstract TPS3633. "A Phase 1 b/2 Study Combining MM-151 + nal-IRI + 5-FU + Leucovorin in RAS-Wildtype Metastatic Colorectal Cancer (mCRC)," J Clin Oncol. 34(15 Suppl):TPS3633 10.1200/JCO.2016.34.15_suppl.TPS3633 (2016), 4 printed pages.

Chauhan V, et. al., "Normalization of Tumour Blood Vessels Improves the Delivery of Nanomedicines in a Size-Dependent Manner," Nat Nanotechnol. 7(6):383-8 (2012), author manuscript version, 15 pages.

Chen J, et al., "Improved Pharmacokinetics and Reduced Toxicity of Brucine After Encapsulation into Stealth Liposomes: Role of Phosphatidylcholine," Int J Nanomedicine 7:3567-77 (2012).

Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 6 printed pages.

Chiang N-J, et al., "A Phase I Dose-Escalation Study of PEP02 (Irinotecan Liposome Injection) in Combination with 5-Fluorouracil and Leucovorin in Advanced Solid Tumors," BMC Cancer. 16(1):907 (2016). doi: 10.1186/s12885-016-2933-6, pp. 1-8.

Chibaudel B, et al., "PEPCOL: a GERCOR Randomized Phase II Study of Nanoliposomal Irinotecan PEP02 (MM-398) or Irinotecan with Leucovorin/5-Fluorouracil as Second-Line Therapy in Metastatic Colorectal Cancer", Cancer Med. 5(4):676-83 (2016).

Chiesa MD, et al., "Sequential Chemotherapy with Dose-Dense Docetaxel, Cisplatin, Folinic Acid and 5-Fluorouracil (TCF-dd) Followed by Combination of Oxaliplatin, Folinic acid, 5-Fluorouracil and Irinotecan (COFFI) in Metastatic Gastric Cancer: Results of a Phase II Trial," Cancer Chemother Pharmacol. 67(1):41-8 (2011), epub 2010.

Chu C-J, et al., "Efficiency of Cytoplasmic Delivery by pH-Sensitive Liposomes to Cells in Culture," Pharm Res. 7(8):824-34 (1990).

Clarke J, et al., "A Phase I Trial of Intravenous Liposomal Irinotecan in Patients With Recurrent High-Grade Gliomas." Poster presented at the American Society of Clinical Oncology (ASCO) Annual Conference, Chicago, IL, May 29-Jun. 2, 2015, 7 pages.

Clarke J, et al., Abstract 2029. "A Phase I Trial of Intravenous Liposomal Irinotecan in Patients With Recurrent High-Grade Gliomas," J Clin Oncol. 33(15_Suppl):2029 DOI: 10.1200/jco.2015.33.15_suppl.2029 (2015), 2 printed pages.

Colbern G, et al., "Encapsulation of the Topoisomerase I Inhibitor GL147211C in Pegylated (STEALTH) Liposomes Pharmacokinetics and Antitumor Activity in HT29 Colon Tumor Xenogralls," Clin Cancer Res. 4(12):3077-82 (1998).

Comella P, et. al., "Irinotecan Plus Leucovorin-Modulated 5-Fluorouracil LV. Bolus Every Other Week May Be a Suitable Therapeutic Option Also for Elderly Patients With Metastatic Colorectal Carcinoma," Br J Cancer. 89(6):992-6 (2003).

Cortés J, et al., Abstract CT154. "Multicenter Open-Label, Phase II Trial, to Evaluate the Efficacy and Safety of Liposomal Irinotecan (nal-IRI) for Progressing Brain Metastases in Patients with HER2-Negative Breast Cancer (The Phenomenal Study)," In Proceedings of the American Association for Cancer Research Annual Meeting 2018; Apr. 14-18, 2018; Chicago, Illinois. Cancer Res. 2018;78(13 Suppl):Abstract nr CT154, 3 printed pages.

Daleke D, et al., "Endocytosis of Liposomes by Macrophages: Binding, Acidification and Leakage of Liposomes Monitored by a New Fluorescence Assay," Biochim Biophys Acta. 1024(2):352-66 (1990).

Abrams T, et al., "Patterns of Chemotherapy Use in a U.S.-Based Cohort of Patients with Metastatic Pancreatic Cancer," Oncologist 22(8):925-933 (2017).

Abushahin L, et al., "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan." Poster presented at the European Society for Medical Oncology Virtual Congress Sep. 19-21, 2020, 6 pages.

Abushahin L, et al., Abstract 1534P. "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan" Ann Oncol. 31(Suppl_4):S881-S897 10.1016/annonc/annonc285 (2020), 2 printed pages.

Abushahin L, et al., Abstract e16780. "Real-World Dosing, Management, and Clinical Outcomes of Patients (pts) With Metastatic Pancreatic Adenocarcinoma (mPDAC) Treated With Liposomal Irinotecan," J Clin Oncol. 38(15_Suppl):e16780 DOI: 10.1200/JCO. 2020.38.15_suppl.e16780 (2020), 2 printed pages.

Ahn D, et al., "Real-World Dosing Patterns of Patients With Metastatic Pancreatic Cancer (mPC) Treated With Liposomal Irinotecan (nal-IRI) in US Oncology Clinics." Poster presented at the European Society for Medical Oncology (ESMO), Munich, Germany, Oct. 19-23, 2018, 8 pages.

Ahn D, et al., Abstract 735P. "Real-World Dosing Patterns of Patients (pts) With Metastatic Pancreatic Cancer (mPC) Treated With Liposomal Irinotecan (nal-IRI) in US Oncology Clinics," Ann Oncol. 29(Suppl_8):viii251 doi:10.1093/annonc/mdy282 (2018).

Amzal B, et al., "Imputing Missing Values to Estimate Health-Related Quality of Life (HR-QoL) in Metastatic Pancreatic Cancer Treated With 5-Fluorouracil and Leucovorin, With and Without Liposomal Irinotecan (nal-IRI)." Poster presented at the International Society for Pharmacoeconomics and Outcomes Research (ISPOR) Annual Meeting, Boston, MA, May 20-24, 2017, 6 pages.

Amzal B, et al., Abstract PCN179. "Imputing Missing Values to Estimate Health-Related Quality of Life (HR-QoL) in Metastatic Pancreatic Cancer (mpc) Treated With 5-Fluorouracil and Leucovorin, With and Without Liposomal Irinotecan (nal-IRI)," Value in Health. 20(5):A119 (2017).

Araneo M, et. al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," Cancer Invest. 21(4):489-96 (2003).

Atkins K, et al., "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)." Poster presented at the American Society of Clinical Oncology Gastrointestinal Cancers Symposium (ASCO GI), San Francisco, CA, Jan. 23-25, 2020, 1 page.

(56) References Cited

OTHER PUBLICATIONS

Atkins K, et al., Abstract TPS780. "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)," J Clin Oncol. 38(4_Suppl):TPS780 DOI: 10.1200/JCO.2020.38.4_suppl.TPS780 (2020), 2 printed pages.

Barbier S, et al., Abstract e16724. "Differentiation of Liposomal Irinotecan From Dose-Dense Non-Liposomal Irinotecan in Patient-Derived Pancreatic Cancer Xenograft Tumor Models," J Clin Oncol. 38(15 Suppl):e16724 DOI 10.1200/JCO.2020.38.15_suppl.e16724 (2020), 5 printed pages.

Barzi A, et al., Abstract e16229. "Real World Outcomes of Metastatic Pancreatic Cancer (mPC) Patients (pts) Treated With Liposomal Irinotecan (nal-IRI) in the US," J Clin Oncol. 36(15_Suppl):e16229 DOI: 10.1200/JCO.2018.36.15_suppl.e16229 (2018), 2 printed pages.

Becker C, et al., "Multivariate Analysis of Health-Related Quality of Life (HR-QoL) in Metastatic Pancreatic Cancer Treated with 5-Fluorouracil and Leucovorin (5-FU/LV), With and Without Liposomal Irinotecan (nal-IRI)." Poster presented at the International Society for Pharmacoeconomics and Outcomes Research (ISPOR) Annual Meeting, Boston, MA, May 20-24, 2017, 7 pages.

Becker C, et al., Abstract PCN182. "Multivariate Analysis of Health-Related Quality of Life (HR-QoL) in Metastatic Pancreatic Cancer (mPC) Treated with 5-Fluorouracil and Leucovorin, With and Without Liposomal Irinotecan (nal-IRI)," Value in Health. 20(5):A120 (2017).

Becker C, et al., Abstract PCN58. "Budget Impact Analysis of Nanoliposomal Irinotecan for Treatment of Pancreatic Cancer Following Progression on Gemcitabine—A US Payer Perspective," Value in Health 19(7):A718-A719 (2016).

Blanc J, et al., "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy." Poster presented at the European Society for Medical Oncology Asia 2017 Congress, Singapore, Nov. 17-19, 2017, 8 pages.

Blanc J, et al., Abstract 228P. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy," Ann Oncol. 28(Suppl 10):x67-x68 doi:10.1093/annonc/mdx660 (2017).

Blanc J, et al., Abstract PD-18. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated With Gemcitabine-Based Therapy," Ann Oncol. 28(Suppl_3):7 doi:10.1093/annonc/mdx263 (2017).

BlueCross Blue Shield of North Carolina Corporate Medical Policy, Bevacizumab in Advanced Adenocarcinoma of the Pancreas, File Name: bevacizumab_in_advanced_adenocarcinoma_of_the_pancreas, Origination: Mar. 2010, Last review: Feb. 2019, 5 pages.

Boeck S and Heinemann V, "Second-Line Therapy in Gemcitabine-Pretreated Patients With Advanced Pancreatic Cancer," J Clin Oncol. 26(7):1178-9 (2008).

Brus C and Saif M, "Second Line Therapy for Advanced Pancreatic Adenocarcinoma: Where Are We and Where Are We Going?," J Pancreas (Online) 11(4):321-3 (2010).

Burris H and Rocha-Lima C, "New Therapeutic Directions for Advanced Pancreatic Cancer: Targeting the Epidermal Growth Factor and Vascular Endothelial Growth Factor Pathways," Oncologist. 13(3):289-98 (2008).

Cascinu S, et al., "Pancreatic Cancer: ESMO Clinical Practice Guidelines for Diagnosis, Treatment and Follow-up," Ann Oncol. 21(Suppl 5):v55-v58 (2010).

Cerenzia W, et al., Abstract e16233. "Identifying Continuing Educational Needs Among Oncologists in Managing Patients With Pancreatic Cancer," J Clin Oncol. 36(15_Suppl):e16233 DOI: 10.1200/JCO.2018.36.15_suppl.e16233 (2018), 2 printed pages.

Chen L, et al., "Expanded Analyses of NAPOLI-1: Phase 3 Study of MM-398 (nal-IRI), with or without 5-Fluorouracil and Leucovorin, versus 5-Fluorouracil and Leucovorin, in Metastatic Pancreatic Cancer (mPAC) Previously Treated with Gemcitabine-based Therapy." Presented Jan. 15, 2015, ASCO GI, 17 pages.

Chen L, et al., "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 10 pages.

Chen L, et al., Abstract PD-023. "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Annals of Oncology. 27(Suppl 2):ii102-ii117 (2016), 1 page.

Chen L-T, et al., "CA19-9 Decrease and Overall Survival (OS) in the NAPOLI-1 Trial of Liposomal Irinotecan (nal-IRI) ±5-Fluorouracil and Leucovorin (5-FU/LV) in Metastatic Pancreatic Ductal Adenocarcinoma (mPDAC) Previously Treated With Gemcitabine-Based Therapy." Poster presented at the European Society for Medical Oncology (ESMO) World Congress on Gastrointestinal Cancer, Barcelona, Spain, Jun. 28-Jul. 1, 2017, 5 pages.

Chen L-T, et al., "CA19-9 Decrease and Overall Survival in the NAPOLI-1 Trial of Liposomal Irinotecan (nal-IRI) ± 5-Fluorouracil and Leucovorin (5-FU/LV) in Metastatic Pancreatic Ductal Adenocarcinoma Previously Treated With Gemcitabine-Based Therapy." Poster presented at the European Society for Medical Oncology Asia 2017 Congress, Singapore, Nov. 17-19, 2017, 8 pages.

Chen L-T, et al., "Early Dose Reduction/Delay and the Efficacy of Liposomal Irinotecan With Fluorouracil and Leucovorin in Metastatic Pancreatic Ductal Adenocarcinoma (mPDAC): A Post Hoc Analysis of NAPOLI-1," Pancreatology. 21(1):192-9 (2021). Epub 2020.

Chen L-T, et al., "Efficacy and Safety of Liposomal Irinotecan (nal-IRI) + 5-Fluorouracil and Leucovorin in Patients With Metastatic Pancreatic Ductal Adenocarcinoma Who Previously Received Gemcitabine-Based Therapy: Post Hoc Analysis of the NAPOLI-1 Trial" Poster presented at the American Society of Clinical Oncology Gastrointestinal Cancers Symposium (ASCO GI), San Francisco, CA, Jan. 19-21, 2017, 9 pages.

Chen L-T, et al., "Final Results of NAPOLI-1: A Phase 3 Study of nal-IRI (MM-398) ± 5-Fluorouracil and Leucovorin 5-FU/LV) vs 5-FU/LV in Metastatic Pancreatic Ductal Adenocarcinoma (mPDAC) Previously Treated With Gemcitabine-Based Therapy." Poster presented at the European Society for Medical Oncology (ESMO) Annual Congress, Copenhagen, Denmark, Oct. 7-11, 2016, 8 pages.

Chen L-T, et al., "Impact of Dose Reduction or Dose Delay on the Efficacy of Liposomal Irinotecan (nal-IRI)+5-Fluorouracil/Leucovorin (5-FU/LV): Survival Analysis From NAPOLI-1." Poster presented at the European Society for Medical Oncology (ESMO) Annual Congress, Munich, Germany, Oct. 19-23, 2018, 9 pages.

Chen L-T, et al., "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)." Poster presented at the European Society for Medical Oneology (ESMO) Annual Congress, Munich, Germany, Oct. 19-23, 2018, 9 pages.

Chen L-T, et al., Abstract 221PD. "Efficacy and Safety of Nanoliposomal Irinotecan (nal-IRI, MM-398, PEP02, BAX-2398) in Patients With Metastatic Pancreatic Cancer in Asia: A Subgroup Analysis of the Phase 3 NAPOLI-1 Study," Ann Oncol. 27(Supp_9):ix69-ix70 doi:10.1093/annonc/mdw582 (2016).

Chen L-T, et al., Abstract 227P. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma mPDAC) Previously Treated With Gemcitabine-Based Therapy," Ann Oncol. 28(Suppl_10):x66-x67 doi:10.1093/annonc/mdx660 (2017).

(56) References Cited

OTHER PUBLICATIONS

Chen L-T, et al., Abstract 303. "Efficacy and Safety of Liposomal Irinotecan (nal-IRI) + 5-Fluorouracil and Leucovorin (5-FU/LV) in Patients (pts) With Metastatic Pancreatic Ductal Adenocarcinoma (mPDAC) Who Previously Received Gemcitabine (Gem)-Based Therapy: Post Hoc Analysis of the NAPOLI-1 Trial," J Clin Oncol. 35(4 Suppl):303 DOI: 10.1200/JCO.2017.35.4_suppl.303 (2017), 2 printed pages.
Chen L-T, et al., Abstract 3707. "Final Results of NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.
Chen L-T, et al., Abstract 734P. "Impact of Dose Reduction or Dose Delay on the Efficacy of Liposomal Irinotecan (nal-IRI)+5-Fluorouracil/Leucovorin (5-FU/LV): Survival Analysis From NAPOLI-1," Ann Oncol. 29(Suppl_8):viii250-viii251 doi:10.1093/annonc/mdy282 (2018).
Chen L-T, et al., Abstract 749P. "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)," Ann Oncol. 29(Suppl 8):viii255-viii256 doi:10.1093/annonc/mdy282 (2018).
Chen L-T, et al., Abstract PD-017. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Supp 3):6-7 doi:10.1093/annonc/mdx263 (2017).
Chin V, et. al., "Chemotherapy and Radiotherapy for Advanced Pancreatic Cancer (Review)," Cochrane Database Syst Rev. 3(3):CD011044 doi: 10.1002/14651858.CD011044.pub2 (2018), 143 pages.
Choi C, et al., "Effects of 5-Fluorouracil and Leucovorin in the Treatment of Pancreatic-Biliary Tract Adenocarcinomas," Am J Clin Oncol. CCT 23(4): 425-8 (2000), 7 printed pages.
Clinical Trials Identifier NCT00426127: Dec. 29, 2017 update, first posted Jan. 24, 2007, "Docetaxel and Liposomal Doxorubicin Chemotherapy With Enoxaparin in Patients With Advanced Pancreatic Cancer," Retrieved from ClinicalTrials.gov archive, 8 printed pages.
Cockrum P, et al., "Impact of Dose Reductions on Clinical Outcomes Among Patients With Metastatic Pancreatic Cancer Treated With Liposomal Irinotecan in Oncology Clinics in the US." Poster presented at the American Society at Clinical Oncology Gastrointestinal Cancers Symposium (ASCO GI), San Francisco, CA, Jan. 23-25, 2020, 8 pages.
Cockrum P, et al., Abstract 665. "Impact of Dose Reductions on Clinical Outcomes Among Patients (pts) With Metastatic Pancreatic Cancer (mPC) Treated With Liposomal Irinotecan (nal-IRI) in Oncology Clinics in the United States," J Clin Oncol. 38(4_Suppl):665 DOI: 10.1200/JCO.2020.38.4_suppl.665 (2020), 2 printed pages.
Cockrum P, et al., Abstract e16739. "National Comprehensive Cancer Network (NCCN) Category I/FDA-Approved Metastatic Pancreatic Adenocarcinoma (mPDAC) Treatments in Commercially Insured Patients: An Analysis of Inpatient (IP) and Emergency Room (ER) Admissions," J Clin Oncol. 38(15_Suppl):e16739 DOI: 10.1200/JCO.2020.38.15_suppl.e16739 (2020), 2 printed pages.
Cockrum P, et al., Abstract PCN134. "An Examination of Quality Metrics: Inpatient and Emergency Department Burden of Commercially Insured Treated Metastatic Pancreatic Cancer (mPC) Patients in the United States (US)," Value in Health. 23(Suppl 1):S46 (2020).
Cockrum P, et al., Abstract PCN167. "An Integrated Delivery Network Focus on Cost Drivers in Chemotherapy: The Economic Burden of Neutropenia and Inpatient Admissions Among Commercially Insured Metastatic Pancreatic Cancer Patients (mPC)," Value in Health. 23(Suppl 1):S52 (2020).
DaunoXome (daunorubicin citrate liposome injection) package insert, rev. Dec. 2011, 11 pages.

Dayyani F, et al., Abstract B14. "CA 19-9 levels in patients with metastatic pancreatic adenocarcinoma receiving first-line therapy with liposomal irinotecan plus 5-fluorouracil/leucovorin and oxaliplatin (NAPOX)," In Proceedings of the AACR Special Conference on Pancreatic Cancer: Advances in Science and Clinical Care; Sep. 6-9, 2019; Boston, MA; Cancer Res. 2019; 79(24 Suppl): Abstract nr B14, 3 printed pages.
Delord J, et al., "A Phase I Clinical and Pharmacokinetic Study of Capecitabine (Xeloda®) and Irinotecan Combination Therapy (XELIRI) in Patients With Metastatic Gastrointestinal Tumours," Br J Cancer. 92(5):820-6 (2005).
Derksen J, et al., "Interaction of Immunoglobulin-Coupled Liposomes with Rat Liver Macrophages In Vitro," Exp Cell Res. 168(1):105-15 (1987).
Dewhirst M, et al., "Microvascular Studies on the Origins of Perfusion-Limited Hypoxia," Br J Cancer Suppl. 27:S247-51 (1996).
Dicko A, et al., "Intra and Inter-Molecular Interactions Dictate the Aggregation State of Irinotecan Co-Encapsulated with Floxuridine Inside Liposomes," Pharm Res. 25(7):1702-13 (2008).
Dos Santos N, et al., "Improved Retention of Idarubicin After Intravenous Injection Obtained for Cholesterol-Free Liposomes," Biochim Biophys Acta 1561(2):188-201 (2002).
Drummond D, et al., "Clinical Development of Histone Deacetylase Inhibitors as Anticancer Agents," Annu Rev Pharmacol Toxicol 45:495-528 and C1-C2 (2005).
Drummond D, et al., "Development of a Highly Stable and Targetable Nanoliposomal Formulation of Topotecan," J Control Release. 141(1):13-21 (2010). Epub 2009.
Drummond D, et al., "Improved Pharmacokinetics and Efficacy of a Highly Stable Nanoliposomal Vinorelbine," J Pharmacol Exp Ther 328(1):321-30 (2009). Epub 2008.
Drummond D, et al., "Liposome Targeting to Tumors using Vitamin and Growth Factor Receptors," Vitam Horm. 60:285-332 (2000).
Drummond D, et al., "Pharmacokinetics and In Vivo Drug Release Rates in Liposomal Nanocarrier Development," J Pharm Sci 97(11):4696-740 (2008).
Drummond D, et al., Chapter 8, "Intraliposomal Trapping Agents for Improving In Vivo Liposomal Drug Formulation Stability," In Liposome Technology, Third Edition, vol. 2, Ed. G. Gregoriadis, pp. 149-168 (2006).
Drummond D, et al., Chapter 9, "Liposomal Drug Delivery Systems for Cancer Therapy," In Drug Discovery Systems in Cancer Therapy, Ed. D Brown, Humana Press, Totowa, NJ, pp. 191-213 (2004).
Duhfour J, et al., "Efficacy of Prophylactic Anti-Diarrhoeal Treatment in Patients Receiving Campto for Advanced Colorectal Cancer," Anticancer Res. 22(6B): 3727-31 (2002).
Elinzano H, et al., "Nanoliposomal Irinotecan and Metronomic Temozolomide for Patients With Recurrent Glioblastoma BrUOG329, A Phase I Brown University Oncology Research Group Trial," Am J Clin Oncol. 44(2):49-52 (2021). Epub 2020 version, pp. 1-4.
Elinzano H, et al., Abstract e14548. "Nanoliposomal Irinotecan and Metronomic Temozolomide for Patients With Recurrent Glioblastoma: BrUOG329, A Phase IB/IIA Brown University Oncology Research Group (BrUOG) Trial," J Clin Oncol. 38(15_Suppl):e14548 DOI: 10.1200/JCO.2020.38.15_suppl.e14548 (2020), 2 printed pages.
Emerson D, et al., "Antitumor Efficacy, Pharmacokinetics, and Biodistribution of NX 211: A Low-Clearance Liposomal Formulation of Lurtotecan," Clin Cancer Res 6(7):2903-12 (2000).
English translation of title and abstract for Hasegawa, Y, "Biomarker as Predictive Safety Testing in Oncology", Igaku No Ayumi (Journal of Clinical and Experimental Medicine), 224(13):1171-4 (2008) (original in Japanese).
EP Patent Application No. 05745505.7: European Search Report dated Sep. 1, 2010, 6 pages.
EP2861210: Proprietor's statement of grounds of appeal to opposition decision dated Dec. 30, 2019, 35 pages.
EP2861210: Proprietor's Main and Auxiliary Requests MR, AR1, AR2, and AR3 with Proprietor's Statement of Grounds of Appeal in Opposition Proceedings filed Dec. 30, 2019, 4 pages.
EP2861210: Proprietor's statement of grounds of appeal to opposition decision dated Dec. 30, 2019, D23 (Declaration of Amy McKee M.D.) including D23A (Hoos W, et al., "Pancreatic Cancer Clinical Trials and Accrual in the United Sates." J Clin Oncol.

(56) References Cited

OTHER PUBLICATIONS

31(27):3432-8 (2013) and accompanying Appendix Table A1, Table A2, and Figure A1) and D23B (Bio Industry Analysis: Clinical Development Success Rates 2006-2015, Jul. 2016), 44 total pages.
EP2861210: Proprietor's statement of grounds of appeal to opposition decision dated Dec. 30, 2019, D24 (Declaration of Bruce Belanger, Ph.D.), 2 pages.
EP2861210: Reply to proprietor's grounds of appeal following opposition and cover letter, dated Jul. 27, 2020, 35 pages.
EP2861210: Reply to proprietor's grounds of appeal to opposition decision dated Jul. 27, 2020, D15c (EU clinical trial database for NAPOLI-1 study from Oct. 12, 2012, corresponds to D15b), 10 pages.
EP2861210: Reply to proprietor's grounds of appeal to opposition decision dated Jul. 27, 2020, D25 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).
EP2861210: Reply to proprietor's grounds of appeal to opposition decision dated Jul. 27, 2020, D26 (Drummond D, et al., "Development of a Highly Active Nanoliposomal Irinotecan Using a Novel Intraliposomal Stabilization Strategy," Cancer Res. 66(6):3271-77 (2006)).
EP2861210: Reply to proprietor's grounds of appeal to opposition decision dated Jul. 27, 2020, D27 (Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013)).
EP2861210: Reply to proprietor's grounds of appeal to opposition decision dated Jul. 27, 2020, D28 (Svenson S, "Clinical Translation of Nanomedicines," Current Opinion in Solid State and Materials Science. 16(6):287-294 (2012), article in press version, 7 pages).
EP2861210: Reply to proprietor's grounds of appeal to opposition decision dated Jul. 27, 2020, D29 (Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011)).
EP2861210: Reply to proprietor's grounds of appeal to opposition decision dated Jul. 27, 2020, D30 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl): Abstract 613 (2012), 5 printed pages).
EP2861210: Reply to proprietor's grounds of appeal to opposition decision dated Jul. 27, 2020, D31 (Cunningham D, et al., "Randomized Phase II Study of PEP02, Irinotecan, or Docetaxel as a Second-Line Therapy in Gastric or Gastroesophageal Junction Adenocarcinoma," J Clin Oncol. 29(4_supp):Abstract 6 (2011), 5 printed pages).
EP2861210: Reply to proprietor's grounds of appeal to opposition decision dated Jul. 27, 2020, D32 (Gerber D, "Miscellaneous Agents-Cytotoxics and Hormonal Agents," J Thorac Oncol. 7(12 Suppl 5):S387-9 (2012)).
EP2861210: Reply to proprietor's grounds of appeal to opposition decision dated Jul. 27, 2020, D33 (Noble C, et al., "Novel Nanoliposomal CPT-11 Infused by Convection-Enhanced Delivery in Intracranial Tumors: Pharmacology and Efficacy," Cancer Res. 66(5):2801-6 (2006)).
EP2861210: Reply to proprietor's grounds of appeal to opposition decision dated Jul. 27, 2020, D34 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007)).
EP2861210: Reply to proprietor's grounds of appeal to opposition decision dated Jul. 27, 2020, D35 (Mullard A, "How Much Do Phase III Trials Cost?" Nat Rev Drug Discov. 17(11):777 (2018)).
EP2861210: Reply to proprietor's grounds of appeal to opposition decision dated Jul. 27, 2020, D36 (The Medicines tor Human Use (Clinical Trials) Regulations, 2004, 86 pages).
Ettrich T, et al., "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," Poster presented at the American Society of Clinical Oncology (ASCO) Annual Meeting, Chicago, Illinois, Jun. 1-5, 2018, 5 pages.
Ettrich T, et al., Abstract TPS4145. "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," J Clin Oncol. 36(15_Suppl):TPS4145 DOI: 10.1200/JCO.2018.36.15_suppl.TPS4145 (2018), 2 printed pages.
European Medicines Agency Assessment Report for Onivyde, Committee for Medicinal Products for Human Use (CHMP), Jul. 21, 2016, 107 pages.
Falcone A, et al., "Sequence Effect of Irinotecan and Fluorouracil Treatment on Pharmacokinetics and Toxicity in Chemotherapy-Naive Metastatic Colorectal Cancer Patients," J Clin Oncol. 19(15):3456-62 (2001).
Fannon M, et al., "Sucrose Octasulfate Regulates Fibroblast Growth Factor-2 Binding, Transport, and Activity: Potential for Regulation of Tumor Growth," J Cell Physiol. 215(2):434-41 (2008), NIH public access author manuscript version, 19 pages.
Farncombe M, "Management of Bleeding in a Patient with Colorectal Cancer: A Case Study," Support Care Cancer. 1(3):159-160 (1993).
FDA, "Draft Guidance on Daunorubicin Citrate," Jul. 2014, 6 pages.
FDA, "Draft Guidance on Doxorubicin Hydrochloride," Recommended Feb. 2010, Revised Nov. 2013, Dec. 2014, 6 pages.
Fioravanti A, et. al., "Metronomic 5-Fluorouracil, Oxaliplatin and Irinotecan in Colorectal Cancer," Eur J Pharmacol. 619(1-3): 8-14(2009).
Fleming G, et. al., "Phase I and Pharmacokinetic Study of 24-Hour Infusion 5-Fluorouracil and Leucovorin in Patients With Organ Dysfunction," Ann Oncol. 14(7):1142-7 (2003).
Freise C, et al., "Characterization of a Cyclosporine-Containing Liposome," Transplant Proc. 23(1 Pt 1):473-4 (1991).
Freise C, et al., "Increased Efficacy of Cyclosporin Liposomes in a Rat Orthotopic Liver Transplant Model," Surgical Forum. 43:395-7 (1992).
ClinicalTrials.gov search results for Onivyde, retrieved from clinicaltrials.gov website on Jan. 27, 2021, 27 pages.
Kraut E, et. al., Abstract 2017. "Final Results of a Phase I Study of Liposome Encapsulated SN-38 (LE-SN38) Safety, Pharmacogenomics, Pharmacokinetics, and Tumor Response," J Clin Oncol. 23(16_Suppl):2017 (2005), 3 printed pages.
Kulke M, et. al., "A Phase II Trial of Irinotecan and Cisplatin in Patients with Metastatic Neuroendocrine Tumors," Dig Dis Sci. 51(6):1033-8 (2006).
Lamichhane N, et. al., "Liposomes: Clinical Applications and Potential for Image-Guided Drug Delivery," Molecules. 23(2):288 doi: 10.3390/molecules2302028 (2018), 17 pages.
Larsen A, et al., "Influence of Liposomal Irinotecan (nal-IRI) and Non-Liposomal Irinotecan, Alone and in Combination, on Tumor Growth and Angiogenesis in Colorectal Cancer (CRC) Models." Poster presented at the American Society of Clinical Oncology Gastrointestinal Cancers Symposium (ASCO GI), San Francisco, CA, Jan. 18-20, 2018, 9 pages.
Larsen A, et al., Abstract 771. "Influence of Liposomal Irinotecan (nal-IRI) and Non-Liposomal Irinotecan, Alone and in Combination, on Tumor Growth and Angiogenesis in Colorectal Cancer (CRC) Models," J Clin Oncol. 36(4_Suppl):711 DOI: 10.1200/JCO.2018.36.4_suppl.711 (2018), 2 printed pages.
Lecovorin Calcium package insert, Teva, revised Oct. 2009, 6 pages.
Lee H, et al., "(64)Cu-MM-302 Positron Emission Tomography Quantifies Variability of Enhanced Permeability and Retention of Nanoparticles in Relation to Treatment Response in Patients with Metastatic Breast Cancer," Clin Cancer Res. 23(15):4190-4202 (2017).

(56) References Cited

OTHER PUBLICATIONS

Lee H, et al., "A Gradient-Loadable (64)Cu-Chelator for Quantifying Tumor Deposition Kinetics of Nanoliposomal Therapeutics by Positron Emission Tomography," Nanomedicine. 11(1):155-65 (2015). Epub 2014.
Liu B, et al., "Mapping Tumor Epitope Space by Direct Selection of Single-Chain Fv Antibody Libraries on Prostate Cancer Cells," Cancer Res. 64(2):704-10 (2004).
Liu B, et al., "Recombinant Full-Length Human IgG1s Targeting Hormone-Refractory Prostate Cancer," J Mol Med (Berl). 85(10):1113-23 (2007).
Liu J-J, et al., "Simple and Efficient Liposomal Encapsulation of Topotecan by Ammonium Sulfate Gradient: Stability, Pharmacokinetic and Therapeutic Evaluation," Anticancer Drugs. 13(7):709-17 (2002).
Lorusso P, et al., "Abstract CT325: Combination of the PARP Inhibitor Veliparib (ABT888) with Irinotecan in Patients with Triple Negative Breast Cancer: Preliminary Activity and Signature of Response." Proceedings: AACR 106th Annual Meeting, Apr. 18-22, 2015, Philadelphia, PA (2015), 3 printed pages.
Lundberg B, et al., "Conjugation of Apolipoprotein B with Liposomes and Targeting to Cells in Culture," Biochim Biophys Acta. 1149(2):305-12 (1993).
Ma W, et al., Abstract e13588. "Population Pharmacokinetics and Exposure-Safety Relationship of Nanoliposomal Irinotecan (MM-398, nal-IRI) in Patients With Solid Tumors," J Clin Oncol. 33(15_Suppl):e13588 DOI: 10.1200/co.2015.33.15_suppl.e13588 (2015), 2 printed pages.
Mabro M, et. al., "A Phase II Study of FOLFIRI-3 (Double Infusion of Irinotecan Combined With LV5FU) After FOLFOX in Advanced Colorectal Cancer Patients," Br J Cancer. 94(9):1287-92 (2006).
Mabro M, et. al., "Bimonthly Leucovorin, Infusion 5-Fluorouracil, Hydroxyurea, and Irinotecan (FOLFIRI-2) for Pretreated Metastatic Colorectal Cancer," Am J Clin Oncol. 26(3):254-8 (2003).
Mackenzie M, et. al., "A Phase I Study of OSI-211 and Cisplatin as Intravenous Infusions Given on Days 1,2 and 3 Every 3 Weeks in Patients With Solid Cancers," Ann Oncol. 15(4):665-70 (2004).
Malet-Martino M and Martino R, "Clinical Studies of Three Oral Prodrugs of 5-Fluorouracil (Capecitabine, UFT, S-1): A Review," Oncologist. 7(4):288-323 (2002).
Mamot C, et al., "Epidermal Growth Factor Receptor (EGFR)-Targeted Immunoliposomes Mediate Specific and Efficient Drug Delivery to EGFR and EGFRvIII-Overexpressing Tumor Cells," Cancer Res. 63(12):3154-61 (2003).
Mamot C, et al., "Liposome-Based Approaches to Overcome Anticancer Drug Resistance," Drug Resist Updat. 6(5):271-9 (2003).
Mancini R and Modlin J, "Chemotherapy Administration Sequence: A Review of the Literature and Creation of a Sequencing Chart," J Hematol Oncol Pharm. 1(1):17-25 (2011).
Martin L, et. al., "VEGF Remains an Interesting Target in Advanced Cancreas Cancer (APCA): Results of a Multi-Institutional Phase II Study of Bevacizumab, Gemcitabine, and Infusional 5-Fluorouracil in Patients With APCA," Ann Oncol. 23(11):2812-20 (2012).
Mathijssen R, et. al., "Clinical Pharmacokinetics and Metabolism of Irinotecan (CPT-11)," Clin Cancer Res. 7(8):2182-94 (2001).
Matsusaka S, et. al., "Differential Effects of Two Fluorouracil Administration Regimens for Colorectal Cancer," Oncol Rep. 10(1):109-13 (2003).
Mayer L, et. al.,"Ratiometric Dosing of Anticancer Drug Combinations: Controlling Drug Ratios After Systemic Administration Regulates Therapeutic Activity in Tumor-Bearing Mice," Mol Cancer Ther. 5(7):1854-63 (2006).
McNamara M, et al., "NET-02: A Multi-Centre, Randomized, Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)." Poster presented at the 17th Annual European Neuroendocrine Tumor Society (ENETS) Conference for the Diagnosis and Treatment of Neuroendocrine Tumor Disease, Virtual Conference, Mar. 11-13, 2020, 4 pages.

McNamara M, et al., Abstract P04. NET-02: A Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC), In Abstracts of the 17th Annual European Neuroendocrine Tumor Society (ENETS) Conference for the Diagnosis and Treatment of Neuroendocrine Tumor Disease, Virtual Conference, Mar. 11-13, 2020, p. 374.
Meerum Terwogt J, et al., "Phase I and Pharmacokinetic Study of SPI-77, a Liposomal Encapsulated Dosage Form of Cisplatin," Cancer Chemother Pharmacol. 49(3):201-10 (2002).
Messerer C, et. al., "Liposomal Encapsulation of Irinotecan and Potential for the Use of Liposomal Drug in the Treatment of Liver Metastases Associated with Advanced Colorectal Cancer," MS Thesis, University of British Columbia, 2000, 90 pages.
Mirtsching B, et al., "Irinotecan-induced Immune Thrombocytopenia," Am J Med Sci. 347(2):167-9 (2014).
Munzone E, "Adverse Side Effects Associated to Metronomic Chemotherapy," Presentation presented at Aiom Cancer Metronomic Therapy, Feb. 26, 2016, Milan, 32 pages.
Myocet liposomal, Summary of product characteristics and labelling and package leaflet, European Medicines Agency, available at ema.europa.eu/en/documents/product-information/myocet-liposomal-previously-myocet-epar-product-information_en.pdf, Date of first authorisation: Jul. 13, 2000, Date of latest renewal: Jul. 2, 2010, 37 pages.
Nakajima T, et. al., "Synergistic Antitumor Activity of the Novel SN-38-Incorporating Polymeric Micelles, NK012, Combined With 5-Fluorouracil in a Mouse Model of Colorectal Cancer, As Compared With That of Irinotecan Plus 5-Fluorouracil," Int J Cancer. 122(9):2148-53 (2008).
Nardi M, et. al., Abstract 14520. "Metronomic Irinotecan and Standard FOLFIRI Regimen as First-Line Chemotherapy in Metastatic Colorectal Cancer (MCRC). Final Results of Phase II Study," J Clin Oncol. 25(18_suppl):14520 (2007), 1 printed page.
National Cancer Institute, "Irinotecan Hydrochloride Liposome,"Posted: Oct. 27, 2015, Updated:Mar. 28, 2019, available at cancer.gov/about-cancer/treatment/drugs/irinotecan-hydrochloride-liposome, 2 pages.
No authors listed. "5HT3-receptor Antagonists as Antiemetics in Cancer," Drug Ther Bull. 43(8):57-62 (2005).
Moble C, et al., "Development of Ligand-Targeted Liposomes for Cancer Therapy," Expert Opin Ther Targets. 8(4):335-53 (2004).
Noordhuis P, et. al., "5-Fluorouracil Incorporation into RNA and DNA in Relation to Thymidylate Synthase Inhibition of Human Colorectal Cancers," Ann Oncol. 15(7):1025-32 (2004).
Ogata Y, et. al., "Dosage Escalation Study of S-1 and Irinotecan in Metronomic Chemotherapy against Advanced Colorectal Cancer," Kurume Med J 56(1-2):1-7 (2009).
Oneology News International, "Experts Debate Bolus vs Continuous Infusion 5-FU." Feb. 1, 2003, vol. 12, Issue 2, 3 printed pages.
O'Reilly S, "Topotecan: What Dose, What Schedule, What Route?" Clin Cancer Res. 5(1):3-5 (1999).
Pal A, et. al., "Preclinical Safety, Pharmacokinetics and Antitumor Efficacy Profile of Liposome-Entrapped SN-38 Formulation," Anticancer Res. 25(1A):331-41 (2005).
Papahadjopoulos D, et al., "Targeting of Drugs to Solid Tumors Using Anti-HER2 Immunoliposomes," J Liposome Res. 8(4):425-42 (1998).
Papahadjopoulos D, et. al., "Sterically Stabilized Liposomes: Improvements in Pharmacokinetics and Antitumor Therapeutic Efficacy," Proc Natl Acad Sci USA. 88(24):11460-4 (1991).
Papi M, et. al., "Clinically Approved PEGylated Nanoparticles Are Covered by a Protein Corona That Boosts the Uptake by Cancer Cells," Nanoscale. 9(29):10327-34 (2017).
Park J, et al., "Anti-HER2 Immunoliposomes for Targeted Therapy of Human Tumors," Cancer Lett. 118(2):153-60 (1997).
Park J, et al., "Development of Anti-p185HER2 Immunoliposomes for Cancer Therapy," Proc Natl Acad Sci U S A. 92(5):1327-31 (1995).
Park J, et al., "Immunoliposomes for Cancer Treatment," Adv Pharmacol. 40:399-435 (1997).

(56) References Cited

OTHER PUBLICATIONS

Park J, et al., "Sterically Stabilized Immunoliposomes: Formulations for Delivery of Drugs and Genes to Tumor Cells in Vivo," In Targeting of Drugs 6: Strategies for Stealth Therapeutic Systems, Gregoriadis G, et al., eds., Plenum Press, New York, pp. 41-47 (1998).
Park J, et al., "Tumor Targeting Using Anti-HER2 Immunoliposomes," J Control Release. 74(1-3):95-113 (2001).
Freise C, et al., "The Increased Efficacy and Decreased Nephrotoxicity of a Cyclosporine Liposome," Transplantation. 57(6):928-932 (1994).
Fugit K, et al., "The Role of pH and Ring-opening Hydrolysis Kinetics on Liposomal Release of Topotecan," J Control Release. 174:88-97 (2014), Epub Nov. 12, 2013, Author manuscript, pp. 1-27.
Gaber M, et al., "Thermosensitive Liposomes: Extravasation and Release of Contents in Tumor Microvascular Networks," Int J Radiat Oncol Biol Phys. 36(5):1177-87 (1996).
Gaber M, et al., "Thermosensitive Sterically Stabilized Liposomes: Formulation and in Vitro Studies on the Mechanism of Doxorubicin Release by Bovine Serum and Human Plasma," Pharm Res. 12(10):1407-16 (1995).
Garcia-Alfonso P, et. al., "Capecitabine in Combination with Irinotecan (XELIRI), Administered As a 2-Weekly Schedule, As First-Line Chemotherapy For Patients With Metastatic Colorectal Cancer: A Phase II Study of the Spanish GOTI Group," Br J Cancer. 101(7):1039-43 (2009).
Garcia-Carbonero R and Supko J, "Current Perspectives on the Clinical Experience, Pharmacology, and Continued Development of the Camptothecins," Clin Cancer Res. 8(3):641-61 (2002).
Garufi C, et. al., "A Phase II Study of Irinotecan Plus Chronomodulated Oxaliplatin, 5-Fluorouracil and Folinic Acid in Advanced Colorectal Cancer Patients," Br J Cancer. 89(10):1870-5 (2003).
Geddie M, et al., "Improving the Developability of an Anti-EphA2 Single-Chain Variable Fragment for Nanoparticle Targeting," MAbs. 9(1):58-67 (2017). Epub 2016.
Gelmon K, et. al., "A Phase 1 Study of OSI-211 Given As an Intravenous Infusion Days 1, 2, and 3 Every Three Weeks in Patients With Solid Cancers," Invest New Drugs. 22(3):263-75 (2004).
Gemzar (gemcitabine HCl) package insert, revision Apr. 1998, 24 pages.
Giles F, et. al., "Phase I and Pharmacokinetic Study of a Low-Clearance, Unilamellar Liposomal Formulation of Lurtotecan, a Topoisomerase 1 Inhibitor, in Patients with Advanced Leukemia," Cancer. 100(7):1149-58 (2004).
Glimelius B, et. al., "A Randomized Phase III Multicenter Trial Comparing Irinotecan in Combination With the Nordic Bolus 5-FU and Folinic Acid Schedule or the Bolus/Infused de Gramont Schedule (Lv5FU2) in Patients With Metastatic Colorectal Cancer," Ann Oncol. 19(5):909-14 (2008).
Glimelius B, et. al., "Prediction of Irinotecan and 5-Fluorouracil Toxicity and Response in Patients With Advanced Colorectal Cancer," Pharmacogenomics J. 11(1):61-71 (2011). Epub 2010.
Goldberg R, et. al., "A Randomized Controlled Trial of Fluorouracil Plus Leucovorin, Irinotecan, and Oxaliplatin Combinations in Patients With Previously Untreated Metastatic Colorectal Cancer," J Clin Oncol. 22(1):23-30 (2004). Epub 2003.
Greiner P, et. al., "Pharmacokinetics of (−)-Folinic Acid After Oral and Intravenous Administration of the Racemate," Br J Clin Pharmacol. 28(3):289-95 (1989).
Guichard S, et. al., "Cellular Interactions of 5-Fluorouracil and the Camptothecin Analogue CPT-11 (Irinotecan) in a Human Colorectal Carcinoma Cell Line," Biochem Pharmacol. 55(5):667-76 (1998).
Guichard S, et. al., "Sequence-Dependent Activity of the Irinotecan-5FU Combination in Human Colon-Cancer Model HT-29 In Vitro and In Vivo," Int J Cancer. 73(5):729-34 (1997).
Han S, et al., Abstract ACTR-33. "A Phase I Study of Convection-Enhanced Delivery of Liposomal-Irinotecan Using Real-Time Imaging With Gadolinium In Patients With Recurrent High Grade Glioma," Neuro-Oncology. 18(Suppl_6):vi9 doi.org/10.1093/neuonc/now212.031 (2016).
Hare J, "Utilization of Liposomes in Combination Cancer Chemotherapy," PhD thesis, University of Alberta, Department of Pharmacology, 2011, 367 pages.
Harker-Murray P, et al., Abstract CT146. "Plasma Pharmacokinetics of Liposomal Irinotecan (nal-iri) in Pediatric Oncology Patients with Recurrent or Refractory Solid Tumors: South Plains Oncology Consortium Study 2012-001," In Proceedings of the American Association for Cancer Research Annual Meeting 2017; Apr. 1-5, 2017. Washington, DC. Cancer Res. 2017;77(13 Suppl):Abstract nr CT146, doi: 10.1158/1538-7445.AM2017-CT146, 4 printed pages.
Hashimoto S, et al., "Depletion of Alveolar Macrophages Decreases Neutrophil Chemotaxis to Pseudomonas Airspace Infections," Am J Physiol. 270(5 Pt 1):L819-28 (1996).
Hattori Y, et al., "Novel Irinotecan-Loaded Liposome Using Phytic Acid with High Therapeutic Efficacy for Colon Tumors," J Control Release. 136(1):30-7 (2009).
Hay M, et. al., "Clinical Development Success Rates for Investigational Drugs," Nature Biotechnol. 32(1):40-51 (2014).
Hayes M, et al., "Genospheres: Self-Assembling Nucleic Acid-Lipid Nanoparticles Suitable for Targeted Gene Delivery," Gene Ther. 13(7):646-51 (2006).
Hayes M, et al., "Increased Target Specificity of Anti-HER2 Genospheres by Modification of Surface Charge and Degree of PEGylation," Mol Pharm. 3(6):726-36 (2006).
Honig A, et al., "Brain Metastases in Breast Cancer—an In Vitro Study to Evaluate New Systemic Chemotherapeutic Options," Anticancer Res. 25(3A):1531-7 (2005).
Hsu M and Juliano R, "Interactions of Liposomes With the Reticuloendothelial System. II: Nonspecific and Receptor-Mediated Uptake of Liposomes by Mouse Peritoneal Macrophages," Biochim Biophys Acta. 720(4):411-419 (1982).
Huang S, et al., "Liposomes and Hyperthermia in Mice: Increased Tumor Uptake and Therapeutic Efficacy of Doxorubicin in Sterically Stabilized Liposomes," Cancer Res. 54(8):2186-91 (1994).
Huang S, et al., "Light Microscopic Localization of Silver Enhanced Liposome-Entrapped Colloidal Gold in Mouse Tissues," Biochim Biophys Acta. 1069(1):117-21 (1991).
Huang S, et al., "Microscopic Localization of Sterically Stabilized Liposomes in Colon-Carcinoma Bearing Mice," Cancer Res. 52(19):5135-43 (1992).
Huang S, et. al., "Pharmacokinetics and Therapeutics of Sterically Stabilized Liposomes in Mice Bearing C-26 Colon Carcinoma," Cancer Res. 52(24):6774-81 (1992).
Ignatiadis M, et al., "A Multicenter Phase II Study of Docetaxel in Combination with Gefitinib in Gemcitabine-Pretreated Patients with Advanced/Metastatic Pancreatic Cancer," Oncology. 71(3-4):159-63 (2006).
Immordino M, et al., "Stealth Liposomes: Review of the Basic Science, Rationale, and Clinical Applications, Existing and Potential," Int J Nanomedicine. 1(3):297-315 (2006).
Jones S, et. al., Abstract 2547. "Phase 1 and Pharmacokinetic (PK) Study of IHL-305 (Pegylated Liposomal Irinotecan) in Patients With Advanced Solid Tumors," J Clin Oncol. 27(15_suppl):2547 and Table 1 (2009), 6 printed pages.
Kalra A, et al., "Evaluating Determinants for Enhanced Activity of MM-398/PEP02; A Novel Nanotherapeutic Encapsulation of Irinotecan (CPT-11)." Poster for abstract 5696 presented at American Association for Cancer Research 103rd Annual Meeting 2012, Mar. 31-Apr. 4, 2012, Chicago, IL, 11 pages.
Kalra A, et al., "The Tumor Microenvironment Modulates the Delivery and Activation of Liposomal Encapsulated Irinotecan, MM-398," Poster for abstract 5622 presented at the 104th Annual Meeting of the American Association of Cancer Research, Apr. 6-10, 2013, Washington DC, 10 pages.
Kalra A, et al., Abstract 2065. "Magnetic Resonance Imaging with an Iron Oxide Nanoparticle Demonstrates the Preclinical Feasibility of Predicting Intratumoral Uptake and Activity of MM-398, a Nanoliposomal Irinotecan (nal-IRI)." In Proceedings of the 105th Annual Meeting of the American Association for Cancer Research;

(56) References Cited

OTHER PUBLICATIONS

Apr. 5-9, 2014. Cancer Res 2014;74(19 Suppl):Abstract nr 2065, doi:10.1158/1538-7445.AM2014-2065, 1 printed page.

Kalra A, et al., Abstract 5622. "The Tumor Microenvironment Modulates the Delivery and Activation of Liposomal Encapsulated Irinotecan, MM-398." In Proceedings of the 104th Annual Meeting of the American Association of Cancer Research; Apr. 6-10, 2013. Cancer Res 2013;73(8 Suppl):Abstract nr 5622, doi:10.1158/1538-7445. AM2013-5622, 2 printed pages.

Kalra A, et al., Abstract 5696. "Evaluating Determinants for Enhanced Activity of MM-398/PEP02; A Novel Nanotherapeutic Encapsulation of Irinotecan (CPT-11)." In Proceedings of the 103rd Annual Meeting of the American Association for Cancer Research; Mar. 31-Apr. 4, 2012; Chicago, IL. Cancer Res 2012; 72(8 Suppl):Abstract nr 5696. doi:1538-7445.AM2012-5696, 3 printed pages.

Khapzory (levoleucovrin) package insert, revised Oct. 2018, accessed from accessdata.fda.gov/drugsatfda_docs/label/2018/211226s000lbl. pdf, 9 pages.

Kim J, et al., "Efficient Prioritization of Potential Diagnostic Biomarkers Using a Systems Pharmacology Approach Case Study of MM-398 (Irinotecan sucrosofate liposome injection)." Presentation presented at the Pharmacokinetics UK 2013 Meeting, Oct. 31, 2013, Harrogate, North Yorkshire, 34 pages.

Kim J, et al., "Efficient Prioritization of Potential Diagnostic Biomarkers Using a Systems Pharmacology Approach Case Study of MM-398, an Irinotecan Sucrosofate Liposome Injection)." Abstract for Pharmacokinetics UK 2013 Meeting, Oct. 30-Nov. 1, 2013, Harrogate, North Yorkshire, 2 pages.

Kim J, et al., "Systems Pharmacology Modeling Identifies Unique Parameters That Drive Tumor SN38 Levels for Liposomal Irinotecan (MM-398) Compared to Irinotecan." Abstract presented at 14th International Conference on Systems Biology; Copenhagen, Denmark; Aug. 29-Sep. 4, 2013, 1 page.

Kim J, et al., "Systems Pharmacology Modeling Identifies Unique Parameters That Drive Tumor SN38 Levels for Liposomal Irinotecan (MM-398) Compared to Irinotecan." Poster presented at 14th International Conference on Systems Biology; Copenhagen, Denmark; Aug. 29-Sep. 4, 2013, 11 pages.

Kim J, et al., Abstract A6. "Sustained Intratumoral Activation of MM-398 Results in Superior Activity Over Irinotecan Demonstrated by Using a Systems Pharmacology Approach," In: Proceedings of the AACR Special Conference on Chemical Systems Biology: Assembling and Interrogating Computational Models of the Cancer Cell by Chemical Perturbations; Jun. 27-30, 2012; Boston, MA. Cancer Res. 2012; 72(13 Suppl):Abstract nr A6, 3 printed pages.

Kirpotin D, et al., "Building and Characterizing Antibody-Targeted Lipidic Nanotherapeutics," Methods Enzymol. 502:139-66 (2012).

Kirpotin D, et al., "Targeting of Liposomes to Solid Tumors: The Case of Sterically Stabilized Anti-HER2 Immunoliposomes," J Liposome Res. 7:391-417 (1997).

Kirpotin D, et al., Chapter 4.7, "Targeting of Sterically Stabilized Liposomes to Cancers Overexpressing HER2/neu Proto-Oncogene," In Medical Applications of Liposomes, Lasic D and Papahadjopoulos D, eds., pp. 325-345 (1998).

Kline C, et al., "Preliminary Observations Indicate Variable Patterns of Plasma 5-Fluorouracil (5-FU) Levels During Dose Optimization of Infusional 5-FU in Colorectal Cancer Patients," Cancer Biol Ther. 12(7):557-68 (2011).

Krauss W, et al., "Emerging Antibody-Based HER2 (ErbB2/neu) Therapeutics," Breast Dis. 11:113-24 (2000).

Park J, et. al., "Anti-HER2 Immunoliposomes for Targeted Drug Delivery," Med Chem Res. 8(7/8):383-91 (1998).

Patankar N, et. al., "Topophore C: A Liposomal Nanoparticle Formulation of Topotecan for Treatment of Ovarian Cancer," Invest New Drugs. 31(1):46-58 (2013). Epub 2012.

Patel M, et al., "Effects of Oxaliplatin and CPT-11 on Cytotoxicity and Nucleic Acid Incorporation of the Fluoropyrimidines," J Cancer Res Clin Oncol. 130(8):453-9 (2004).

Pavai S and Yap S, "The Clinical Significance of Elevated Levels of Serum CA19-9," Med J Malaysia. 58(5):667-72 (2003).

Pavillard V, et al., "Determinants of the Cytotoxicity of Irinotecan in Two Human Colorectal Tumor Cell Lines," Cancer Chemother Pharmacol. 49(4):329-35 (2002).

Paz N, et al., "MM-398/PEP02, A Novel Liposomal Formulation of Irinotecan Demonstrates Stromal-Modifying Anti-Cancer Properties," Poster for abstract A63 presented at the AACR Special Conference on Pancreatic Cancer: Progress and Challenges; Jun. 18-21, 2012; Lake Tahoe, NV, 9 pages.

Paz N, et al., Abstract A63. "MM-398/PEP02, A Novel Liposomal Formulation of Irinotecan, Demonstrates Stromal-Modifying Anticancer Properties," In Proceedings of the AACR Special Conference on Pancreatic Cancer: Progress and Challenges; Jun. 18-21, 2012; Lake Tahoe, NV. Cancer Res. 2012;72(12 Suppl):Abstract nr A63, 3 printed pages.

Paz-Ares L, et al., "Efficacy and Safety of Irinotecan Liposome Injection (nal-IRI) in Patients with Small Cell Lung Cancer (SCLC)," Presentation presented at 2019 World Conference on Lung Cancer; Sep. 7-10, 2019; Barcelona, Spain; 9 pages.

Paz-Ares L, et al., "RESILIENT part 2: An Open-Label, Randomized, Phase 3 Study of Liposomal Irinotecan Injection in Patients With Small-Cell Lung Cancer Who Have Progressed With Platinum-Based First-Line Therapy." Poster presented at the American Society of Clinical Oncology (ASCO) Annual Conference, virtual format, May 29-Jun. 2, 2020, 7 pages.

Paz-Ares L, et al., Abstract TPS9081. "RESILIENT part II: An Open-Label, Randomized, Phase III Study of Liposomal Irinotecan Injection in Patients With Small-Cell Lung Cancer Who Have Progressed With Platinum-Based First-Line Therapy," J Clin Oncol. 38(15_Suppl):TPS9081 DOI: 10.1200/JCO.2020.38.15_suppl. TPS9081 (2020), 2 printed pages.

Paz-Ares Rodriguez L, et al., Abstract OA03.03. "Initial Efficacy and Safety Results of Irinotecan Liposome Injection (NAL-IRI) in Patients With Small Cell Lung Cancer," 2019 World Conference on Lung Cancer Abstracts; Sep. 7-10, 2019; Barcelona, Spain; pp. 220-221.

PCT/GB2017/053293: PCT International Preliminary Reporton Patentability dated May 7, 2019, 7 pages.

PCT/GB2017/053293: PCT International Search Report and Written Opinion dated Feb. 2, 2018, 12 pages.

PCT/US2005/015349: PCT International Search Report and Written Opinion dated Aug. 18, 2005, 14 pages.

PCT/US2016/027515: PCT International Preliminary Report on Patentability dated Oct. 17, 2017, 8 pages.

PCT/US2016/027515: PCT International Search Report dated Jun. 27, 2016, 4 pages.

PCT/US2016/057247: PCT International Preliminary Report on Patentability dated Apr. 17, 2018, 8 pages.

PCT/US2016/057247: PCT International Search Report dated Dec. 23, 2016, 4 pages.

Peikov V, et al., "pH-Dependent Association of SN-38 with Lipid Bilayers of a Novel Liposomal Formulation," Int J Pharm. 299(1-2):92-9 (2005).

Peinert S, et al., "Safety and Efficacy of Weekly 5-Fluorouracil/Folinic Acid/Oxaliplatin/Irinotecan in the First-Line Treatment of Gastrointestinal Cancer," Ther Adv Med Oncol. 2(3):161-74 (2010).

PharmaEngine, www.pharmaengine.com/pep02.html Webpage titled "PEP02". Aug. 4, 2011, 4 printed pages.

Pillai G, "Nanomedicines for Cancer Therapy: An Update of FDA Approved and Those under Various Stages of Development," SOJ Pharm Pharm Sci. 1(2):13 (2014), 13 pages.

Ponce S, et al., "RESILIENT Part 1: Pharmacokinetics of Second-Line (2L) Liposomal Irinotecan in Patients with Small Cell Lung Cancer (SCLC)," Poster presented at the European Society for Medical Oncology (ESMO) Virtual Congress 2020, virtual format, Sep. 19-21, 2020, 8 pages.

Ponce S, et al., Abstract 1793P. "RESILIENT Part 1: Pharmacokinetics of Second-Line (2L) Liposomal Irinotecan in Patients with Small Cell Lung Cancer (SCLC)," Ann Oncol. 31(S4):S1038-S1039 (2020).

Poplin E, et. al.,"Phase III Southwest Oncology Group 9415/Intergroup 0153 Randomized Trial of Fluorouracil, Leucovorin, and

(56) References Cited

OTHER PUBLICATIONS

Levamisole Versus Fluorouracil Continuous Infusion and Levamisole for Adjuvant Treatment of Stage III and High-Risk Stage II Colon Cancer," J Clin Oncol. 23(9):1819-25 (2005).
Ramsay E, et. al., "Irinophore C: A Liposome Formulation of Irinotecan With Substantially Improved Therapeutic Efficacy Against a Panel of Human Xenograft Tumors," Clin Cancer Res. 14(4):1208-17 (2008).
Raymond E, et al., "Multicentre Phase II Study and Pharmacokinetic Analysis of Irinotecan in Chemotherapy-Naive Patients with Glioblastoma," Ann Oncol. 14(4):603-14 (2003).
Rea D, et al., "A Phase I/II and Pharmacokinetic Study of Irinotecan in Combination with Capecitabine as First-Line Therapy for Advanced Colorectal Cancer," Ann Oncol. 16(7):1123-32 (2005).
Reynolds J, et al., "HER2-Targeted Liposomal Doxorubicin Displays Enhanced Anti-Tumorigenic Effects Without Associated Cardiotoxicity," Toxicol Appl Pharmacol. 262(1):1-10 (2012).
Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.
Rosenecker J, et al., "Increased Liposome Extravasation in Selected Tissues: Effect of Substance P," Proc Natl Acad Sci USA. 93(14):7236-41 (1996).
Roth A, et al., "Anti-CD166 Single Chain Antibody-Mediated Intracellular Delivery of Liposomal Drugs to Prostate Cancer Cells," Mol Cancer Ther. 6(10):2737-46 (2007).
Rothenberg M, et. al., "Alternative Dosing Schedules for Irinotecan," Oncology. 12(8 Suppl 6):68-71 (1998). Available at cancernetwork. com/view/alternative-dosing-schedules-irinotecan, 16 printed pages.
Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013).
Rubesova E, et al., "Gd-Labeled Liposomes for Monitoring Liposome-Encapsulated Chemotherapy: Quantification of Regional Uptake in Tumor and Effect on Drug Delivery," Acad Radiol. 9(Suppl 2):S525-7 (2002).
Sachdev J, et al., "Phase I Expansion Study of Irinotecan Liposome Injection (nal-IRI) in Patients with Metastatic Breast Cancer (mBC)." Poster presented at the American Association for Cancer Research Annual Meeting 2019; Mar. 29-Apr. 3, 2019; Atlanta, GA, 9 printed pages.
Sachdev J, et al., Abstract CT048. "Phase I Expansion Study of Irinotecan Liposome Injection (nal-IRI) in Patients with Metastatic Breast Cancer (mBC)," Cancer Res. In Proceedings of the American Association for Cancer Research Annual Meeting 2019; Mar. 29-Apr. 3, 2019; Atlanta, GA Cancer Res. 2019; 79(13 Suppl):Abstract nr CT048, 4 printed pages.
Sadzuka Y, et al., "Effective Irinotecan (CPT-11)-containing Liposomes: Intraliposomal Conversion to the Active Metabolite SN-38." Jpn J Cancer Res. 90(2):226-32 (1999).
Saif M, et. al., "Pharmacokinetically Guided Dose Adjustment of 5-Fluorouracil: A Rational Approach to Improving Therapeutic Outcomes," J Natl Cancer Inst. 101(22):1543-52 (2009).
Saltz L, "Clincial Use of Irinotecan: Current Status and Future Considerations," Oncologist. 2(6):402-9 (1997).
Saltz LB, et. al., "Phase I Clinical and Pharmacokinetic Study of Irinotecan, Fluorouracil, and Leucovorin in Patients With Advanced Solid Tumors," J Clin Oncol. 14(11):2959-67 (1996).
Satoh T, et. al., "Pharmacokinetic Assessment of Irinotecan, SN-38, and SN-38-Glucuronide: A Substudy of the FIRIS Study," Anticancer Res. 33(9):3845-53 (2013).
Scheithauer W, et. al., "Fluorouracil Plus Racemic Leucovorin Versus Fluorouracil Combined With the Pure I-Isomer of Leucovorin for the Treatment of Advanced Colorectal Cancer: A Randomized Phase III Study," J Clin Oncol. 15(3):908-14 (1997).
Schroen A, et. al., "Challenges to Accrual Predictions to Phase III Cancer Clinical Trials: A Survey of Study Chairs and Lead Statisticians of 248 NCI Sponsored Trials," Clin Trials. 8(5):591-600 (2011), author manuscript version, 14 pages.
Serwer L, et al., "Investigation of Intravenous Delivery of Nanoliposomal Topotecan For Activity Against Orthotopic Glioblastoma Xenografts," Neuro Oncol. 13(12):1288-95 (2011).
Skof E, et. al., "Capecitabine Plus Irinotecan (XELIRI Regimen) Compared to 5-FU/LV Plus Irinotecan (FOLFIRI Regimen) As Neoadjuvant Treatment for Patients With Unresectable Liver-Only Metastases of Metastatic Colorectal Cancer: A Randomised Prospective Phase II Trial," BMC Cancer. 9:120 doi: 10.1186/1471-2407-9-120 (2009), 9 pages.
Spigel D, et al., "Liposomal Irinotecan in Adults with Small Cell Lung Cancer Who Progressed on Platinum-Based Therapy: Subgroup Analyses by Platinum Sensitivity." Poster presented at the International Association for the Study of Lung Cancer (IASLC) 2020 North America Conference on Lung Cancer (NACLC): virtual meeting, Oct. 16-17, 2020, 9 pages.
Spigel D, et al., "RESILIENT Part 1, An Open-Label, Safety Run-In of Liposomal Irinotecan in Adults With Small Cell Lung Cancer (SCLC) Who Have Progressed With Platinum-Based First-Line Therapy: Subgroup Analyses by Platinum Sensitivity." Poster presented at the American Society of Clinical Oncology (ASCO) Annual Conference, virtual format, May 29-Jun. 2, 2020, 6 pages.
Spigel D, et al., Abstract 9069. "RESILIENT Part I, An Open-Label, Safety Run-In of Liposomal Irinotecan in Adults Nith Small Cell Lung Cancer (SCLC) Who Have Progressed With Platinum-Based First-Line (1L) Therapy: Subgroup Analyses by Platinum Sensitivity," J Clin Oncol. 38(15_Suppl):9069 DOI: 10 1200/JCO.2020.38. 15_suppl.9069 (2020), 2 printed pages.
Spigel D, et al., Abstract MO01.39. "Liposomal Irinotecan in Adults with Small Cell Lung Cancer Who Progressed on Platinum-Based Therapy: Subgroup Analyses by Platinum Sensitivity," IASLC 2020 North America Conference on Lung Cancer Abstracts, p. 80 (2020).
Wang-Gillam A, et al., Abstract 459. "Nomogram for Predicting Overall Survival (OS) in Patients (pts) Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1," J Clin Oncol. 36(4_Suppl):459 DOI: 10.1200/JCO.2018.36.4_suppl.459 (2018), 2 printed pages.
Wang-Gillam A, et al., Abstract e15795. "The Prognostic Value of Baseline Neutrophil-to-Lymphocyte Ratio (NLR) and Platelet-to-Lymphocyte ratio (PLR) for Predicting Clinical Outcome in Patients with Metastatic Pancreatic Ductal Adenocarcinoma (mPDAC) Treated With Liposomal Irinotecan (nalIRI; MM398) + 5-Fluorouracil and Leucovorin (5-FU/LV) vs 5-FU/LV," J Clin Oncol. 35(15_Suppl):e15795 DOI: 10.1200/JCO.2017.35.15_suppl.e 15795 (2017), 3 printed pages.
Wang-Gillam A, et al., Abstract e16204. "A Survival Prediction Nomogram for Liposomal Irinotecan (nal-IRI)+5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(15_Suppl):e16204 DOI: 10.1200/JCO.2018.36.15_suppl.e16204 (2018), 2 printed pages.
Wang-Gillam A, et. al., letter to editor, "Nanoliposomal Irinotecan in the Clinical Practice Guideline for Metastatic Pancreatic Cancer: Applicability to Clinical Situations," J Clin Oncol. 35(6):689-90 (2017). Epub 2016.
Xiong H, et. al., "Phase 2 Trial of Oxaliplatin Plus Capecitabine (XELOX) as Second-line Therapy for Patients With Advanced Pancreatic Cancer," Cancer 113(8):2046-52 (2008).
Yu K, et al., "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," Poster presented at the Academy of Managed Care Pharmacy, Nexus (AMCP, Nexus): virtual meeting, week of Oct. 19, 2020, 9 pages.
Yu K, et al., Abstract C3. "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," J Manag Care Spec Pharm. 26(10-a):S19 (2020).

(56) References Cited

OTHER PUBLICATIONS

Yu K, et al., "A US Multicenter Chart Review Study of Patients With Metastatic Pancreatic Ductal Adenocarcinoma Receiving Liposomal Irinotecan after Gemcitabine-Based Therapy." Poster presented at the International Conference on Pharmacoepidemiology & Therapeutic Risk Management (ICPE) All Access, Sep. 16-17, 2020, 8 pages.

Yu K, et al., "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review." Poster presented at the European Society for Medical Oncology (ESMO) Virtual Congress 2020, Sep. 19-21, 2020, 9 pages.

Yu K, et al., Abstract 1555P. "Real-World Treatment Patterns and Effectiveness of Liposomal Irinotecan in a NAPOL11-Based Regimen Among Patients With Metastatic Pancreatic Ductal Adenocarcinoma (mPDAC): A Multi-Academic Center Chart Review," Ann Oncol. 31(Suppl_4):S950-S951 doi.org/10.1016/j.annonc.2020.08.2038 (2020), 2 printed pages.

Yu K, et al., Abstract e16733. "A Multicenter Chart Review Study of Patients with Metastatic Pancreatic Ductal Adenocarcinoma Receiving Liposomal Irinotecan after Gemcitabine-Based Therapy," J Clin Oncol. 38(15_Suppl): e16733 DOI: 10.1200/JCO.2020.38.15_suppl.e16733 (2020), 4 printed pages.

Yu K, et al., Abstract PO-3727. "A US Multicenter Chart Review Study of Patients With Metastatic Pancreatic Ductal Adenocarcinoma Receiving Liposomal Irinotecan after Gemcitabine-Based Therapy," International Conference on Pharmacoepidemiology & Therapeutic Risk Management (ICPE), Sep. 14, 2020, available at eventscribe.com/2020/ICPEAllAccess/PosterTitles.asp?pfp=PosterTitles, 1 page.

Yu X, et. al., "Targeted Drug Delivery in Pancreatic Cancer," Biochim Biophys Acta. 21805(1):97-104 (2010). Epub 2009, author manuscript version, 16 pages.

Alese O, et al., "A Phase 1 Trial of Trifluridine/Tipiracil in Combination With Nanoliposomal Irinotecan in Advanced GI Cancers," Abstract PD-4, doi.org/10.1016/j.annonc2021.05.022, Annals Oncol. 32(S3):S200 (2021).

Bai L, et al., "A Phase 2 Study of Liposomal Irinotecan With 5-Fluorouracil and Leucovorin in Squamous Cell Carcinoma of Head and Neck or Esophagus After Prior Platinum-Based Chemotherapy or Chemoradiotherapy," J Clin Oncol. 39(15_suppl):6025-6025, DOI: 10.1200/JCO.2021.39.15_suppl.6025 (2021), 4 printed pages.

Choi G, et al., "Safety and Effectiveness of Prospective Observational Postmarketing Surveillance Study for Pancreatic Adenocarcinoma Treated by Liposomal Irinotecan Plus 5-Flurouracil/Leucovorin in Korea," Abstract P196, 2nd American Association for Cancer Research—Korean Cancer Association Joint Conference on Precision Medicine in Solid Tumors, Nov. 10-11, 2021 (EST), 1 page.

Chotzagiannoglou V, et al., Abstract PCN154. "Budget Impact Analysis of Liposomal Irinotecan for Treatment of Metastatic Adenocarcinoma of Pancreas Following Progression on Gemcitabine-Based Therapies from Greek Payer's Perspective," Value in Health. 23(S2):S450 (2020).

Dieguez G et al., "Risk Adjustment and Total Cost of Care Per Month of Overall Survival Among Medicare Fee-for-Service (FFS) Patients Receiving NCCN Category-1 Treatments for Metastatic Pancreatic Cancer," Abstract, doi.org/10.1093/ajhp/zxab362, Found at American Journal of Health-System Pharmacy, 78(20):1831-1918 (2021), 2 printed pages.

Dieguez G, et al., "Trends in Treatment Patterns Among Medicare Fee-For-Service (FFS) Patients Receiving Treatment for Metastatic Pancreatic Cancer," Abstract 1478P, doi.org/10.1016/j.annonc.2021.08.805, Annals Oncol. 32(S5):S1091-S1092 (2021).

Dieguez G, et al., "Trends in Use of One, Two, and Three-Line NCCN Category 1 Regimens Among Medicare Fee-For-Service (FFS) Patients Receiving Treatment for Metastatic Pancreatic Cancer," J Clin Oncol. 39(28_suppl):297-297, DOI:10.1200/JCO.2020.39.28_suppl.297 (2021), 4 printed pages.

Elias R, et al., "Comparison of First-Line (1L) Treatment (Tx) Patterns and Overall Survival by Age at Diagnosis Among Patients With Metastatic Pancreatic Ductal Adenocarcinoma (mPDAC)," J Clin Oncol. 39(3 suppl):388-388, DOI: 10.1200/JCO.2021.39.3_suppl.388, (2021), 5 printed pages.

George B, et al., "Real-World Impact of Prior Surgery on Outcomes of Patients With Metastatic Ductal Adenocarcinoma (mPDAC) Treated With Liposomal Irinotecan-Based Regimens," Abstract PCN17, Value in Health. 24(Suppl 1):S21 (2021).

George B, et al., "Real-World Serum CA19-9 Level Monitoring Patterns and Its Association With Clinical Outcomes Among Patients With Metastatic Pancreatic Ductal Adenocarcinoma (mPDAC)," https://doi.org/10.1158/1538-7445.AM2021-765, Cancer Res. 81(13_Suppl):765 (2021), 4 printed pages.

George B, et al., "The Association Between Real-World CA19-9 Level Monitoring Patterns and With Clinical Outcomes Among Patients With Metastatic Pancreatic Ductal Adenocarcinoma (mPDAC) in the Second- and Third-Line of Therapy," J Clin Oncol. 39(15_suppl):e16251, DOI: 10.1200/JCO.2021.39.15_suppl.e16251 (2021), 4 printed pages.

Gourzoulidis G, et al., Abstract PCN108. "The Cost-Effectiveness of Liposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece," Value in Health. 23(S2):S442 (2020).

Kim G, et al., "Real-World Characteristics and Outcomes of Patients With Metastatic Ductal Adenocarcinoma (mPDAC) Treated With Liposomal Irinotecan-Based Regimens by Race," Abstract PCN27, Value in Health. 24(Suppl 1):S23 (2021).

Kim G, et al., "Real-World One-Year Overall Survival Among Patients With Metastatic Pancreatic Ductal Adenocarcinoma (mPDAC) Treated With Liposomal Irinotecan in the NAPOLI-1 Based Regimen," J Clin Oncol. 39(3_suppl):392-392, DOI: 10.1200/JCO.2021.39.3_suppl.392, (2021), 4 printed pages.

Kim G, et al., "Real-World Progression Outcomes Among Patients (pts) With Metastatic Pancreatic Ductal Adenocarcinoma (mPDAC) Treated With Liposomal Irinotecan-Based Regimens in the United States," Abstract 1480P, doi.org/10.1016/j.annonc.2021.08.807, Annals Oncol. 32(S5):S1092-S1093 (2021).

Kim G, et al., "Real-World Safety and Medication Use of Second-Line (2L) 5-Fluorouracil (5-FU)-Based Regimens Among Patients (pts) With Metastatic Pancreatic Ductal Adenocarcinoma (mPDAC)," J Clin Oncol. 39(15 suppl):e16248, DOI: 10.1200/JCO.2021.39.15_suppl.e16248 (2021), 5 printed pages.

Kim G, et al., "Real-World Safety Data and Differentiation of Second-Line (2L) 5-Fluorouracil (5-FU) Based Regimens Among Patients With Metastatic Pancreatic Ductal Adenocarcinoma (mPDAC)," J Clin Oncol. 39(3 suppl):390-390, DOI: 10.1200/JCO.2021.39.3_suppl.390, (2021), 5 printed pages.

Kim G, et al., "Real-World Treatment Discontinuation Patterns Among Patients (pts) With Metastatic Pancreatic Ductal Adenocarcinoma (mPDAC) Treated With Liposomal Irinotecan-Based Regimens in the United States," Abstract 1513P, doi.org/10.1016/j.annonc.2021.08.842, Annals Oncol. 32(S5):S1107-S1108 (2021).

Kokhreidze J, et al., "Psychometric Properties of Patient Reported Outcome (PRO) Instruments in Patients With Small Cell Lung Cancer (SCLC) in RESILIENT Part 1," J Clin Oncol. 39(15_suppl):e24027, DOI: 10.1200/JCO.2021.39.15_suppl.e24027, (2021), 4 printed pages.

Latimer H, et al., "Dispersion in Total Cost of Care for Medicare Fee-For-Service (FFS) Patients With Metastatic Pancreatic Cancer Receiving FDA-Approved/NCCN Category 1 Regimens at 340B Versus Non-340B Institutions," J Clin Oncol. 39(15_suppl):e18843, DOI: 10.1200/JCO.2021.39.15_suppl.e18843 (2021), 4 printed pages.

Latimer H, et al., "Dispersion in Total Cost of Care for Medicare Fee-For-Service (FFS) Patients With Metastatic Pancreatic Cancer Receiving FDA-Approved/NCCN Category 1 Regimens at Teaching Versus Non-Teaching Institutions," J Clin Oncol. 39(15 suppl):e16244, DOI: 10.1200/JCO.2021.39.15 suppl.e16244 (2021), 4 printed pages.

Latimer H, et al., "Total Cost of Care and Utilization Among Medicare Fee-For-Service (FFS) Patients With Metastatic Pancreatic Cancer Treated With FDA-Approved/NCCN® Category 1

(56) References Cited

OTHER PUBLICATIONS

Regimens at Teaching vs. Non-Teaching Hospitals," Abstract PDB2, Value in Health. 24(Suppl 1):S78 (2021).
Laursen A, et al., "Real-World Patterns of Pain Medication Use Among Patients With Metastatic Pancreatic Ductal Adenocarcinoma (mPDAC)," J Clin Oncol. 39(28_suppl):302-302, DOI: 10.1200/JCO.2020.39.28_suppl.302 (2021), 4 printed pages.
O'Reilly E, et al., "Real-World Overall Survival of Patients Diagnosed With Recurrent Versus de novo Metastatic Pancreatic Ductal Adenocarcinoma (PDAC)," J Clin Oncol. 39(15_suppl):e16250, DOI: 10.1200/JCO.2021.39.15_suppl.e16250 (2021), 4 printed pages.
Paluri R, et al., "Impact of the COVID-19 Pandemic on Care Delivery and Outcomes for Patients With Metastatic Pancreatic Ductal Adenocarcinoma (mPDAC)," J Clin Oncol. 39(15_suppl):4137-4137, DOI: 10.1200/JCO.2021.39.15_suppl.4137 (2021), 4 printed pages.
Paz-Ares L, et al., "RESILIENT Part 1: Safety and Efficacy of Second-Line Liposomal Irinotecan in Patients With Small Cell Lung Cancer," Abstract FP10.04, J Thoracic Oncol. 16(3S):S216 (2021).
Paz-Ares L, et al., "RESILIENT Part 2: A Phase 3 Study of Liposomal Irinotecan in Patients With Small-Cell Lung Cancer in the Second-Line Setting," Abstract P48.14, J Thoracic Oncol. 16(3S):S505 (2021).
Perkhofer L, et al., "Nal-IRI With 5-Fluorouracil (5-FU) and Leucovorin or Gemcitabine Plus Cisplatin in Advanced Biliary Tract Cancer: Final Results of the NIFE-trial (AIO-YMO HEP-0315), A Randomized Phase II Study of the AIO Biliary Tract Cancer Group," Abstract LBA10, doi.org/10.1016/j.annonc.2021.08.2082, Annals Oncol. 32(S5):S1282 (2021).
Rogers S, et al., "A Phase II, Open-Label Pilot Study Evaluating the Safety and Activity of Liposomal Irinotecan (Nal-IRI) in Combination With 5-FU and Oxaliplatin (NALIRIFOX) in Preoperative Treatment of Pancreatic Adenocarcinoma (NEO-Nal-IRI study) (NCT03483038)," J Clin Oncol. 39(15 suppl):TPS4170, DOI: 10.1200/JCO.2021.39.3_suppl.TPS446 (2021), 4 printed pages.
Taieb J, et al., "Real-World Study of Treatment Patterns and Outcomes Among Patients With Metastatic Pancreatic Ductal Adenocarcinoma (PDAC) in Europe," J Clin Oncol. 39(3_suppl):391-391, DOI: 10.1200/JCO.2021.39.3_suppl.391 (2021), 4 printed pages.
Taieb J, et al., "Treatment Sequences and Prognostic Factors in Metastatic Pancreatic Ductal Adenocarcinoma Univariate and Multivariate Analyses of a Real-World Study in Europe," Abstract SO-3, doi.org/10.1016/j.annonc.2021.05.027, Annals Oncol. 32(S3):S203 (2021).
Tomicki S, et al., "Total Cost of Care and Utilization Among Medicare Fee-For-Service (FFS) Patients With Metastatic Pancreatic Cancer Treated With FDA-Approved/NCCN® Category 1 Regimens at 340B vs. Non-340B Hospitals," Abstract PDB17, Value in Health. 24(Suppl 1):S80-S81 (2021).
Yoo C, et al., "Liposomal Irinotecan (nal-IRI) in Combination With Fluorouracil (5-FU) and Leucovorin (LV) for Patients With Metastatic Biliary Tract Cancer (BTC) After Progression on Gemcitabine Plus Cisplatin (GemCis): Multicenter Comparative Randomized Phase 2b Study (NIFTY)," J Clin Oncol. 39(15_suppl):4006-4006, DOI: 10.1200/JCO.2021.39.15_suppl.4006 (2021), 4 printed pages.
Yu K, et al., "Population-Based, Real-World Prognostic Factors Related to Survival Among Patients With Metastatic Pancreatic Ductal Adenocarcinoma (mPDAC)," J Clin Oncol. 39(3_suppl):389-389, DOI: 10.1200/JCO.2021.39.3_suppl.389, (2021), 4 printed pages.
Zhu Z, et al., "Assessing Real-World Survival Outcomes of Patients (pts) With Metastatic Pancreatic Ductal Adenocarcinoma (mPDAC) Treated With First-Line FOLFIRINOX Compared to Patients From a Phase 1/2 Trial Treated With NALIRIFOX," J Clin Oncol. 39(15_suppl):e16252, DOI: 10.1200/JCO.2021.39.15_suppl.e1625 (2021), 4 printed pages.

EP3337478: Proprietor's Submission in Response to Oppositions, dated Dec. 7, 2021, including main request and auxiliary requests 1-3, 62 pages.
EP3337478: Proprietor's Submission in Response to Oppositions, dated Dec. 7, 2021, D18 (Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021)).
EP3337478: Proprietor's Submission in Response to Oppositions, dated Dec. 7, 2021, D19 (Declaration of Dr. Bin Zhang, including Annex A and Annex B, 15 pages).
EP3337478: Proprietor's Submission in Response to Oppositions, dated Dec. 7, 2021, D20 (Eisenhauer E, et al., "New Response Evaluation Criteria in Solid Tumours: Revised RECIST Guideline (version 1.1)," Eur J Cancer. 45(2):228-47 (2009)).
EP3337478: Proprietor's Submission in Response to Oppositions, dated Dec. 7, 2021, D21 (Jang G, et al., "Comparison of RECIST Version 1.0 and 1.1 in Assessment of Tumor Response by Computed Tomography in Advanced Gastric Cancer," Chin J Cancer Res. 25(6):689-694 (2013)).
EP3337478: Proprietor's Submission in Response to Oppositions, dated Dec. 7, 2021, D22 (Kim J, et al., "Comparison of RECIST 1.0 and RECIST 1.1 in Patients with Metastatic Cancer: A Pooled Analysis," J Cancer. 6(4):387-393 (2015)).
EP3337478: Proprietor's Submission in Response to Oppositions, dated Dec. 7, 2021, D23 (Trial Protocol for Conroy T, et al., "FOLFIRINOX versus Gemcitabine for Metastatic Pancreatic Cancer," N Engl J Med. 364(19):1817-25 (2011), 88 pages).
EP3337478: Proprietor's Submission in Response to Oppositions, dated Dec. 7, 2021, D24 (Package leaflet for Campto 20 mg/mL concentration for solution for infusion irinotecan hydrochloride, trihydrate, last revised May 2021, 11 pages).
EP3337478: Sandoz AG Response to Proprietor's Reply to the Notice of Opposition dated Feb. 1, 2022, 17 pages.
EP3337478: Sandoz AG Response to Proprietor's Reply to the Notice of Opposition dated Feb. 1, 2022, D25 (Tsai C, et al., "Nanovector-Based Therapies in Advanced Pancreatic Cancer," J Gastroint Oncol 2(3):185-94 (2011)).
EP3337478: Sandoz AG Response to Proprietor's Reply to the Notice of Opposition dated Feb. 1, 2022, D26 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP3337478: Sandoz AG Response to Proprietor's Reply to the Notice of Opposition dated Feb. 1, 2022, D27 (Kalra A, et al., "Preclinical Activity of Nanoliposomal Irinotecan Is Governed by Tumor Deposition and Intratumor Prodrug Conversion," Cancer Res. 74(23):7003-13 (2014)).
EP3337478: Proprietor's Response to Sandoz AG's Submission of Feb. 1, 2022, dated Feb. 28, 2022, 17 pages.
Brendel K, et al., "Population Pharmacokinetics of Liposomal Irinotecan in Patients With Cancer and Exposure-Safety Analyses in Patients With Metastatic Pancreatic Cancer," CPT Pharmacometrics Syst Pharmacol. 10(12):1550-63, doi: 10.1002/psp4.12725 (2021).
Gebauer F, et al., "Study Protocol of an Open-Label, Single Arm Phase II Trial Investigating the Efficacy, Safety and Duality of Life of Neoadjuvant Chemotherapy With Liposomal Irinotecan Combined With Oxaliplatin and 5-Fluorouracil/Folinic Acid Followed by Curative Surgical Resection in Patients With Hepatic Oligometastatic Adenocarcinoma of the Pancreas (HOLIPANC)," BMC Cancer. 21(1):1239, doi: 10.1186/s12885-021-08966-3, pp. 1-11 (2021).
George B, et al., "The Association of Real-World CA 19-9 Level Monitoring Patterns and Clinical Outcomes Among Patients With Metastatic Pancreatic Ductal Adenocarcinoma," Front Oncol. 11:754687, doi: 10.3389/fonc.2021.754687, pp. 1-8 (2021).
Paz-Ares L, et al., "RESILIENT Part 1: A Phase 2 Dose-Exploration and Dose-Expansion Study of Second-Line Liposomal Irinotecan in Adults With Small Cell Lung Cancer," Cancer, doi: 10.1002/cncr.34123, online ahead of print, pp. 1-11 (2022).
Sachdev J, et al., "Phase I Study of Liposomal Irinotecan in Patients With Metastatic Breast Cancer: Findings from the Expansion Phase," Breast Cancer Res Treat..185(3):759-71 (2021), Epub 2020.

(56) References Cited

OTHER PUBLICATIONS

Tomicki S, et al., "Real-World Cost of Care for Commercially Insured Versus Medicare Patients With Metastatic Pancreatic Cancer Who Received Guideline-Recommended Therapies," Am Health Drug Benefits 14(2):70-78 (2021).

Yoo C, et al., "Liposomal Irinotecan Plus Fluorouracil and Leucovorin Versus Fluorouracil and Leucovorin for Metastatic Biliary Tract Cancer After Progression on Gemcitabine Plus Cisplatin (NIFTY): A Multicentre, Open-Label, Randomized, Phase 2b Study," Lancet Oncol. 22(11):1560-1572, doi: 10.1016/S1470-2045(21)00486-1, pp. 1-13 (2021).

Yu K, et al., "Clinical Outcomes Among Patients With Metastatic Pancreatic Ductal Adenocarcinoma Treated With Liposomal Irinotecan," Front Oncol. 11:678070. doi: 10.3389/fonc.2021.678070, pp. 1-9 (2021).

Yu K, et al., "Real-World Prognostic Factors for Survival Among Treated Patients With Metastatic Pancreatic Ductal Adenocarcinoma," Cancer Med. 10(24):8934-43 (2021).

U.S. Appl. No. 15/664,976: Apr. 21, 2021 Notice of Allowance including Examiner's Reasons for Allowance, 14 pages.

U.S. Appl. No. 15/809,815: Aug. 26, 2021 Non-Final Office Action, 14 pages.

U.S. Appl. No. 16/012,351: Mar. 8, 2021 Notice of Allowance including Examiner's Reasons for Allowance, 9 pages.

U.S. Appl. No. 16/012,372: Feb. 11, 2021 Notice of Allowance including Examiner's Reasons for Allowance, 9 pages.

U.S. Appl. No. 16/302,050: Aug. 11, 2021 Non-Final Office Action, 17 pages.

U.S. Appl. No. 16/567,902: Mar. 8, 2021 Notice of Allowance including Examiner's Reasons for Allowance and Examiner Interview Summary, 22 pages.

U.S. Appl. No. 16/711,072: Dec. 10, 2021 Non-Final Office Action, 19 pages.

U.S. Appl. No. 16/906,601: Jan. 7, 2022 Non-Final Office Action, 21 pages.

Bai L, et al., "A Phase 2 Study of Liposomal Irinotecan With 5-Fluorouracil and Leucovorin in Squamous Cell Carcinoma of Head and Neck or Esophagus After Prior Platinum-Based Chemotherapy or Chemoradiotherapy," Poster presented at American Society of Clinical Oncology 2021 Meeting, Jun. 4-8, 2021, 6 pages.

Dieguez G et al., "Risk Adjustment and Total Cost of Care Per Month of Overall Survival Among Medicare Fee-for-Service (FFS) Beneficiaries Receiving Treatment for Metastatic Pancreatic Cancer," Poster presented at American Society of Health-System Pharmacists (ASHP) Midyear Clinical Meeting & Exhibition, Dec. 6-7, 2021, 6 pages.

Dieguez G, et al., "Trends in Treatment Patterns Among Medicare Fee-For-Service (FFS) Patients Receiving Treatment for Metastatic Pancreatic Cancer," Poster presented at European Society for Medical Oncology (ESMO) Congress 2021, Sep. 16-21, 2021, 5 pages.

Dieguez G, et al., "Trends in Use of One, Two, and Three-Line NCCN Category 1 Regimens Among Medicare Fee-For-Service (FFS) Patients Receiving Treatment for Metastatic Pancreatic Cancer," Poster presented at ASCO Quality Care Symposium 2021, Sep. 24-25, 2021, 5 pages.

Elias R, et al., "Comparison of First-Line (1L) Treatment (Tx) Patterns and Overall Survival by Age at Diagnosis Among Patients With Metastatic Pancreatic Ductal Adenocarcinoma (mPDAC)," Poster Presented at the American Society of Clinical Oncology Gastrointestinal Cancer Symposium (ASCO GI) 2021, Jan. 15-17, 2021, Virtual Congress, 6 pages.

George B, et al., "Real-World Impact of Prior Surgery on Outcomes of Patients With Metastatic Ductal Adenocarcinoma (mPDAC) Treated With Liposomal Irinotecan-Based Regimens," Presented at International Society tor Pharmacoeconomics and Outcomes, May 17-19, 2021, Virtual poster, 10 pages.

George B, et al., "Real-World Serum CA19-9 Level Monitoring Patterns and Its Association With Clinical Outcomes Among Patients With Metastatic Pancreatic Ductal Adenocarcinoma (mPDAC)," Poster presented at the American Association for Cancer Research (AACR) 2021 Virtual Congress, Apr. 10-15, 2021, 8 pages.

Kim G, et al., "Real-World Characteristics and Outcomes of Patients With Metastatic Ductal Adenocarcinoma (mPDAC) Treated With Liposomal Irinotecan-Based Regimens by Race," Presented at International Society for Pharmacoeconomics and Outcomes, May 17-19, 2021, Virtual poster, 9 pages.

Kim G, et al., "Real-World One-Year Overall Survival Among Patients With Metastatic Pancreatic Ductal Adenocarcinoma (mPDAC) Treated With Liposomal Irinotecan in the NAPOLI-1 Based Regimen," Poster presented at the American Society of Clinical Oncology Gastrointestinal Cancer Symposium (ASCO GI) 2021, Jan. 15-17, 2021, Virtual Congress, 6 printed pages.

Kim G, et al., "Real-World Progression Outcomes Among Patients (pts) With Metastatic Pancreatic Ductal Adenocarcinoma (mPDAC) Treated With Liposomal Irinotecan-Based Regimens in the United States," Poster presented at European Society for Medical Oncology (ESMO) Congress,, Virtual Congress, Sep. 16-21, 2021, 5 pages.

Kim G, et al., "Real-World Safety Data and Differentiation of Second-Line (2L) 5-Fluorouracil (5-FU) Based Regimens Among Patients With Metastatic Pancreatic Ductal Adenocarcinoma (mPDAC)," Poster presented at the American Society of Clinical Oncology Gastrointestinal Cancer Symposium (ASCO GI) 2021, Jan. 15-17, 2021, Virtual Congress, 7 pages.

Kim G, et al., "Real-World Treatment Discontinuation Patterns Among Patients (pts) With Metastatic Pancreatic Ductal Adenocarcinoma (mPDAC) Treated With Liposomal Irinotecan-Based Regimens in the United States," Presented at European Society for Medical Oncology (ESMO) Congress, Virtual Congress, Sep. 16-21, 2021, 5 pages.

Latimer H, et al., "Total Cost of Care and Utilization Among Medicare Fee-For-Service (FFS) Patients With Metastatic Pancreatic Cancer Treated With FDA-Approved/NCCN® Category 1 Regimens at Teaching vs. Non-Teaching Hospitals," Presented at International Society for Pharmacoeconomics and Outcomes, May 17-19, 2021, Virtual poster, 11 pages.

Laursen A, et al., "Real World Patterns of Pain Medication Use Among Patients With Metastatic Pancreatic Ductal Adenocarcinoma (mPDAC)," Poster presented at ASCO Quality Care Symposium 2021. Boston, MA, Online, Sep. 24-25, 2021, 4 pages.

Paluri R, et al., "Impact of the COVID-19 Pandemic on Metastatic Pancreatic Ductal Adenocarcinoma (mPDAC) Care Delivery," Presented at the American Society for Clinical Oncology (ASCO) Annual Meeting: Jun. 4-8, 2021; Virtual, 6 pages.

Paz-Ares L, et al., "RESILIENT Part 1: A Phase II Dose-Exploration and Dose-Expansion Study of Second-Line Liposomal Irinotecan Monotherapy in Adults With Small Cell Lung Cancer," Presented at World Conference on Lung Cancer, Jan. 28-31, 2021, Virtual event, 12 pages.

Paz-Ares L, et al., "RESILIENT Part 2: A Phase III Study of Liposomal Irinotecan in Patients With Small-Cell Lung Cancer in the Second-Line Setting," Presented at World Conference on Lung Cancer, Jan. 28-31, 2021, Virtual event, 9 pages.

Perkhofer L, et al., "Nal-IRI With 5-FU and Leucovorin or Gemcitabine Plus Cisplatin in Advanced Biliary Tract Cancer: Final Results of the Randomized Phase 2 NIFE Trial (AIO-YMO HEP-0315)," Presentation at the European Society for Medical Oncology (ESMO) Congress, Virtual Congress! Sep. 16-21, 2021, 9 pages.

Ramnaraign B, et al., "A Phase II, Open-Label Pilot Study Evaluating the Safety and Activity of Nal-IRI in Combination With 5-FU and Oxaliplatin (NALIRIFOX) in Preoperative Treatment of Pancreatic Adenocarcinoma (NEO-Nal-IRI study)," Poster presented at the American Society of Clinical Oncology Gastrointestinal Cancer Symposium (ASCO GI) 2021, Jan. 15-17, 2021, Virtual Congress, 4 pages.

Taieb J, et al., "Real-World Study of Treatment Patterns and Outcomes Among Patients With Metastatic Pancreatic Ductal Adenocarcinoma (PDAC) in Europe," Poster presented at the American Society of Clinical Oncology Gastrointestinal Cancer Symposium (ASCO GI) 2021, Jan. 15-17, 2021, Virtual Congress, 6 pages.

Tomicki S, et al., "Total Cost of Care and Utilization Among Medicare Fee-For-Service (FFS) Patients With Metastatic Pancreatic Cancer Treated With FDA-Approved/NCCN® Category 1

(56) References Cited

OTHER PUBLICATIONS

Regimens at 340B vs. Non-340B Hospitals," Presented at International Society for Pharmacoeconomics and Outcomes, May 17-19, 2021, Virtual poster, 11 pages.

Yoo C, et al., "Liposomal Irinotecan (nal-IRI) in Combination With Fluorouracil (5-FU) and Leucovorin (LV) for Patients (pts) With Metastatic Biliary Tract Cancer (BTC) After Progression on Gemcitabine Plus Cisplatin (GemCis) Multicenter Comparative Randomized Phase 2B Study (NIFTY)," Presented at the American Society of Clinical Oneology 2021 Meeting, Jun. 4-8, 2021, 18 pages.

Yu K, et al., "Population-Based, Real-World Prognostic Factors Related to Survival Among Patients With Metastatic Pancreatic Ductal Adenocarcinoma (mPDAC)," Poster presented at the American Society of Clinical Oncology Gastrointestinal Cancer Symposium (ASCO GI) 2021, Jan. 15-17, 2021, Virtual Congress, 7 pages.

Marsh R, et al., "Pancreatic Cancer and FOLFIRINOX: A New Era and New Questions," Cancer Med. 4(6):853-63 (2015).

Chang E, et al. "The Role of Tumor Size in the Radiosurgical Management of Patients with Ambiguous Brain Metastases," Neurosurgery 53(2):272-280; discussion at 280-281 (2003).

De Forni M, et al., "Phase I and Pharmacokinetic Study of the Camptothecin Derivative Irinotecan, Administered on a Weekly Schedule in Cancer Patients," Cancer Res. 54(16):4347-4354 (1994).

EP3337467: Sandoz AG Opposition dated Sep. 9, 2021, 24 pages.

EP3337467: Sandoz AG Opposition dated Sep. 9, 2021, D1 (Lorusso P, et al., "Phase I Study of the Safety, Pharmacokinetics (PK), and Pharmacodynamics (PD) of the Poly(ADP-ribose) Polymerase (PARP) Inhibitor Veliparib (ABT-888; V) in Combination with Irinotecan (CPT-11; Ir) in Patients (pts) with Advanced Solid Tumors," J Clin Oncol. 29(15) Suppl:3000 (2011), 2 pages).

EP3337467: Sandoz AG Opposition dated Sep. 9, 2021, D1a (Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages).

EP3337467: Sandoz AG Opposition dated Sep. 9, 2021, D2 (Berlin J, et al., "A Phase 1 Dose-Escalation Study of Veliparib with Bimonthly FOLFIRI in Patients with Advanced Solid Tumors," J Clin Oncol. 32(15) Suppl:2574 (2014), 4 pages).

EP3337467: Sandoz AG Opposition dated Sep. 9, 2021, D3 (Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014)).

EP3337467: Sandoz AG Opposition dated Sep. 9, 2021, D4 (Neijzen R, et al., "Irinophore C™, a Lipid Nanoparticle Formulation of Irinotecan, Improves Vascular Function, Increases the Delivery of Sequentially Administered 5-FU in HT-29 Tumors, and Controls Tumor Growth in Patient Derived Xenografts of Colon Cancer," J Control Release. 199:72-83 (2015), Epub 2014).

EP3337467: Sandoz AG Opposition dated Sep. 9, 2021, D5 (Clinical Trials Identifier NCT01770353: May 5, 2015 update submitted, "A Pilot Study in Patients Treated with MM-398 to Determine Tumor Drug Levels and to Evaluate the Feasibility of Ferumoxytol Magnetic Resonance Imaging to Measure Tumor Associated Macrophages." 5 pages).

EP3337467: Sandoz AG Opposition dated Sep. 9, 2021, D6 (Shah M, et al., "The Relevance of Drug Sequence in Combination Chemotherapy," Drug Resist Updat. 3(6):335-356 (2000)).

EP3337467: Sandoz AG Opposition dated Sep. 9, 2021, D7 (O'Sullivan C, et al., "Beyond Breast and Ovarian Cancers: PARP Inhibitors for BRCA Mutation-Associated and BRCA-Like Solid Tumors," Front Oncol. 4:42 doi: 10.3389/fonc.2014.00042 (2014), 13 pages).

EP3337467: Sandoz AG Opposition dated Sep. 9, 2021, D8 (Onivyde package insert, revision Oct. 22, 2015, 18 pages).

EP3337467: Sandoz AG Opposition dated Sep. 9, 2021, D9 (Carnevale J and Ko A, "MM-398 (Nanoliposomal Irinotecan): Emergence of a Novel Therapy for the Treatment of Advanced Pancreatic Cancer," Future Oncol. 12(4):453-64 (2016). Epub 2015).

EP3337467: Sandoz AG Opposition dated Sep. 9, 2021, D10 (Clinical Trials Identifier NCT02631733 Dec. 15, 2015 submitted, "A Phase I Study of a Combination of MM-398 and Veliparib in Solid Tumors." 7 pages).

EP3337467: Sandoz AG Opposition dated Sep. 9, 2021, D11 (Koshkaryev A, et al., "Differential Tissue Clearance Results in Improved Therapeutic Index for Irinotecan Liposome Injection (Onivyde) When Combined with the PARP Inhibitor Veliparib in Preclinical Cervical Tumors," In: Proceedings of the 107th Annual Meeting of the American Association for Cancer Research; Apr. 16-20, 2016; Cancer Res. 76(14 Suppl):Abstract nr 2075 (2016), 2 pages).

EP3337467: Sandoz AG Opposition dated Sep. 9, 2021, D12 (Livraghi L, et al., "PARP Inhibitors in the Management of Breast Cancer: Current Data and Future Prospects," BMC Med. 13:188; doi: 10.1186/s12916-015-0425-1 (2015), 16 pages)).

EP3337467: Proprietor's Submission in Response to Oppositions, dated Feb. 3, 2022, including main request and auxiliary requests 1-23, 140 pages.

EP3337467: Proprietor's Submission in Response to Oppositions, dated Feb. 3, 2022, D13 (Written transcript of the presentation associated with D1a: Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," American Society of Clinical Oncology 2011 Meeting), 7 pages).

EP3337467: Proprietor's Submission in Response to Oppositions, dated Feb. 3, 2022, D14 (Shah M, et al., "A Phase I Clinical Trial of the Sequential Combination of Irinotecan Followed by Flavopiridol," Clin Cancer Res. 11(10):3836-45 (2005)).

EP3337467: Proprietor's Submission in Response to Oppositions, dated Feb. 3, 2022, D15 (Sadetzki S, et al., "Childhood Exposure to External Ionising Radiation and Solid Cancer Risk," Br J Cancer. 100(7):1021-25 (2009)).

EP3337467: Proprietor's Submission in Response to Oppositions, dated Feb. 3, 2022, D16 (Practical Medical Oncology Textbook, Eds Russio A, et al., Springer Nature Switzerland AG, Table of Contents, pp. I-XI (2021)).

EP3337467: Proprietor's Submission in Response to Oppositions, dated Feb. 3, 2022, D17 (Camptosar package insert, 2014, 39 pages).

EP2861210: Proprietor's response to opponent's reply to proprietor's grounds of appeal following opposition, dated Jun. 30, 2021, 23 pages.

EP2861210: Proprietor's response to opponent's reply to proprietor's grounds of appeal following opposition, dated Jun. 30, 2021, D37 (Declaration of Carla Schoonderbeek) including D37A (Directive 2001/20/EC of the European Parliament and of the Counsel of Apr. 4, 2001 ("the Clinical Trials Directive" or CTD)), 26 total pages.

EP2861210: Proprietor's response to opponent's reply to proprietor's grounds of appeal following opposition, dated Jun. 30, 2021, D38 (Declaration of Grant H. Castle, Ph.D.) including D38A (European Commission: "Communication from the Commission—Detailed guidance on the request to the competent authorities for authorisation of a clinical trial on a medicinal product for human use, the notification of substantial amendments and the declaration of the end of the trial (CT-1)"), 23 total pages.

EP2861210: Communication of the Board of Appeals, Preliminary Opinion, dated Aug. 9, 2021, 21 pages.

EP2861210: Proprietor Response to the Board of Appeals' Preliminary Opinion, dated Dec. 21, 2021, 12 pages.

EP3266456: EPO Notice of Sandoz AG Opposition dated Feb. 1, 2022, 6 pages.

EP3266456: Sandoz AG Opposition dated Feb. 1, 2022, 23 pages.

EP3266456: EPO Notice of Teva Pharmaceuticals Industries Ltd. Opposition dated Feb. 2, 2022, 6 pages.

EP3266456: Teva Pharmaceutical Industries Ltd. Opposition dated Feb. 2, 2022, 12 pages.

EP3266456: EPO Notice of Generics [UK] Limited Opposition dated Feb. 4, 2022, 5 pages.

(56) References Cited

OTHER PUBLICATIONS

EP3266456: Generics [UK] Ltd. Opposition dated Feb. 4, 2022, 13 pages.
EP3266456: EPO Opposition Consolidated List of Citations, Feb. 4, 2022, 2 pages.
EP3266456: Consolidated Opposition dated Feb. 2022, D1 (Chen L, et al., "Phase I Study of Liposome Irinotecan (PEP02) in Combination with Weekly Infusion of 5-FU/LV in Advanced Solid Tumors," J Clin Oncol. 28(15_suppl):abstract e13024 (2010), 2 pages).
EP3266456: Consolidated Opposition dated Feb. 2022, D2 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 2 pages).
EP3266456: Consolidated Opposition dated Feb. 2022, D3 (Ko A, et al., "A Multinational Phase II Study of Liposome Irinotecan (PEP02) for Patients with Gemcitabine-Refractory Metastatic Pancreatic Cancer," J Clin Oncol. 29(4_suppl):Abstract 237 (2011), 2 pages).
EP3266456: Consolidated Opposition dated Feb. 2022, D4 (Chen L, et al., "Phase I Study of Liposome Encapsulated Irinotecan (PEP02) in Advanced Solid Tumor Patients," J Clin Oncol., 26(15_suppl):abstract 2565 (2008), 2 pages).
EP3266456: Consolidated Opposition dated Feb. 2022, D5 ((Clinical Trials Identifier NCT01494506: May 29, 2012 version submitted, "A Randomized, Open Label Phase 3 Study of MM-398 Versus 5-Fluorouracil and Leucovorin in Patients With Metastatic Pancreatic Cancer." 6 pages).
EP3266456: Consolidated Opposition dated Feb. 2022, D5a ((Clinical Trials Identifier NCT01494506: Aug. 8, 2012 submitted, "A Randomized, Open Label Phase 3 Study of MM-398, With or Without 5-Fluorouracil and Leucovorin, Versus 5-Fluorouracil and Leucovorin in Patients with Metastatic Pancreatic Cancer Who Have Failed Prior Gemcitabine-based Therapy." 7 pages).
EP3266456: Consolidated Opposition dated Feb. 2022, D6 ((Clinical Trials Identifier NCT01375816: Jun. 16, 2011 Version submitted, "A Randomized Phase II Study of PEP02 or Irinotecan in Combination with Leucovorin and 5-Fluorouracil in Second Line Therapy of Metastatic Colorectal Cancer." 6 pages).
EP3266456: Consolidated Opposition dated Feb. 2022, D7 (Tsai C, et al., "Nanovector-Based Therapies in Advanced Pancreatic Cancer," J Gastroint Oncol 2(3):185-94 (2011)).
EP3266456: Consolidated Opposition dated Feb. 2022, D8 (Camptosar package insert, 2009, 37 pages).
EP3266456: Consolidated Opposition dated Feb. 2022, D9 (Fusilev package insert, 2008, 7 pages).
EP3266456: Consolidated Opposition dated Feb. 2022, D10 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP3266456: Consolidated Opposition dated Feb. 2022, D11 (Drummond D, et al., "Development of a Highly Active Nanoliposomal Irinotecan Using a Novel Intraliposomal Stabilization Strategy," Cancer Res. 66(6):3271-77 (2006)).
EP3266456: Consolidated Opposition dated Feb. 2022, D12 (Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008)).
EP3266456: Consolidated Opposition dated Feb. 2022, D13 (Venditto V, et al., "Cancer Therapies Utilizing the Camptothecins: A Review of the in Vivo Literature," Mol Pharm. 7(2):307-349 (2010)).
EP3266456: Consolidated Opposition dated Feb. 2022, D14 (Tardi P, et al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006).
EP3266456: Consolidated Opposition dated Feb. 2022, D15 (Opposition Division's decision to revoke EP2861210, dated Aug. 28, 2019, 24 pages).
EP3266456: Consolidated Opposition dated Feb. 2022, D16 (EP2861210: Communication of the Board of Appeals, Preliminary Opinion, dated Aug. 9, 2021, 21 pages).
EP3266456: Consolidated Opposition dated Feb. 2022, D17 (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." 2 pages).
EP3266456: Consolidated Opposition dated Feb. 2022, D18 (Hoskins J, et al., "UGT1A1*28 Genotype and Irinotecan-Induced Neutropenia: Dose Matters," J Natl Cancer Inst. 99(17):1290-95 (2007)).
EP3266456: Consolidated Opposition dated Feb. 2022, D19 (Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011)).
EP3266456: Consolidated Opposition dated Feb. 2022, D20 (Infante J, et al., "Phase 1 and Pharmacokinetic Study of IHL-305 (PEGylated Liposomal Irinotecan) in Patients with Advanced Solid Tumors," Cancer Chemother Pharmacol. 70(5):699-705 (2012)).
EP3266456: Consolidated Opposition dated Feb. 2022, D23 (European Commission Implementing Decision granting marketing authorisation for Onivyde, Oct. 14, 2016, 39 pages).
EP3266456: Consolidated Opposition dated Feb. 2022, D24 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015)).
EP3266456: Consolidated Opposition dated Feb. 2022, D25 (FDA News Release, "FDA Approves New Treatment for Advanced Pancreatic Cancer." http://ww.fda.gov/NewsEvents/Newsroom/PressAnnouncements/ucm468654.htm, Oct. 22, 2015, 3 pages).
EP3266456: Consolidated Opposition dated Feb. 2022, D26 (MHRA Public Assessment Report for 5-Fluorouracil 2006, 60 pages).
EP3266456: Consolidated Opposition dated Feb. 2022, D27 (Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010)).
EP3266456: Consolidated Opposition dated Feb. 2022, D28 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).

\* cited by examiner

| | Control | MM-398 | IRI | NAPOLI | FOLFIRI | NAPOX | FOLFIRINOX |
|---|---|---|---|---|---|---|---|
| Tumor Vol (mean mm³, d35) | 779 | 562 | 753 | 321 | 523 | 255 | 445 |
| TGI (% at d35) | n/a | 27.9% | 3.4% | 58.8% | 32.9% | 67.3% | 42.9% |
| Median Days to 1000mm³ | 50.5 (n=8 of 8) | 68 (6 of 8, 2 est) | 43.5 (8 of 8) | 70 (6 of 8, 2 est) | 56 (7 of 7) | 77 (8 of 8) | 56 (8 of 8) |
| Stable Disease (-30% - +30%) | 0 | 3 | 1 | 2 | 3 | 2 | 4 |
| PR (30%-95% reduction) | 0 | 0 | 0 | 3 | 0 | 4 | 0 |
| CR (≥95% reduction) | 0 | 0 | 0 | 0 | 0 | 0 | 0 |
| Response Rate (≥30% reduction) | 0% | 0% | 0% | 38% | 0% | 50% | 0% |
| Disease Control Rate (ORR + SD) | 0% | 38% | 13% | 63% | 38% | 75% | 50% |
| Median Progression Free Survival (days) | 5 | 12 | 3 | 36.5 | 10 | 47 | 14 |
| Median OS (days) | 80 | 83 | 68 | 100 | 80 | 105 | 80 |

FIG. 8

METHODS FOR TREATING METASTATIC PANCREATIC CANCER USING COMBINATION THERAPIES COMPRISING LIPOSOMAL IRINOTECAN AND OXALIPLATIN

RELATED APPLICATIONS

This application is a continuation of U.S. application Ser. No. 15/241,106, filed Aug. 19, 2016, which claims the benefit of priority to U.S. Provisional Application Nos. 62/208,209, filed Aug. 21, 2015, 62/216,736, filed Sep. 10, 2015, 62/273,244, filed Dec. 30, 2015, 62/281,473, filed Jan. 21, 2016, 62/302,341, filed Mar. 2, 2016, 62/323,245, filed Apr. 15, 2016 and 62/343,313, filed May 31, 2016. The entire contents of which are incorporated herein by reference.

TECHNICAL FIELD

This disclosure relates to novel therapies useful in the treatment of pancreatic cancer, including the use of liposomal irinotecan in combination with 5-fluorouracil and oxaliplatin for the (first line) treatment of patients diagnosed with previously untreated pancreatic cancer.

BACKGROUND

Pancreatic cancer is chemotherapy-resistant, with an extremely poor prognosis. It is the fourth leading cause of cancer death in the United States; the 5-year survival rate is 6%. The incidence of pancreatic cancer has increased during the past several decades and in 2014, an estimated 46,420 patients were diagnosed with pancreatic cancer and 39,590 died. Pancreatic cancer is projected to surpass liver, breast, prostate, and colorectal cancers to become the second-leading cause of cancer-related death by 2030. These statistics reflect the dire nature of the disease and lack of effective therapies. The location of the tumor results in few early symptoms and is often diagnosed at a late stage as a result. The absence of effective screening tools, and a limited understanding of risk factors, means that patients have advanced or metastatic disease at the time of diagnosis. Given the poor prognosis and the low median survival rates of less than one year for patients with metastatic disease, new treatment options are still needed.

Tolerability of multi-drug regimens is important in cancer treatment. The longer the duration of manageable treatment should translate into improved outcome due to longer drug exposure. During the last 5 years, one combination chemotherapy regimen that has emerged as standard of care for first-line treatment of metastatic pancreatic cancer is the combination therapy of 5-fluorouricil (5-FU)/leucovorin (LV)+irinotecan+oxaliplatin (FOLFIRINOX). However, FOLFIRINOX is known to have significant toxicity, and use is limited to patients with better performance status (i.e. ECOG performance score of 0 or 1). With prolonged FOLFIRINOX treatment, oxaliplatin is often discontinued from the regimen due to toxicity. Therefore, if equally effective double regimens can be identified, patients may be able to tolerate prolonged treatment better, and even poor performance status patients may receive benefit. Although the FOLFIRINOX regimen has been recommended by the National Comprehensive Cancer Network (NCCN) as a preferred option for first-line metastatic disease since 2011, there are some concerns about the toxicity associated with FOLFIRINOX. One dose regimen of FOLFIRINOX is 85 mg/m$^2$ oxaliplatin, 180 mg/m$^2$ irinotecan, and fluorouracil at a dose of 400 mg/m$^2$ administered by IV bolus followed by a continuous infusion of 2400 mg/m$^2$. Yet due to toxicity, modified FOLFIRINOX regimens are often used (e.g. elimination of the 5-FU bolus) with unknown effects on the efficacy and safety of modified schedules.

CPT-11 is irinotecan hydrochloride trihydrate, marketed as Camptosar® in the United States. MM-398 is a liposomal irinotecan and is marketed in the U.S. as the FDA-approved product ONIVYDE® in combination with 5-fluorouracil and leucovorin for the treatment of patients with metastatic adenocarcinoma of the pancreas after disease progression following gemcitabine-based therapy.

SUMMARY

Improved antineoplastic therapies for the treatment of pancreatic cancer provide the administration of liposomal irinotecan in combination with oxaliplatin and 5-fluorouracil to patients with previously untreated pancreatic cancer (e.g., untreated metastatic pancreatic adenocarcinoma, or mPAC). The 5-fluorouracil can be administered in combination with leucovorin. The improved antineoplastic therapies can provide improved therapeutic index (e.g., improved toxicity profiles) relative to prior FOLFIRINOX regimens.

A method of treating pancreatic cancer can comprise the administration of an antineoplastic therapy of liposomal irinotecan, oxaliplatin, and 5-fluorouracil once every two weeks to the patient. Optionally, leucovorin can also be administered prior to each administration of the 5-fluorouracil. Each administration of the liposomal irinotecan can be administered in a total dose of 60 mg/m$^2$ liposomal irinotecan (dose based on the amount of irinotecan hydrochloride trihydrate, as defined herein). A total of 2,400 mg/m$^2$ 5-fluorouracil can be administered over hours starting on each day when the liposomal irinotecan is administered. A total of 60, 75 or 85 mg/m$^2$ oxaliplatin can be administered on each day the liposomal irinotecan is administered. A total of 200 mg/m$^2$ (l) leucovorin can be administered prior to each administration of the 5-flurouracil (e.g., optionally administered as 400 mg/m$^2$ of (l+d) leucovorin). The antineoplastic therapy can be administered starting on days 1 and 15 of a 28-day treatment cycle, with the liposomal irinotecan, oxaliplatin, and optionally leucovorin administered on days 1 and 15 and initiating the 46-hour administration of the 5-fluorouracil on days 1 and 15.

The invention is based in part on several pre-clinical discoveries. First, liposomal irinotecan improved anti-tumor activity of the topoisomerase 1 inhibitor SN-38 (an active metabolite of irinotecan) relative to exposure-matched doses of non-liposomal irinotecan. Second, liposomal irinotecan combined with 5-fluorouracil and oxaliplatin consistently improved tumor growth inhibition and survival in mouse xenograft models of pancreatic cancer relative to non-liposomal irinotecan, without exacerbating the baseline toxicities of these agents.

In addition, the invention is based in part on the discovery that the administration of a dose of mg/m$^2$ liposomal irinotecan was not well tolerated in humans when administered in combination with 60 mg/m$^2$ oxaliplatin, 2400 mg/m$^2$ 5-fluorouracil and 400 mg/m$^2$ (l+d) leucovorin. Accordingly, preferred methods of treating (previously untreated) pancreatic cancer provide for the administration of a human-tolerated antineoplastic therapy once every two weeks, where each administration of the antineoplastic therapy is a combination of the antineoplastic agents liposomal irinotecan, oxaliplatin and 5-fluorouracil provided herein. Preferably, the antineoplastic therapy administered once every two weeks consists of: (a) a total dose of 60 mg/m$^2$ liposomal irinotecan (dose based on the amount of irinotecan hydrochloride trihydrate, as defined herein), (b) a total dose of 60-85 mg/m$^2$ oxaliplatin (including, e.g., 60 or 85 mg/m$^2$), and (c) a total of 2,400 mg/m$^2$ 5-fluorouracil optionally administered in combination with leucovorin. Optionally, the combination can include administration of a total of 200 mg/m$^2$ (l) leucovorin (optionally administered as 400 mg/m$^2$ of (l+d) leucovorin), prior to initiating the administration of the 5-fluorouracil. Preferably, no other antineoplastic agent is administered during the antineoplastic therapy, other than amounts of SN-38 produced within the patient from the liposomal irinotecan, after administration of the liposomal irinotecan. For example, the antineoplastic therapy can be administered without (non-liposomal) CPT-11 irinotecan. Preferably, the liposomal irinotecan, oxaliplatin, and (optionally) leucovorin are consecutively administered as separate infusions on a single (first) day and the 5-fluorouracil is administered starting on the first day after the administration of the leucovorin (if administered) and continuing into the following day (e.g., over a total of 46 hours).

BRIEF DESCRIPTION OF THE DRAWINGS

FIG. 8 is a table showing the results obtained from a patient-derived xenograft (PDX #19015) pancreatic cancer mouse efficacy model after treatment with MM-398 liposomal irinotecan alone, non-liposomal irinotecan alone (monotherapy), MM-398 liposomal irinotecan in combination with 5FU (NAPOLI, double therapy), MM-398 liposomal irinotecan in combination with 5FU+oxaliplatin (NAPOX, triple therapy) and non-liposomal irinotecan combined with oxaliplatin and 5-fluorouracil (FOLFIRINOX).

DETAILED DESCRIPTION

Unless otherwise indicated, the dose of liposomal irinotecan or irinotecan liposome as recited herein refers to the amount of irinotecan hydrochloride trihydrate providing an amount of irinotecan encapsulated in the liposome of the liposomal irinotecan or irinotecan liposome. For example, a dose of 60 mg/m$^2$ liposomal irinotecan refers to an amount of the liposomal irinotecan providing the same amount of liposome encapsulated irinotecan that is present in 60 mg/m$^2$ of irinotecan hydrochloride trihydrate, and is equivalent to a dose of about 50 mg/m$^2$ of liposomal irinotecan based on the amount of the irinotecan free base encapsulated in the liposomal irinotecan.

As used herein, unless otherwise indicated, the term "nal-IRI" (nanoliposomal irinotecan) and "MM-398" refer to a form of liposomal irinotecan. The term "CPT-11" refers to (non-liposomal) irinotecan hydrochloride trihydrate.

As used herein, "5-FU" and "5FU" and used interchangeably and refer to 5-fluorouracil.

All cited documents are incorporated herein by reference.

Figure 1A:
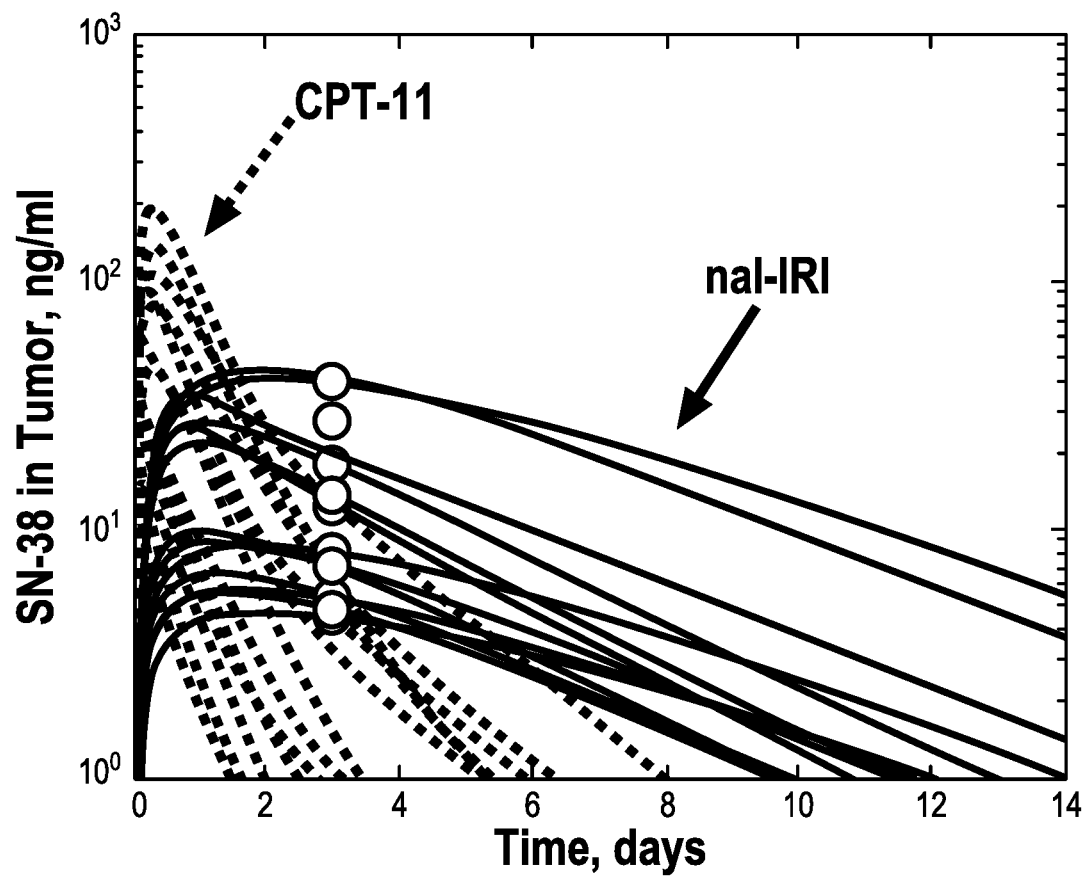
FIG. 1A is a graph showing the simulated levels of the active irinotecan metabolite SN-38 over time based on liposomal irinotecan human clinical biopsy data and human clinical trial data.
Figure 1B:
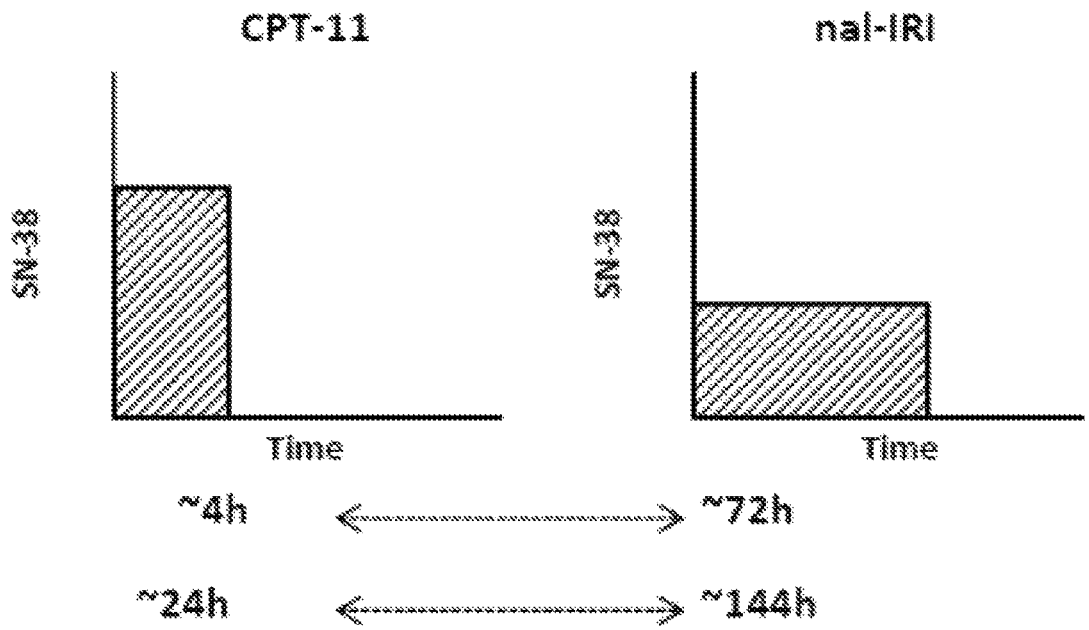
FIG. 1B is a schematic showing how the tumor exposure of SN-38 over time observed with liposomal irinotecan (MM-398) is prolonged compared to SN-38 tumor exposure from non-liposomal irinotecan (CPT-11).
Figure 1C:
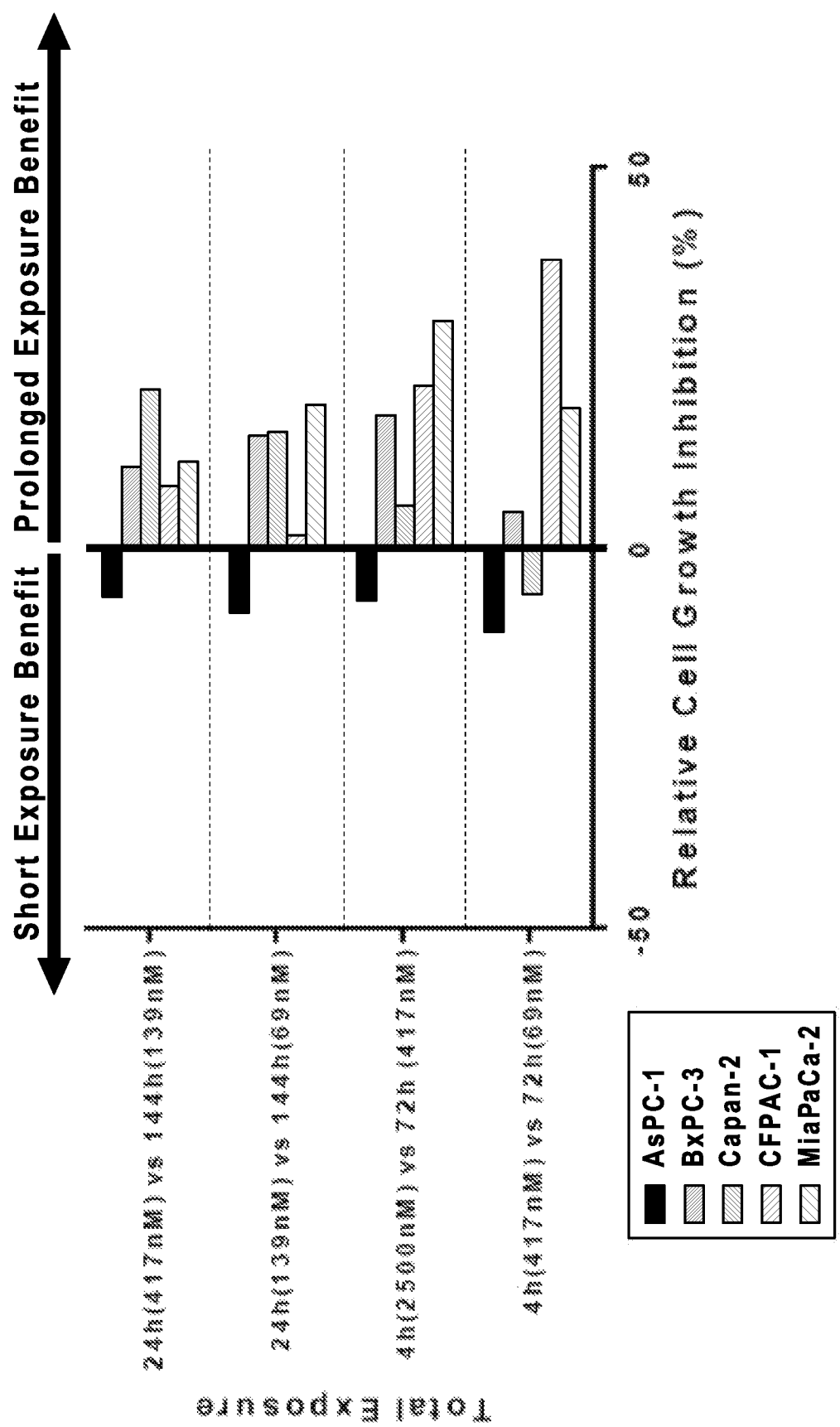
FIG. 1C is a graph showing the percent relative cell growth inhibition of SN-38 based on various times of total SN-38 cell exposure for 5 different cell lines.
Figure 1D:
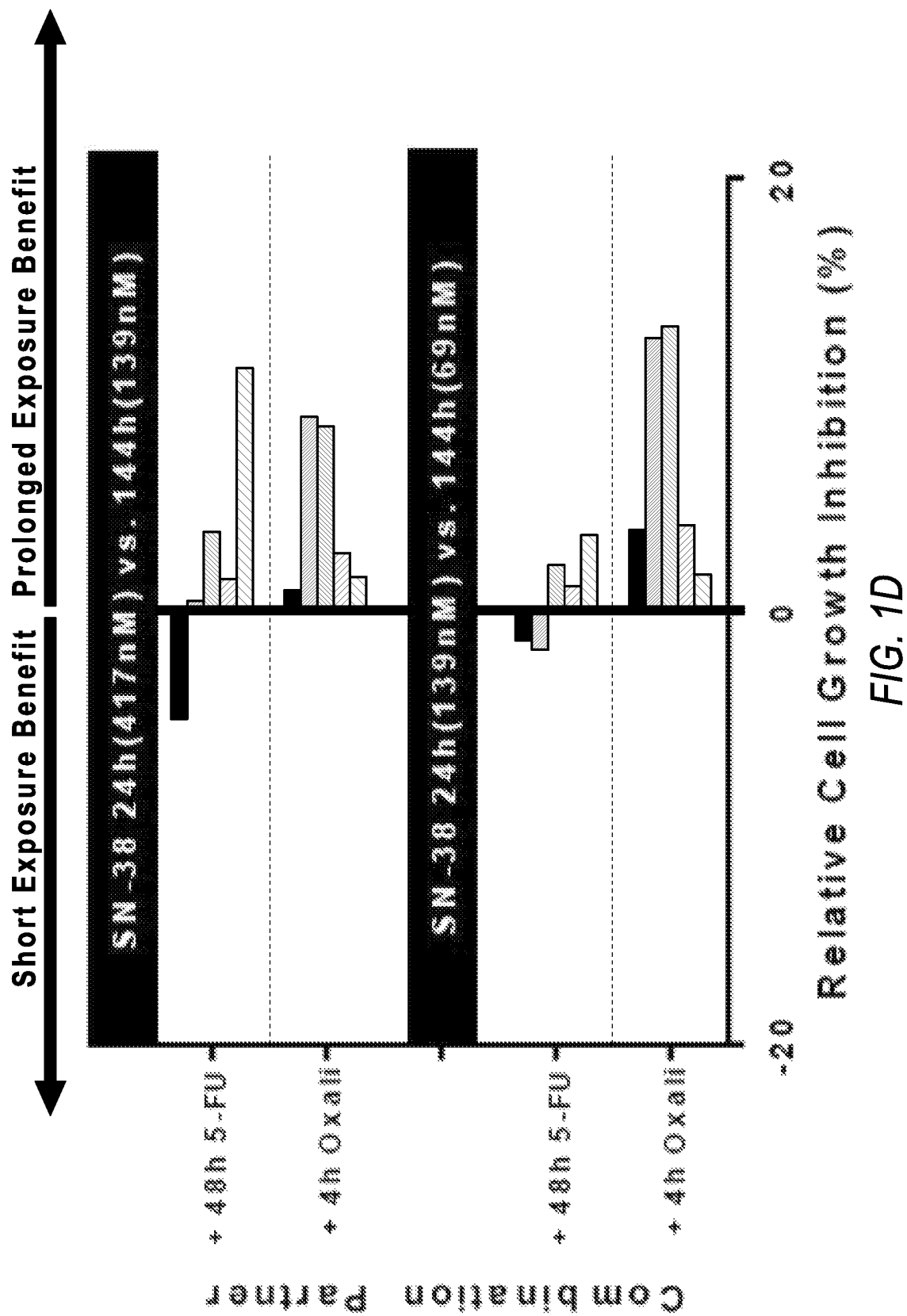
FIG. 1D is a graph showing the percent relative cell growth inhibition of the cell lines tested in FIG. 1C at different exposure times (4 hours or 48 hours) for different combinations of SN-38 with 5-fluorouracil (5-FU) or oxaliplatin (oxali).

Using pancreatic cancer cell lines (Example 1), we demonstrated enhanced cell death when liposomal irinotecan treatment is simulated using prolonged exposure of SN-38 (the active metabolite of irinotecan) in combination with 5-FU and oxaliplatin. FIG. 1 shows that prolonged exposure of SN-38 simulates MM-398 treatment in vitro. Referring to FIG. 1A, MM-398 treatment results in prolonged tumor exposure to the active metabolite, SN-38, compared to non-liposomal irinotecan (CPT-11). Referring to FIG. 1B, prolonged low-dose exposure of SN-38 mimics MM-398 tumor delivery in vitro. Referring to FIG. 1C, prolonged low-dose exposure resulted in greater cell growth inhibition in multiple pancreatic cancer cell lines. The graph comprises four sections, and for each section the cell line data is presented with AsPC-1 data at the top, followed next by BxPC-3, Capan-2, CFPAC-1, and finally MaPaCa-2 on the bottom. Referring to FIG. 1D, the benefit of prolonged exposure to low concentrations of SN-38 was also observed when combined with 5-FU (20.7 mM for 48 h) or oxaliplatin (12.3 mM for 4 h). Both combinations also increased sensitivity of resistance cell lines to prolonged low-dose SN-38.

Figure 2A:
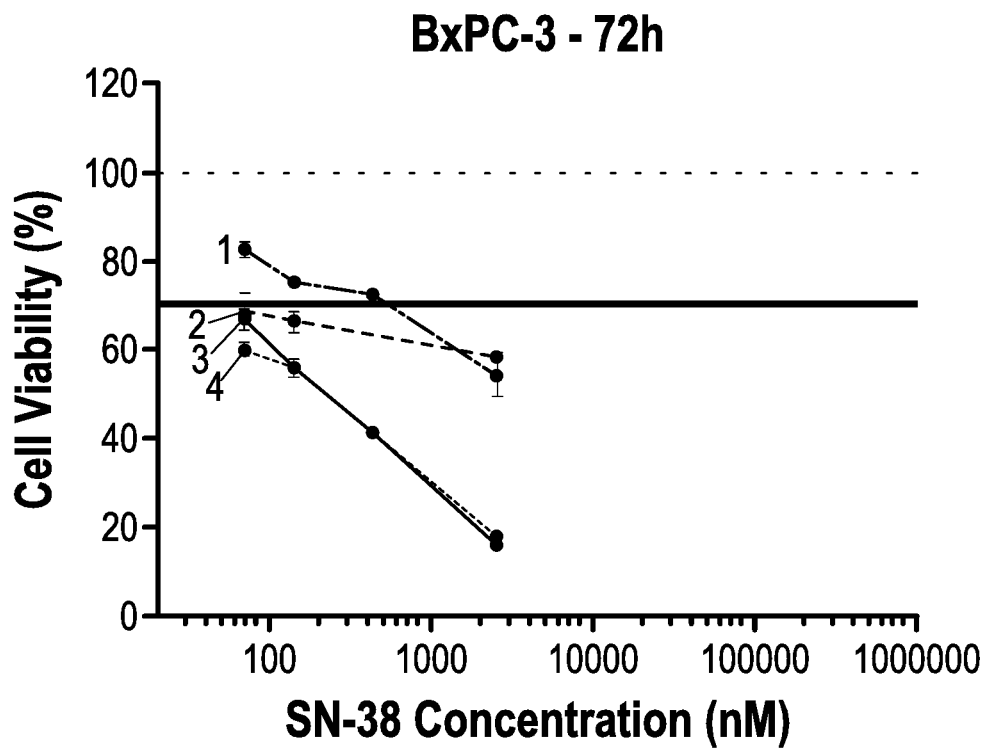
FIG. 2A is a graph showing the cell viability as a function of SN-38 exposure for BxPC-3 pancreatic cancer cells.
Figure 2B:
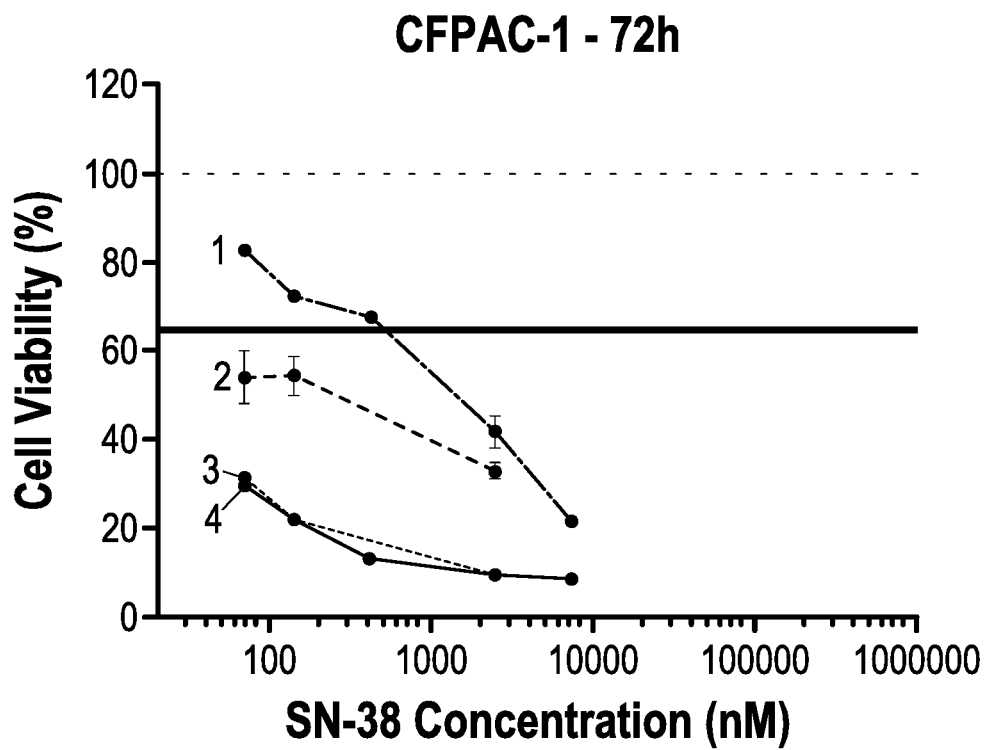
FIG. 2B is a graph showing the cell viability as a function of SN-38 exposure for CFPAC-1 pancreatic cancer cells.

FIG. 2 is two line graphs that depict cell viability following treatment with SN-38 as a single agent or the combination of SN-38 and oxaliplatin. BxPC-3 (FIG. 2A) or CFPAC-1 (FIG. 2B) cells were treated for 4 h or 72 h, washed and then incubated for an additional 24 h or 144 h with fresh media, following which cell viability was assessed. The data traces are labeled "1" (SN-38 alone for four hours followed by a 24 hour incubation; "2" SN-38+oxaliplatin for four hours followed by a 24 hour incubation; "3" SN-38 alone for 72 hours followed by a 144 hour incubation; and "4" SN-38+oxaliplatin for 72 hours followed by a 144 hour incubation. Treatment of the cells with a combination of SN-38 and oxaliplatin decreased the IC-50 when cells were treated for 4 h only as compared to treatment with single agents in both cell lines tested.

Testing of cell line-derived and patient-derived xenograft models of pancreatic cancer in Example 2 demonstrated improved anti-tumor activity of liposomal irinotecan relative to exposure-matched doses of non-liposomal irinotecan. In the mouse animal studies in Example 2, a dose of "x" mg/kg liposomal irinotecan provides about the same exposure to the topoisomerase 1 inhibitor (irinotecan and/or SN-38) as a dose of "5x" non-liposomal irinotecan (CPT-11). The liposomal irinotecan consistently improved tumor growth inhibition and survival relative to non-liposomal irinotecan in preclinical models, both as a monotherapy and in combination with 5-FU and oxaliplatin. The addition of MM-398 to 5-FU and/or oxaliplatin did not exacerbate the baseline toxicities of these agents, including weight loss and neutropenia, and tolerability could be further improved by delaying the administration of oxaliplatin to 1 day post-MM-398. These findings illustrate the therapeutic potential of liposomal irinotecan in combination with 5-FU/LV and oxaliplatin and support an ongoing Phase 2 trial (NCT02551991) of this triplet regimen in first-line PDAC (Example 2).

An animal model of the FOLFIRINOX regimen was tested against the MM-398+5-FU/LV+oxaliplatin regimen in a pancreatic tumor xenograft mouse model. Liposomal irinotecan (MM-398) performed better than conventional (non-liposomal) irinotecan (CPT-11) at equivalent exposure doses (5 mg/kg MM-398 vs. 25 mg/kg free IRI) in the BxPC-3 pancreatic xenograft cancer models (Example 2) either alone (e.g., FIG. 3A), or in combination with oxaliplatin and/or 5-FU (e.g., FIG. 3B).

Figure 3A:
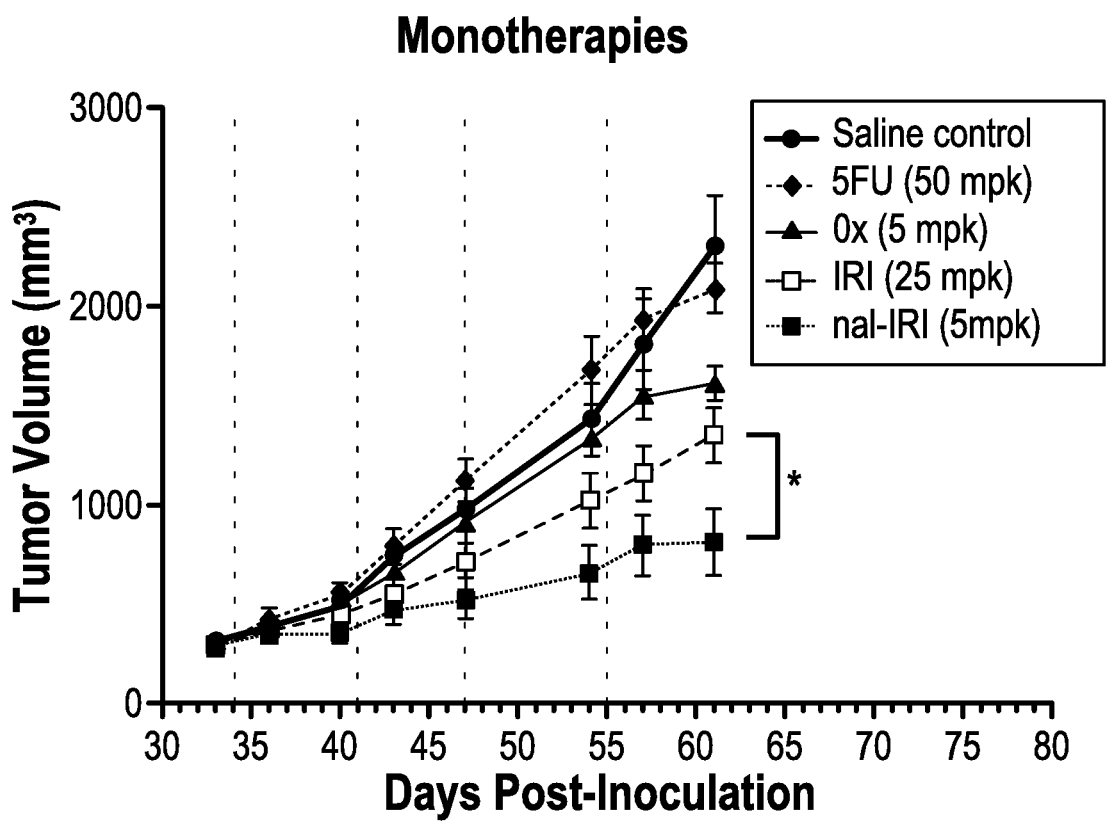
FIG. 3A is a graph showing the tumor volume over time measured in a BxPC-3 pancreatic cancer xenograft mouse efficacy model after treatment with individual antineoplastic agents: including 5-fluorouracil (5FU), oxaliplatin (Ox), (non-liposomal) irinotecan (IRI) and MM-398 liposomal irinotecan (nal-IRI).
Figure 3B:
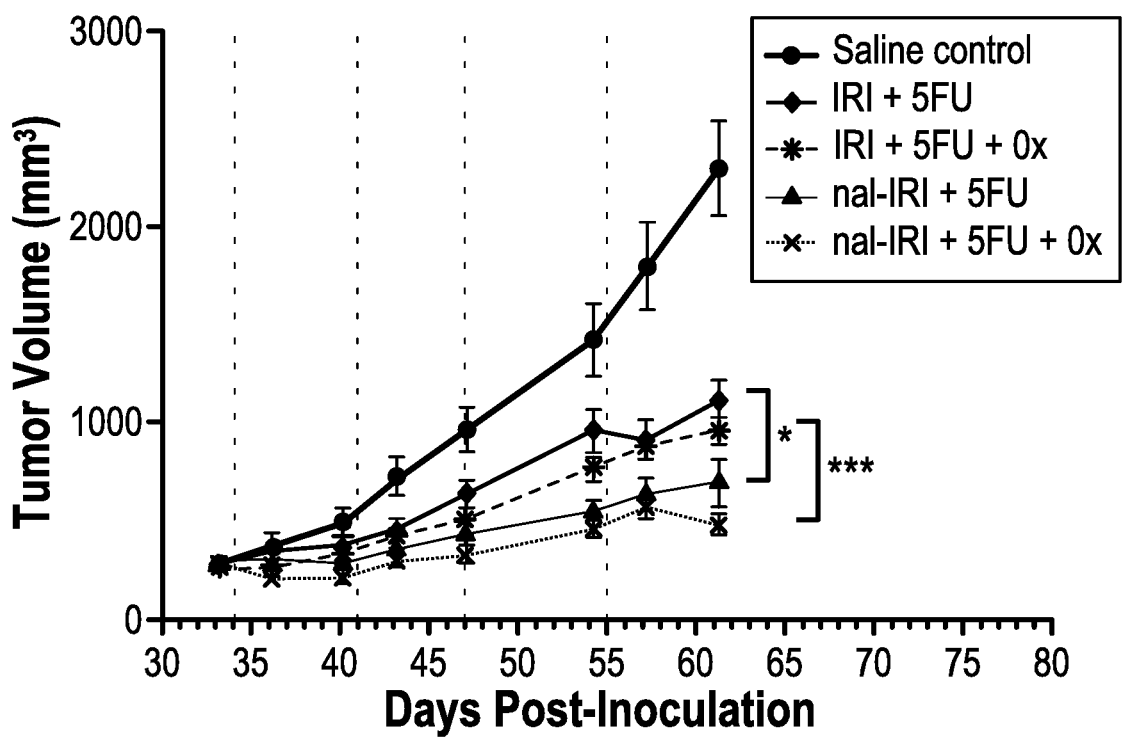
FIG. 3B is a graph showing the tumor volume over time measured in a BxPC-3 pancreatic cancer xenograft mouse efficacy model after treatment with various combinations of antineoplastic agents: (non-liposomal) irinotecan (IRI) and 5FU; (non-liposomal)irinotecan (IRI), oxaliplatin and 5FU; MM-398 liposomal irinotecan (nal-IRI) and 5FU; and 398 liposomal irinotecan (nal-IRI), oxaliplatin and 5FU.

In the mouse model tested in Example 2, efficacy of MM-398 in a 5-FU insensitive pancreatic cancer model (BxPC-3) was evaluated. Cancer cells were implanted subcutaneously in mice; when tumors were well established and had reached mean volumes of 300 mm$^3$, IV treatment with free irinotecan (IRI), MM-398, 5-FU, oxaliplatin (Ox) or control was initiated. Doses are indicated above for each treatment, and were given weekly ×4 weeks, at time points indicated by dashed lines on graphs. FIG. 3A depicts a line graph representing tumor growth after treatment with various individual treatment agents. FIG. 3B depicts a line graph representing tumor growth after treatment with various combinations of treatment agents.

Efficacy of MM-398 in a 5-FU insensitive pancreatic cancer model (BxPC-3). Cancer cells were implanted subcutaneously in mice; when tumors were well established and had reached mean volumes of 300 mm$^3$, IV treatment with doublet or triplet regimens containing either IRI or MM-398 in combination with oxaliplatin and/or 5-FU was initiated. Doses are indicated above for each treatment, and were given weekly ×4 weeks, at time points indicated by dashed lines on graphs. In comparison to FIG. 4A (discussed below), doublet or triplet regimens containing either IRI or MM-398 in combination with oxaliplatin and/or 5-FU demonstrate that the MM-398-containing doublet and triplet regimens inhibit tumor growth significantly better than the IRI-containing regimens. The addition of oxaliplatin to the doublet combinations of FOLFIRI or MM-398+5-FU/LV causes a slight increase in tumor growth inhibition (FIG. 3B: compare IRI+5FU to IRI+5FU+Ox for FOLFIRI vs. FOLFIRINOX; compare nal-IRI+5FU to nal-IRI+5FU+Ox for MM-398+5-FU/LV vs. MM-398+5-FU/LV+Ox). However, comparison of FOLFIRI versus the MM-398+5-FU/LV doublet (IRI+5FU vs. nal-IRI+5FU), and FOLFIRINOX vs. the MM-398+5-FU/LV+Ox triplet (IRI+5FU+Ox vs. nal-IRI+5FU+Ox), demonstrates significantly more tumor growth inhibition with the MM-398-containing regimens. Further, the MM-398-containing doublet regimen performed better than the FOLFIRINOX triplet (nal-IRI+5FU vs. IRI+5FU+Ox), owing to the improved efficacy of MM-398 compared to conventional irinotecan.

Figure 4A:
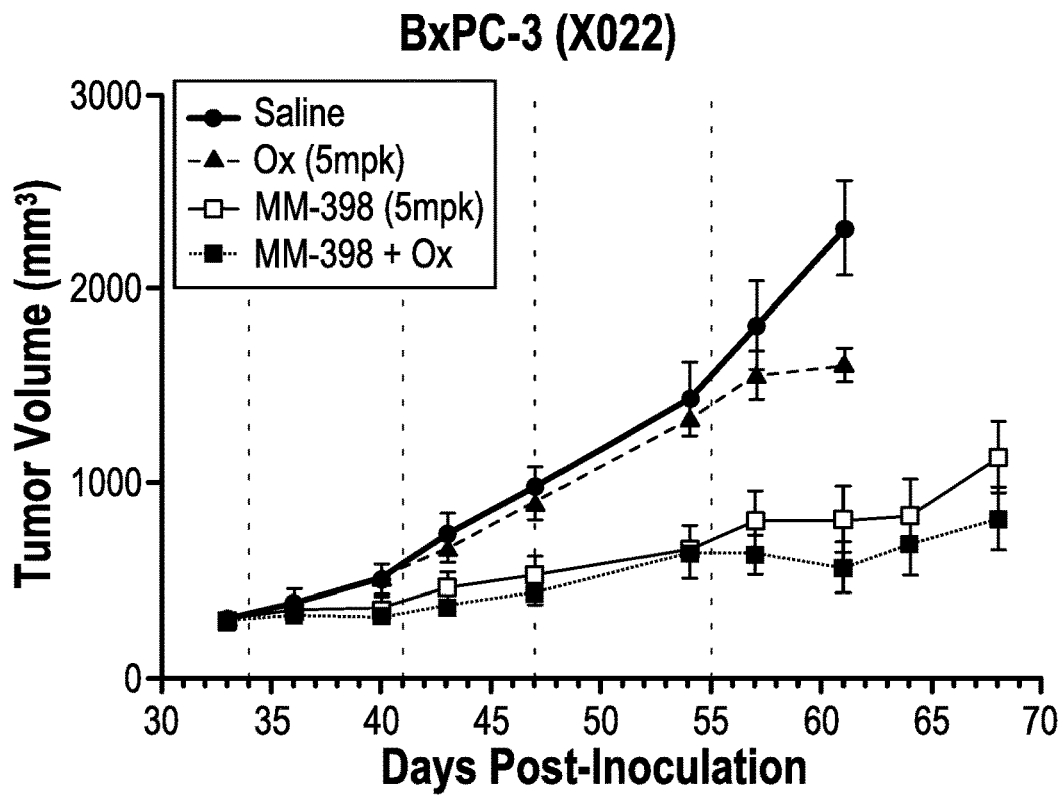
FIG. 4A is a graph showing the tumor volume over time measured in a BxPC-3 pancreatic cancer xenograft mouse efficacy model after treatment with oxaliplatin monotherapy, MM-398 liposomal irinotecan (nal-IRI) monotherapy, and a combination of MM-398 liposomal irinotecan (nal-IRI) and oxaliplatin (Ox).
Figure 4B:
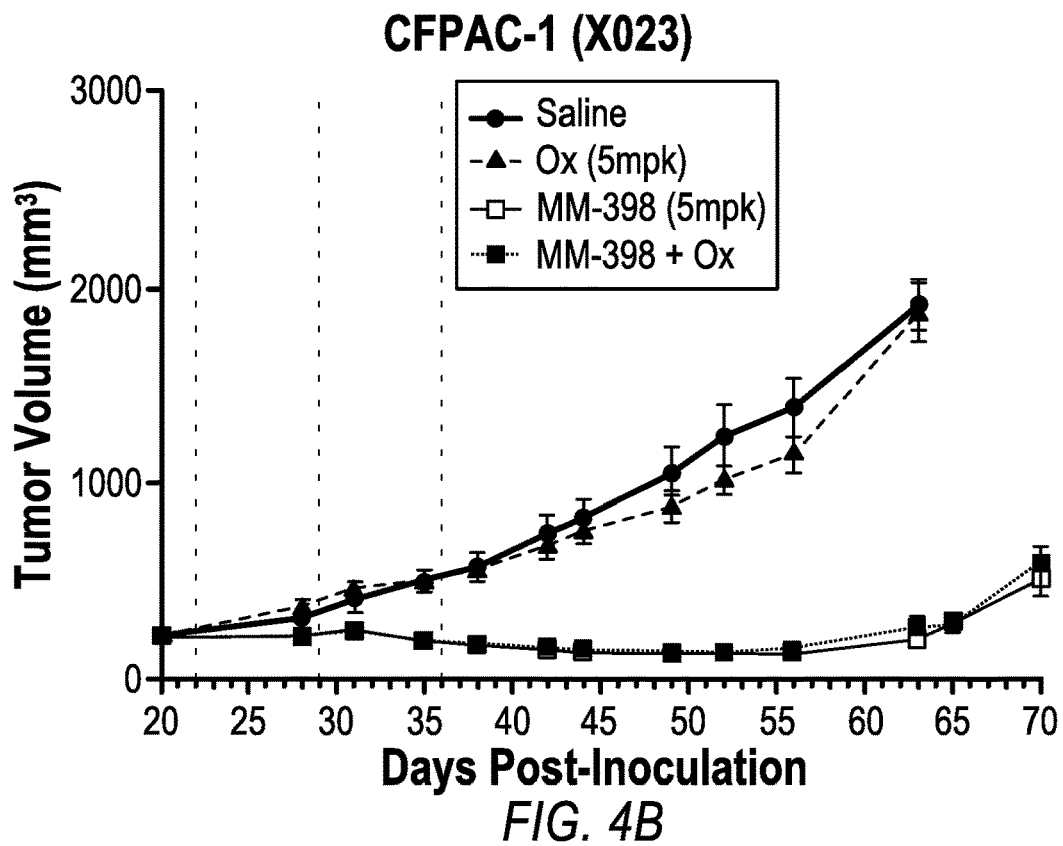
FIG. 4B is a graph showing the tumor volume over time measured in a CFPAC-1 pancreatic cancer xenograft mouse efficacy model after treatment with oxaliplatin monotherapy, MM-398 liposomal irinotecan (nal-IRI) monotherapy, and a combination of MM-398 liposomal irinotecan (nal-IRI) and oxaliplatin (Ox).

Single agent results of the individual treatments are shown in FIG. 4A, demonstrating that MM-398 significantly inhibits tumor growth compared to free IRI. FIGS. 4A and 4B are two line graphs depicting tumor growth in mouse xenograft models following intravenous treatment with saline (control, circles), 5 mg/kg oxaliplatin (triangles), 5 mg/kg MM-398 (light squares), or the combination of BxPC-3 (FIG. 4A) or CFPAC-1 (FIG. 4B) tumor cells were implanted subcutaneously in mice. Treatment was initiated after tumors were well established, and treatments were given four times (BxPC-3 model) or three times (CFPAC-1 model) at the time points indicated by dashed lines on the graphs.

FIGS. 5A, 5B, 5C, 6A, 6B, 6C, 6D and 7 are graphs obtained by measuring tumor growth inhibition in mice following various treatments. Tumor cells (PDX model 19015) were implanted subcutaneously in mice. When tumors were well-established, and had reached a mean volume of 250 mm$^3$, IV treatment with MM-398 or non-liposomal irinotecan alone, or in combination with 5-FU or 5-FU+oxaliplatin, was initiated. Treatment doses are indicated in the figure beside each treatment, and were given 4 times.

Figure 5A:
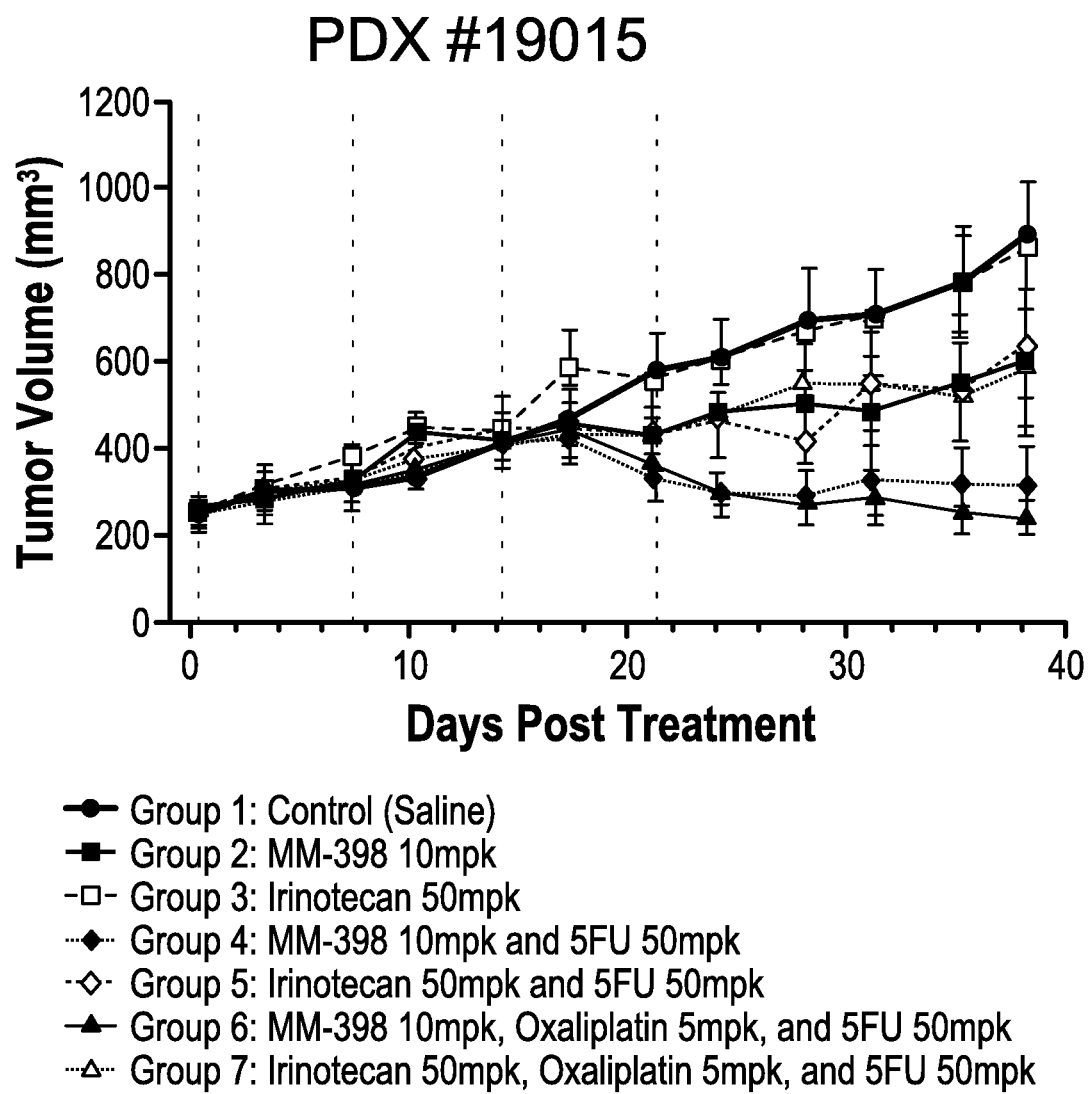
FIG. 5A is a graph showing the tumor volume over time measured in a patient-derived xenograft (PDX #19015) pancreatic cancer mouse efficacy model after treatment with MM-398 liposomal irinotecan (nal-IRI) monotherapy, (non-liposomal) irinotecan monotherapy (irinotecan), and various combination therapies: MM-398 liposomal irinotecan (nal-IRI) and 5-fluorouracil (5FU); (non-liposomal) irinotecan (irinotecan) and 5FU; MM-398 liposomal irinotecan (nal-IRI), oxaliplatin and 5FU; and (non-liposomal) irinotecan, oxaliplatin and 5FU.
Figure 5B:
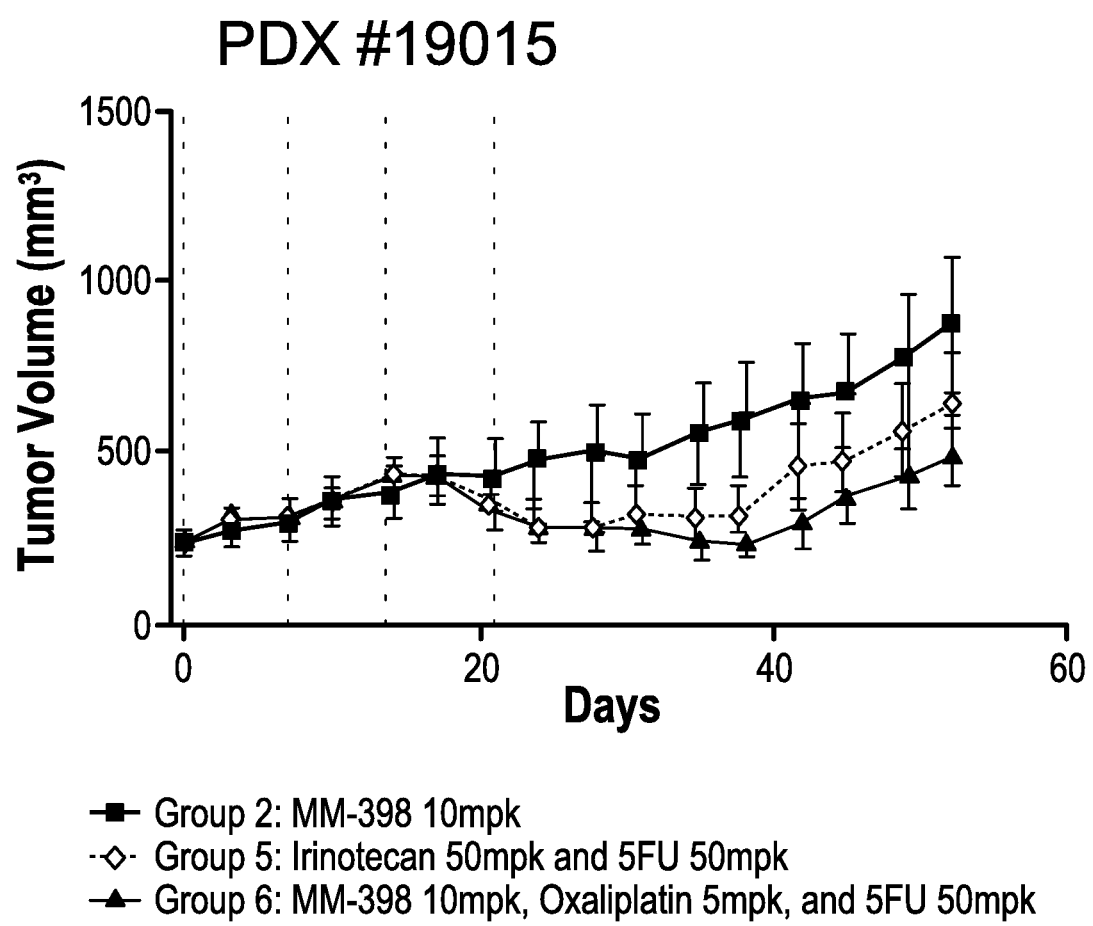
FIG. 5B is a graph showing the tumor volume over time measured in a patient-derived xenograft (PDX #19015) pancreatic cancer mouse efficacy model after treatment with the MM-398 containing combination therapies shown in FIG. 5A: MM-398 liposomal irinotecan (nal-IRI) and 5-fluorouracil (5FU), MM-398 liposomal irinotecan (nal-IRI), oxaliplatin and 5FU; and (non-liposomal) irinotecan, oxaliplatin and 5FU.
Figure 5C:
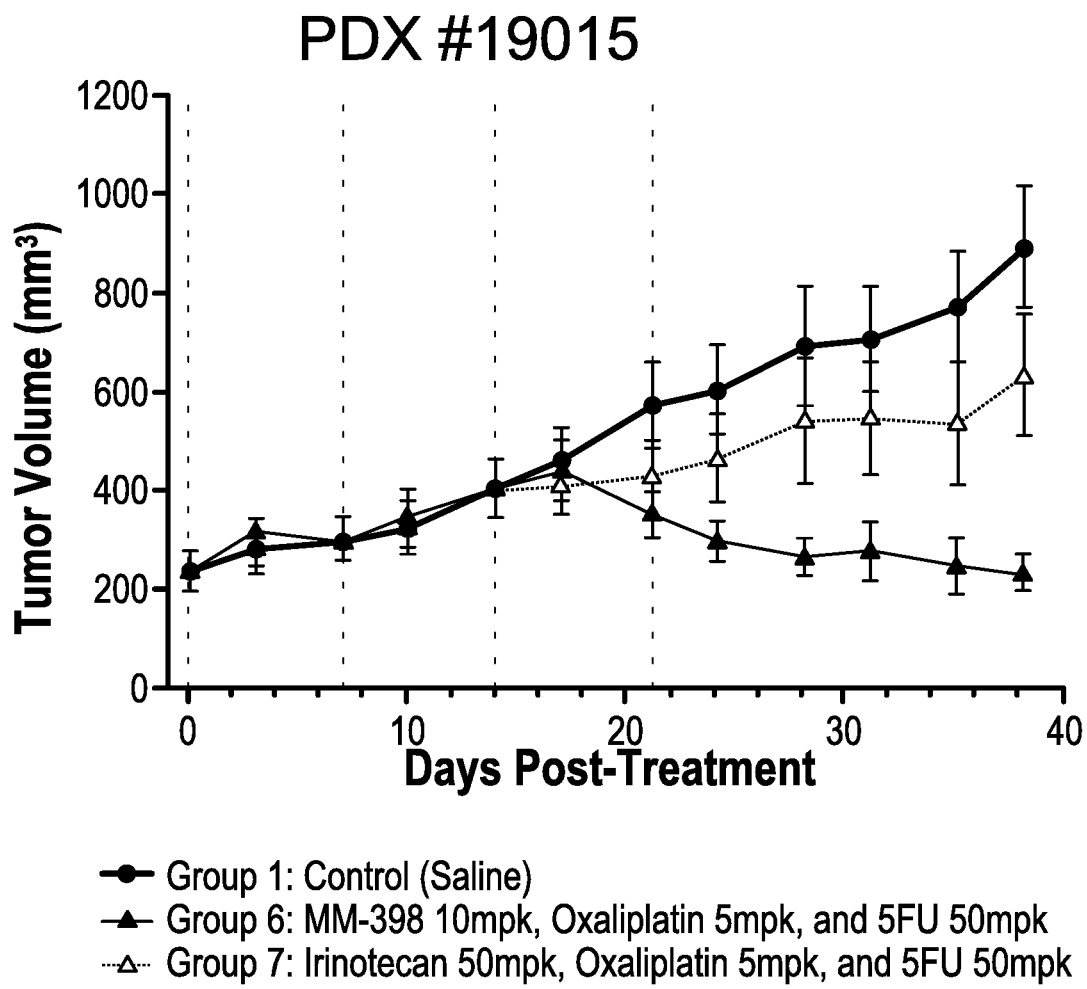
FIG. 5C is a graph showing the tumor volume over time measured in a patient-derived xenograft (PDX #19015) pancreatic cancer mouse efficacy model after treatment with the oxaliplatin containing combination therapies shown in FIG. 5A: MM-398 liposomal irinotecan (nal-IRI), oxaliplatin and 5FU; and (non-liposomal) irinotecan, oxaliplatin and 5FU.

FIGS. 5A-5C are three line graphs depicting tumor growth inhibition in mice following various treatments. Tumor cells, PDX 19015 model, were implanted subcutaneously in mice. When tumors were well-established, and had reached a mean volume of 250 mm$^3$, IV treatment with MM-398 or non-liposomal irinotecan as monotherapy, or in combination with 5-FU and Oxaliplatin, was initiated. Treatment doses are indicated in the legend beside each treatment, and were given four times, at time points indicated by dashed lines on the graphs. The addition of 5-FU to MM-398 or non-liposomal irinotecan significantly improved tumor growth inhibition relative to the respective monotherapies. The addition of oxaliplatin to MM-398+5-FU further improves response by significantly delaying tumor progression as compared to MM-398 monotherapy. The delay in tumor progression was not significant in the group treated with the double therapy of MM-398+5-FU. FIG. 5A is a line graph comprising data from all of the combinations (both those with MM-398 and those with irinotecan), and shows that the combination of MM-398, oxaliplatin, and 5-FU resulted in the most inhibition of tumor growth (lowest line trace), although the combination of MM-398 and 5-FU also inhibited tumor growth (next lowest line). FIG. 5B is a line graph comprising data from the MM-398 combinations only (no irinotecan combinations or control line) for the purpose of comparison. As can be seen in the graph, the triple combination treatment resulted in the most tumor growth inhibition (lowest line), and the double combination of irinotecan and 5-FU (middle line) was better than MM-398 alone (highest line) in inhibiting tumor growth. FIG. 5C is a subset of the same data that allows comparison of the oxaliplatin combinations to the saline control.

Figure 6A:
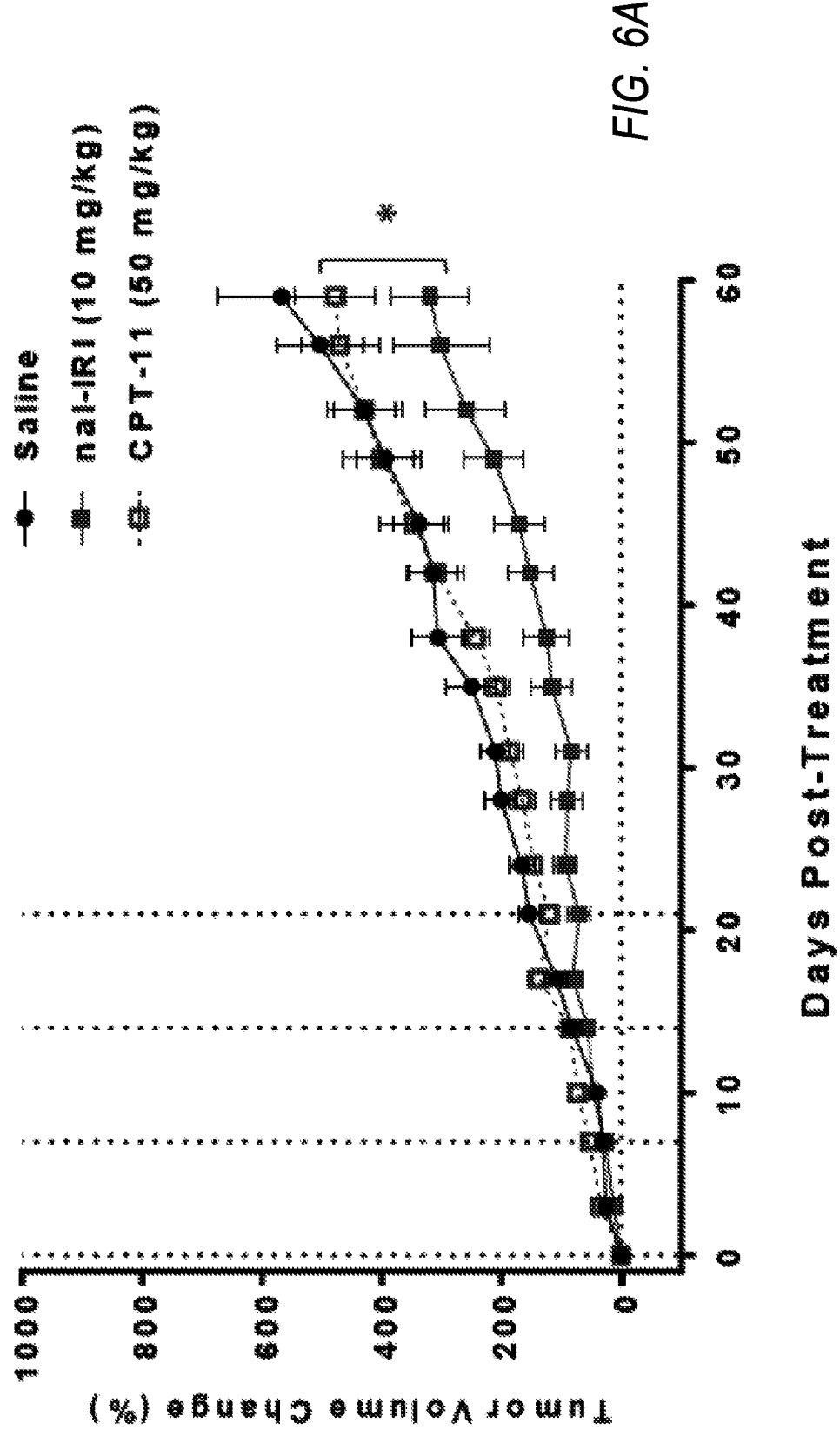
FIG. 6A is a graph showing the percent tumor volume change over time measured in a patient-derived xenograft (PDX #19015) pancreatic cancer mouse efficacy model after treatment with a saline control, MM-398 liposomal irinotecan (nal-IRI) monotherapy, or (non-liposomal) irinotecan monotherapy (irinotecan).
Figure 6B:
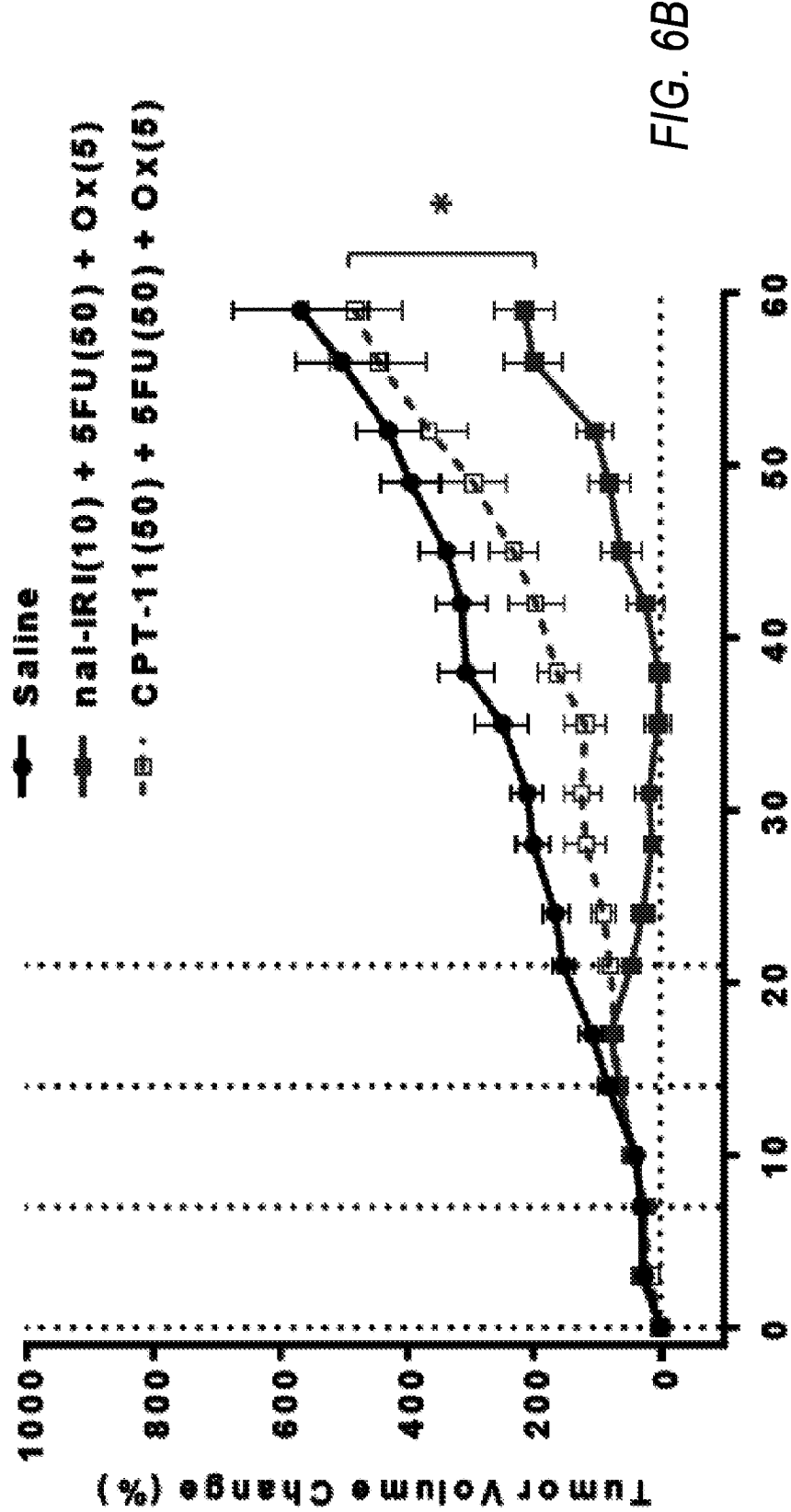
FIG. 6B is a graph showing the percent tumor volume change over time measured in a patient-derived xenograft (PDX #19015) pancreatic cancer mouse efficacy model after treatment with saline control or two oxaliplatin containing combination therapies: MM-398 liposomal irinotecan (nal-IRI), oxaliplatin and 5FU; and (non-liposomal) irinotecan, oxaliplatin and 5FU.
Figure 6C:
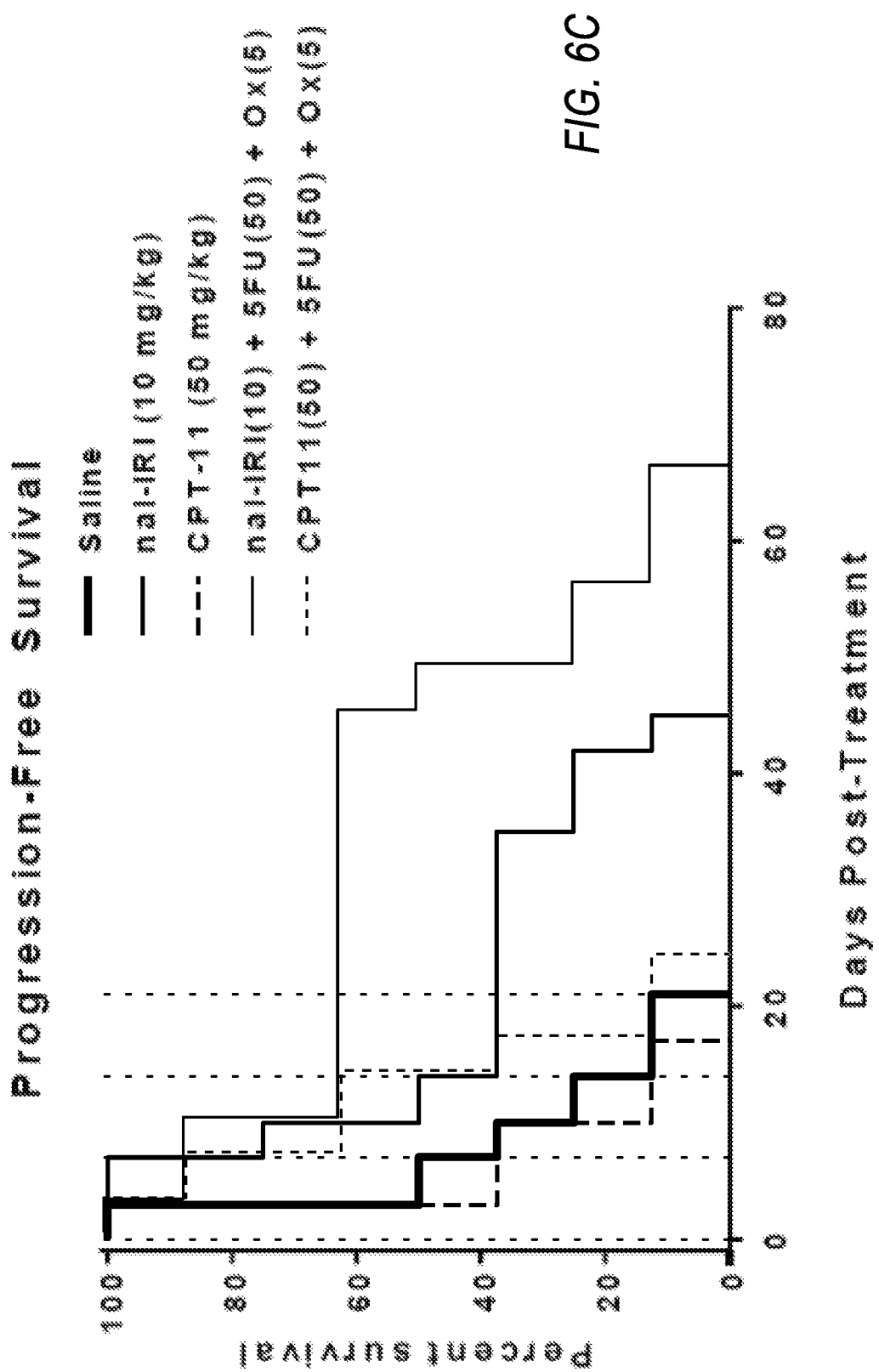
FIG. 6C is a graph of the progression free survival measured in a patient-derived xenograft (PDX #19015) pancreatic cancer mouse efficacy model after treatment with two oxaliplatin containing combination therapies: MM-398 liposomal irinotecan (nal-IRI), oxaliplatin and 5FU; and (non-liposomal) irinotecan, oxaliplatin and 5FU.
Figure 6D:
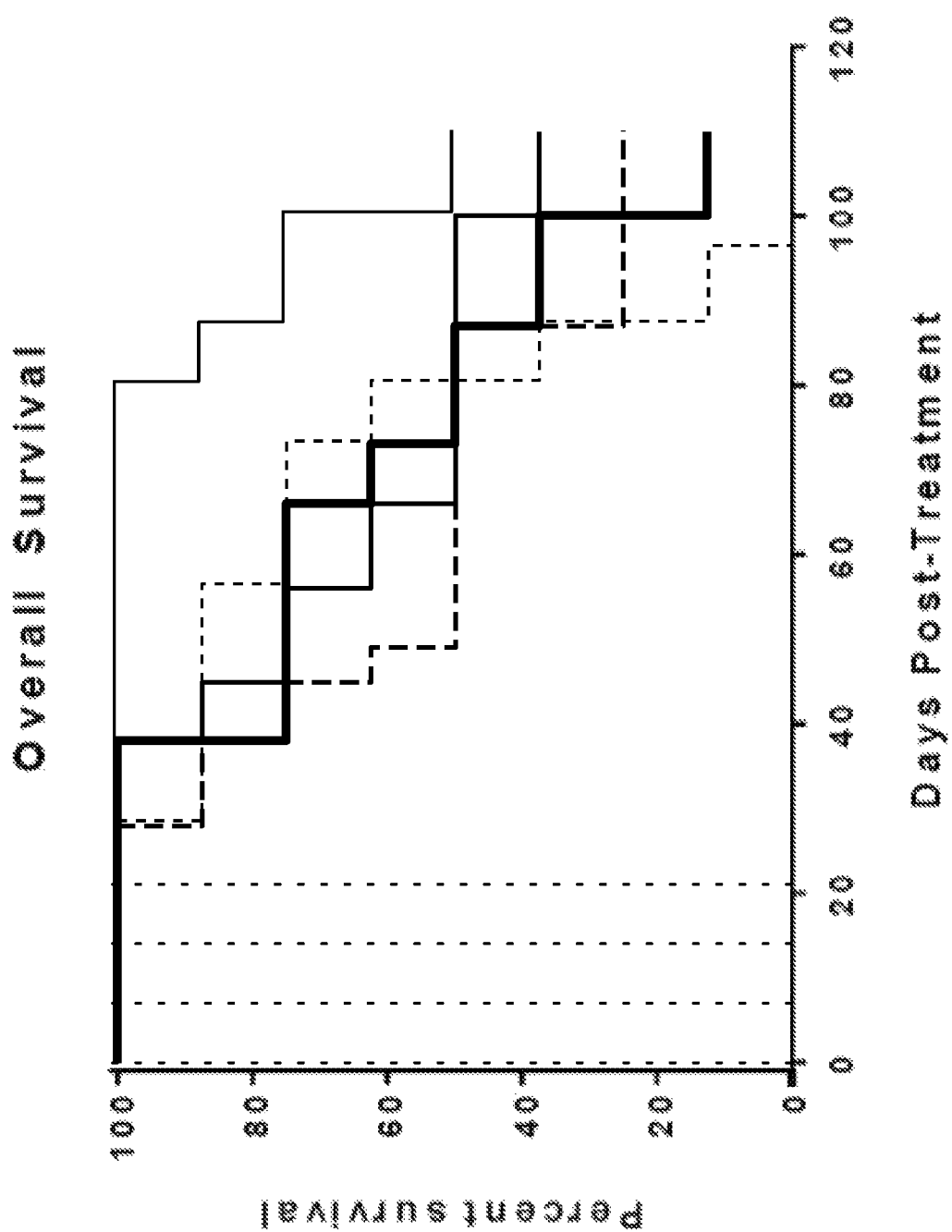
FIG. 6D is a graph of the overall survival measured in a patient-derived xenograft (PDX #19015) pancreatic cancer mouse efficacy model after treatment with two oxaliplatin containing combination therapies: MM-398 liposomal irinotecan (nal-IRI), oxaliplatin and 5FU; and (non-liposomal) irinotecan, oxaliplatin and 5FU.
Figure 7:
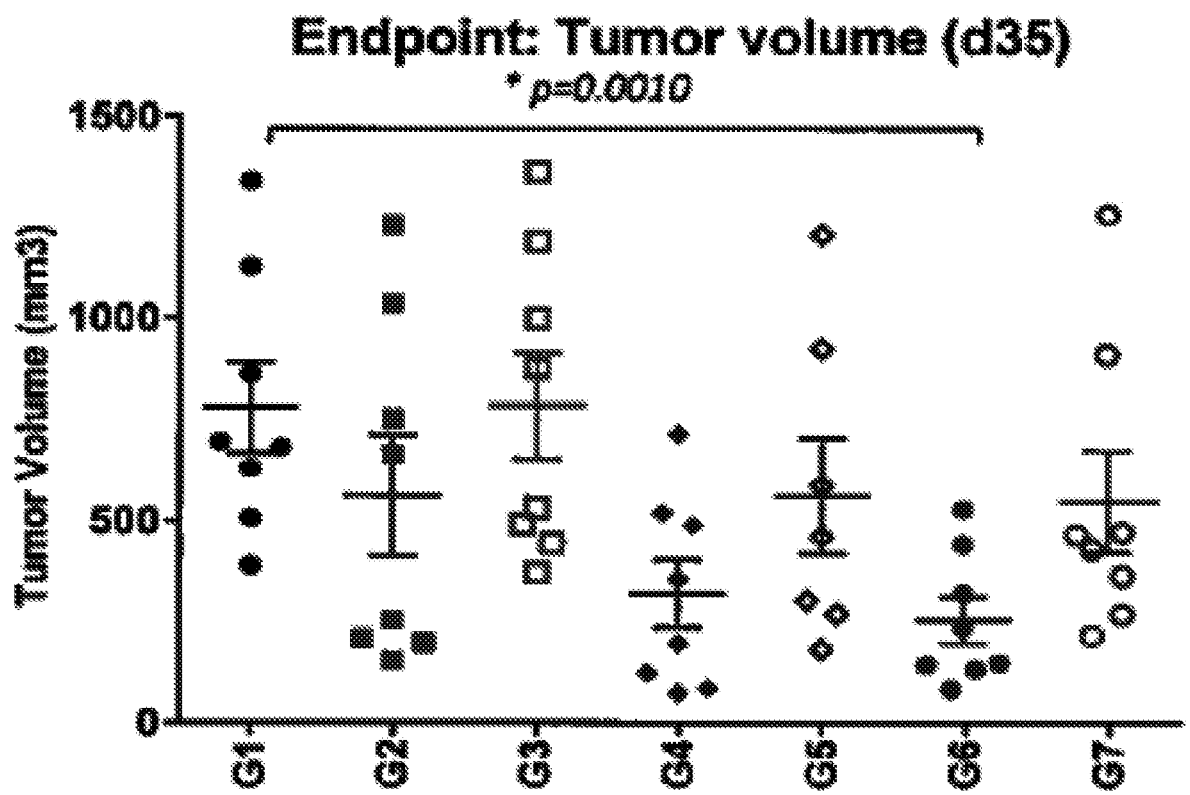
FIG. 7 is a graph showing the tumor volume measured in a patient-derived xenograft (PDX #19015) pancreatic cancer mouse efficacy model after treatment with MM-398 liposomal irinotecan (nal-IRI) monotherapy, (non-liposomal) irinotecan monotherapy (irinotecan), and various combination therapies: MM-398 liposomal irinotecan (nal-IRI) and 5-fluorouracil (5FU); (non-liposomal) irinotecan (irinotecan) and 5FU; MM-398 liposomal irinotecan (nal-IRI), oxaliplatin and 5FU; and (non-liposomal) irinotecan, oxaliplatin and 5FU.

FIG. 6A is a graph showing the percent tumor volume change over time measured in a PDX 19015 pancreatic cancer xenograft mouse efficacy model after treatment with a saline control, MM-398 liposomal irinotecan (MM-398) monotherapy, or (non-liposomal) irinotecan monotherapy (irinotecan). The data in FIG. 6A shows a significantly greater reduction in the percent tumor volume change for administration of 10 mg/kg liposomal irinotecan (MM-398) compared to non-liposomal irinotecan (CPT-11) at 50 mg/kg, each administered on days 0, 7, 14 and 21 followed by observation for a total of about 60 days. FIG. 6B is a graph showing the percent tumor volume change over time measured in a PDX 19015 pancreatic cancer xenograft mouse efficacy model after treatment with saline control or two oxaliplatin containing combination therapies: MM-398 liposomal irinotecan (MM-398), oxaliplatin and 5FU; and (non-liposomal) irinotecan, oxaliplatin and 5FU. Mice receiving the combination of liposomal irinotecan (MM-398, also called MM-398) with 5FU and oxaliplatin on days 0, 7, 14 and 21 showed significantly reduced tumor volume percent change through the observation period of about 60 days, compared to mice receiving the combination of non-liposomal irinotecan (CPT-11) with oxaliplatin and 5-FU on days 0, 7, 14 and 21. Referring to FIG. 6C, the addition of oxaliplatin to MM-398+5-FU significantly improves progression free survival of mice bearing PDX 19015 tumors, as compared to the control group and MM-398 monotherapy. The difference between MM-398+5FU and MM-398 monotherapy is not statistically significant. Referring to FIG. 6D, the addition of 5-FU and oxaliplatin to MM-398 significantly improve overall survival relative to the control group. No benefit of added 5-FU or oxaliplatin was observed with non-liposomal irinotecan. Referring to FIG. 7, the addition of oxaliplatin to MM-398+5-FU significantly delays tumor progression relative to MM-398 monotherapy, as indicated by significantly reduced tumor volume at day 35.

Figure 9:
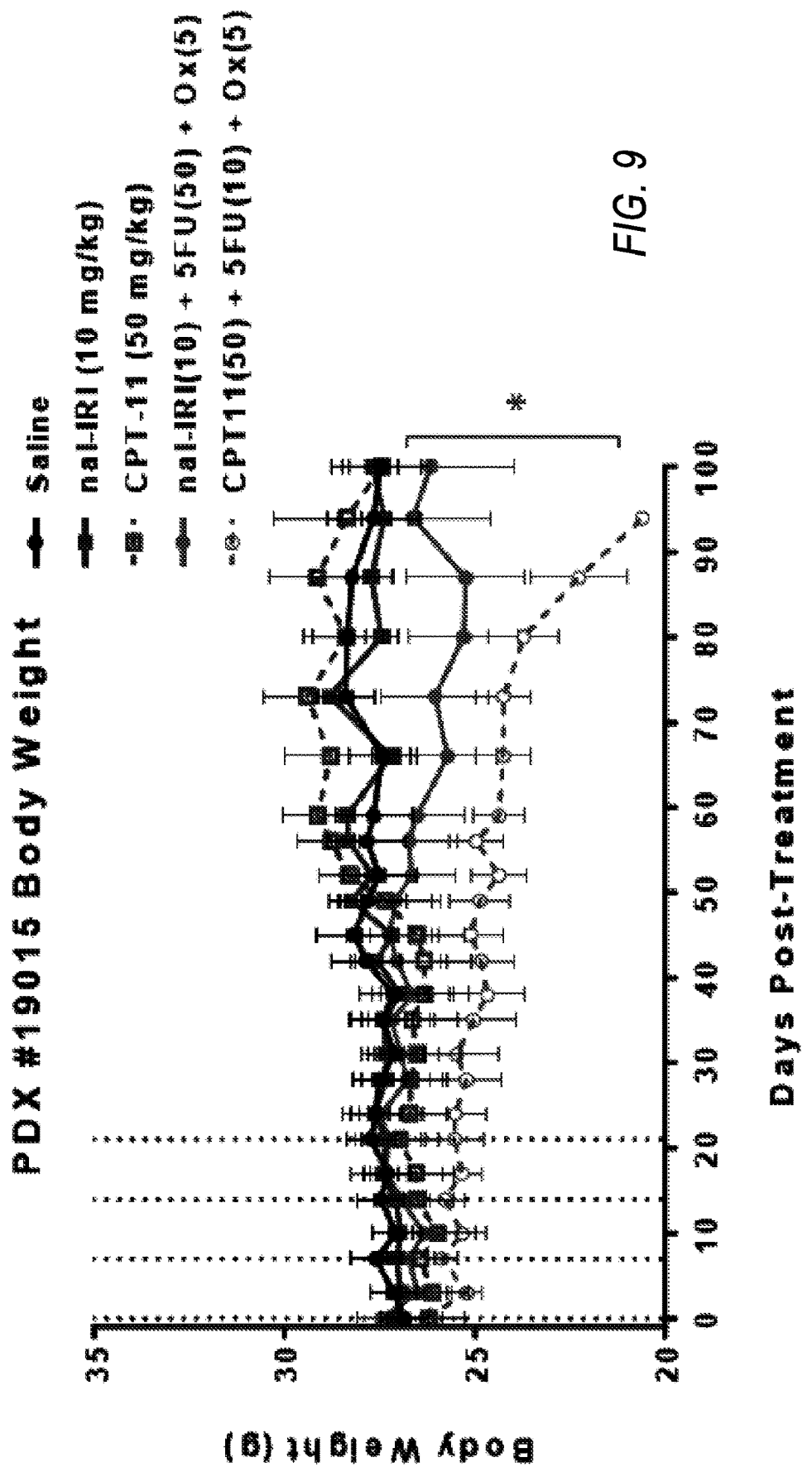
FIG. 9 is a graph showing the tolerability of various therapies in a mouse model, measured by recording the body weight of the mouse after administration of a saline control, liposomal irinotecan (nal-IRI), a combination of nanoliposomal irinotecan, 5-FU and oxaliplatin or a combination of non-liposomal irinotecan (CPT11), 5FU and oxaliplatin on days 0, 7, 14 and 21.

FIG. 8 is a table showing results of tumor growth and survival in mice following various treatments. Tumor cells (PDX 19015 model) were implanted subcutaneously in mice. When tumors were well-established, and had reached a mean volume of 250 mm$^3$, IV treatment with MM-398 or non-liposomal irinotecan alone (monotherapy), or in combination with 5-FU (NAPOLI, double therapy) or 5-FU+oxaliplatin (NAPOX, triple therapy), was initiated. Mice treated with the triple therapy, NAPOX (50%) had the best Overall Response Rate (ORR), as compared to double NAPOLI (38%), or monotherapy MM-398 monotherapy (0%). Further, triple therapy treated mice also had a better Disease Control Rate (DCR): NAPOX (75%), NAPOLI (63%), MM-398 monotherapy (38%), and Progression Free Survival (PFS): NAPOX was 47 days, relative to 36.5 days for NAPOLI and 12 days for MM-398 monotherapy. NAPOX PFS was significantly better than the monotherapy, whereas NAPOLI is not significantly better than the monotherapy. Notably, the combination of liposomal irinotecan with 5FU and oxaliplatin was better tolerated than the combination of an SN-38 exposure-matched dose of non-liposomal irinotecan with 5FU and oxaliplatin in a mouse tolerability study over 100 days. FIG. 9 is a graph showing the body weight of mice after administration of various regimens: a saline control, liposomal irinotecan (MM-398), a combination of nanoliposomal irinotecan, 5-FU and oxaliplatin or a combination of non-liposomal irinotecan (CPT11), 5FU and oxaliplatin. Liposomal irinotecan improved tolerability in a mouse model following repeated dosing in mice relative to non-liposomal irinotecan when combined with 5-FU and oxaliplatin. Significance was determined by ordinary 2-way analysis of variance (ANOVA). The regimens were administered on days 0, 7, 14 and 21 of the study. The administration of 10 mg/kg liposomal irinotecan and the 50 mg/kg dose of non-liposomal free irinotecan (CPT11) provide a comparable dose of SN-38 to tumor cells in the mouse model.

Figure 10A:
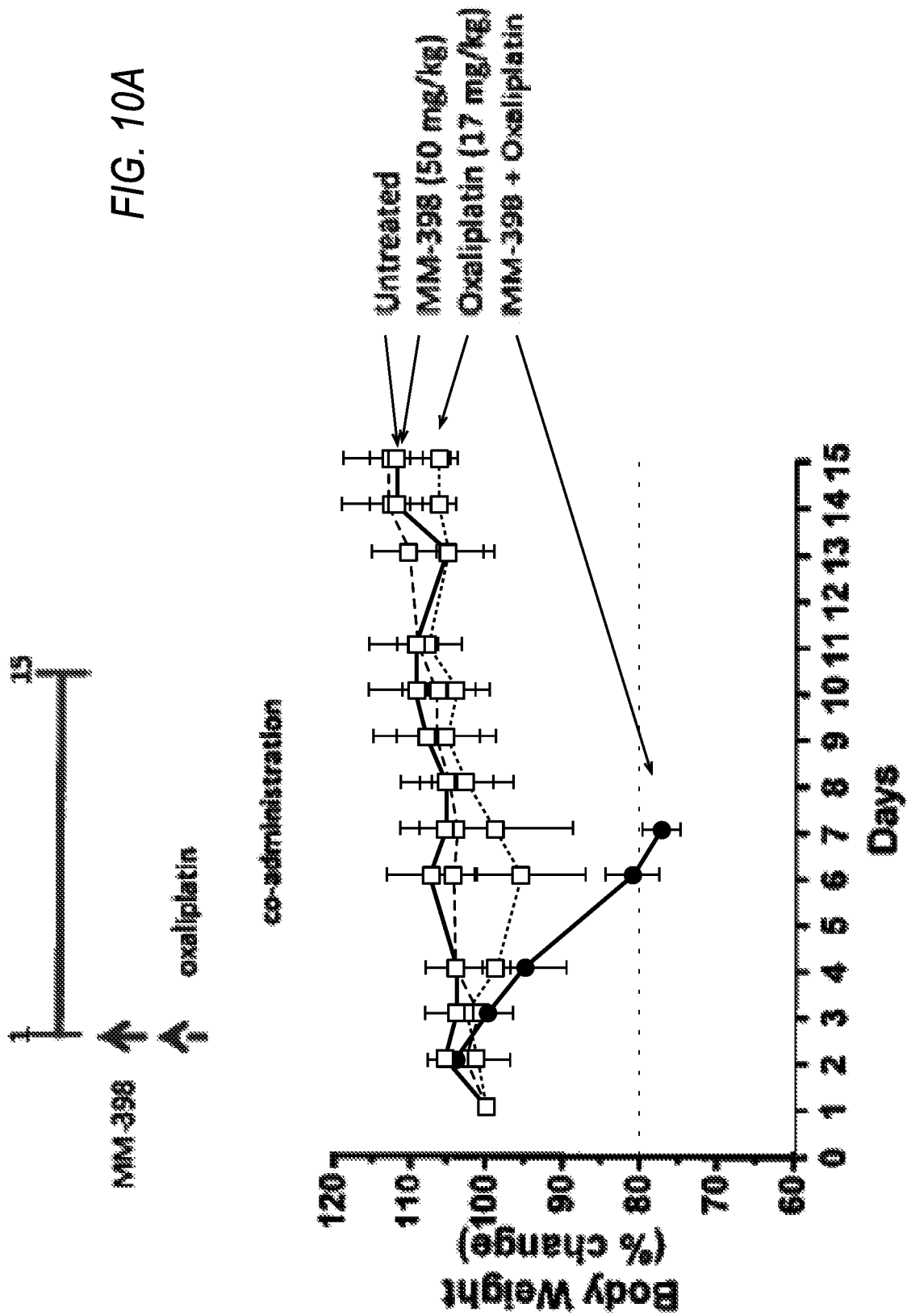
FIG. 10A is a graph showing the tolerability of various therapies in a mouse model, measured by recording the body weight of the mouse after administration of high doses of MM-398 liposomal irinotecan (nal-IRI), oxaliplatin and a combination of MM-398 liposomal irinotecan and oxaliplatin given together on the same day.
Figure 10B:
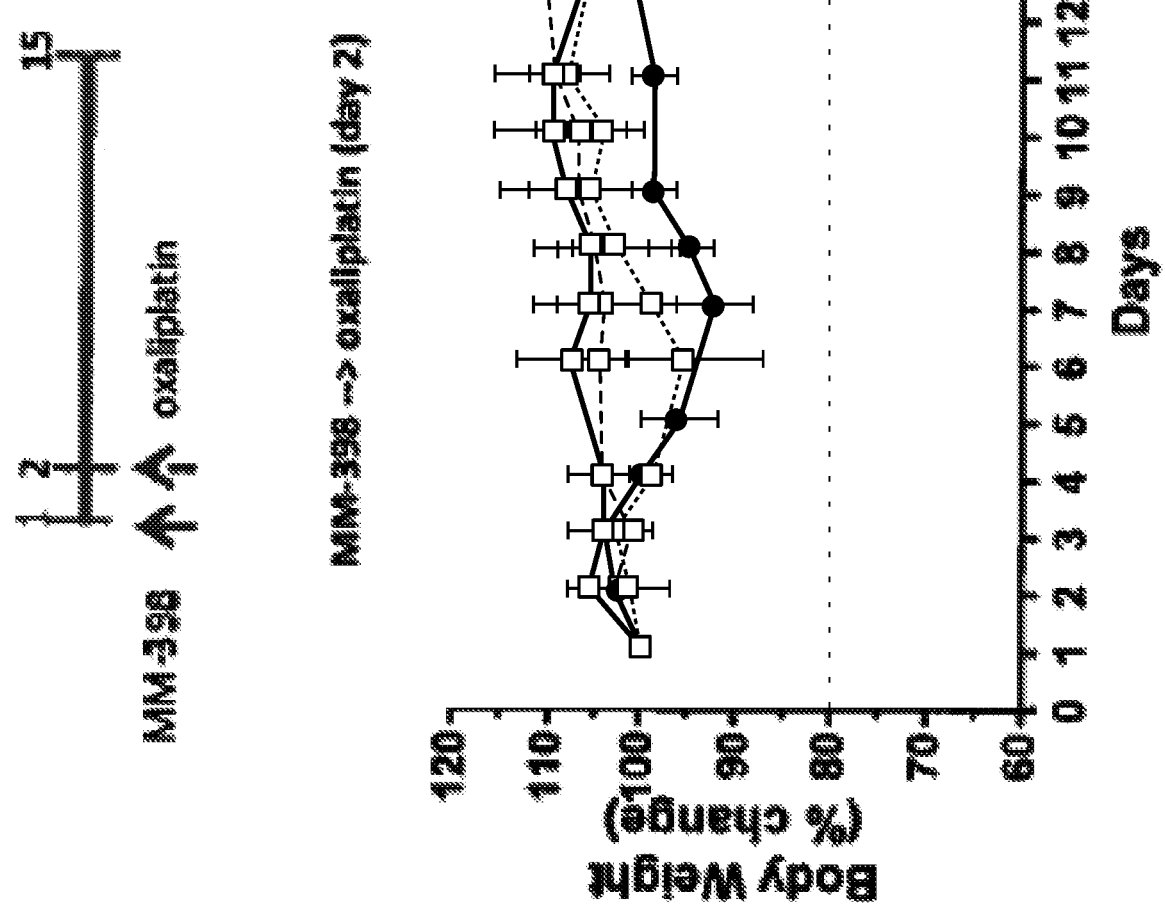
FIG. 10B is a graph showing the tolerability of various therapies in a mouse model, measured by recording the body weight of the mouse after administration of high doses of MM-398 liposomal irinotecan (nal-IRI), oxaliplatin and a combination of MM-398 liposomal irinotecan and oxaliplatin given sequentially on separate successive days with the MM-398 administered on day 1 and the oxaliplatin administered on day 2.
Figure 11A:
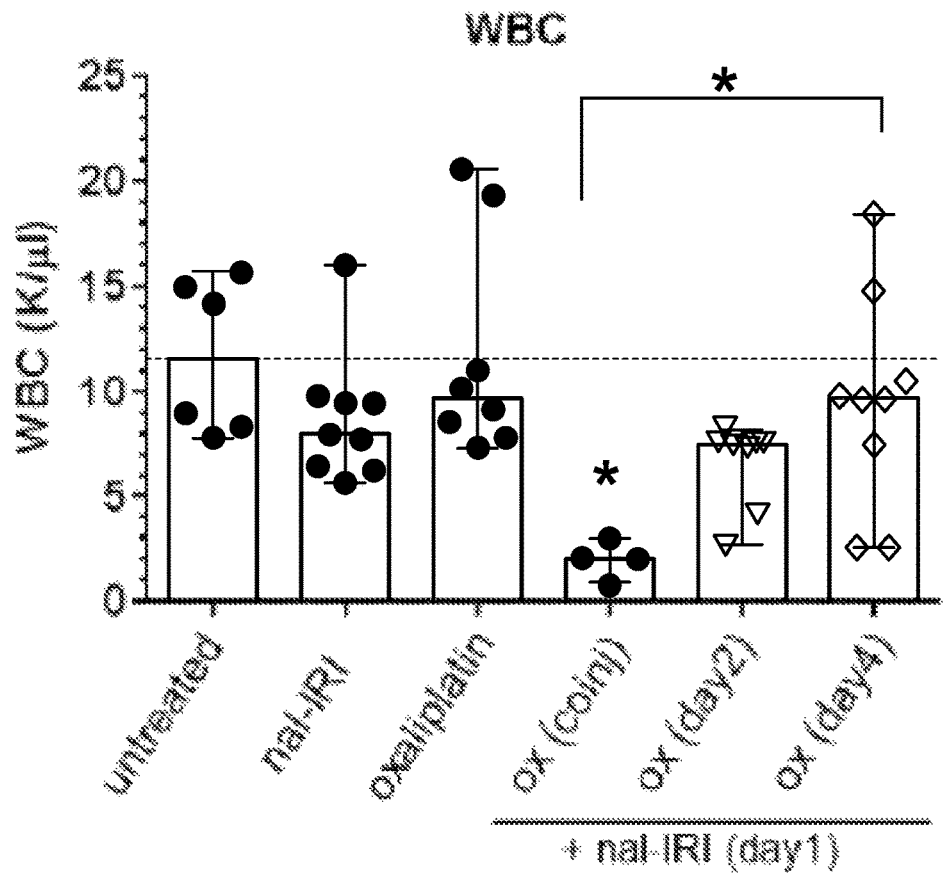
FIGS. 11A, 11B and 11C are bar graphs depicting hematological toxicities observed in mice after administration of high doses of MM-398 liposomal irinotecan (nal-IRI) and oxaliplatin administered on the same day or with oxaliplatin administered at least one day after administration of MM-398: A. White blood cells; B. Neutrophils; and C. Lymphocytes.
Figure 11B:
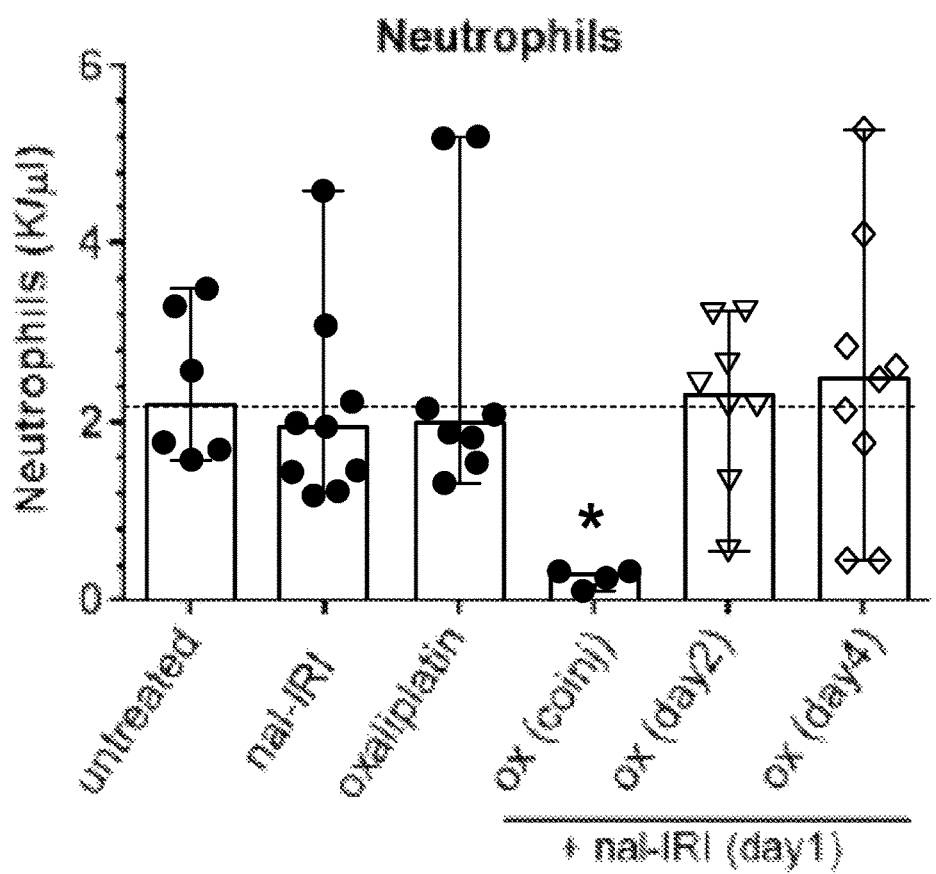
Figure 11C:
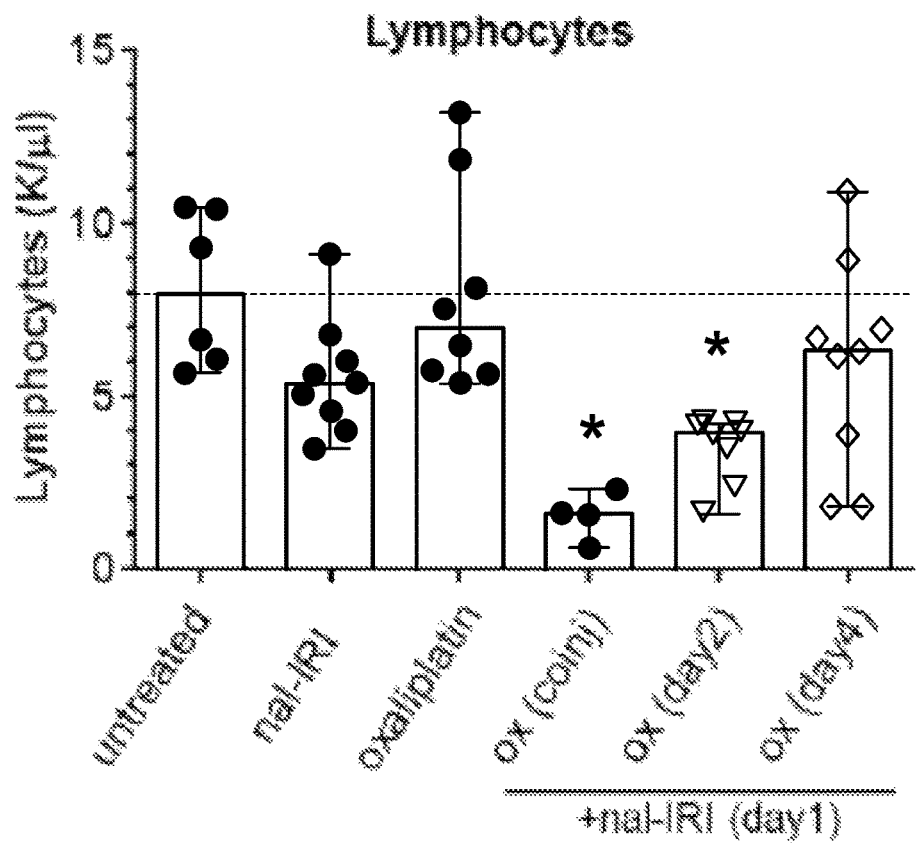
Figure 11D:
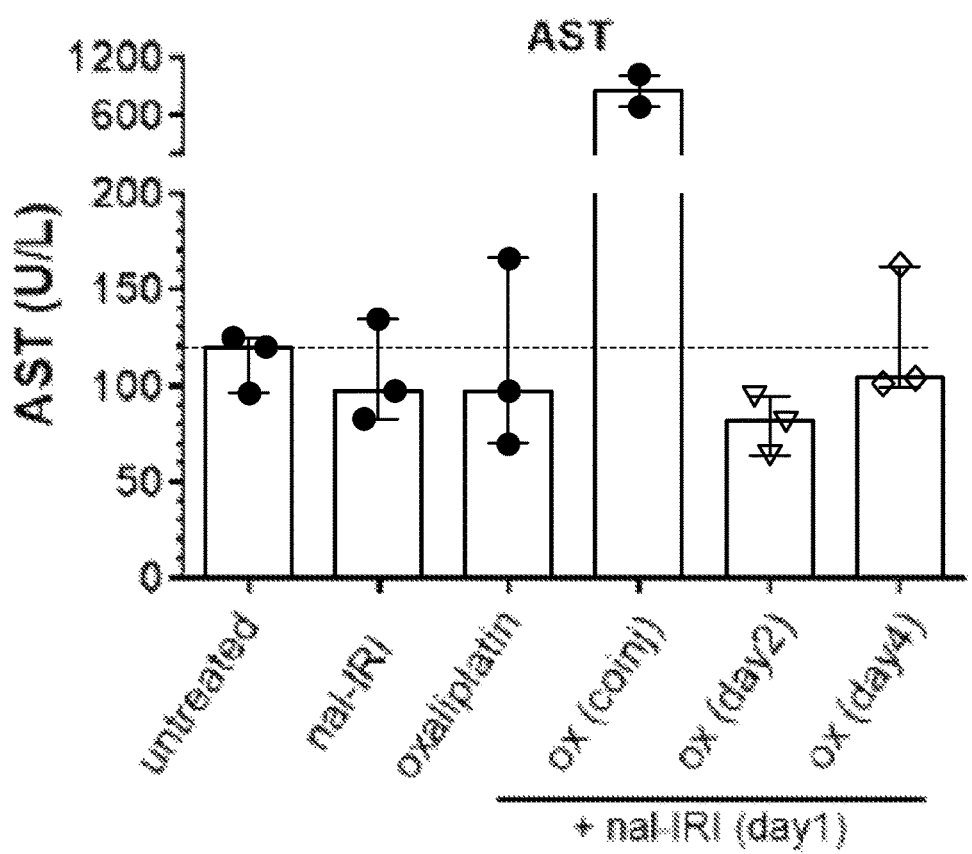
FIGS. 11D, 11E and 11F is bar graphs depicting liver enzyme levels observed in mice after administration of high doses of MM-398 liposomal irinotecan (nal-IRI) and oxaliplatin administered on the same day or with oxaliplatin administered at least one day after administration of MM-398: D. aspartate aminotransferase (AST); E. alanine transaminase (ALT); F. alkaline phosphatase (ALKP).
Figure 11E:
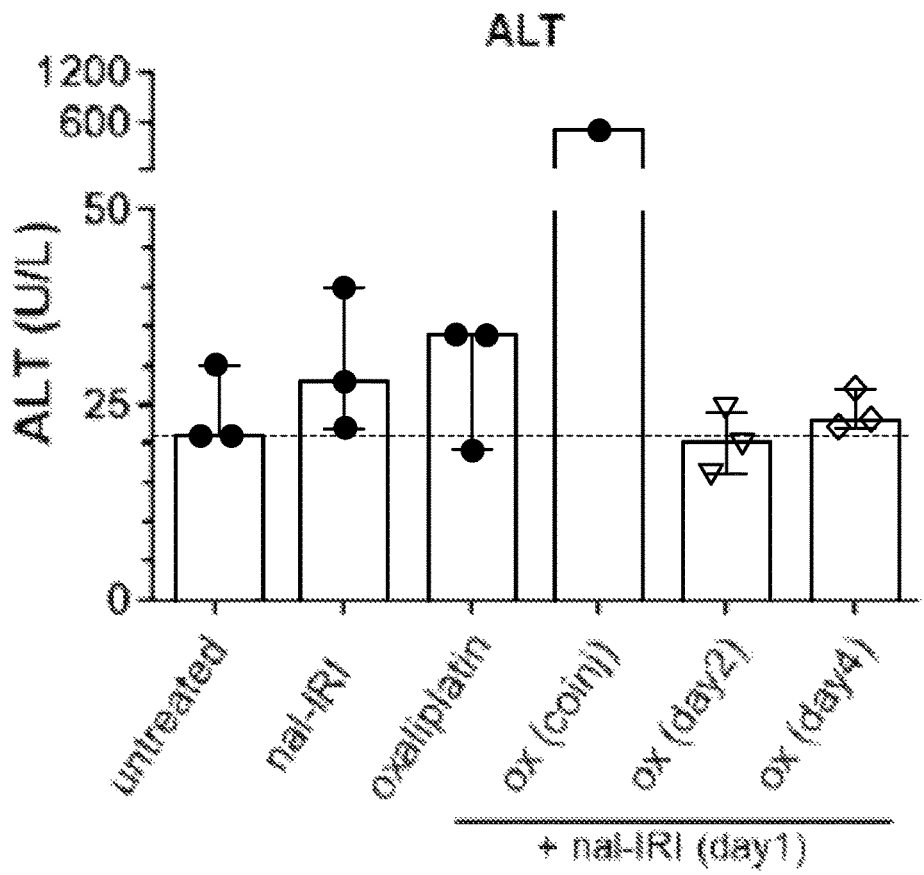
Figure 11F:
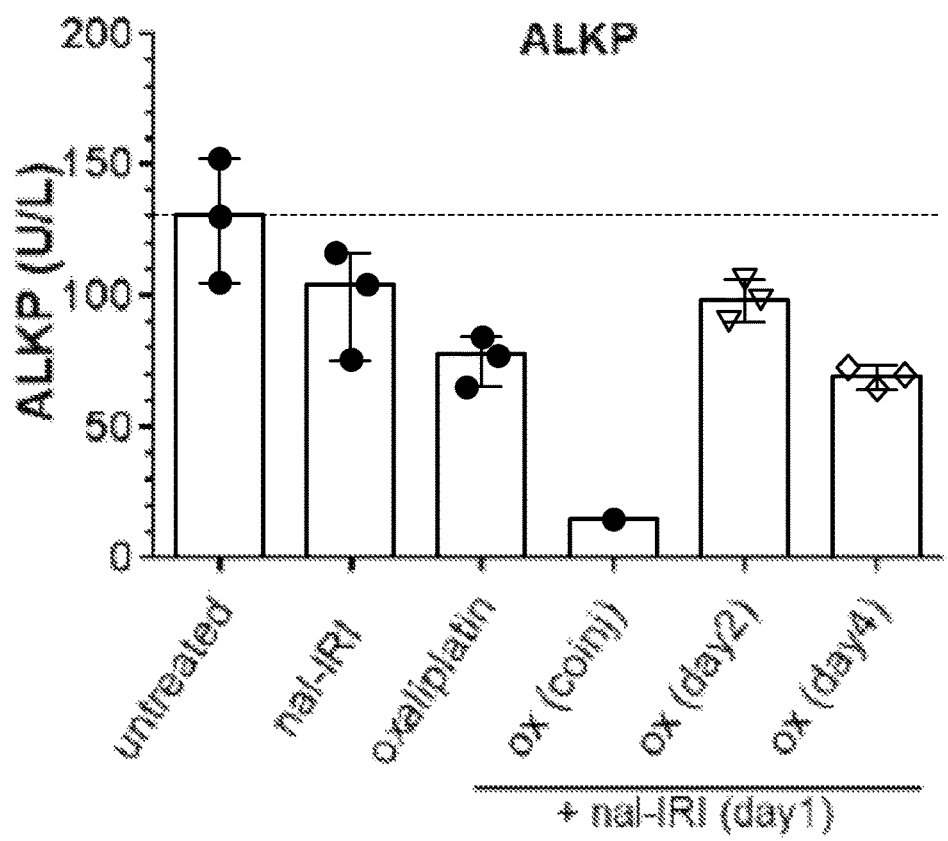

The tolerability of combinations of MM-398 liposomal irinotecan and oxaliplatin was improved in mouse models when the oxaliplatin was administered one day after the administration of the MM-398. FIGS. 10A and 10B depict line graphs demonstrating the toxicities associated with MM-398 and oxaliplatin given as monotherapy or combined therapy given concurrently (A) or staggered, with oxaliplatin given 1 day after MM-398 administration (B). Co-administration of MM-398 and oxaliplatin leads to significant toxicities as measured by loss of body weight, whereas delaying oxaliplatin administration by 24 h after MM-398 does not lead to significant changes in body weight.

FIG. 11A-11F are bar graphs depicting hematological and liver toxicities following treatment with MM-398 with or without oxaliplatin given either concurrently or sequentially with MM-398. Hematological toxicities (A-C) were improved by delayed administration of oxaliplatin. Liver enzymes (D-F) remained comparable to monotherapies when oxaliplatin administration was delayed.

Figure 12:
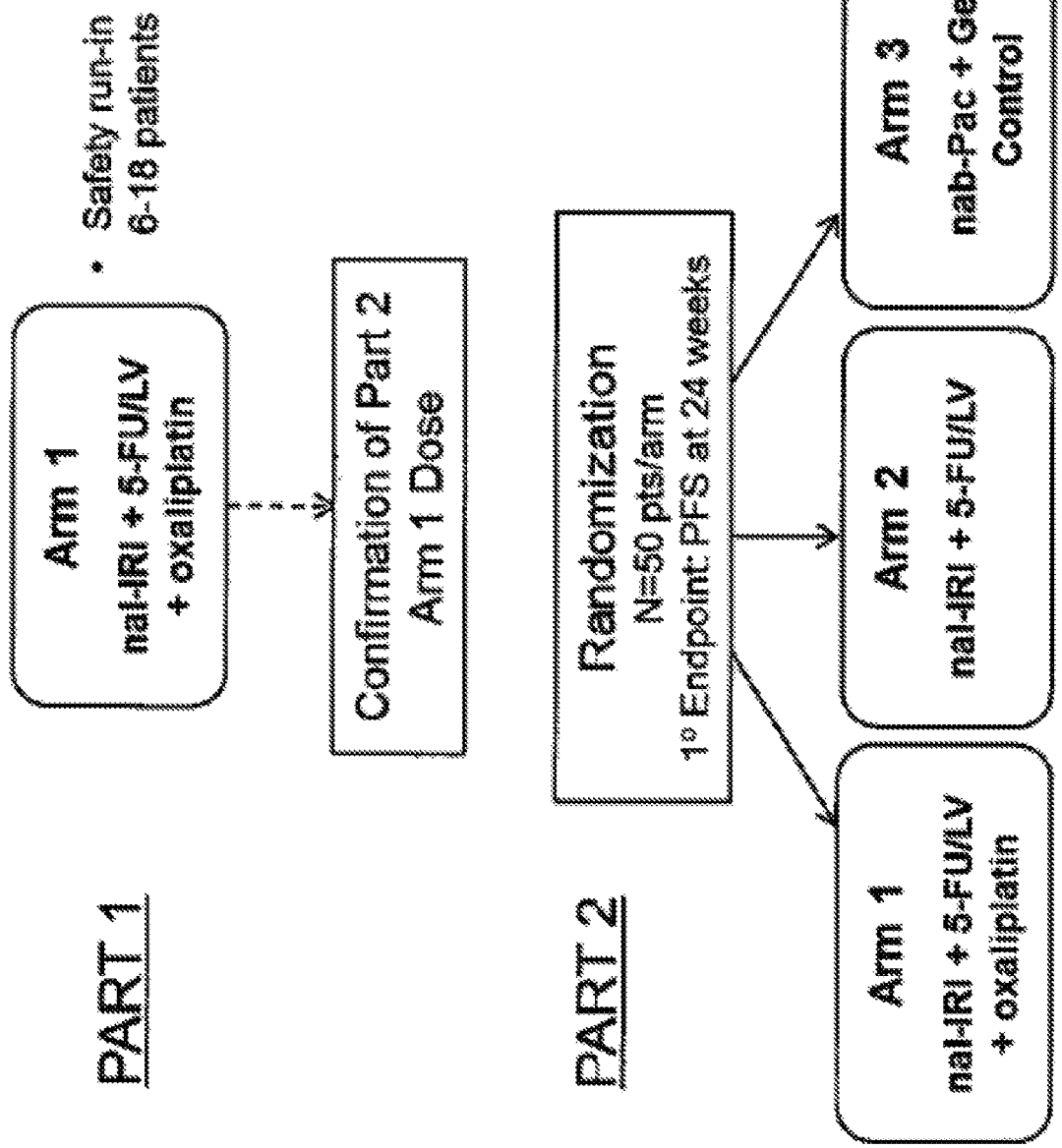
FIG. 12 is a schematic of methods of treating pancreatic cancer, including methods comprising the administration of liposomal irinotecan, oxalipaltin, 5-fluorouracil and leucovorin.

These preclinical findings support the therapeutic use of liposomal irinotecan in combination with 5-FU/LV and oxaliplatin and an ongoing Phase 2 trial (NCT02551991) of this triplet regimen in first-line PDAC (Example 2). FIG. 12 depicts a graphical representation of the study design employing the combination of MM-398+5-FU/LV+oxaliplatin in (Arm 1) and MM-398+5-FU/LV (Arm 2), and nab-paclitaxel+gemcitabine (Arm 3) as described herein.

For example, use of a combination of liposomal irinotecan, oxaliplatin, and 5-fluorouracil in treating metastatic adenocarcinoma of the pancreas in a human patient who has not previously received chemotherapy to treat the metastatic adenocarcinoma of the pancreas, the use comprising administering an antineoplastic therapy to the patient a total of once every two weeks, the antineoplastic therapy consisting of: (a) 60 mg/m$^2$ of liposomal irinotecan, 60 mg/m$^2$ oxaliplatin, 200 mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient; (b) 60 mg/m$^2$ of liposomal irinotecan, 85 mg/m$^2$ oxaliplatin, 200 mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient; (c) 60 mg/m$^2$ of liposomal irinotecan, 60 mg/m$^2$ oxaliplatin, 200 mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient wherein the liposomal irinotecan, oxaliplatin and leucovorin is administered on days 1 and 15 of a 28-day treatment cycle; (d) 60 mg/m$^2$ of liposomal irinotecan, 85 mg/m$^2$ oxaliplatin, 200 mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient, wherein the liposomal irinotecan, oxaliplatin and leucovorin is administered on days 1 and 15 of a 28-day treatment cycle; (e) 60 mg/m$^2$ of liposomal irinotecan, 60 mg/m$^2$ oxaliplatin, 200 mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient wherein the liposomal irinotecan is administered, followed by administering the oxaliplatin, followed by administering the leucovorin, followed by administering the 5-fluorouracil; (f) 60 mg/m$^2$ of liposomal irinotecan, 85 mg/m$^2$ oxaliplatin, mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient wherein the liposomal irinotecan is administered, followed by administering the oxaliplatin, followed by administering the leucovorin, followed by administering the 5-fluorouracil; or (g) 60 mg/m$^2$ of liposomal irinotecan, 60 mg/m$^2$-85 mg/m$^2$ oxaliplatin, 200 mg/m$^2$ of (l)-form of leucovorin or 400 mg/m$^2$ of the (l+d) racemic form of leucovorin, and 2,400 mg/m$^2$ 5-fluorouracil to treat the metastatic adenocarcinoma of the pancreas in the human patient wherein the liposomal irinotecan, oxaliplatin and leucovorin is administered on days 1 and 15 of a 28-day treatment cycle, wherein the liposomal irinotecan is administered, followed by administering the oxaliplatin, followed by administering the leucovorin, followed by administering the 5-fluorouracil, wherein the administration of the oxaliplatin begins 2 hours after completing each administration of the liposomal irinotecan. Each of these exemplary uses can be modified to replace the doses of liposomal irinotecan, oxaliplatin, leucovorin and 5-flurouracil disclosed herein in the following passages relating to these specific components. Sometimes the liposomal irinotecan comprises irinotecan sucrose octasulfate encapsulated in liposomes. Sometimes, the liposomal irinotecan comprises irinotecan encapsulated in liposome vesicles consisting of 1,2-distearoyl-sn-glycero-3-phosphocholine (DSPC), cholesterol, and a N-(carbonylmethoxypolyethlyene glycol-2000)-1,2-distearoly-sn-glycero-3-phosphoethanolamine (MPEG-2000-DSPE).

As provided herein, irinotecan can be administered in an irinotecan liposome preparation. Preferably, the liposomal irinotecan is irinotecan sucrose sulfate liposome injection (otherwise termed "irinotecan sucrose octasulfate salt liposome injection" or "irinotecan sucrosofate liposome injection"), the formulation referred to herein as "MM-398" (also known as PEP02, see U.S. Pat. No. 8,147,867) is a form of "nanoliposomal irinotecan" (also called "irinotecan liposome" or "liposomal Irinotecan"). MM-398 is irinotecan as the irinotecan sucrose octasulfate salt encapsulated in a nanoliposome drug delivery system.

The liposomal irinotecan can be a pharmaceutical composition prepared for human intravenous administration. For example, the liposomal irinotecan may be provided as a sterile, injectable parenteral liquid for intravenous injection. The required amount of liposomal irinotecan may be diluted, e.g., in 500 mL of 5% dextrose injection USP, to provide a variety of concentrations, for example, 5 mg/mL, and may be infused over a 90 minute period.

The active ingredient of the MM-398 injection, irinotecan, is a member of the topoisomerase I inhibitor class of drugs and is a semi-synthetic and water soluble analog of the naturally-occurring alkaloid, camptothecin. Topoisomerase I inhibitors work to arrest uncontrolled cell growth by preventing the unwinding of DNA and therefore preventing replication. The pharmacology of irinotecan is complex, with extensive metabolic conversions involved in the activation, inactivation, and elimination of the drug. Irinotecan is a pro-drug that is converted by nonspecific carboxylesterases into a 100-1000 fold more active metabolite, SN-38. SN-38 is cleared via glucuronidation, (for which major pharmacogenetic differences have been shown), and biliary excretion. These drug properties contribute to the marked differences in efficacy and toxicity observed in clinical studies with irinotecan.

The liposomal irinotecan can be a unilamellar lipid bilayer vesicle of approximately 80-140 nm in diameter that encapsulates an aqueous space that contains irinotecan complexed in a gelated or precipitated state as a salt with sucrose octasulfate. The lipid membrane of the liposome is composed of phosphatidylcholine, cholesterol, and a polyethyleneglycol-derivatized phosphatidyl-ethanolamine in the amount of approximately one polyethyleneglycol (PEG) molecule for every 200 phospholipid molecules.

The amount of liposomal irinotecan administered to the human patient can range from about 40 mg/m$^2$ to about 180 mg/m$^2$, preferably 60 mg/m$^2$ when administered in combination with oxaliplatin and 5-fluorouracil for treatment of pancreatic cancer (dose expressed in terms of the amount of irinotecan hydrochloride trihydrate salt). The plasma pharmacokinetics of total irinotecan and total SN-38 were evaluated in patients with cancer who received MM-398, as a single agent or as part of combination chemotherapy, at doses between 50 and 155 mg/m$^2$ (amount of irinotecan base, equivalent to 60-180 mg/m$^2$ dose expressed in terms of the amount of irinotecan hydrochloride trihydrate salt) and 353 patients with cancer using population pharmacokinetic analysis. Over the dose range of 50 to 155 mg/m$^2$, the $C_{max}$ and AUC of total irinotecan increases with dose. Additionally, the $C_{max}$ of total SN-38 increases proportionally with dose; however, the AUC of total SN-38 increases less than proportionally with dose.

The combination treatment described herein encompasses administration of MM-398 liposomal irinotecan in combination with multiple additional active agents: oxaliplatin, leucovorin and 5-fluorouracil, in doses and schedules to human patients with metastatic pancreatic cancer not previously treated with a prior chemotherapeutic agent in the metastatic setting as described herein.

5-Fluorouracil is a pyrimidine antagonist that interferes with nucleic acid biosynthesis. The deoxyribonucleotide of the drug inhibits thymidylate synthetase, thus inhibiting the formation of thymidylic acid from deoxyuridylic acid, thus interfering in the synthesis of DNA. It also interferes with RNA synthesis. An exemplary effective amount of 5-fluorouracil administered to a human patient can range from about 2,000 mg/m$^2$ to about 3,000 mg/m$^2$. In some embodiments, the amount of 5-fluorouracil administered to the human patient is 2,400 mg/m$^2$.

Leucovorin is optionally administered prior to the 5-fluorouracil. Leucovorin acts as a biochemical cofactor for 1-carbon transfer reactions in the synthesis of purines and pyrimidines. Leucovorin does not require the enzyme dihydrofolate reductase (DHFR) for conversion to tetrahydrofolic acid. The effects of methotrexate and other DHFR-antagonists are inhibited by leucovorin. Leucovorin can potentiate the cytotoxic effects of fluorinated pyrimidines (i.e., fluorouracil and floxuridine). After 5-FU is activated within the cell, it is accompanied by a folate cofactor, and inhibits the enzyme thymidylate synthetase, thus inhibiting pyrimidine synthesis. Leucovorin increases the folate pool, thereby increasing the binding of folate cofactor and active 5-FU with thymidylate synthetase. Leucovorin has dextro- and levo-isomers, only the latter one being pharmacologically useful. As such, the bioactive levo-isomer ("levo-leucovorin") has also been approved by the FDA for treatment of cancer. The dosage of leucovorin is that of the racemic mixture containing both dextro (d) and levo (l) isomers, or optionally the (l) form of leucovorin at half the dosage of the (l+d) racemic form. An exemplary effective amount of leucovorin administered to the human patient can include an amount of (l)-form leucovorin ranging from about 100 mg/m$^2$ to about 300 mg/m$^2$. In some embodiments, the amount of (l)-form leucovorin administered to the human patient is 200 mg/m$^2$. In other embodiments, the leucovorin administered is the (l+d)-form of leucovorin, in an amount ranging from about 200 mg/m$^2$ to about 600 mg/m$^2$. In some embodiments, the amount of (l+d)-form of leucovorin administered is 400 mg/m$^2$.

Oxaliplatin is a platinum-based drug that acts as a DNA cross-linking agent to effectively inhibit DNA replication and transcription, resulting in cytotoxicity which is cell-cycle non-specific. Oxaliplatin is typically used in combination with infusional 5-FU/LV, and is approved for use in advanced colorectal cancer (refer to package insert for more details). The effective amount of oxaliplatin administered to the human patient can range from about 30 mg/m$^2$ to about 150 mg/m$^2$, for example, from about 40 mg/m$^2$ to about 100 mg/m$^2$, or an amount of oxaliplatin of mg/m$^2$, 55 mg/m$^2$, 60 mg/m$^2$, 65 mg/m$^2$, 70 mg/m$^2$, 75 mg/m$^2$, 80 mg/m$^2$, 85 mg/m$^2$, 90 mg/m$^2$, or 95 mg/m$^2$.

Dose modifications may be made to methods of administering the combination treatment described herein as a result of adverse events, include hematological and non-hematological adverse events.

In some embodiments, methods of administering the combination treatment described herein to patients having one or more characteristics can include reducing or otherwise modifying the dose of MM-398 administered according to the embodiments herein. In some embodiments, the dose of MM-398 is modified according to Table 1.

TABLE 1A

Examples of Dose Modifications for MM-398 (salt)

| Toxicity NCI CTCAE v4.0 | Occurrence | MM-398 adjustment in patients receiving 60 mg/m²‡ (salt) | Patients homozygous for UGT1A1*28 without previous increase to 60 mg/m² (salt) |
|---|---|---|---|
| Grade 3 or 4 adverse reactions | | Withhold MM-398. Initiate loperamide for late onset diarrhea of any severity. Administer intravenous or subcutaneous atropine 0.25 to 1 mg (unless clinically contraindicated) for early onset diarrhea of any severity. Upon recovery to ≤ Grade 1 or baseline grade resume MM-398 at: | |
| | First | 45 mg/m² | 35 mg/m² |
| | Second | 35 mg/m² | 30 mg/m² |
| | Third | Discontinue MM-398 | Discontinue MM-398 |
| Interstitial Lung Disease | First | Discontinue MM-398 | Discontinue MM-398 |
| Anaphylactic Reaction | First | Discontinue MM-398 | Discontinue MM-398 |

In some embodiments, the first, second or any subsequent dose of MM-398 can be reduced by 20-30% (including dose reductions of 20%, 25% and/or 30%) in response to patient tolerability considerations such as an adverse reaction to a first or subsequent dose of MM-398 and/or other antineoplastic agent, and/or identifying a patient as being homozygous for the UGT1A1*28 allele. In some embodiments, the second or subsequent dose of MM-398 is reduced by about 20%, 25% or 30% (e.g., a dose reduction from 60 mg/m2 to. In some embodiments, the dose of MM-398 is reduced by 25%. In some embodiments, the dose of MM-398 is reduced by 30%. In some embodiments, the reduced dose of MM-398 is in a range starting from 30 mg/m² to (and including) 55 mg/m². In some embodiments, the dose of MM-398 is reduced to 60 mg/m². In some embodiments, the dose of MM-398 is reduced to 45 mg/m². In some embodiments, the dose of MM-398 is reduced to 35 mg/m².

Other dose reduction schedules are provided Tables 1B-1E below. When the starting (initial) dose of MM-398 is 60 mg/m², 5FU 2400 mg/m², LV(l+d) 400 mg/m² and Oxaliplatin is either 85 mg/m2 OR 60 mg/m2, then the first dose reduction in response to a grade III or IV hematotoxicity is preferably a 25% dose reduction for each of the MM-398, 5-FU and Oxaliplatin doses for each administration of the antineoplastic therapy. For persistent toxicities despite the first dose reduction, an additional 25% dose reduction in each of the antineoplastic agents of MM-398, 5-fluorouracil and oxaliplatin is preferred. Further toxicity will then lead to discontinuation of treatment in some instances. For non-hematologic toxicities, the same dose reduction schema can be followed as for hematotoxicity, except for the specific toxicities associated with the drug (ie 5FU hand foot syndrome, and oxaliplatin neuropathy) which can be selected based on the medically appropriate dose for the patient.

TABLE 1B

Examples of Reduced Doses of MM-398 and oxaliplatin

| Dose | MM-398 (mg/m2) (salt) | Oxaliplatin (mg/m2) | 5-fluorouracil (5FU) (mg/m2) |
|---|---|---|---|
| Initial | 60 | 60 | 2400 |
| First Reduction | 45 | 45 | 1800 |
| Second Reduction | 35 | 35 | 1350 |

TABLE 1C

Examples of Reduced Doses of MM-398 and oxaliplatin

| Dose | MM-398 (mg/m2) (salt) | Oxaliplatin (mg/m2) | 5-fluorouracil (5FU) (mg/m2) |
|---|---|---|---|
| Initial | 60 | 80 | 2400 |
| First Reduction | 45 | 60 | 1800 |
| Second Reduction | 35 | 45 | 1350 |

TABLE 1D

Examples of Reduced Doses of MM-398 and oxaliplatin

| Dose | MM-398 (mg/m2) (salt) | Oxaliplatin (mg/m2) | 5-fluorouracil (5FU) (mg/m2) |
|---|---|---|---|
| Initial | 60 | 60 | 2400 |
| First Reduction | 45 | 45 | 2400 |
| Second Reduction | 35 | 35 | 1800 |

TABLE 1E

Examples of Reduced Doses of MM-398 and oxaliplatin

| Dose | MM-398 (mg/m2) (salt) | Oxaliplatin (mg/m2) | 5-fluorouracil (5FU) (mg/m2) |
|---|---|---|---|
| Initial | 60 | 80 | 2400 |
| First Reduction | 45 | 60 | 2400 |
| Second Reduction | 35 | 45 | 1800 |

In some embodiments, methods of administering the combination treatment described herein to patients having one or more characteristics can include reducing or otherwise modifying the dose of Oxaliplatin administered according to the embodiments herein. In some embodiments, the dose of Oxaliplatin is reduced by 20-30%. In some embodiments, the, the dose of Oxaliplatin is reduced by 20%. In some embodiments, the, the dose of Oxaliplatin is reduced by 25%. In some embodiments, the, the dose of Oxaliplatin is reduced by 30%. In some embodiments, the reduced dose of Oxaliplatin is in a range from 30 mg/m² to 75 mg/m². In some embodiments, the dose of Oxaliplatin is reduced to 75 mg/m². In some embodiments, the dose of Oxaliplatin is reduced to 65 mg/m². In some embodiments, the dose of Oxaliplatin is reduced to 60 mg/m². In some embodiments, the dose of Oxaliplatin is reduced to 45 mg/m². In some embodiments, the dose of Oxaliplatin is reduced to 45 mg/m². In some embodiments, the dose of Oxaliplatin is reduced to 34 mg/m².

In some embodiments, methods of administering the combination treatment described herein to patients having one or more characteristics can include reducing or otherwise modifying the dose of 5-fluorouracil administered according to the embodiments herein. In some embodiments, the dose of 5-fluorouracil is reduced by 20-30%. In some embodiments, the, the dose of 5-fluorouracil is reduced by 20%. In some embodiments, the, the dose of 5-fluorouracil is reduced by 25%. In some embodiments, the, the dose of 5-fluorouracil is reduced by 30%. In some embodiments, the reduced dose of 5-fluorouracil is in a range from 1000 mg/m² to 1800 mg/m². In some embodiments, the dose of 5-fluorouracil is reduced to 1800 mg/m². In some embodiments, the dose of 5-fluorouracil is reduced to 1350 mg/m². In some embodiments, the dose of 5-fluorouracil is reduced to 1200 mg/m².

In some embodiments, methods of administering the combination treatment described herein to patients having one or more characteristics can include further reducing or otherwise modifying the dose of MM-398, Oxaliplatin and/or 5-fluorouracil administered according to the embodiments herein.

In some embodiments, methods of administering the combination treatment described herein to patients having one or more characteristics can include reducing or otherwise modifying the dose of more than one of MM-398, Oxaliplatin and 5-fluorouracil administered according to the embodiments herein.

Additional dose modifications for MM-398, Oxaliplatin and/or 5-fluorouracil can be found in the respective Package Inserts, which are incorporated herein by reference.

In one embodiment, the method of administering the combination treatment comprises 34, 45, or 60 mg/m² of liposomal irinotecan, 34, 42, 45, 60 or 85 mg/m² oxaliplatin, 200 mg/m² of (l)-form of leucovorin or 400 mg/m² of the (l+d) racemic form of leucovorin, and 1,200, 1,350, 1,800 or 2,400 mg/m² 5-fluorouracil to treat the metastatic adenocarcinoma of the pancreas in the human patient.

Thus, in some embodiments, the method of administering the combination treatment to treat the metastatic adenocarcinoma of the pancreas in the human patient comprises:

(A) (i) 35 mg/m² of liposomal irinotecan, 35 mg/m² oxaliplatin, 200 mg/m² (l)-form or 400 mg/m² racemic leucovorin, and 1,200 mg/m² 5-FU; (ii) 35 mg/m² of liposomal irinotecan, 35 mg/m² oxaliplatin, 200 mg/m² (l)-form or 400 mg/m² racemic leucovorin, and 1,350 mg/m² 5-FU; (iii) 35 mg/m² of liposomal irinotecan, 35 mg/m² oxaliplatin, 200 mg/m² (l)-form or 400 mg/m² racemic leucovorin, and 1,800 mg/m² 5-FU; (iv) 35 mg/m² of liposomal irinotecan, 35 mg/m² oxaliplatin, 200 mg/m² (l)-form or 400 mg/m² racemic leucovorin, and 2,400 mg/m² 5-FU; (v) 35 mg/m² of liposomal irinotecan, 45 mg/m² oxaliplatin, 200 mg/m² (l)-form or 400 mg/m² racemic leucovorin, and 1,200 mg/m² 5-FU; (vi) 35 mg/m² of liposomal irinotecan, 45 mg/m² oxaliplatin, 200 mg/m² (l)-form or 400 mg/m² racemic leucovorin, and 1,350 mg/m² 5-FU; (vii) 35 mg/m² of liposomal irinotecan, 45 mg/m² oxaliplatin, 200 mg/m² (l)-form or 400 mg/m² racemic leucovorin, and 1,800 mg/m² 5-FU; (viii) 35 mg/m² of liposomal irinotecan, 45 mg/m² oxaliplatin, 200 mg/m² (l)-form or 400 mg/m² racemic leucovorin, and 2,400 mg/m² 5-FU; (ix) 35 mg/m² of liposomal irinotecan, 45 mg/m² oxaliplatin, 200 mg/m² (l)-form or 400 mg/m² racemic leucovorin, and 1,200 mg/m² 5-FU; (x) 35 mg/m² of liposomal irinotecan, 45 mg/m² oxaliplatin, 200 mg/m² (l)-form or 400 mg/m² racemic leucovorin, and 1,350 mg/m² 5-FU; (xi) 35 mg/m² of liposomal irinotecan, 45 mg/m² oxaliplatin, 200 mg/m² (l)-form or 400 mg/m² racemic leucovorin, and 1,800 mg/m² 5-FU; (xii) 35 mg/m² of liposomal irinotecan, 45 mg/m² oxaliplatin, 200 mg/m² (l)-form or 400 mg/m² racemic leucovorin, and 2,400 mg/m² 5-FU; (xiii) 35 mg/m² of liposomal irinotecan, 60 mg/m² oxaliplatin, 200 mg/m² (l)-form or 400 mg/m² racemic leucovorin, and 1,200 mg/m² 5-FU; (xiv) 35 mg/m² of liposomal irinotecan, 60 mg/m² oxaliplatin, 200 mg/m² (l)-form or 400 mg/m² racemic leucovorin, and 1,350 mg/m² 5-FU; (xv) 35 mg/m² of liposomal irinotecan, 60 mg/m² oxaliplatin, 200 mg/m² (l)-form or 400 mg/m² racemic leucovorin, and 1,800 mg/m² 5-FU; (xvi) 35 mg/m² of liposomal irinotecan, 60 mg/m² oxaliplatin, 200 mg/m² (l)-form or 400 mg/m² racemic leucovorin, and 2,400 mg/m² 5-FU; (xvii) 35 mg/m² of liposomal irinotecan, 85 mg/m² oxaliplatin, 200 mg/m² (l)-form or 400 mg/m² racemic leucovorin, and 1,200 mg/m² 5-FU; (xviii) 35 mg/m² of liposomal irinotecan, 85 mg/m² oxaliplatin, 200 mg/m² (l)-form or 400 mg/m² racemic leucovorin, and 1,350 mg/m² 5-FU; (xix) 35 mg/m² of liposomal irinotecan, 85 mg/m² oxaliplatin, 200 mg/m² (l)-form or 400 mg/m² racemic leucovorin, and 1,800 mg/m² 5-FU; or (xx) 35 mg/m² of liposomal irinotecan, 85 mg/m² oxaliplatin, 200 mg/m² (l)-form or 400 mg/m² racemic leucovorin, and 2,400 mg/m² 5-FU; (B) (i) 45 mg/m² of liposomal irinotecan, 35 mg/m² oxaliplatin, 200 mg/m² (l)-form or 400 mg/m² racemic leucovorin, and 1,200 mg/m² 5-FU; (ii) 45 mg/m² of liposomal irinotecan, 35 mg/m² oxaliplatin, 200 mg/m² (l)-form or 400 mg/m² racemic leucovorin, and 1,350 mg/m² 5-FU; (iii) 45 mg/m² of liposomal irinotecan, 35 mg/m² oxaliplatin, 200 mg/m² (l)-form or 400 mg/m² racemic leucovorin, and 1,800 mg/m² 5-FU; (iv) 45 mg/m² of liposomal irinotecan, 35 mg/m² oxaliplatin, 200 mg/m² (l)-form or 400 mg/m² racemic leucovorin, and 2,400 mg/m² 5-FU; (v) 45 mg/m² of liposomal irinotecan, 45 mg/m² oxaliplatin, 200 mg/m² (l)-form or 400 mg/m² racemic leucovorin, and 1,200 mg/m² 5-FU; (vi) 45 mg/m² of liposomal irinotecan, 45 mg/m² oxaliplatin, 200 mg/m² (l)-form or 400 mg/m² racemic leucovorin, and 1,350 mg/m² 5-FU; (vii) 45 mg/m² of liposomal irinotecan, 45 mg/m² oxaliplatin, 200 mg/m² (l)-form or 400 mg/m² racemic leucovorin, and 1,800 mg/m² 5-FU; (viii) 45 mg/m² of liposomal irinotecan, 45 mg/m² oxaliplatin, 200 mg/m² (l)-form or 400 mg/m² racemic leucovorin, and 2,400 mg/m² 5-FU; (ix) 45 mg/m² of liposomal irinotecan, 45 mg/m² oxaliplatin, 200 mg/m² (l)-form or 400 mg/m² racemic leucovorin, and 1,200 mg/m² 5-FU; (x) 45 mg/m² of liposomal irinotecan, 45 mg/m² oxaliplatin, 200 mg/m² (l)-form or 400 mg/m² racemic leucovorin, and 1,350 mg/m² 5-FU; (xi) 45 mg/m² of liposomal irinotecan, 45 mg/m² oxaliplatin, 200 mg/m² (l)-form or 400 mg/m² racemic leucovorin, and 1,800 mg/m² 5-FU; (xii) 45 mg/m² of liposomal irinotecan, 45 mg/m² oxaliplatin, 200 mg/m² (l)-form or 400 mg/m² racemic leucovorin, and 2,400 mg/m² 5-FU; (xiii) 45 mg/m² of liposomal irinotecan, 60 mg/m² oxaliplatin, 200 mg/m² (l)-form or 400 mg/m² racemic leucovorin, and 1,200 mg/m² 5-FU; (xiv) 45 mg/m² of liposomal irinotecan, 60 mg/m² oxaliplatin, 200 mg/m² (l)-form or 400 mg/m² racemic leucovorin, and 1,350 mg/m² 5-FU; (xv) 45 mg/m² of liposomal irinotecan, 60 mg/m² oxaliplatin, 200 mg/m² (l)-form or 400 mg/m² racemic leucovorin, and 1,800 mg/m² 5-FU; (xvi) 45 mg/m² of liposomal irinotecan, 60 mg/m² oxaliplatin, 200 mg/m² (l)-form or 400 mg/m² racemic leucovorin, and 2,400 mg/m² 5-FU; (xvii) 45 mg/m² of liposomal irinotecan, 85 mg/m² oxaliplatin, 200 mg/m² (l)-form or 400 mg/m² racemic leucovorin, and 1,200 mg/m² 5-FU; (xviii) 45 mg/m² of liposomal irinotecan, 85 mg/m² oxaliplatin, 200 mg/m² (l)-form or 400 mg/m² racemic leucovorin, and 1,350 mg/m² 5-FU; (xix) 45 mg/m² of liposomal irinotecan, 85 mg/m² oxaliplatin, 200 mg/m² (l)-form or 400 mg/m² racemic leucovorin, and 1,800 mg/m² 5-FU; or (xx) 45 mg/m² of liposomal irinotecan, 85 mg/m² oxaliplatin, 200 mg/m² (l)-form or 400 mg/m² racemic leucovorin, and 2,400 mg/m² 5-FU; or (C) (i) 60 mg/m² of liposomal irinotecan, 35 mg/m² oxaliplatin, 200 mg/m² (l)-form or 400 mg/m² racemic leucovorin, and 1,200 mg/m² 5-FU; (ii) 60 mg/m² of liposomal irinotecan, 35 mg/m² oxaliplatin, 200 mg/m² (l)-form or 400 mg/m² racemic leucovorin, and 1,350 mg/m² 5-FU; (iii) 60 mg/m² of liposomal irinotecan, 35 mg/m² oxaliplatin, 200 mg/m² (l)-form or 400 mg/m² racemic leucovorin, and 1,800 mg/m² 5-FU; (iv) 60 mg/m² of liposomal irinotecan, 35 mg/m² oxaliplatin, 200 mg/m² (l)-form or 400 mg/m² racemic leucovorin, and 2,400 mg/m² 5-FU; (v) 60 mg/m² of liposomal irinotecan, 45 mg/m² oxaliplatin, 200 mg/m² (l)-form or 400 mg/m² racemic leucovorin, and 1,200 mg/m² 5-FU; (vi) 60 mg/m² of liposomal irinotecan, 45 mg/m² oxaliplatin, 200 mg/m² (l)-form or 400 mg/m² racemic leucovorin, and 1,350 mg/m² 5-FU; (vii) 60 mg/m² of liposomal irinotecan, 45 mg/m² oxaliplatin, 200 mg/m² (l)-form or 400 mg/m² racemic leucovorin, and 1,800 mg/m² 5-FU; (viii) 60 mg/m² of liposomal irinotecan, 45 mg/m2 oxaliplatin, 200 mg/m² (l)-form or 400 mg/m² racemic leucovorin, and 2,400 mg/m² 5-FU; (ix) 60 mg/m² of liposomal irinotecan, 45 mg/m² oxaliplatin, 200 mg/m² (l)-form or 400 mg/m² racemic leucovorin, and 1,200 mg/m² 5-FU; (x) 60 mg/m² of liposomal irinotecan, 45 mg/m² oxaliplatin, 200 mg/m² (l)-form or 400 mg/m² racemic leucovorin, and 1,350 mg/m² 5-FU; (xi) 60 mg/m² of liposomal irinotecan, 45 mg/m² oxaliplatin, 200 mg/m² (l)-form or 400 mg/m² racemic leucovorin, and 1,800 mg/m² 5-FU; (xii) 60 mg/m² of liposomal irinotecan, 45 mg/m² oxaliplatin, 200 mg/m² (l)-form or 400 mg/m² racemic leucovorin, and 2,400 mg/m² 5-FU; (xiii) 60 mg/m² of liposomal irinotecan, 60 mg/m² oxaliplatin, 200 mg/m² (l)-form or 400 mg/m² racemic leucovorin, and 1,200 mg/m² 5-FU; (xiv) 60 mg/m² of liposomal irinotecan, 60 mg/m² oxaliplatin, 200 mg/m² (l)-form or 400 mg/m² racemic leucovorin, and 1,350 mg/m² 5-FU; (xv) 60 mg/m² of liposomal irinotecan, 60 mg/m² oxaliplatin, 200 mg/m² (l)-form or 400 mg/m² racemic leucovorin, and 1,800 mg/m² 5-FU; (xvi) 60 mg/m² of liposomal irinotecan, 60 mg/m² oxaliplatin, 200 mg/m² (l)-form or 400 mg/m² racemic leucovorin, and 2,400 mg/m² 5-FU; (xvii) 60 mg/m² of liposomal irinotecan, 85 mg/m² oxaliplatin, 200 mg/m² (l)-form or 400 mg/m² racemic leucovorin, and 1,200 mg/m² 5-FU; (xviii) 60 mg/m² of liposomal irinotecan, 85 mg/m² oxaliplatin, 200 mg/m² (l)-form or 400 mg/m² racemic leucovorin, and 1,350 mg/m² 5-FU; (xix) 60 mg/m² of liposomal irinotecan, 85 mg/m² oxaliplatin, 200 mg/m² (l)-form or 400 mg/m² racemic leucovorin, and 1,800 mg/m² 5-FU; or (xx) 60 mg/m² of liposomal irinotecan, 85 mg/m² oxaliplatin, 200 mg/m² (l)-form or 400 mg/m² racemic leucovorin, and 2,400 mg/m² 5-FU.

Liposomal irinotecan is preferably administered intravenously, in combination with oxaliplatin, 5-fluorouracil (5-FU) and leucovorin. In one embodiment, liposomal irinotecan is administered prior to oxaliplatin, 5-FU and leucovorin. In another embodiment, leucovorin is administered prior to 5-FU. In another embodiment, the MM-398 liposomal irinotecan is administered followed by administration of the oxaliplatin, followed by administration of the leucovorin, and followed by the administration of the 5-fluorouracil. In certain embodiments, the liposomal irinotecan is administered to the patient intravenously over 90 minutes. In another embodiment, the oxaliplatin is administered to the patient intravenously over 120 minutes. In another embodiment, 5-FU is administered intravenously over 46 hours. In one embodiment, the oxaliplatin is administered from about 6 to about 72 hours after administration of the liposomal irinotecan. In another embodiment, the oxaliplatin is administered for example, 6 hours, 12 hours, 24 hours, 36 hours, 48 hours, 60 hours, or 72 hours, after administration of the liposomal irinotecan. In another embodiment, leucovorin is administered intravenously over 30 minutes. In various embodiments the liposomal irinotecan is MM-398. In various embodiments, the human patient with metastatic pancreatic cancer is pre-medicated with dexamethasone and a 5-HT3 antagonist or other anti-emetic prior to administering the MM-398 liposomal irinotecan, and other active agents.

FURTHER EMBODIMENTS OF THE INVENTION

The following methods and embodiments can be considered alone, in combination other embodiments in this section, or in combination with the methods disclosed above. The invention provides methods for treating pancreatic cancer in a human patient, such as in a patient not previously treated with a chemotherapeutic agent in the metastatic setting, the method comprising administering to the patient liposomal irinotecan, also referred to as MM-398 (e.g., irinotecan sucrose octasulfate salt liposome injection) in combination with oxaliplatin, leucovorin and 5-FU.

1. A method for treating pancreatic cancer in a human subject who has not previously received chemotherapy to treat the pancreatic cancer, the method comprising: administering to the subject a therapeutically effective amount of MM-398 liposomal irinotecan in combination with oxaliplatin, leucovorin, and 5-FU to treat the pancreatic cancer in the human subject.

2. The method of embodiment 1, wherein the amount of MM-398 liposomal irinotecan administered is administered is 60 mg/m² or 80 mg/m².

3. A method for treating pancreatic cancer in a human subject who has not previously received chemotherapy to treat the pancreatic cancer, the method comprising: administering to the subject mg/m² of MM-398 liposomal irinotecan in combination with oxaliplatin, leucovorin, and 5-FU to treat the pancreatic cancer in the human subject.

4. The method of any one of embodiments 1-3, wherein the amount of oxaliplatin administered is from about 50 mg/m² to about 100 mg/m², such as about 60 mg/m² to about 85 mg/m², for example 60 mg/m², 75 mg/m², or 85 mg/m².

5. The method of any one of embodiments 1-4, wherein the leucovorin administered at a dosage of 400 mg/m² of the (l+d) racemic form, or 200 mg/m² of the (l) form.

6. The method of any one of embodiments 1-5, wherein the amount of 5-FU administered is 2,400 mg/m².

7. The method of any one of embodiments 1-6, wherein the MM-398 liposomal irinotecan, oxaliplatin, leucovorin, and 5-FU are administered at least once, such as wherein the MM-398, oxaliplatin, leucovorin, and 5-FU are administered on days 1 and 15 of a 28-day cycle.

8. The method of any one of embodiments 1-7, wherein multiple cycles are administered.

9. The method of any one of embodiments 1-8, wherein the pancreatic cancer is adenocarcinoma of the pancreas, such as unresectable, locally advanced or metastatic adenocarcinoma of the pancreas, for example, wherein the pancreatic cancer is metastatic adenocarcinoma of the pancreas; or wherein the metastatic pancreatic cancer is an exocrine metastatic pancreatic cancer selected from the group consisting of Duct cell carcinoma, Acinar cell carcinoma, Adenosquamous carcinoma, Cyst adenocarcinoma (serous and mucinous types), Giant cell carcinoma, Invasive adenocarcinoma associated with cystic mucinous neoplasm or intraductal papillary mucinous neoplasm, Mixed type (ductal-endocrine or acinar-endocrine), Mucinous carcinoma, Pancreatoblastoma, Papillary-cystic neoplasm (Frantz tumor), Papillary mucinous carcinoma, Signet ring carcinoma, Small cell carcinoma, Unclassified, Undifferentiated carcinoma, serous cystadenocarcinoma, and Solid and Pseudopapillary tumors.

11. The method of any one of embodiments 1-10, wherein the oxaliplatin is administered to the patient prior to the leucovorin, such as wherein the leucovorin is administered to the patient prior to the 5-FU, optionally wherein the MM-398 liposomal irinotecan is administered to the patient prior to the oxaliplatin, leucovorin, and 5-FU.

12. The method of embodiment 11, wherein the MM-398 is administered over 90 minutes, followed by administration of the oxaliplatin over 120 minutes, followed by administration of the leucovorin over 30 minutes, followed by the administration of the 5-FU over 46 hours. In a particular embodiment, a human patient with metastatic adenocarcinoma of the pancreas who has not previously been treated with any chemotherapeutic agent in the metastatic setting, is treated with a combination regimen of the present disclosure, the method comprising, intravenously administering to the patient, beginning on day 1 of a 2-week cycle, 80 mg/m$^2$ of MM-398 liposomal irinotecan over 90 minutes, followed by 60-85 mg/m$^2$ oxaliplatin, followed by 200 mg/m$^2$ of the (l) form of leucovorin, or 400 mg/m$^2$ of the (l+dl) racemic form of leucovorin, followed by 2,400 mg/m$^2$ 5-FU, wherein the human patient is treated with one or multiple cycles. In the embodiments disclosed herein, the effective amount of MM-398 liposomal irinotecan administered to the human patient can range from about 40 mg/m$^2$ to about 100 mg/m$^2$, for example, from about 60 mg/m$^2$ to about 80 mg/m$^2$. In various embodiments, the amount of MM-398 liposomal irinotecan administered to the human patient is 60 mg/m$^2$ or 80 mg/m$^2$. In the embodiments disclosed herein, the effective amount of Oxalyplatin administered to the human patient can range from about 40 mg/m$^2$ to about 100 mg/m$^2$, for example, from about 60 mg/m$^2$ to about 85 mg/m$^2$. In various embodiments, the amount Oxalyplatin administered to the human patient is 60 mg/m$^2$ or 85 mg/m$^2$. In one variant of this embodiment, oxaliplatin is administered over 120 minutes, leucovorin is administered over 30 minutes, and 5-FU is administered over 46 hours.

EXAMPLES

Example 1: In Vitro Pancreatic Cancer Cell Exposure to Topoisomerase 1 Inhibitor Simulated tumor exposure of SN-38 in patients administered with free irinotecan or MM-398 were shown in FIG. 1A. MM-398 is shown to result in prolonged SN-38 duration in tumors compared to free irinotecan (CPT-11). The effect of various SN-38 durations on cell growth inhibition was studied in a panel of pancreatic cell lines (AsPC-1, BxPC-3, Capan-2, CFPAC-1, and MiaPaCa-2). FIG. 1B illustrates the in vitro conditions for mimicking this clinically comparable SN-38 exposure of the 2 drugs, where cells exposed to SN-38 at high concentrations for a short period of time approximates for free irinotecan, and at low concentrations for a long period of time for MM-398. The results and experimental conditions are summarized in FIG. 1C. For example, cells incubated with 139 nM of SN-38 for 144 h vs. 417 nM for 24 h have similar SN-38 tumor exposure ratios of MM-398 vs. free irinotecan in patient tumors. Under these clinically relevant conditions, prolonged exposure (i.e. MM-398) primarily resulted in more pancreatic cancer cell growth inhibition compared to short exposure at high concentrations (i.e. free irinotecan). Similar results were also obtained when SN-38 were combined with 5-FU or oxaliplatin, demonstrating that prolonged exposure also led to increased cell growth inhibition when combined with these other chemotherapeutics agents that are used in the FOLFIRINOX regimen.

Example 2: Evaluation of In Vivo Tolerability and Efficacy of Combination Therapies in an Animal Model BxPC-3 and CFPAC-1 Mouse Xenograft Studies (Efficacy):
Tissue culture: BxPC-3 cells were cultured in RPMI growth media supplemented with 10% FBS and 1% penicillin/streptomycin. CFPAC-1 cells were also cultured in RPMI growth media supplemented with 10% FBS and 1% penicillin/streptomycin.

Animals: Experiments were performed according to approved guidelines. Female NOD.scid mice were obtained from Charles River Laboratories (Wilmington, Mass.). BxPC-3 or CFPAC-1 cells were inoculated into the right hind flank at 5e6 cells in a total volume of 50 uL per mouse. Eight animals were treated per group, unless otherwise indicated. Animals were randomized and dosing initiated when tumors reached an average volume of 200-250 mm$^3$ (range 100-400 mm$^3$), unless otherwise indicated.

Treatment efficacy: MM-398, irinotecan and oxaliplatin were administered intravenously. 5-FU was administered intraperitoneally. Administration of the indicated doses of each agent was initiated when tumors reached an average volume of 200-250 mm$^3$ and continued for a total of weekly doses. Tumor volumes were measured weekly until tumors reached 1000-2000 mm$^3$, as indicated, animals were in poor general health, or 2 weeks post post-final dose.

PDX19015 Mouse Xenograft Study (Efficacy and Tolerability):

Animals: Experiments were performed according to approved guidelines. Female CB.17 SCID mice were obtained from Roswell Park Cancer Institute (Buffalo, N.Y.), initially at 6-8 weeks of age. Per treatment group, 8 animals were treated, unless otherwise indicated. Tumor pieces were derived from donor mice and engrafted subcutaneously. Animals were randomized and dosing initiated when tumors reached an average volume of 200-250 mm$^3$ (range 100-400 mm$^3$), unless otherwise indicated.

Treatment efficacy: MM-398, irinotecan and oxaliplatin were administered intravenously. 5-FU was administered intraperitoneally. Administration of the indicated doses of each agent was initiated when tumors reached an average volume of 200-250 mm$^3$ and continued for a total of weekly doses. Tumor volumes were measured twice weekly during the dosing cycle, then once weekly until tumors reached 1000-2000 mm$^3$, as indicated, animals were in poor general health, or 100 days post-first dose. Tolerability: Mouse weights were measured once weekly to monitor treatment tolerability. Mice were euthanized when body weight declined to ≥20% below baseline, or they exhibited overt signs of poor general health.

Delayed Dosing of Oxaliplatin:

Animals: Experiments were performed according to approved guidelines. Female CD-1 mice were obtained from Charles River Laboratories (Wilmington, Mass.). Tolerability studies were performed in naïve (non-tumor-bearing) mice. Three animals were treated per group.

Treatment tolerability: Agents were administered intravenously at their pre-defined maximum tolerated doses (MM-398, 50 mg/kg; oxaliplatin, 17 mg/kg). Each drug was administered individually, or in combination. Combinations were given in one of 3 independent dosing schedules: coinjection (drugs administered simultaneously), MM-398 given on day 1 and oxaliplatin given on day 2 (24 h delay), or MM-398 given on day 1 and oxaliplatin given on day 4 (72 h delay). A single administration of each drug was given. Mouse body weights were measured daily for up to 2 weeks post-treatment. Mice were euthanized when body weight declined to ≥20% below baseline, they exhibited overt signs of poor general health, or at 2 weeks post-treatment (end of study).

Measurement of hematologic and liver toxicities: At the end of study, terminal bleeds were performed for each mouse via cardiac puncture. Hematologic function (blood cell count) was measured by Hemavet (Drew Scientific, Miami Lakes, Fla.), according to manufacturer's protocol. Liver function (enzyme levels) was measured by CatalystDx (Idexx Laboratories, Westbrook, Me.) according to the manufacturer's protocol.

Example 3: Treatment of Pancreatic Cancer

As schematically shown in FIG. 12, the present study is an open-label, phase 2 comparative study to assess the safety, tolerability, and efficacy of MM-398 in combination with other anticancer therapies, compared to nab-paclitaxel+gemcitabine, in patients with metastatic pancreatic adenocarcinoma who have not received prior chemotherapy. This study assesses the following regimens: (1) MM-398+5-FU/LV+oxaliplatin (Arm 1), (2) MM-398+5-FU/LV (Arm 2) and (3) nab-paclitaxel+gemcitabine (Arm 3).

This phase 2 study evaluates the preliminary safety and efficacy of MM-398+5-FU/LV with or without oxaliplatin versus nab-paclitaxel+gemcitabine in patients with previously untreated mPAC. The study may also provide important information on the impact of MM-398 combination treatment on patient HRQL and identify potential biomarkers of response.

In the study, MM-398 is administered instead of conventional irinotecan to improve the safety, tolerability, and ultimately efficacy of a FOLFIRINOX regimen. The addition of oxaliplatin to the NAPOLI-1 regimen is included to increase DNA damage and potentiate efficacy. Further, due to the MM-398 prolonged PK properties and sustained tumor exposure, using MM-398 instead of conventional irinotecan is designed to further improve upon the efficacy of FOLFIRINOX.

A modified triplet combination regimen of liposomal irinotecan, oxaliplatin, 5-fluorouracil (5-FU)/leucovorin is provided herein, whereby no bolus of 5-FU will be administered. The target dose of oxaliplatin (60-85 mg/m$^2$) is evaluated in the Arm 1 combination regimen with the continuous infusion dose of 5-FU (excluding the bolus), and the every 2 week dose of MM-398 previously shown to be tolerable and efficacious in combination with 5-FU. Note that with MM-398 dosing, the $C_{max}$ of SN-38 is expected to be lower than would be expected for standard dosing with free irinotecan.

The study is conducted in two parts, as illustrated in the schematic of FIG. 12: 1) a safety run-in of the MM-398+5-FU/LV+oxaliplatin regimen, and 2) a randomized, efficacy study of the MM-398+5-FU/LV+oxaliplatin regimen, the MM-398+5-FU/LV combination that previously demonstrated efficacy in the Phase 3 NAPOLI-1 trial (i.e. the NAPOLI regimen), and a nab-paclitaxel+gemcitabine control arm.

Part 1:

Part 1 consists of an open-label safety run-in of the combination regimen in Arm 1: MM-398+5-FU/LV+oxaliplatin. The Arm 2 and Arm 3 regimens have established doses, and MM-398+5-FU/LV has been demonstrated tolerable, yielding antitumor responses in a Phase 3 study of patients with relapsed metastatic pancreatic cancer, and therefore was not included in this part of the study. The safety run-in enrolls small cohorts of patients following a traditional 3+3 dose escalation design in order to confirm the target dose of oxaliplatin. Dose limiting toxicities (DLTs) are evaluated during the first cycle of treatment (i.e. 28 days per cycle; or 14 days after the 2$^{nd}$ dose of study treatment if there is a treatment delay in cohorts of patients to determine if the target combination dose is tolerable (note: the target combination dose is based on the established dose of the FOLFIRINOX regimen)). If there are no DLTs within the safety evaluation period, then the subsequent cohort is initiated following agreement between the Investigators, Medical Monitor, and the Sponsor. If one DLT occurs, then the cohort is expanded to 6 patients. If 2 or more patients have DLTs within a given dose level, that dose is considered to exceed the safety and tolerability criteria of the combination, and the dose is not be escalated further; however, lower doses can be explored. The Part 2 dose is then defined as the next lower dose level in which 6 patients were treated and ≤1 patient experienced a toxicity that qualifies as a DLT.

Additionally, UGT1A1*28 allele status is considered when evaluating DLTs. Based on previous experience with irinotecan, individuals who are homozygous for the UGT1A1*28 allele (UGT1A1 7/7 genotype) are at increased risk for neutropenia following initiation of irinotecan treatment. According to the prescribing information for irinotecan, in a study of 66 patients who received single-agent irinotecan (350 mg/m$^2$ once every-3-weeks), the incidence of grade 4 neutropenia in patients homozygous for the UGT1A1*28 allele was as high as 50%, and in patients heterozygous for this allele (UGT1A1 6/7 genotype) the incidence was 12.5%. Importantly, no grade 4 neutropenia was observed in patients homozygous for the wild-type (WT) allele (UGT1A1 6/6 genotype). In other studies, a lower prevalence of accompanying life threatening neutropenia is described (for details refer to the prescribing information for irinotecan). Population PK studies of MM-398 have not identified a relationship between UGT1A1*28 homozygosity and increased SN-38 exposure (see Investigator Brochure). In a Phase I study, no differences in toxicity were seen in cohorts of heterozygous or WT patients, and DLTs of diarrhea with or without accompanying dehydration or fatigue, were seen in both cohorts. For these reasons, and because the prevalence of UGT1A1*28 homozygosity is relatively low, testing results are not required prior to the first dose of MM-398 on this study and the starting dose for all patients will be 80 mg/m$^2$. However, if patients are known to be homozygous for UGT1A1*28, the dose of MM-398 may be reduced as described herein.

Part 2:

Part 2 consists of an open-label, randomized, Phase 2 study where patients will be randomized to treatment (1:1:1)

to either MM-398+5-FU/LV+oxaliplatin, MM-398+5-FU/LV, or nab-paclitaxel+gemcitabine. The randomization is stratified based on region (East Asia vs. rest of the world) and performance status (ECOG 0 vs. 1).

The following adverse events are common (≥40%) with past oxaliplatin treatment in combination with 5-FU/LV and are to be expected with the MM-398-containing combination regimen: peripheral sensory neuropathy, neutropenia, thrombocytopenia, anemia, nausea, increases in transaminases and alkaline phosphatase, diarrhea, fatigue, emesis, and stomatitis. Additional adverse events may be anticipated, as described in the package insert for oxaliplatin, including allergic and anaphylactic reactions. In a Phase 3 study of the FOLFIRINOX combination, the most common (>5%) Grade 3-4 adverse events were: neutropenia, fatigue, vomiting, diarrhea, thrombocytopenia, sensory neuropathy, anemia, elevated alanine aminotransferase (ALT) level, thromboembolism, and febrile neutropenia. Considering these expected toxicities, Arm 1 is evaluated for safety and tolerability in Part 1 of the study as described below.

A dose of oxaliplatin of 85 mg/m$^2$ is the target dose for Part 2 of this study. The purpose of Part is to confirm whether this dose is compatible when MM-398 is used instead of conventional irinotecan. In case there are any unexpected toxicities, 3 to 6 patients are initially treated at a lower dose of oxaliplatin (60 mg/m$^2$, see Table 1) prior to administration of oxaliplatin at the highest proposed dose of 85 mg/m$^2$. The dose of the triplet combination to be administered in Part 2 of the study is defined as the highest dose level at which a DLT is experienced by fewer than 2 patients in a cohort of 3 to 6 patients. If one patient experiences a treatment-related toxicity that qualifies as a DLT, up to 3 additional patients are enrolled at that dose level, for no more than 6 total patients per cohort. If no additional DLTs are observed, the dose escalation resumes. If a second patient experiences a treatment-related toxicity that qualifies as a DLT at that dose, that dose is considered to exceed the optimal safety and tolerability criteria of the combination. The dose to be used in Part 2 is then defined as the next lower dose level in which 6 patients were treated and ≤1 patient experienced a toxicity that qualifies as a DLT.

Dosing of patient cohorts begins at dose level −1 with planned escalation to dose level −2B (target dose), in which the dose for one of the three drugs is increased while the other two drugs will maintain a constant dose. If the −1 dose level is evaluated and deemed to be safe, escalation to the −2B dose level may be initiated. Any decisions to de-escalate, as well as enrollment at alternative doses following de-escalation, must be made according to the established decision process for dose escalation, as described herein. Planned dose escalation for the Arm 1 combination regimen is outlined in Table 2 below; additional details on dose administration as described herein in the section "Study Treatment".

TABLE 2

Part 1 Dose Escalation Table (MM-398 + 5-FU/LV + oxaliplatin)

| Level | Oxaliplatin | | 5-FU/LV | | MM-398 (nal-IRI) | |
| --- | --- | --- | --- | --- | --- | --- |
| | Dose (mg/m$^2$)$^a$ | Dose Day$^c$ | Dose (mg/m$^2$) | Dose Day$^c$ | Dose (mg/m$^2$)$^b$ | Dose Day$^c$ |
| −1 | 60 | 1, 15 | 2400/400 | 1, 15 | 60 | 1, 15 |
| −2B | 85 | 1, 15 | 2400/400 | 1, 15 | 60 | 1, 15 |

$^a$First dose administration in conjunction with first dose of MM-398; oxaliplatin to be administered 2 hours after the completion of the nal-IRI infusion in Part 1.
$^b$46 hour infusion, no bolus is given; leucovorin and 5-FU will be administered last, following the completion of the oxaliplatin infusion
$^c$Day indicated is part of a 28-day cycle Arm 1: MM-398+5-FU/LV+Oxaliplatin The order of the infusions to be administered in the clinic is as follows: MM-398 administered first, followed by oxaliplatin, then LV, followed by 5-FU.

In Part 1, patients receive the oxaliplatin infusion 2 hours after the completion of the MM-398 infusion. If no infusion reactions are seen, Part 2 patients can receive oxaliplatin directly after completion of the MM-398 infusion. If any grade 3 or higher infusion reactions are seen in Part patients, the DSMB may elect to revert back to administration of oxaliplatin two hours after the completion of the MM-398 infusion.

Arm 1 Premedication

All patients must be premedicated prior to MM-398 infusion, 5-FU/LV infusion, and oxaliplatin infusion with standard doses of dexamethasone and a 5-HT3 antagonist, or equivalent other anti-emetics according to standard institutional practices for irinotecan, 5-FU, and oxaliplatin administration, or the Summary of Product Characteristics (SmPC) for sites located in the European Union (EU). Atropine may be prescribed prophylactically for patients who experienced acute cholinergic symptoms in the previous cycles.

Arm 2: MM-398+5-FU/LV

The order of the infusions to be administered in the clinic will be as follows: MM-398 will be administered first, followed by LV, followed by 5-FU.

Arm 2 Premedication

All patients must be premedicated prior to MM-398 infusion and 5-FU/LV infusion with standard doses of dexamethasone and a 5-HT3 antagonist, or equivalent other anti-emetics according to standard institutional practices for irinotecan and 5-FU administration, or the SmPC for sites located in the EU. Atropine may be prescribed prophylactically, according to standard institutional practices, for patients who experienced acute cholinergic symptoms in the previous cycles.

Doses and Administration of MM-398 (Arms 1 and 2)

MM-398 is administered by intravenous (IV) infusion over 90 minutes (±10 minutes) every two weeks. The first cycle Day 1 is a fixed day; subsequent doses should be administered on the first day of each cycle+/−2 days.

Prior to administration, the appropriate dose of MM-398 must be diluted in 5% Dextrose Injection solution (D5W) or normal saline to a final volume of 500 mL. Care should be taken not to use in-line filters or any diluents other than D5W or normal saline. MM-398 can be administered at a rate of up to 1 mL/sec (30 mg/sec).

The actual dose of MM-398 to be administered will be determined by calculating the patient's body surface area at the beginning of each cycle. A +/−5% variance in the calculated total dose will be allowed for ease of dose administration. Since MM-398 vials are single-use vials, site staff must not store any unused portion of a vial for future use and they must discard unused portions of the product.

Doses and Administration of 5-FU and Leucovorin (Arms 1 and 2)

Leucovorin is administered at a dose of 400 mg/m$^2$ of the (l+d)-racemic form, or (l) form 200 mg/m$^2$, as an IV infusion over 30 minutes (±5 minutes), on Days 1 and 15 of each 28-day cycle 5-FU is administered at a dose of 2400 mg/m$^2$ as an IV infusion over 46-hours (±60 minutes), on Days 1 and 15 of each 28-day cycle Leucovorin should be reconstituted per the instructions on the package insert, SmPC or standard institutional guidelines for reconstitution of leucovorin.

Leucovorin should be administered prior to the 5-FU infusion (on Arm 1, leucovorin will be given concurrently with oxaliplatin). Actual dose of 5-FU and leucovorin to be administered is determined by calculating the patient's body surface area prior to each cycle. A +/−5% variance in the calculated total dose will be allowed for ease of dose administration.

Doses and Administration of Oxaliplatin (Arm 1 Only)

In Part 1, oxaliplatin is administered at increasing dose levels as indicated in Table 2 (from 60 mg/m$^2$-85 mg/m$^2$), IV over 120 minutes (±10 minutes), on Days 1 and 15 of each 28-day cycle In Part 2, oxaliplatin is administered at a dose of 85 mg/m$^2$, IV over 120 minutes (±10 minutes), on Days 1 and 15 of each 28-day cycle (if target dose is confirmed in accordance with methods described herein).

Oxaliplatin should be prepared according to the instructions on the package insert, SmPC or per standard institutional guidelines for preparation and administration of oxaliplatin.

Oxaliplatin should be administered following MM-398 infusion; in Part 1, the first 3 patients in Dose Level 1 begin the oxaliplatin infusion two hours after the completion of the MM-398 infusion. Actual dose of oxaliplatin to be administered is determined by calculating the patient's body surface area prior to each cycle. A +/−5% variance in the calculated total dose is allowed for ease of dose administration.

Arm 3: Nab-Paclitaxel+Gemcitabine

The order of the infusions to be administered in the clinic is as follows: nab-paclitaxel will be administered first, followed by gemcitabine.

Arm 3 Premedication

All patients receiving nab-paclitaxel and gemcitabine should be pre-medicated per the respective package inserts. If different institutional guidelines exist for premedication of weekly nab-paclitaxel and/or gemcitabine, the investigator should use their standard practice or the SmPC for sites located in the EU.

Doses and Administration of Nab-Paclitaxel and Gemcitabine (Arm 3)

The nab-paclitaxel will be administered at 125 mg/m$^2$ IV over 35 minutes (±5 minutes), on Days 1, 8 and 15 of each 28-day cycle.

The gemcitabine will be administered at 1000 mg/m$^2$ IV over 30 minutes (±5 minutes), on Days 1, 8 and 15 of each 28-day cycle.

Dose Limiting Toxicities (DLTs)

For MM-398 administered in combination with 5-FU/LV and oxaliplatin, the following adverse events are considered as dose limiting toxicities (DLTs) if they occur during the first cycle of treatment and are deemed related to the study treatment regimen:

Grade 4 neutropenia or thrombocytopenia that does not resolve within 7 days despite optimal therapy (withholding study drug and administering concomitant medication, e.g. G-CSF administration for neutropenia);

Grade 4 neutropenia complicated by fever ≥38.5° C. (i.e. febrile neutropenia) and/or Grade 3 neutropenia with infection;

Inability to begin subsequent treatment course within 14 days of the scheduled date, due to drug-related toxicity; and Any grade 4 non-hematologic toxicity with the specific exclusion of: Fatigue/asthenia <2 weeks in duration, increases in alkaline phosphatase level, nausea and vomiting ≤3 days duration (only considered dose limiting if they last >72 hours after treatment with an optimal anti-emetic regimen), and diarrhea ≤3 days duration (only considered dose limiting if diarrhea lasts >72 hours after treatment with an optimal anti-diarrheal regimen)

Any toxicity that is related to disease progression will not be considered a DLT.

The safety assessment period for purposes of DLT evaluation and dose escalation decisions is one cycle of treatment (i.e. 28 days; or 14 days after the 2nd dose of study treatment if there is a treatment delay according as described herein). The dose can escalate to the next level only after the safety data have been evaluated at the current dose level (once the last patient enrolled in the cohort completes the first cycle of treatment) and the criteria for safety and tolerability of the optimal dose have not been exceeded (see Section Part 2 dose definition). In addition, any drug-related toxicities of Grade 3 or higher that arise after Cycle 1 (if applicable) are assessed for their potential relationship to cumulative MM-398 or combination therapy doses and considered in the decision to escalate the dose. PK data may be available, but is not be required for decisions on dose escalation.

| Inclusion Criteria | Exclusion Criteria |
| --- | --- |
| In order for inclusion into the study, patients must have/be: Pathologically confirmed adenocarcinoma of the pancreas that has not been previously treated in the metastatic setting Part 1: unresectable, locally advanced or metastatic disease is allowed, diagnosed within 6 weeks prior to enrollment Part 2: must have metastatic disease diagnosed within 6 weeks prior to randomization; locally advanced disease is not allowed | Patients must meet all the inclusion criteria and none of the following exclusion criteria: Prior treatment of pancreatic cancer in the metastatic setting with surgery, radiotherapy, chemotherapy or investigational therapy (note: placement of biliary stent is allowed) Prior treatment of pancreatic cancer with cytotoxic doses of chemotherapy (patients receiving prior treatment with chemotherapy as a radiation sensitizer are eligible if ≥6 months has elapsed from completion of therapy) Known metastasis to the central nervous system Clinically significant gastrointestinal disorder including hepatic disorders, bleeding, inflammation, occlusion, diarrhea > grade 1, malabsorption syndrome, ulcerative colitis, inflammatory bowel disease, or partial bowel obstruction History of any second malignancy in the last 3 years; patients with prior history of in-situ cancer or basal |

| Inclusion Criteria | Exclusion Criteria |
|---|---|
| Measurable or non-measurable disease as defined by RECIST v1.1 | or squamous cell skin cancer are eligible. Patients with a history of other malignancies are eligible if they have been continuously disease free for at least 3 years. |
| ECOG performance status of 0 or 1 | Known hypersensitivity to any of the components of MM-398, other liposomal products, or any components of 5-FU, leucovorin or oxaliplatin |
| Adequate biological parameters as evidenced by the following blood counts: | Known hypersensitivity to any of the components of nab-paclitaxel or gemcitabine (Part 2 only) |
| ANC >1,500 cells/µl without the use of hematopoietic growth factors, | Concurrent illnesses that would be a relative contraindication to trial participation such as active cardiac or liver disease, including: |
| Platelet count >100,000 cells/µl, and | Severe arterial thromboembolic events (myocardial infarction, unstable angina pectoris, stroke) less than 6 months before inclusion |
| Hemoglobin >9 g/dL | |
| Adequate hepatic function as evidenced by: | NYHA Class III or IV congestive heart failure, ventricular arrhythmias or uncontrolled blood pressure |
| Serum total bilirubin ≤ ULN (biliary drainage is allowed for biliary obstruction), and | Known historical or active infection with HIV, hepatitis B, or hepatitis C |
| AST and ALT ≤2.5 × ULN (≤5 × ULN is acceptable if liver metastases are present) | Active infection or an unexplained fever >38.5° C. during screening visits or on the first scheduled day of dosing (at the discretion of the investigator, patients with tumor fever may be enrolled), which in the investigator's opinion might compromise the patient's participation in the trial or affect the study outcome |
| Adequate renal function as evidenced by serum creatinine ≤1.5 × ULN, and calculated clearance ≥60 mL/min/1.72 m² for patients with serum creatinine levels above or below the institutional normal value. Actual body weight should be used for calculating creatinine clearance using the Cockcroft-Gault Equation (CreatClear = Sex * ((140 − Age)/(SerumCreat)) * (Weight/72); for patients with body mass index (BMI) >30 kg/m², lean body weight should be used instead. | Use of strong CYP3A4 inhibitors or inducers, or presence of any other contraindications for irinotecan |
| | Presence of any contraindications for 5-FU, leucovorin, or oxaliplatin |
| | Use of strong CYP2C8 inhibitors or inducers, or presence of any other contraindications for nab-paclitaxel or gemcitabine (Part 2 only) |
| | Any other medical or social condition deemed by the Investigator to be likely to interfere with a patient's ability to sign informed consent, cooperate and participate in the study, or interfere with the interpretation of the results |
| Normal ECG or ECG without any clinically significant findings | |
| Recovered from the effects of any prior surgery or radiotherapy | Pregnant or breast feeding; females of child-bearing potential must test negative for pregnancy at the time of enrollment based on a urine or serum pregnancy test. Both male and female patients of reproductive potential must agree to use a highly effective method of birth control, during the study and for 3 months following the last dose of study drug. |
| ≥18 years of age | |
| Agreeable to submit unstained archived tumor tissue for analysis, if available | |
| Able to understand and sign an informed consent (or have a legal representative who is able to do so) | |

Dose Modifications

The toxicity of each cycle must be recorded prior to the administration of a subsequent cycle and graded according to the National Cancer Institute Common Terminology Criteria for Adverse Events (NCI CTCAE) (Version 4.03). All dose reductions for all arms should be based on the worst preceding toxicity.

Dosing may be held for up to 2 weeks from when it was due to allow for recovery from toxicity related to the study treatment. If the time required for recovery from toxicity is more than 2 weeks, the patient should be discontinued from the study, unless the patient is benefiting from the study treatment, in which case the patient's continuation on study should be discussed between Investigator and Sponsor regarding risks and benefits of continuation. If oxaliplatin is not well tolerated in patients enrolled in Arm 1, oxaliplatin may be discontinued and patients may continue to receive MM-398+5-FU/LV at the discretion of the Investigator.

If a patient's dose is reduced during the study due to toxicity, it should remain reduced for the duration of the study; dose re-escalation to an earlier dose is not permitted. Any patient who has 2 dose reductions and experiences an adverse event that would require a third dose reduction must be discontinued from study treatment.

Dose Modifications

Prior to each dosing, patients must have: ANC≥1500/mm³, WBC≥3500/mm³, Platelet count≥100,000/mm³ and Diarrhea≤Grade 1.

Treatment should be delayed to allow sufficient time for recovery to levels noted above, and upon recovery, treatment should be administered according to the guidelines in the tables below. If the patient had febrile neutropenia, the ANC must have resolved to ≥1500/mm³ and the patient must have recovered from infection. For Grade 3 or 4 non-hematological toxicities, treatment should be delayed until they resolve to Grade 1 or baseline. Guidelines for dose adjustments of each individual treatment within the regimen are found in the tables below for Arm 1 (Table 3), and for Arm 2 (Tables 6 through 14). In case a patient experiences an infusion reaction, either institutional guidelines or the guidelines provided for infusion reaction management should be followed.

For all tables below, patient should be withdrawn from study treatment if more than 2 dose reductions are required or if MM-398 reductions lower than 35 mg/m$^2$ are required. No dose adjustments for toxicity are required for leucovorin. Leucovorin must be given immediately prior to each 5-FU dose; hence, if 5-FU dose is held, leucovorin dose should be held as well. Treatment discontinuation that is required due to MM-398 or 5-FU toxicity will result in discontinuation from the study. However, for Arm 1, toxicity that requires discontinuation from oxaliplatin only (e.g. neuropathy) will result in the option to continue on study treatment with MM-398+5-FU/LV only for all future dosing.

Arm 1 Dose Modifications

The starting dose of ONIVYDE will be 60 mg/m$^2$, 5FU 2400 mg/m$^2$, LV 400 mg/m$^2$ and Oxaliplatin either 85 mg/m$^2$ or 60 mg/m$^2$. Dose reduction will be 25% reduction in all agents for any grade III-IV Hematotoxicity. For persistent toxicities despite the first dose reduction, and additional 25% dose reduction in all agents will occur. Further toxicity will then lead to discontinuation from trial.

For non-hematologic toxicities, the dose reduction will be the same dose reduction schema as for hematotoxicity, except for the specific toxicities associated with the drug (ie 5FU hand foot syndrome, and oxaliplatin neuropathy) which will be as shown in Table 3.

TABLE 3

Arm 1 Dose Modifications

| Worst Toxicity by CTCAE Grade | MM-398 | 5-FU | Oxaliplatin |
|---|---|---|---|
| Hematological Toxicities | | | |
| Grade 2 neutropenia (ANC <1500-1000 cells/mm$^3$) | 100% of previous dose | 100% of previous dose | 1$^{st}$ occurrence: 100% of previous dose |
| Grade 3 or 4 neutropenia (ANC ≤1000/mm$^3$) or febrile neutropenia$^a$ | 1$^{st}$ occurrence: Reduce dose to 45 mg/m$^2$ 2$^{nd}$ occurrence: Reduce dose to 35 mg/m$^2$ | 1$^{st}$ occurrence: Reduce dose by 25% 2$^{nd}$ occurrence: Reduce dose another 25% | 1$^{st}$ occurrence: Reduce dose from 85 mg/m$^2$ to 65 mg/m$^2$ or from 60 mg/m$^2$ to 45 mg/m$^2$ 2$^{nd}$ occurrence: Reduce dose from 65 mg/m$^2$ to 50 mg/m$^2$ or from 45 mg/m$^2$ to 35 mg/m$^2$ |
| ≥Grade 2 thrombocytopenia (Grade 2: platelets ≤75,000/mm$^3$-50,000/mm$^3$ OR Grade 3-4: platelets <50,000/mm$^3$) | If Grade 2: 100% of previous dose If ≥ Grade 3: 1$^{st}$ occurrence: Reduce dose to 45 mg/m$^2$ 2$^{nd}$ occurrence: Reduce dose to 35 mg/m$^2$ | If Grade 2: 100% of previous dose If ≥ Grade 3: 1$^{st}$ occurrence: Reduce dose by 25% 2$^{nd}$ occurrence: Reduce dose another 25% (50% of original dose) | 1$^{st}$ occurrence: Reduce dose from 85 mg/m$^2$ to 65 mg/m$^2$ or from 60 mg/m$^2$ to 45 mg/m$^2$ 2$^{nd}$ occurrence: Reduce dose from 65 mg/m$^2$ to 50 mg/m$^2$ or from 45 mg/m$^2$ to 35 mg/m$^2$ |
| Other hematologic toxicities not specifically listed above | If ≤ Grade 2: 100% of previous dose If ≥ Grade 3: 1$^{st}$ occurrence: Reduce dose to 45 mg/m$^2$ 2$^{nd}$ occurrence: Reduce dose to 35 mg/m$^2$ | If ≤ Grade 2: 100% of previous dose If ≥ Grade 3: 1$^{st}$ occurrence: Reduce dose by 25% 2$^{nd}$ occurrence: Reduce dose another 25% | If ≤ Grade 2: 100% of previous dose If ≥ Grade 3: 1$^{st}$ occurrence: Reduce dose from 85 mg/m$^2$ to 65 mg/m$^2$ or from 60 mg/m$^2$ to 45 mg/m$^2$ 2$^{nd}$ occurrence: Reduce dose from 65 mg/m$^2$ to 50 mg/m$^2$ or from 45 mg/m$^2$ to 35 mg/m$^2$ |

TABLE 3-continued

Arm 1 Dose Modifications

| Worst Toxicity by CTCAE Grade | MM-398 | 5-FU | Oxaliplatin |
|---|---|---|---|
| Non-Hematological Toxicities Other than Asthenia and Grade 3 Anorexia[b] | | | |
| Grade 1 or 2, including diarrhea[c] | 100% of previous dose | 100% of previous dose, except for Grade 2 hand foot syndrome, Grade 2 cardiac toxicity, or any grade neurocerebellar toxicity | 100% of previous dose |
| Grade 3 or 4, including diarrhea[d] (except nausea and vomiting) | 1st occurrence: Reduce dose to 45 mg/m$^2$ 2nd occurrence: Reduce dose to 35 mg/m$^2$ | 1st occurrence: Reduce dose by 25% 2nd occurrence: Reduce dose another 25% *except for Grade 3 or 4 hand foot syndrome | 1st occurrence: Reduce dose from 85 mg/m$^2$ to 65 mg/m$^2$ or from 60 mg/m$^2$ to 45 mg/m$^2$ 2nd occurrence: Reduce dose from 65 mg/m$^2$ to 50 mg/m$^2$ or from 45 mg/m$^2$ to 35 mg/m$^2$ |
| Grade 3 or 4 nausea and/or vomiting despite anti-emetic therapy | Optimize anti-emetic therapy AND 1st occurrence: Reduce dose to 45 mg/m$^2$ 2nd occurrence: Reduce dose to 35 mg/m$^2$ | Optimize anti-emetic therapy AND reduce dose by 25%; if the patient is already receiving a reduced dose, reduce dose an additional 25% | 1st occurrence: Reduce dose from 85 mg/m$^2$ to 65 mg/m$^2$ or from 60 mg/m$^2$ to 45 mg/m$^2$ 2nd occurrence: Reduce dose from 65 mg/m$^2$ to 50 mg/m$^2$ or from 45 mg/m$^2$ to 35 mg/m$^2$ |
| Grade 2 hand foot syndrome | 100% of previous dose[d] | 1st occurrence: Reduce dose by 25% 2nd occurrence: Reduce dose another 25% | 100% of previous dose |
| Grade 3 or 4 hand foot syndrome | 1st occurrence: Reduce dose to 45 mg/m$^2$ 2nd occurrence: Reduce dose to 35 mg/m$^2$ | Discontinue therapy | No dose modifications required |
| Any grade neurocerebellar or ≥ Grade 2 cardiac toxicity | No dose modifications required[e] | Discontinue therapy | No dose modifications required |
| Sensory neuropathy | No dose modifications required[e] | No dose modifications required[e] | Grade 2, persistent: Reduce dose from 85 mg/m$^2$ to 60 mg/m$^2$ or from 60 mg/m$^2$ to 45 mg/m$^2$ Grade 3, recovers prior to next cycle: Reduce dose from 85 mg/m$^2$ to 60 mg/m$^2$ or from 60 mg/m$^2$ to 45 mg/m$^2$ Grade 3, persistent: Discontinue therapy Grade 4: Discontinue therapy |

[a]Consider the use of G-CSF for patients who experience ≥ Grade 3 neutropenia or febrile neutropenia.
[b]Asthenia and Grade 3 Anorexia do not require dose modification
[c]Grade 1 diarrhea: 2-3 stools/day > pretreatment; Grade 2 diarrhea: 4-6 stools/day > pretreatment
[d]Grade 3 diarrhea: 7-9 stools/day > pretreatment; Grade 4 diarrhea: >10 stools/day > pretreatment Arm 2 Dose Modifications Dosing may be held for up to 3 weeks from when it was due, to allow for recovery from toxicity related to the study treatments. If the time required for recovery from toxicity is more than 3 weeks, the patient should be discontinued from the study, unless the patient is benefiting from the study treatment, in which case the patient's continuation on study should be discussed between Investigator and Sponsor or its designee regarding risks and benefits of continuation.

If a patient's dose is reduced during the study due to toxicity, it should remain reduced for the duration of the study; dose re-escalation to an earlier dose is not permitted. Any patient who has 2 dose reductions and experiences an adverse event that would require a third dose reduction must be discontinued from study treatment.

Infusion reactions will be monitored. Infusion reactions will be defined according to the National Cancer Institute CTCAE (Version 4.0) definition of an allergic reaction/infusion reaction and anaphylaxis, as defined below:

TABLE 4

Grade 1: Transient flushing or rash, drug fever <38° C. (<100.4° F.); intervention not indicated
Grade 2: Intervention or infusion interruption indicated; responds promptly to symptomatic treatment (e.g., antihistamines, NSAIDS, narcotics); prophylactic medications indicated for <24 hrs
Grade 3: Symptomatic bronchospasm, with or without urticaria; parenteral intervention indicated; allergy-related edema/angioedema; hypotension
Grade 4: Life-threatening consequences; urgent intervention indicated Study site policies or the following treatment guidelines shall be used for the management of infusion reactions.

TABLE 5

Grade 1

Slow infusion rate by 50%
Monitor patient every 15 minutes for worsening of condition
Grade 2

Stop infusion
Administer diphenhydramine hydrochloride 50 mg IV, acetaminophen 650 mg orally, and oxygen TABLE 5-continued Resume infusion at 50% of the prior rate once infusion reaction has resolved
Monitor patient every 15 minutes for worsening of condition
For all subsequent infusions, premedicate with diphenhydramine hydrochloride 25-50 mg IV
Grade 3

Stop infusion and disconnect infusion tubing from patient
Administer diphenhydramine hydrochloride 50 mg IV, dexamethasone 10 mg IV, bronchodilators for bronchospasm, and other medications or oxygen as medically necessary
No further treatment with MM-398 will be permitted
Grade 4

Stop the infusion and disconnect infusion tubing from patient
Administer epinephrine, bronchodilators or oxygen as indicated for bronchospasm
Administer diphenhydramine hydrochloride 50 mg IV, dexamethasone 10 mg IV
Consider hospital admission for observation
No further treatment with MM-398 will be permitted For patients who experience a Grade 1 or Grade 2 infusion reaction, future infusions may be administered at a reduced rate (over 120 minutes), with discretion.

For patients who experience a second grade 1 or 2 infusion reaction, administer dexamethasone 10 mg IV. All subsequent infusions should be premedicated with diphenhydramine hydrochloride 50 mg IV, dexamethasone 10 mg IV, and acetaminophen 650 mg orally.

MM-398 Dose Modifications for Hematological Toxicities

Prior to initiating a new cycle of therapy, the patients must have:

ANC≥1500/m m$^3$

Platelet count≥100,000/mm$^3$

Treatment should be delayed to allow sufficient time for recovery and upon recovery, treatment should be administered according to the guidelines in the tables below. If the patient had febrile neutropenia, the ANC must have resolved to ≥1500/mm$^3$ and the patient must have recovered from infection.

TABLE 6

MM-398 Dose Modifications for Neutrophil Count

| | MM-398 Dose for Next Cycle | | |
|---|---|---|---|
| ANC: cells/mm$^3$ (Worst CTCAE grade) | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
| ≥1000 to 1999 (Grade 1 or 2) | 100% of previous dose | 100% of previous dose | 100% of previous dose |
| <1000 (Grade 3/4) or febrile neutropenia | Reduce dose by 20 mg/m$^2$ to a minimum dose of 40 mg/m$^2$ | Reduce dose to 45 mg/m$^2$ for the first occurrence and to 35 mg/m$^2$ for the second occurrence | Reduce dose to 45 mg/m$^2$ for the first occurrence and to 35 mg/m$^2$ for the second occurrence |

TABLE 7

MM-398 Dose Modifications for Other Hematologic Toxicity

MM-398 Dose for Next Cycle

| Worst Toxicity CTCAE Grade | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
|---|---|---|---|
| ≤Grade 2 | 100% of previous dose | 100% of previous dose | 100% of previous dose |
| Grade 3/4 | Reduce dose by 20 mg/m² to a minimum dose of 40 mg/m² | Reduce dose to 45 mg/m² for the first occurrence and to 35 mg/m² for the second occurrence | Reduce dose to 45 mg/m² for the first occurrence and to 35 mg/m² for the second occurrence |

MM-398 Dose Modifications for Non-Hematological Toxicities

Treatment should be delayed until diarrhea resolves to ≤Grade 1, and for other Grade 3 or 4 non-hematological toxicities, until they resolve to Grade 1 or baseline. Guidelines for dose adjustment of MM-398 for drug related diarrhea and other Grade 3 or 4 non-hematological toxicities are provided below. Infusion reactions should be handled as described above.

TABLE 8

MM-398 Dose Modifications for Diarrhea

MM-398 Dose for Next Cycle$^a$

| Worst Toxicity CTCAE Grade | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
|---|---|---|---|
| Grade 1 or 2 (2-3 stools/day > pretreatment or 4-6 stools/day > pretreatment) | 100% of previous dose | 100% of previous dose | 100% of previous dose |
| Grade 3 (7-9 stools/day > pretreatment) or Grade 4 (>10 stools/day > pretreatment) | Reduce dose by 20 mg/m² to a minimum dose of 40 mg/m² | Reduce dose to 45 mg/m² for the first occurrence and to 35 mg/m² for the second occurrence | Reduce dose to 45 mg/m² for the first occurrence and to 35 mg/m² for the second occurrence |

TABLE 9

MM-398 Dose Modifications for Non-Hematological Toxicities Other than Diarrhea, Asthenia and Grade 3 Anorexia MM-398 Dose for Next Cycle

| Worst Toxicity CTCAE Grade | Arm A: Patients Not Homozygous for UGT1A1*28 | Arm A: Patients Homozygous for UGT1A1*28 Arm C: Patients Not Homozygous for UGT1A1*28 | Arm C: Patients Homozygous for UGT1A1*28 |
|---|---|---|---|
| Grade 1 or 2 | 100% of previous dose | 100% of previous dose | 100% of previous dose |
| Grade 3 or 4 (except nausea and vomiting) | Reduce dose by 20 mg/m² to a minimum dose of 40 mg/m² | Reduce dose to 45 mg/m² for the first occurrence and to 35 mg/m² for the second occurrence | Reduce dose to 45 mg/m² for the first occurrence and to 35 mg/m² for the second occurrence |
| Grade 3 or 4 nausea and or vomiting despite anti emetic therapy | Optimize anti-emetic therapy AND reduce dose by 20 mg/m² to a minimum dose of 40 mg/m² | Optimize anti-emetic therapy AND reduce dose to 40 mg/m² | Optimize anti-emetic therapy AND reduce dose to 40 mg/m² |

5-FU and Leucovorin Dose Modifications

Guidelines for 5-FU dose modifications are provided below. No dose adjustments for toxicity are required for leucovorin. Leucovorin must be given immediately prior to each 5-FU dose; hence, if 5-FU dose is held, leucovorin dose should be held as well. In case a patient experiences an infusion reaction, either institutional guidelines or the guidelines provided for MM-398 infusion reaction management should be used.

5-FU Dose Modifications for Hematological Toxicities

Prior to the next dose in a cycle or prior to initiating a new cycle of therapy, the patients must have:

ANC≥1500/mm$^3$
WBC≥3500/mm$^3$
Platelet count≥75,000/mm$^3$ (according to the European summary of product characteristics for 5-FU, the platelets should have recovered to ≥100,000/mm$^3$ prior to initiating therapy)

Treatment should be delayed to allow sufficient time for recovery and upon recovery, treatment should be administered according to the guidelines provided in the table below. The duration of the cycles is fixed at 6 weeks, and if a patient is unable to receive the D8, D15 or D22 dose due to toxicity, the dose will be considered as skipped.

MM-398 Dose Modifications for UGT1A1*28 Positive Patients (Arms 1 and 2)

Patients are tested for UGT1A1*28 status during screening, however the result of the test is not required prior to the initial dose of MM-398. All patients will begin dosing at 80 mg/m$^2$ (salt), however future doses may be reduced for patients who are positive (i.e. homozygous) for UGT1A1*28 7/7 genotype. For Part 1 patients receiving 80 mg/m$^2$ (salt) of MM-398: depending on the overall safety profile seen after the first dose, the dose may be reduced to 60 mg/m$^2$ (salt) after discussion between the PI, Sponsor and Medical Monitor. Any Part 1 patients who receive a reduced dose during Cycle 1 due to UGT1A1*28 homozygosity will not be evaluable for the cohort and are replaced.

Arm 3 Dose Modifications

Dose level reductions required due to toxicities related to nab-paclitaxel and gemcitabine should be made following the guidelines outlined in Table 12.

TABLE 12

Dose Level Reductions for nab-Paclitaxel and Gemcitabine

| Dose Level | Nab-paclitaxel (mg/m$^2$) | Gemcitabine (mg/m$^2$) |
| --- | --- | --- |
| Full dose | 125 | 1000 |
| 1$^{st}$ dose reduction | 100 | 800 |

TABLE 10

5-FU Dose Modifications for Hematological Toxicities (Arm B & C)

| ANC (cells/mm$^3$) | | Platelets (cells/mm$^3$) | 5-FU Dose for D8, D15, D22$^a$ | 5-FU Dose for Next Cycle$^a$ |
| --- | --- | --- | --- | --- |
| ≥1000 | and | ≥50,000 | 100% of previous dose | 100% of previous dose |
| 500-999 | Or | <50,000-25,000 | Hold; when resolved, reduce dose by 25%$^b$ | Reduce dose by 25%$^b$ |
| <500 or febrile neutropenia | Or | <25,000 or thrombocytopenia with bleeding | Hold dose; when resolved, reduce dose by 25%$^b$ | Reduce dose by 25%$^b$ |

$^a$All dose modifications should be based on the worst preceding toxicity
$^b$Patients who require more than 2 dose reductions must be withdrawn from the study 5-FU Dose Modifications for Non-Hematological Toxicities Treatment should be delayed until all Grade 3 or 4 non-hematological toxicities resolve to Grade 1 or baseline. Guidelines for dose adjustment of 5-FU related toxicities are provided below. The duration of the cycles is fixed at 6 weeks, and if a patient is unable to receive the D8, D15 or D22 dose due to toxicity, the dose will be considered as skipped.

TABLE 11

5-FU Dose Modifications for Non-Hematological Toxicities Other than Asthenia and Grade 3 Anorexia$^c$

| Worst Toxicity CTCAE Grade | 5-FU Dose for D8, D15, D22$^a$ | 5-FU Dose for Next Cycle$^a$ |
| --- | --- | --- |
| Grade 1 or 2 | 100% of previous dose, except for Grade 2 hand foot syndrome, Grade 2 cardiac toxicity, or any grade neurocerebellar toxicity | 100% of previous dose, except for Grade 2 hand and foot syndrome, Grade 2 cardiac toxicity, or any grade neurocerebellar toxicity |
| Grade 2 hand foot syndrome | Reduce dose by 25%$^b$ | Reduce dose by 25%$^b$ |
| Any grade neurocerebellar or ≥ Grade 2 cardiac toxicity | Discontinue therapy | Discontinue therapy |
| Grade 3 or 4 | Hold; when resolved, reduce dose by 25%$^b$, except for Grade 3 or 4 hand foot syndrome | Reduce dose by 25%$^b$, except for Grade 3 or 4 hand foot syndrome |
| Grade 3 or 4 hand foot syndrome | Discontinue therapy | Discontinue therapy |

$^a$All dose modifications should be based on the worst preceding toxicity
$^b$Patients who require more than 2 dose reductions must be withdrawn from the study
$^c$Asthenia and Grade 3 Anorexia do not require dose modification TABLE 12-continued Dose Level Reductions for nab-Paclitaxel and Gemcitabine

| Dose Level | Nab-paclitaxel (mg/m$^2$) | Gemcitabine (mg/m$^2$) |
|---|---|---|
| 2$^{nd}$ dose reduction | 75 | 600 |
| If additional dose reductions required | Discontinue | Discontinue |

Recommended dose modifications for neutropenia and thrombocytopenia are provided in Table 13 and adjustments related to other toxicities are provided in Table 14.

TABLE 13 nab-Paclitaxel and Gemcitabine Dose Modifications at the Start of Each Cycle or Within a Cycle for Neutropenia and/or Thrombocytopenia.

| Cycle Day | ANC (cells/mm$^3$) | | Platelet count (cells/mm$^3$) | Nab-paclitaxel/Gemcitabine |
|---|---|---|---|---|
| Day 1 | <1500 | OR | <100,000 | Delay doses until recovery |
| Day 8 | 500 to <1000 | OR | 50,000 to <75,000 | Reduce 1 dose level |
| | <500 | OR | <50,000 | Withhold doses |
| Day 15: IF day 8 doses were reduced or given without modification: | | | | |
| | 500 to <1000 | OR | 50,000 to <75,000 | Reduce 1 dose level from Day 8 |
| | <500 | OR | <50,000 | Withhold doses |
| Day 15: IF day 8 doses were withheld: | | | | |
| | ≥1000 | OR | ≥75,000 | Reduce 1 dose level from Day 1 |
| | 500 to <1000 | OR | 50,000 to <75,000 | Reduce 2 dose levels from Day 1 |
| | <500 | OR | <50,000 | Withhold doses |

ANC = absolute neutrophil count

TABLE 14 nab-Paclitaxel and Gemcitabine Dose Modifications for Other Adverse Drug Reactions

| Adverse Drug Reaction | Nab-paclitaxel | Gemcitabine |
|---|---|---|
| Febrile Neutropenia: Grade 3 or 4 | Withhold until fever resolves and ANC ≥1500; resume at next lower dose level | |
| Peripheral Neuropathy: Grade 3 or 4 | Withhold until improves ≤ Grade 1; resume at next dose level | No dose reduction |
| Cutaneous Toxicity: Grade 2 or 3 | Reduce to next lower dose level; discontinue treatment if toxicity persists | |
| Gastrointestinal Toxicity: Grade 3 mucositis or diarrhea | Withhold until improves to ≤ Grade 1; resume at next dose level | |

Disease Evaluation

Tumor responses are evaluated according to the Response Evaluation Criteria in Solid Tumors (RECIST) version 1.1, to establish disease progression by CT or MRI. In addition, other imaging procedures, as deemed appropriate by the Investigator, are performed to assess sites of neoplastic involvement. The same method of assessment must be used throughout the study. Investigators should select target and non-target lesions in accordance with RECIST v1.1 guidelines. Follow up measurements and overall response should also be in accordance with these guidelines.

Tumor assessments should be completed until it has been determined that the patient has progressive disease (in accordance with RECIST v1.1). For patients who do not have documented disease progression per RECIST v. 1.1 at the time of treatment termination, imaging studies should be continually performed into the follow-up period every 8 weeks until disease progression is documented. Continued imaging follow-up on schedule is recommended to reduce potential bias in the evaluations of the impacts of the experimental treatments on disease.

EORTC-QLQ-C30 and EQ-5D-5L (Part 2 Only)

Health-related quality of life (HRQL) is assessed by the EORTC-QLQ-C30 and EQ-5D-5L instruments. The EORTC-QLQ-C30 is a reliable and valid measure of the quality of life of cancer patients in multicultural clinical research settings. It incorporates nine multi-item scales: five functional scales (physical, role, cognitive, emotional, and social); three symptom scales (fatigue, pain, and nausea and vomiting); and a global health and quality-of-life scale. Several single-item symptom measures are also included.

EQ-5D is a generic, preference-based measurement of HRQL. The EQ-5D-5L descriptive system comprises the following 5 dimensions: mobility, self-care, usual activities, pain/discomfort and anxiety/depression. Each dimension has 5 levels: no problems, slight problems, moderate problems, severe problems, and unable to do.

Patients are required to complete both questionnaires at time points outlined in the Schedule of Assessments. On days that the patient is to receive study drug, assessments should be completed prior to study drug administration. Only those patients for whom validated translations of the questionnaires are available will be required to complete the questionnaire.

Efficacy Analysis

In the assessments of efficacy, each MM-398-containing arm is compared to the control arm. Efficacy comparisons use stratified analyses, incorporating randomization strata. Each comparison uses 0.10 level one-sided testing to evaluate whether the MM-398-containing arm improves the efficacy parameter. Confidence intervals are presented at two-sided 95% level for descriptive purposes. Hypothesis tests and confidence intervals are not adjusted for multiple comparisons. The primary efficacy comparisons are based on the ITT population, which includes all randomized patients.

Tumor evaluation is measured according to RECIST v1.1. For each patient, progression free survival time is determined as the time from randomization (for patients in Part 1, the reference start time will be date of first study drug) to the first documented radiographical Progression of Disease (PD), per investigator using RECIST 1.1, or death from any cause, whichever comes first. If the progression or death occurs at a time point that is greater than 12 weeks after the non-PD last tumor assessment, then progression-free survival time is censored at the time of the last non-PD tumor assessment.

A primary analysis is conducted when the Week 24 progression-free status for all randomized patients can be determined, anticipated at approximately 24 weeks after the last patient is randomized. A subsequent analysis for PFS and other endpoints is performed when PFS events have occurred in at least 120 (i.e. 80% of randomized patients) patients.

Primary Efficacy Analysis

In the intention-to-treat (ITT) analysis, a patient is considered to have achieved progression-free survival at 24 weeks if the patient has data to indicate the patient has not progressed at 24 weeks. That is, a patient is considered a responder if there is at least one non-PD assessment, prior to progression or new anticancer therapy, at Week 24 or later.

Patients who do not meet the 24-week progression-free achievement criteria (e.g. patients progressed/died up to Week 24, patients censored prior to Week 24), if progression or death occurs at a time point that is greater than 12 weeks after the non-PD last tumor assessment.

For each arm, the progression-free survival achievement rate at 24 weeks is estimated by the number of patients meeting the 24 week achievement criteria divided by the number of ITT patients in the arm. The rate estimates are presented with corresponding 95% confidence intervals. Each MM-398 containing arm is assessed for increase in rate relative to the control arm using a one-sided Cochran-Mantel-Haenszel test, incorporating randomization stratification factors, at 0.10 level of significance.

Secondary Efficacy Analyses

Progression-Free Survival (PFS) is descriptively summarized for each arm using Kaplan-Meier methodology. Median PFS time and corresponding 95% confidence limits are presented. For each MM-398-containing arm, PFS is compared to the control arm. Hypothesis tests are conducted for differences in PFS using a one-sided stratified log-rank test. Hazard ratios (with 95% confidence interval) for PFS are estimated using stratified Cox models.

Best Overall Response (BOR) is defined as the best response as recorded from the start of study drug until disease progression. Patients without a post-baseline tumor assessment are considered to be non-evaluable for BOR. To classify BOR as stable disease (SD), there should be a qualifying SD assessment at least 6 weeks from randomization. Objective Response Rate (ORR) is defined as the proportion of patients with a BOR characterized as either a Complete Response (CR) or Partial Response (PR) relative to the total number of evaluable patients. Only patients with measurable disease at baseline will be included in the analysis of the objective response. Estimates of objective response rate and its corresponding 95% CI are calculated for each treatment arm. For each MM-398-containing arm, ORR is compared to the control arm. Differences in objective response rate between each MM-398-containing arm and control arm are provided with 95% CIs. Cochran-Mantel-Haenszel tests, adjusting by randomization strata, are used to compare objective response rates.

The maximum reduction (% change from baseline) in CA19-9 is computed, including analyses by time period (up to Week 8, 16 and 24 visits). CA 19-9 response analyses is carried out using 3 thresholds for maximum reduction: ≥20%, ≥50%, ≥90%. A patient without post-baseline CA19-9 measurement is considered as a non-responder. Only patients with CA 19-9 elevated (>37 U/mL) at baseline are included in the analysis of the CA19-9 response. For each threshold and time period, the proportion of CA19-9 response is estimated, along with corresponding 95% confidence intervals, by treatment arm.

Overall Survival (OS) is the time from randomization to the date of death from any cause. Patients who are alive or lost to follow-up at the time of the analysis will be censored at the last known alive date. OS is descriptively summarized for each arm using Kaplan-Meier methodology. For each MM-398-containing arm, OS is compared to the control arm. Hypothesis tests are conducted for differences in OS using a one-sided stratified log-rank test. Hazard ratios (with 95% confidence interval) for PFS are estimated using stratified Cox models.

Quality of Life Analyses

Quality of life analyses are performed using patients in the analysis populations for each quality of life instrument (EORTC-QLC-C30, EQ-5D-5L). EORTC-QLQ-30 and EQ-5D-5L results will be summarized at each visit by treatment group For each EORTC QLQ-C30 administered, scores are computed for the following scales: Global Health Status, Physical Functioning, Role Functioning, Emotional Functioning, Cognitive Functioning, Social Functioning, Fatigue, Nausea and vomiting, Pain, Dyspnea, Insomnia, Appetite Loss, Constipation, Diarrhea, Financial difficulties.

Scoring is carried out as described in the EORTC QLQ-C30 Scoring Manual (Fayers, Aaronson, Bjordal, Curran, & Groenvald, 2001). Linear transformations are applied to the raw scores so that the reported score will have range 0-100 for all scales. Summary statistics are presented for each subscale. A summary health state index value is computed for each EQ-5D-5L assessment. Summary statistics are presented for summary health state index. For each EQ-5D-5L attribute (mobility, self-care, usual activities, pain/discomfort, and anxiety/depression), responses are tabulated.

Safety Analysis

Safety analyses (adverse events and laboratory analyses) will be performed using the safety population. Adverse events are reported by the MedDRA version 17.1 or higher. Toxicity is graded according to the NCI CTCAE version 4.03.

Safety analysis of patients in Part 1 is to include a summary of dose-limiting toxicity events.

The period for treatment-emergent adverse events and safety findings is from the time of first study drug administration to 30 days after the date of last study drug administration. If an adverse event begins on the date of first study drug administration with no time recorded, the event is then considered as treatment-emergent.

Tabular summaries are to be presented for all adverse events, pre-treatment adverse events, treatment-emergent adverse events (TEAE), serious adverse events, adverse events leading to study drug discontinuation, TEAE-related to study drug and TEAE Grade 3/4. Adverse events are to be summarized by System Organ Class and preferred term. All adverse event data is to be listed by patient.

Laboratory data is presented by cycle. Abnormal laboratory values are assessed using all available data and toxicity grading will be assigned according to NCI CTCAE toxicity scale, where criteria are available to do so. Maximum and minimum decrease/increase in continuous laboratory data are reported. Frequency and percent of abnormal laboratory values (L/ULN, 2*L/ULN) are assessed. Shift to most severe toxicity grade are summarized.

Vital signs and ECG are tabulated for the change from baseline by time point. Additional analyses may be performed as described in detail within the SAP.

Vital signs are tabulated for the change from baseline by time point. Additional analyses may be performed as described in detail within the SAP.

Biomarker Subgroup Analysis

Analyses are performed to assess the associations between potential biomarkers (from plasma and archived tissue) and efficacy parameters (ORR, percent change in target lesion size, and PFS or as appropriate). Graphical displays are performed when appropriate.

Pharmacokinetics Analysis

Plasma concentrations of MM-398 and oxaliplatin can be used to characterize PK parameters. Due to the sparse PK sampling schedule, PK parameters for individual patients can be estimated based on the Empirical Bayesian Estimation method with priors from the previously estimated (MM-398) or published (oxaliplatin) population PK model parameters. The model simulated exposures, e.g., $C_{max}$, AUC (area under the curve), are used to examine any possible interactions between MM-398 and oxaliplatin by comparing the least squares geometric mean ratios (LS-GMR) of drug exposures. NONMEM®, Version 7.3, is used to estimate individual PK parameters and simulate plasma exposures.

Example 4: Tolerability of Antineoplastic Therapies in Human Clinical Trial

The tolerability of antineoplastic therapies combining liposomal irinotecan, 5-FU/leucovorin and oxaliplatin was evaluated in a human clinical trial described in Example 3, using two different doses: 80 mg/m$^2$ (salt) of liposomal irinotecan (MM-398) and 60 mg/m$^2$ (salt) of liposomal irinotecan (MM-398). Table 15 summarizes three dosing regimens for the treatment of previously untreated (frontline) pancreatic cancer in humans over a 28 day treatment cycle.

TABLE 15

Part 1 Dose Escalation Table (MM-398 + 5-FU/LV + oxaliplatin)

| Level | Oxaliplatin | | 5-FU/LV | | MM-398 (nal-IRI) | |
|---|---|---|---|---|---|---|
| | Dose (mg/m$^2$)$^a$ | Dose Day$^c$ | Dose (mg/m$^2$) | Dose Day$^c$ | Dose (mg/m$^2$)$^b$ | Dose Day$^c$ |
| 1 | 60 | 1, 15 | 2400/400 | 1, 15 | 80 | 1, 15 |
| 2 | 85 | 1, 15 | 2400/400 | 1, 15 | 80 | 1, 15 |
| -2A$^d$ | 75 | 1, 15 | 2400/400 | 1, 15 | 80 | 1, 15 |

$^a$First dose administration in conjunction with first dose of nal-IRI; oxaliplatin to be administered 2 hours after the completion of the nal-IRI infusion in Part 1.
$^b$46 hour infusion, no bolus is given; leucovorin and 5-FU will be administered last, following the completion of the oxaliplatin infusion
$^c$Day indicated is part of a 28-day cycle
Note:
The dose of nal-IRI and 5-FU/LV in Dose Level 1 and 2 above is the same dose and schedule that was previously used in the NAPOLI-1 Phase 3 study.

Initially, a combination of oxaliplatin, MM-398 liposomal irinotecan, leucovorin and 5-fluorouracil at dose level 1 in Table 15 above. The results are summarized in Table 16 for dose level 1 in Table 15 above (for 80 mg/m$^2$ (salt) M-398 dose), showing that the 80 mg/m$^2$ (salt) dose of liposomal irinotecan (MM-398) in combination with oxaliplatin and 5-fluorouracil/leucovorin at dose level 1 was not tolerated in humans.

TABLE 16

Antineoplastic Therapy with 80 mg/m$^2$ liposomal irinotecan in combination with oxaliplatin/5FU/leucovorin in human clinical trials

| Patient | Cycle 1 Day 1 | Cycle 1 Day 15 | Cycle 2 Day 1 | Cycle 2 Day 15 | Cycle 3 Day 1 | Cycle 3 Day 15 |
|---|---|---|---|---|---|---|
| 1 | ✓ | ✓ | X | X | X | X |
| 2 | ✓ | R | R | R | X | X |
| 3 | ✓ | X | X | X | X | X |
| 4 | ✓ | ✓ | X | X | X | X |
| 5 | ✓ | X | X | X | X | X |
| 6 | ✓ | ✓ | R | R | R | R |
| 7 | ✓ | X | X | X | X | X |

Table 16 summarizes the results from treating a total of seven (7) patients as part of Part 1 of Arm 1 shown in FIG. 12. All seven patients met the applicable inclusion criteria specified below, including a diagnosis of pancreatic cancer.

A "check mark" (✓) in Table 16 indicates the patient received the antineoplastic therapy of dose level 1 in Table 15 above, starting on the indicated days of 3 consecutive 28-day treatment cycles: 80 mg/m$^2$ liposomal irinotecan (MM-398, dose based on the corresponding amount of irinotecan hydrochloride trihydrate salt), 60 mg/m$^2$ oxaliplatin, 400 mg/m$^2$ (l+d) leucovorin and 2,400 mg/m$^2$ 5-fluorouracil, as described in the protocol of Example 3.

A "R" in Table 16 indicates the patient received a reduced dose of antineoplastic therapy of dose level −1 in Table 2 (Example 3 above) on the corresponding cycle and day: 60 mg/m$^2$ liposomal irinotecan (MM-398, dose based on the corresponding amount of irinotecan hydrochloride trihydrate salt), 60 mg/m$^2$ oxaliplatin, 400 mg/m$^2$ (l+d) leucovorin and 2,400 mg/m$^2$ 5-fluorouracil, as described in the protocol of Example 3.

An "X" in Table 16 indicates the patient did not receive an antineoplastic therapy combining liposomal irinotecan, oxaliplatin, 5-fluorouracil and leucovorin or combining liposomal irinotecan, oxaliplatin, and 5-fluorouracil. After cycle 1, day 1 and prior to cycle 1, day 15, patient 2 was determined to be homozygous for the UGT1A1*28 allele, and subsequent reduced doses of the antineoplastic therapy were administered on days indicated in Table 16, based on the protocol of Example 3. Patients 1 and 3-7 were not homozygous for UGT1A1*28 allele.

The antineoplastic therapy of dose level 1 in Table 15 (Example 4) was only administered to 2 of these 6 patients on day 15 of (28-day) cycle 1, no patients received dose level 1 for more than 2 consecutive doses, and none of the patients received this therapy after cycle 1.

Accordingly, as noted in the Table 16, antineoplastic therapies combining a dose of 80 mg/m$^2$ liposomal irinotecan with 60 mg/m$^2$ oxaliplatin and doses of 2,400 and 400 mg/m$^2$ of 5-fluorouracil and (l+d) leucovorin were not well tolerated in a human clinical trial (resulting in dose limiting toxicities). Examples of antineoplastic therapies combining a dose of 80 mg/m$^2$ liposomal irinotecan with 60 mg/m$^2$ oxaliplatin and doses of 2,400 and 400 mg/m$^2$ of 5-fluorouracil and (l+d) leucovorin include the therapies in Table 15.

In contrast, as noted in Table 18 below, antineoplastic therapies combining a dose of 60 mg/m$^2$ liposomal irinotecan with 60 mg/m$^2$ oxaliplatin and doses of 2,400 and 400 mg/m2 of 5-fluorouracil and (l+d) leucovorin were tolerated in a human clinical trial. In particular, dose level −1 in Table 17 (a 60 mg/m$^2$ (salt) M-398 dose) was administered two or more consecutive times to multiple human patients in the clinical trial described in Example 3. These antineoplastic therapies comprising the reduced 60 mg/m$^2$ (salt) of liposomal irinotecan (MM-398) in combination with oxaliplatin and 5-fluorouracil/leucovorin were better tolerated in humans than dose level 1 in Table 15. In other embodiments, patients are administered the therapy of dose level −2B in Table 17.

TABLE 17

Part 1 Dose Escalation Table (MM-398 + 5-FU/LV + oxaliplatin)

| Level | Oxaliplatin | | 5-FU/LV | | MM-398 (nal-IRI) | |
|---|---|---|---|---|---|---|
| | Dose (mg/m²)[a] | Dose Day[c] | Dose (mg/m²) | Dose Day[c] | Dose (mg/m²)[b] | Dose Day[c] |
| −1 | 60 | 1, 15 | 2400/400 | 1, 15 | 60 | 1, 15 |
| −2B | 85 | 1, 15 | 2400/400 | 1, 15 | 60 | 1, 15 |

[a]First dose administration in conjunction with first dose of MM-398; oxaliplatin to be administered 2 hours after the completion of the nal-IRI infusion in Part 1.
[b]46 hour infusion, no bolus is given; leucovorin and 5-FU will be administered last, following the completion of the oxaliplatin infusion
[c]Day indicated is part of a 28-day cycle

TABLE 18

Antineoplastic Therapy with 60 mg/m² liposomal irinotecan in combination with oxaliplatin/5FU/leucovorin in human clinical trials

| Patient | Cycle 1 Day 1 | Cycle 1 Day 15 | Cycle 2 Day 1 | Cycle 2 Day 15 | Cycle 3 Day 1 |
|---|---|---|---|---|---|
| 1 | ✓ | ✓ | R2 | R2 | R2 |
| 2 | ✓ | ✓ | ✓ | | |
| 3 | ✓ | ✓ | ✓ | | |
| 4 | ✓ | ✓ | | | |
| 5 | ✓ | ✓ | ✓ | | |

Table 18 summarizes the results from treating a total of five (5) patients as part of Part 1 of Arm 1 shown in FIG. 12. All five patients met the applicable inclusion criteria specified in Example 3, including a diagnosis of pancreatic cancer. A "check mark" (✓) in Table 18 indicates the patient received the antineoplastic therapy of dose level −1 in Table 17 above, starting on the indicated days of 3 consecutive 28-day treatment cycles: 60 mg/m² liposomal irinotecan (MM-398, dose based on the corresponding amount of irinotecan hydrochloride trihydrate salt), 60 mg/m² oxaliplatin, 400 mg/m² (l+d) leucovorin and 2,400 mg/m² 5-fluorouracil, as described in the protocol of Example 3.

In contrast to the antineoplastic therapy of dose level 1 in Table 14, the antineoplastic therapy of dose level −1 in Table 2 (Example 3) was administered repeatedly to patients 2 and 6 for at least 3 consecutive administrations (including 4 consecutive administrations for patient 6). The antineoplastic therapy of dose level −1 in Table 2 (Example 3) was administered to 5 of 5 patients on days 1 and 15 of (28-day) cycle 1, and days 1 and 15 of (28 day) to 3 of 4 patients in the study, with no dose limiting toxicities. The antineoplastic therapy of dose level −1 was administered repeatedly to all 5 patients for at least 2 consecutive administrations.

A "check mark" (✓) in Table 18 indicates the patient received the antineoplastic therapy of dose level −1 in Table 17 above, starting on the indicated days of 3 consecutive 28-day treatment cycles: 80 mg/m² liposomal irinotecan (MM-398, dose based on the corresponding amount of irinotecan hydrochloride trihydrate salt), 60 mg/m² oxaliplatin, 400 mg/m² (l+d) leucovorin and 2,400 mg/m² 5-fluorouracil, as described in the protocol of Example 3.

A "R2" in Table 18 indicates the patient received a reduced dose of antineoplastic therapy of dose on the corresponding cycle and day: 50 mg/m² liposomal irinotecan (MM-398, dose based on the corresponding amount of irinotecan hydrochloride trihydrate salt), 60 mg/m² oxaliplatin, mg/m² (l+d) leucovorin and 1,800 mg/m² 5-fluorouracil (a 25% reduction compared to dose level −1 dose), as described in the protocol of Example 3. One patient in Table 18 received this reduced dose in response to Grade II symptoms (non-hematologic), but without a dose limiting toxicity.

Accordingly, as noted in the Table 18, antineoplastic therapies combining a dose of 60 mg/m² liposomal irinotecan with 60 mg/m² oxaliplatin and doses of 2,400 and 400 mg/m² of 5-fluorouracil and (l+d) leucovorin were well tolerated in a human clinical trial. Examples of antineoplastic therapies combining a dose of 80 mg/m² liposomal irinotecan with 60 mg/m² oxaliplatin and doses of 2,400 and 400 mg/m² of 5-fluorouracil and (l+d) leucovorin include the therapies in Table 17.

Example 5: ONIVYDE® (Irinotecan Liposome Injection) Liposomal Irinotecan

One preferred example of an irinotecan liposome described herein is the product marketed as ONIVYDE® (irinotecan liposome injection). ONIVYDE® is a topoisomerase inhibitor, formulated with irinotecan in a liposomal dispersion, for intravenous use.

The finished ONIVYDE® product is a white to slightly yellow opaque sterile concentrate for infusion. It consists of an isotonic dispersion of liposomes containing irinotecan hydrochloride trihydrate. The liposomes are small unilamellar lipid bilayer vesicles, approximately 110 nm in diameter, enclosing an aqueous compartment that contains irinotecan in a gelated or precipitated state, as sucrosofate salt. The vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. Each mL also contains 2-[4-(2-hydroxyethyl)piperazin-1-yl]ethanesulfonic acid (HEPES) as a buffer 4.05 mg/mL and sodium chloride as an isotonicity reagent 8.42 mg/mL. The liposomes are dispersed in an aqueous buffered solution.

The ONIVYDE® product contains irinotecan sucrosofate encapsulated in a liposome, obtained from an irinotecan hydrochloride trihydrate starting material. The chemical name of irinotecan is (S)-4,11-diethyl-3,4,12,14-tetrahydro-4-hydroxy-3,14-dioxo1H-pyrano[3',4': 6,7]-indolizino[1,2-b]quinolin-9-yl-[1,4'bipiperidine]-1'-carboxylate. The dosage of ONIVYDE® can be calculated based on the equivalent amount of irinotecan trihydrate hydrochloride starting material used to prepare the irinotecan liposomes, or based on the amount of irinotecan in the liposome. There are about 866 mg of irinotecan per gram of irinotecan trihydrate hydrochloride. For example, an ONIVYDE® dose of 80 mg based on the amount of irinotecan hydrochloride trihydrate starting material actually contains about 0.866×(80 mg) of irinotecan in the final product (i.e., a dose of 80 mg/m² of ONIVYDE® based on the weight of irinotecan hydrochloride starting material is clinically equivalent to about 70 mg/m² of irinotecan in the final product). Each 10 mL single-dose vial contains 43 mg irinotecan free base at a concentration of 4.3 mg/mL.

The invention claimed is:
1. A method of treating metastatic adenocarcinoma of the pancreas in a human patient who has not previously received an antineoplastic agent to treat the metastatic adenocarcinoma of the pancreas, the method comprising administering an antineoplastic therapy to the patient once every two weeks, the antineoplastic therapy consisting of:
- a. 60 mg/m$^2$ of liposomal irinotecan,
- b. 60 mg/m$^2$ oxaliplatin,
- c. 200 mg/m$^2$ of the (1)-form of leucovorin or 400 mg/m$^2$ of the (l+d) racemic form of leucovorin, and
- d. 2,400 mg/m$^2$ 5-fluorouracil;

to treat the metastatic adenocarcinoma of the pancreas in the human patient.

2. The method of claim 1, wherein each administration of the oxaliplatin begins 2 hours after completing each administration of the liposomal irinotecan.

3. The method of claim 1, wherein the 5-fluorouracil is administered as an infusion over 46 hours.

4. The method of claim 1, wherein the leucovorin is administered immediately prior to the 5-fluorouracil.

5. The method of claim 1, wherein the liposomal irinotecan, oxaliplatin and leucovorin are administered on days 1 and 15 of a 28-day treatment cycle.

6. The method of claim 1, wherein the liposomal irinotecan is administered as an infusion over about 90 minutes.

7. The method of claim 1, wherein the liposomal irinotecan is administered, followed by administering the oxaliplatin, followed by administering the leucovorin, followed by administering the 5-fluorouracil.

8. The method of claim 1, wherein the liposomal irinotecan comprises irinotecan sucrose octasulfate encapsulated in liposomes.

9. The method of claim 1, wherein the liposomal irinotecan comprises irinotecan encapsulated in liposomes comprising 1,2-distearoyl-sn-glycero-3-phosphocholine (DSPC), cholesterol, and a N-(carbonylmethoxypolyethlyene glycol-2000)-1,2-distearoly-sn-glycero-3-phosphoethanolamine (MPEG-2000-DSPE).

10. The method of claim 1, wherein the liposomal irinotecan comprises irinotecan sucrose octasulfate encapsulated in liposomes comprising 1,2-distearoyl-sn-glycero-3-phosphocholine (DSPC), cholesterol, and a N-(carbonylmethoxypolyethlyene glycol-2000)-1,2-distearoly-sn-glycero-3-phosphoethanolamine (MPEG-2000-DSPE).

11. The method of claim 10, wherein the liposomal irinotecan, oxaliplatin, leucovorin, and 5-fluorouracil are administered beginning on days 1 and 15 of a 28-day treatment cycle; each administration of the liposomal irinotecan is administered prior to each administration of the leucovorin; each administration of the leucovorin is administered immediately prior to each administration of the 5-fluorouracil; and each administration of the 5-fluorouracil is administered as an infusion over 46 hours.

12. A method of treating metastatic adenocarcinoma of the pancreas in a human patient who has not previously received gemcitabine to treat the metastatic adenocarcinoma of the pancreas, the method comprising administering an antineoplastic therapy to the patient once every two weeks, the antineoplastic therapy consisting of:
- a. 60 mg/m$^2$ of liposomal irinotecan,
- b. 60 mg/m$^2$ oxaliplatin,
- c. 200 mg/m$^2$ of the (1)-form of leucovorin or 400 mg/m$^2$ of the (l+d) racemic form of leucovorin, and
- d. 2,400 mg/m$^2$ 5-fluorouracil;

to treat the metastatic adenocarcinoma of the pancreas in the human patient.

13. The method of claim 1, wherein the liposomal irinotecan, oxaliplatin, leucovorin, and 5-fluorouracil are administered beginning on days 1 and 15 of a 28-day treatment cycle; each administration of the liposomal irinotecan is administered prior to each administration of the leucovorin; each administration of the leucovorin is administered prior to each administration of the 5-fluorouracil; and each administration of the 5-fluorouracil is administered as an infusion over 46 hours.

14. The method of claim 12, wherein the liposomal irinotecan, oxaliplatin, leucovorin, and 5-fluorouracil are administered beginning on days 1 and 15 of a 28-day treatment cycle; each administration of the liposomal irinotecan is administered prior to each administration of the leucovorin; each administration of the leucovorin is administered prior to each administration of the 5-fluorouracil; and each administration of the 5-fluorouracil is administered as an infusion over 46 hours.

15. The method of claim 1, wherein each administration of the oxaliplatin begins after completing each administration of the liposomal irinotecan, and the method further comprises administering a corticosteroid and an anti-emetic to the patient prior to the antineoplastic therapy.

* * * * *